(12) United States Patent
McCall et al.

(10) Patent No.: US 10,953,012 B2
(45) Date of Patent: *Mar. 23, 2021

(54) HETEROCYCLIC COMPOUNDS FOR THE INHIBITION OF PASK

(75) Inventors: John M. McCall, Boca Grande, FL (US); Robert C. Kelly, San Francisco, CA (US); Donna L. Romero, Chesterfield, MO (US)

(73) Assignee: BioEnergenix LLC, San Francisco, CA (US)

(*) Notice: Subject to any disclaimer, the term of this patent is extended or adjusted under 35 U.S.C. 154(b) by 107 days.

This patent is subject to a terminal disclaimer.

(21) Appl. No.: 13/456,838

(22) Filed: Apr. 26, 2012

(65) Prior Publication Data

US 2012/0277224 A1    Nov. 1, 2012

Related U.S. Application Data

(60) Provisional application No. 61/479,161, filed on Apr. 26, 2011.

(51) Int. Cl.
| | |
|---|---|
| *A61P 3/10* | (2006.01) |
| *A61P 3/04* | (2006.01) |
| *A61P 3/06* | (2006.01) |
| *A61P 3/00* | (2006.01) |
| *C07D 487/04* | (2006.01) |
| *A61K 31/519* | (2006.01) |
| *A61K 31/5377* | (2006.01) |
| *C07D 401/14* | (2006.01) |
| *C07D 401/04* | (2006.01) |
| *C07D 265/32* | (2006.01) |
| *C07D 487/22* | (2006.01) |
| *C07D 407/06* | (2006.01) |

(52) U.S. Cl.
CPC ........ *A61K 31/519* (2013.01); *A61K 31/5377* (2013.01); *C07D 487/04* (2013.01)

(58) Field of Classification Search
CPC ............................ C07D 487/04; A61K 31/519
USPC ........................................ 544/281; 514/259.3
See application file for complete search history.

(56) References Cited

U.S. PATENT DOCUMENTS

| | | | |
|---|---|---|---|
| 5,420,128 A | 5/1995 | Kiyokawa et al. | |
| 5,843,951 A | 12/1998 | Inoue et al. | |
| 6,197,774 B1 * | 3/2001 | Yamada et al. | 514/259.3 |
| 9,278,973 B2 | 3/2016 | Mccall | |
| 10,392,389 B2 | 8/2019 | Mccall | |
| 2005/0004159 A1 | 1/2005 | Hibi | |
| 2005/0136065 A1 | 6/2005 | Valiante et al. | |
| 2005/0282827 A1 | 12/2005 | Goetschi et al. | |
| 2006/0025426 A1 | 2/2006 | Fraley et al. | |
| 2006/0040958 A1 | 2/2006 | Guzi et al. | |
| 2006/0041131 A1 | 2/2006 | Guzi et al. | |
| 2006/0089362 A1 | 4/2006 | Seno et al. | |
| 2006/0094706 A1 | 5/2006 | Paruch et al. | |
| 2006/0128725 A1 | 6/2006 | Guzi et al. | |
| 2007/0072879 A1 | 3/2007 | McArthur et al. | |
| 2007/0281951 A1 | 12/2007 | Guzi et al. | |
| 2008/0050384 A1 | 2/2008 | Guzi et al. | |
| 2009/0176778 A1 | 7/2009 | Schmitz et al. | |
| 2009/0182142 A1 | 7/2009 | Furukubo et al. | |
| 2009/0215778 A1 | 8/2009 | Nitz et al. | |
| 2015/0274740 A1 | 10/2015 | Mccall | |
| 2015/0284395 A1 | 10/2015 | Mccall | |
| 2016/0235755 A1 | 8/2016 | Mccall | |

FOREIGN PATENT DOCUMENTS

| | | | |
|---|---|---|---|
| EP | 2264035 A1 * | 12/2010 | ........... C07D 487/04 |
| JP | 2004277337 | 10/2004 | |
| JP | 2005008581 | 1/2005 | |
| JP | 2006045156 | 2/2006 | |
| WO | WO9841526 | 9/1998 | |
| WO | WO2004022062 | 3/2004 | |
| WO | WO2004022559 | 3/2004 | |
| WO | WO2004022560 | 3/2004 | |
| WO | WO2004026229 | 4/2004 | |
| WO | WO2007015866 | 2/2007 | |
| WO | WO2007048066 | 4/2007 | |
| WO | 2008057601 | 5/2008 | |
| WO | WO2008130569 | 10/2008 | |
| WO | WO2008134035 | 11/2008 | |
| WO | 2010056631 | 5/2010 | |
| WO | WO 2011114148 * | 9/2011 | |
| WO | 2012149157 | 11/2012 | |
| WO | 2014066743 | 5/2014 | |
| WO | 2014066795 | 5/2014 | |

OTHER PUBLICATIONS

J. Med. Chem., 1981, 24(5), 610-13.
Zhurnal Organicheskoi Khimii, 1982, 18(5), 1079-84 (partial translation).
Hao, Huai-Xiang, et al. "PAS kinase is required for normal cellular energy balance." Proceedings of the National Academy of Sciences 104.39 (2007): 15466-15471.
Borisov et al., J. of Comb. Chem., 2009, 11 (6), pp. 1023-1029.
PCT Patent Application No. PCT/US2013/066782, International Preliminary Report on Patentability, dated Apr. 28, 2015, 7 pages.
PCT Patent Application No. PCT/US2013/066782, International Search Report, dated Feb. 21, 2014, 4 pages.

(Continued)

*Primary Examiner* — Susanna Moore
(74) *Attorney, Agent, or Firm* — Dennis A. Bennett; Brock Levin

(57) ABSTRACT

Disclosed herein are new heterocyclic compounds and compositions and their application as pharmaceuticals for the treatment of disease. Methods of inhibiting PAS Kinase (PASK) activity in a human or animal subject are also provided for the treatment of diseases such as diabetes mellitus.

2 Claims, No Drawings

(56) References Cited

OTHER PUBLICATIONS

Stella, J. Pharmaceutical Sciences, 2010, 99(12), pp. 4755-4765.
Auzzi, G. et al. "Synthesis of 3-(1,3,4-Thiadiazol-2-Yl)Pyrazolo(1,5-a)Pyrimidine Derivatives as Potential Antimicrobial Agents", Farmaco, 45(11):1193-205, (1990).
International Application No. PCT/US2012/035209; International Preliminary Report on Patentability, dated Oct. 29, 2013; 7 pages.
International Application No. PCT/US2012/035209; International Preliminary Report or Patentability, dated Oct. 29, 2013; 07 pages.
International Application No. PCT/US2012/035209; International Search Report and Written Opinion of the International Search Authority, dated Jan. 3, 2013; 12 pages.
International Application No. PCT/US2013/066782; Written Opinion of the International Search Authority, dated Feb. 21, 2014; 06 pages.
International Application No. PCT/US2013/066869; International Preliminary Report or Patentability, dated Apr. 28, 2015; 07 pages.
International Application No. PCT/US2013/066869; International Search Report and Written Opinion of the International Search Authority, dated Feb. 21, 2014; 10 pages.
PubChem (SID#4262975, pp. 1-8, downloaded May 5, 2018).
U.S. Appl. No. 14/438,261; Advisory Action dated Jul. 31, 2017; 02 pages.
U.S. Appl. No. 14/438,261; Final Office Action dated Mar. 30, 2017; 06 pages.
U.S. Appl. No. 14/438,261; Final Office Action dated Sep. 8, 2017; 06 pages.
U.S. Appl. No. 14/438,261; Non-Final Office Action dated Sep. 22, 2016; 10 pages.
U.S. Appl. No. 14/438,268; Notice of Allowance dated Oct. 30, 2015; 08 pages.
U.S. Appl. No. 15/010,619; Final Office Action dated Sep. 27, 2017; 06 pages.
U.S. Appl. No. 15/010,619; Non-Final Office Action dated Feb. 24, 2017; 10 pages.
U.S. Appl. No. 15/010,619; Non-Final Office Action dated May 11, 2018; 06 pages.
STN structure database search (Registry# 1338651-46-9, Oct. 28, 2011, p. 1).
U.S. Appl. No. 14/438,261; Non-Final Office Action dated May 31, 2018; 7 pages.
U.S. Appl. No. 14/438,261; Final Office Action dated Jan. 18, 2019; 10 pages.
PubChem (SID#4260883, pp. 1-8, downloaded May 5, 2018).
U.S. Appl. No. 15/010,619; Final Office Action dated Aug. 30, 2018; 12 pages.
U.S. Appl. No. 14/438,261; Examiner-Initiated Interview Summary, dated Apr. 12, 2019; 1 page.
U.S. Appl. No. 14/438,261; Notice of Allowance, dated Apr. 12, 2019; 9 pages.
PubChem (SID 4260883, CID: 1266395, available date Aug. 24, 2005, downloaded <https://pubchem.ncbi.nlm.hih.gov/compound/661929>, Jun. 23, 2019, pp. 1-15).
U.S. Appl. No. 15/010,619; Non-Final Office Action dated Jul. 2, 2019; 14 pages.
STN search ChemBridge Corp. (RN# 1087600-51-8, available date Dec. 21, 2008, see STN search, p. 37).
U.S. Appl. No. 15/010,619; Final Office Action, dated Jan. 2, 2020; 11 pages.

* cited by examiner

HETEROCYCLIC COMPOUNDS FOR THE INHIBITION OF PASK

This application claims the benefit of priority of U.S. Provisional Application No. 61/479,161, filed Apr. 26, 2011, the disclosure of which is hereby incorporated by reference as if written herein in its entirety.

Disclosed herein are new heterocyclic compounds and compositions and their application as pharmaceuticals for the treatment of disease. Methods of inhibiting PAS Kinase (PASK) activity in a human or animal subject are also provided for the treatment of diseases such as diabetes mellitus.

The regulation of glycogen metabolism is critical for the maintenance of glucose and energy homeostasis in mammals. Glycogen, a large branched polymer of glucose, acts as a reserve of carbon and energy in a variety of organisms. In mammals, the most important stores are found in the liver and skeletal muscle (1). Liver glycogen is required to efficiently buffer blood glucose levels during fasting, whereas muscle glycogen is primarily used locally as a fuel for muscle contraction (2). Dysregulation of glycogen metabolism has been implicated in the development of many diseases, including type 2 diabetes mellitus (3, 4).

The synthesis of glycogen is primarily controlled through regulation of the enzyme glycogen synthase (GYS, various isoforms), which catalyzes bulk glycogen synthesis (5, 6, 7). The muscle isoform of glycogen synthase (GYS1) is inactivated by reversible phosphorylation that occurs at nine distinct sites within the enzyme (8, 9, 10). In the best characterized form of glycogen synthase, the phosphorylation sites are clustered at the N and C termini (14). Glycogen synthase kinase-3 (GSK-3), an insulin-dependent kinase which has long been implicated in the stepwise phosphorylation of four key sites in the C terminus of glycogen synthase including Ser-640 (one of the most important endogenous regulatory phosphorylation sites in mammalian glycogen synthase (15, 32) and Ser-644 (10, 11-13, 24, 25). GSK-3, however, is not the sole kinase that phosphorylates C-terminal regulatory sites; GSK-3-independent mechanisms also exist, since serine-to-alanine substitutions at Ser-7 and Ser-10 block GSK-3-mediated phosphorylation of the important regulatory sites Ser-640 and Ser-644, and phosphorylation at these sites still occurs.

PASK (purine-analog sensitive kinase, PAS kinase) is a PAS domain-containing serine/threonine kinase, and genetic experiments in *S. cerevisiae* yeast have implicated PASK as a physiological regulator of glycogen synthase and glycogen accumulation (16, 17). As with the entire glycogen synthase regulatory system, PASK is highly conserved from yeast to man. Human PASK (hPASK) phosphorylates glycogen synthase primarily at Ser-640, causing near complete inactivation. It is interesting to note that the exact site of PASK-dependent phosphorylation is similar but not identical in yeast and mammalian glycogen synthase (18, 19); yeast PASK phosphorylates glycogen synthase at the site analogous to Ser-644, four residues C-terminal (18). It appears that the hPASK mid region (residues 444-955) is required for efficient phosphorylation of glycogen synthase in vitro and for interaction with glycogen synthase in cells: an hPASK mutant (Δ955) lacking the noncatalytic N terminus was unable to efficiently phosphorylate glycogen synthase. Since this region is not required for the phosphorylation of generic, nonphysiological substrates, such as histones and synthetic peptides, it has been proposed that the mid region of hPASK is essential for substrate-targeting. A similar substrate region has been discovered in many protein kinases (26-29). Unlike GSK-3, the activity of hPASK has been shown to be independent of insulin and probably regulated instead by a more direct metabolic signal (23).

Genetic and proteomic screens using yeast PASK identified a number of substrates and implicated this kinase in the regulation of carbohydrate metabolism and translation (18). It has previously been shown that yeast PASK phosphorylates glycogen synthase in vitro and that strains lacking the PASK genes (PSK1 and PSK2) had elevated glycogen synthase activity and an approximately 5- to 10-fold accumulation of glycogen relative to wild-type strains, consistent with impaired ability to phosphorylate glycogen synthase in vivo (18). Because glycogen synthesis and translation are two processes tightly regulated in response to nutrient availability and because PAS domains are frequently involved in metabolic sensing, a role for PASK in the cellular response to metabolic status has been proposed. Indeed, it was recently demonstrated that mammalian PASK plays a role in the cellular response to nutrients. The catalytic activity of PASK in pancreatic islet β-cells is rapidly increased in response to glucose addition, and PASK is required for the glucose-responsive expression of some β-cell genes, including preproinsulin (23).

PASK catalytic activity is not responsive to glucose alone, however. The interaction between the hPASK midregion and glycogen synthase is regulated by at least two factors. First, the PAS domain of PAS kinase plays a negative role in regulating this interaction. If the PAS domain is deleted or disrupted, hPASK associates more stably with glycogen synthase. PAS domain function is usually controlled by the metabolic status of the host cell, as has been suggested for the PASK PAS domain (23). This observation raises the intriguing possibility that the hPASK-glycogen synthase interaction is regulated by the metabolic status of the cell, thereby enabling an additional layer of metabolic regulation of glycogen synthesis. Second, glycogen negatively regulates the hPASK-glycogen synthase interaction, which would initially seem counterintuitive, since glycogen would thereby stimulate its own continued synthesis. It is possible, however, that this mechanism exists to spatially coordinate the synthesis of glycogen. It is becoming increasingly apparent that glycogen is synthesized in cells in a highly organized spatial pattern (30). Perhaps one function of hPASK is to maintain free, unlocalized glycogen synthase in a phosphorylated, inactive form until it is properly localized to an existing, properly organized glycogen particle. These data strongly suggest that the hPASK midregion plays an important role in targeting hPASK catalytic activity to specific substrates within the cell.

Since hPASK has been recently implicated in glucose-sensing and glucose-responsive transcription, it appears likely that glucose signaling by means of hPASK affects glycogen metabolism in vivo. It is well-established that derangement in glycogen metabolism is one of the hallmarks of both Type 1 and Type 2 diabetes (20) and related conditions (21), including a panoply of life-threatening cardiovascular conditions (22). Using PASK1 mice, it has further been demonstrated that PASK is indeed required for normal insulin secretion by pancreatic β cells, and that PASK deletion results in nearly complete resistance to the phenotypes caused by a high-fat diet, including obesity, insulin resistance and hepatic fat accumulation. Therefore, PASK inhibition would comprise a system for the metabolic control of glucose utilization and storage in mammalian cells, and offer a new method to treat metabolic diseases including but not limited to diabetes and its complications, the metabolic syndrome, insulin resistance, and various cardiovascular conditions.

Novel compounds and pharmaceutical compositions, certain of which have been found to inhibit PASK have been discovered, together with methods of synthesizing and using the compounds including methods for the treatment of PAS K-mediated diseases in a patient by administering the compounds.

In an embodiment, compounds have structural Formula I

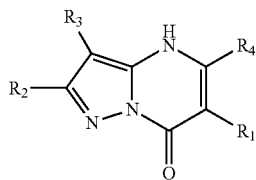

(I)

or a pharmaceutically acceptable salt, ester, or prodrug thereof, wherein:

$R_1$ is chosen from hydrogen, hydroxyl, cyano, lower alkyl, haloalkyl, aryl and arylalkyl, any of which may be optionally substituted;

$R_2$ is chosen from hydrogen, hydroxy, alkoxy, amino, alkylamino, dialkylamino, $NHCOR_{20}$, lower alkyl, lower haloalkyl, aryl, arylalkyl, heteroaryl and heteroarylalkyl, any of which may be optionally substituted;

$R_3$ is chosen from hydrogen, lower alkyl, cycloalkyl, aryl, heteroaryl, heterocycloalkyl, cycloalkylalkyl, arylalkyl, heteroarylalkyl, heterocycloalkylalkyl, cyano, $CONR_6R_7$, $CO_2R_8$, and $COR_9$, any of which may be optionally substituted;

$R_4$ is chosen from lower alkyl, $CH_2CO_2R_5$, alkoxyalkyl, aryl, heteroaryl, cycloalkyl, arylalkyl, heteroarylalkyl, and cycloalkylalkyl, any of which may be optionally substituted, or optionally, $R_1$ and $R_4$ may be taken together to form a cycloalkyl or aryl;

$R_5$ is chosen from hydrogen and lower alkyl;

$R_6$ and $R_7$ are independently chosen from hydrogen, lower alkyl, cycloalkyl, aryl, heteroaryl, heterocycloalkyl, cycloalkylalkyl, arylalkyl, heteroarylalkyl, heterocycloalkylalkyl, any of which may be optionally substituted, or $R_6$ and $R_7$ can be taken together to form a heterocycloalkyl or heteroaryl, any of which may be optionally substituted;

$R_8$ is chosen from hydrogen and lower alkyl;

$R_9$ is chosen from hydrogen, lower alkyl, cycloalkyl, aryl, heteroaryl, heterocycloalkyl, cycloalkylalkyl, arylalkyl, heteroarylalkyl, heterocycloalkylalkyl, any of which may be optionally substituted; and $R_{20}$ is chosen from lower alkyl, arylalkyl, aryl, heteroaryl, and heteroarylalkyl.

Certain compounds disclosed herein may possess useful PASK modulating activity, and may be used in the treatment or prophylaxis of a disease or condition in which PASK plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for modulating PASK. Other embodiments provide methods for treating a PAS K-mediated disorder in a patient in need of such treatment, comprising administering to said patient a therapeutically effective amount of a compound or composition according to the present invention. Also provided is the use of certain compounds disclosed herein for use in the manufacture of a medicament for the treatment of a disease or condition ameliorated by the inhibition of PASK.

In an embodiment, if $R_1$ is hydrogen, and $R_2$ is hydrogen, then $R_3$ is chosen from heteroaryl, heterocycloalkyl, cycloalkylalkyl, arylalkyl, heteroarylalkyl, and heterocycloalkylalkyl, any of which may be optionally substituted;

if $R_1$ is hydrogen, $R_2$ is hydroxyl, and $R_3$ is arylalkyl or heteroarylalkyl, then $R_4$ is not phenyl;

if $R_1$ is hydrogen, $R_2$ is amino, and $R_3$ is arylalkyl, $CO_2R_8$, or $COR_9$, then $R_4$ is not phenyl; and if $R_1$ is hydrogen, $R_2$ is alkoxyalkyl, and $R_3$ is phenyl, then $R_4$ is not phenyl or pyridyl.

In an embodiment, compounds have structural formula I wherein $X_1$ is $CR_3$ and $R_3$ is chosen from hydrogen, heteroaryl, heterocycloalkyl, heterocycloalkylalkyl, and aryl, any of which may be optionally substituted.

In an embodiment, compounds have structural formula I wherein $X_2$ is $CR_2$ and $R_2$ is chosen from hydrogen, hydroxyl, alkoxy, lower alkyl, lower haloalkyl, aryl, arylalkyl, heteroaryl, amino, alkylamino, dialkylamino, and heteroarylalkyl, any of which may be optionally substituted.

In an embodiment, compounds have structural formula I wherein $R_3$ is chosen from pyridyl and phenyl, either of which may be optionally substituted.

In an embodiment, compounds have structural formula II:

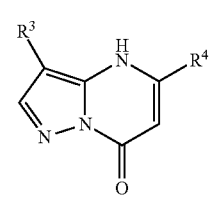

II or a salt, ester or prodrug thereof, wherein:

$R_3$ is chosen from heteroaryl, heterocycloalkyl, cycloalkylalkyl, arylalkyl, $CONR_6R_7$, heteroarylalkyl, and heterocycloalkylalkyl, any of which may be optionally substituted;

$R_4$ is chosen from aryl, heteroaryl, cycloalkyl, arylalkyl, heteroarylalkyl, and cycloalkylalkyl, any of which may be optionally substituted; and $R_6$ and $R_7$ are independently chosen from hydrogen, lower alkyl, cycloalkyl, aryl, heteroaryl, heterocycloalkyl, cycloalkylalkyl, arylalkyl, heteroarylalkyl, heterocycloalkylalkyl, any of which may be optionally substituted, or $R_6$ and $R_7$ can be taken together to form a heterocycloalkyl or heteroaryl, any of which may be optionally substituted.

In an embodiment, compounds have structural formula II wherein $R_3$ is chosen from heterocycloalkyl and heteroaryl.

In an embodiment, compounds have structural formula II wherein $R_3$ is arylalkyl.

In an embodiment, compounds have structural formula II wherein $R_3$ is chosen from heterocycloalkylalkyl and heteroarylalkyl.

In an embodiment, compounds have structural formula I wherein $R_3$ is pyridyl, which may be optionally substituted.

In an embodiment, compounds have structural formula III:

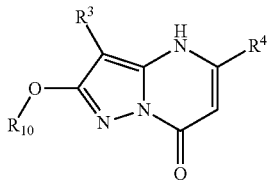

or a salt, ester or prodrug thereof, wherein:

$R_3$ is chosen from lower alkyl, cycloalkyl, aryl, heteroaryl, heterocycloalkyl, cycloalkylalkyl, arylalkyl, heteroarylalkyl, heterocycloalkylalkyl, $CONR_6R_7$, $CO_2R_8$, and $COR_9$, any of which may be optionally substituted;

$R_4$ is chosen from aryl, heteroaryl, cycloalkyl, arylalkyl, heteroarylalkyl, and cycloalkylalkyl, any of which may be optionally substituted;

$R_6$ and $R_7$ are independently chosen from hydrogen, lower alkyl, cycloalkyl, aryl, heteroaryl, heterocycloalkyl, cycloalkylalkyl, arylalkyl, heteroarylalkyl, heterocycloalkylalkyl, any of which may be optionally substituted, or $R_6$ and $R_7$ can be taken together to form a heterocycloalkyl or heteroaryl, any of which may be optionally substituted;

$R_8$ is chosen from hydrogen and lower alkyl;

$R_9$ is chosen from hydrogen, lower alkyl, cycloalkyl, aryl, heteroaryl, heterocycloalkyl, cycloalkylalkyl, arylalkyl, heteroarylalkyl, heterocycloalkylalkyl, any of which may be optionally substituted;

$R_{10}$ is chosen from hydrogen and lower alkyl; and if $R_3$ is arylalkyl or heteroarylalkyl and $R_{10}$ is hydrogen, then $R_4$ is not unsubstituted phenyl.

In an embodiment, compounds have structural formula III wherein $R_3$ is $CONR_6R_7$.

In an embodiment, compounds have structural formula III wherein $R_3$ is chosen from $CO_2R_8$ and $COR_9$.

In an embodiment, compounds have structural formula III wherein $R_3$ is lower alkyl.

In an embodiment, compounds have structural formula III wherein $R_3$ is cycloalkyl.

In an embodiment, compounds have structural formula III wherein $R_3$ is aryl.

In an embodiment, compounds have structural formula III wherein $R_3$ is chosen from heterocycloalkyl and heteroaryl.

In an embodiment, compounds have structural formula III wherein $R_3$ is arylalkyl.

In an embodiment, compounds have structural formula III wherein $R_3$ is chosen from heterocycloalkylalkyl and heteroarylalkyl.

In an embodiment, compounds have structural formula III wherein $R_3$ is chosen from pyridyl and phenyl, either of which may be optionally substituted.

In an embodiment, compounds have structural formula IV:

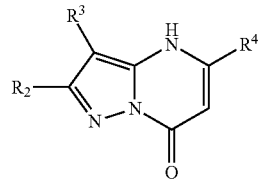

or a salt, ester or prodrug thereof, wherein:

$R_2$ is chosen from aryl, arylalkyl, heteroaryl and heteroarylalkyl, any of which may be optionally substituted;

$R_3$ is chosen from hydrogen, lower alkyl, cycloalkyl, aryl, heteroaryl, heterocycloalkyl, cycloalkylalkyl, arylalkyl, heteroarylalkyl, heterocycloalkylalkyl, cyano, $CONR_6R_7$, $CO_2R_8$, and $COR_9$, any of which may be optionally substituted;

$R_4$ is chosen from lower alkyl, $CH_2CO_2R_5$, alkoxyalkyl, aryl, heteroaryl, cycloalkyl, arylalkyl, heteroarylalkyl, and cycloalkylalkyl, any of which may be optionally substituted, or optionally, $R_1$ and $R_4$ may be taken together to form a cycloalkyl or aryl;

$R_5$ is chosen from hydrogen and lower alkyl;

$R_6$ and $R_7$ are independently chosen from hydrogen, lower alkyl, cycloalkyl, aryl, heteroaryl, heterocycloalkyl, cycloalkylalkyl, arylalkyl, heteroarylalkyl, heterocycloalkylalkyl, any of which may be optionally substituted, or $R_6$ and $R_7$ can be taken together to form a heterocycloalkyl or heteroaryl, any of which may be optionally substituted;

$R_8$ is chosen from hydrogen and lower alkyl;

$R_9$ is chosen from hydrogen, lower alkyl, cycloalkyl, aryl, heteroaryl, heterocycloalkyl, cycloalkylalkyl, arylalkyl, heteroarylalkyl, heterocycloalkylalkyl, any of which may be optionally substituted; and $R_{20}$ is chosen from lower alkyl, arylalkyl, aryl, heteroaryl, and heteroarylalkyl.

In an embodiment, compounds have structural formula IV wherein $R_3$ is $CONR_6R_7$.

In an embodiment, compounds have structural formula IV wherein $R_3$ is chosen from $CO_2R_8$ and $COR_9$.

In an embodiment, compounds have structural formula IV wherein $R_3$ is lower alkyl.

In an embodiment, compounds have structural formula IV wherein $R_3$ is cycloalkyl.

In an embodiment, compounds have structural formula IV wherein $R_3$ is aryl.

In an embodiment, compounds have structural formula IV wherein $R_3$ is chosen from heterocycloalkyl and heteroaryl.

In an embodiment, compounds have structural formula IV wherein $R_3$ is arylalkyl.

In an embodiment, compounds have structural formula IV wherein $R_3$ is chosen from heterocycloalkylalkyl and heteroarylalkyl.

In an embodiment, compounds have structural formula IV wherein $R_3$ is chosen from pyridyl and phenyl, either of which may be optionally substituted.

In an embodiment, compounds have structural formula V:

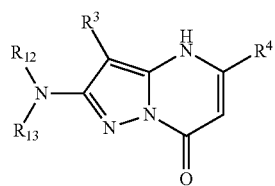

or a salt, ester or prodrug thereof, wherein:
$R_3$ is chosen from lower alkyl, cycloalkyl, aryl, heteroaryl, heterocycloalkyl, cycloalkylalkyl, arylalkyl, heteroarylalkyl, heterocycloalkylalkyl, $CONR_6R_7$, $CO_2R_8$, and $COR_9$, any of which may be optionally substituted;
$R_4$ is chosen from aryl, heteroaryl, cycloalkyl, arylalkyl, heteroarylalkyl, and cycloalkylalkyl, any of which may be optionally substituted;
$R_6$ and $R_7$ are independently chosen from hydrogen, lower alkyl, cycloalkyl, aryl, heteroaryl, heterocycloalkyl, cycloalkylalkyl, arylalkyl, heteroarylalkyl, heterocycloalkylalkyl, any of which may be optionally substituted, or $R_6$ and $R_7$ can be taken together to form a heterocycloalkyl or heteroaryl, any of which may be optionally substituted;
$R_8$ is chosen from hydrogen and lower alkyl;
$R_9$ is chosen from hydrogen, lower alkyl, cycloalkyl, aryl, heteroaryl, heterocycloalkyl, cycloalkylalkyl, arylalkyl, heteroarylalkyl, heterocycloalkylalkyl, any of which may be optionally substituted;
$R_{12}$ and $R_{13}$ are independently chosen from hydrogen, lower alkyl, and $COR_{21}$;
$R_{21}$ is chosen from lower alkyl, arylalkyl, and heteroarylalkyl; and
if $R_{12}$ and $R_{13}$ are each hydrogen, $R_3$ is $CO_2R_8$, and $R_8$ is ethyl, then $R_4$ is not unsubstituted phenyl or nitrophenyl; and
$R_{12}$ and $R_{13}$ cannot both be $COR_{21}$.

In an embodiment, compounds have structural formula V wherein $R_3$ is $CONR_6R_7$.

In an embodiment, compounds have structural formula V wherein $R_3$ is chosen from $CO_2R_8$ and $COR_9$.

In an embodiment, compounds have structural formula V wherein $R_3$ is lower alkyl.

In an embodiment, compounds have structural formula V wherein $R_3$ is cycloalkyl.

In an embodiment, compounds have structural formula V wherein $R_3$ is aryl.

In an embodiment, compounds have structural formula V wherein $R_3$ is chosen from heterocycloalkyl and heteroaryl.

In an embodiment, compounds have structural formula V wherein $R_3$ is arylalkyl.

In an embodiment, compounds have structural formula V wherein $R_3$ is chosen from heterocycloalkylalkyl and heteroarylalkyl.

In an embodiment, compounds have structural formula V wherein $R_3$ is chosen from pyridyl and phenyl, either of which may be optionally substituted.

Further provided is a compound as disclosed above for use as a medicament.

Further provided is a compound as disclosed above for use in the manufacture of a medicament for the prevention or treatment of a disease or condition ameliorated by the inhibition of PASK.

Further provided is a compound as disclosed above for use in the manufacture of a medicament for the prevention or treatment of a disease or condition ameliorated by the inhibition of PASK.

Further provided is a pharmaceutical composition comprising a compound as recited above together with a pharmaceutically acceptable carrier.

Further provided is a method of inhibiting PASK comprising contacting PASK with a compound as disclosed above.

Further provided is a method of treatment of a disease comprising the administration of a therapeutically effective amount of a compound as disclosed above to a patient in need thereof.

Further provided is the method as recited above wherein said disease is chosen from cancer and a metabolic disease.

Further provided is the method as recited above wherein said disease is a metabolic disease.

Further provided is the method as recited above wherein said metabolic disease is chosen from metabolic syndrome, diabetes, dyslipidemia, fatty liver disease, non-alcoholic steatohepatitis, obesity, and insulin resistance.

Further provided is the method disclosed above wherein said diabetes is Type II diabetes.

Further provided is the method as disclosed above wherein said dyslipidemia is hyperlipidemia.

Further provided is a method for achieving an effect in a patient comprising the administration of a therapeutically effective amount of a compound as disclosed above to a patient, wherein the effect is selected from the group consisting of reduction of triglycerides, reduction of cholesterol, and reduction of hemoglobin A1c.

Further provided is the method as disclosed above wherein said cholesterol is chosen from LDL and VLDL cholesterol.

Further provided is the method as disclosed above wherein said triglycerides are chosen from plasma triglycerides and liver triglycerides.

Further provided is a method of treatment of a PASK-mediated disease comprising the administration of:
 a. a therapeutically effective amount of a compound as disclosed above; and
 b. another therapeutic agent.

Not to be bound by any theory or mechanism, the compounds disclosed herein can be used to treat or modulate metabolic disease (including but not limited to diabetes, metabolic disorder, dyslipidemia, fatty liver disease, non-alcoholic steatohepatitis, obesity, and insulin resistance, as well as to reduce triglycerides, cholesterol, and hemoglobin A1c) and cancer.

Further provided is a method of inhibiting CK2 in a cell, comprising contacting the cell, in which inhibition of CK2 is desired with a compound having structural formula I.

Further provided is a method of treating a disease or condition that involves CK2 comprising administering to a patient, in need of said treatment with a compound having structural formula I.

Further provided is a method of treating a disease or condition that involves CK2 comprising administering to a patient, in need of said treatment, a pharmaceutical composition comprising a compound having structural formula I and a pharmaceutically acceptable carrier, excipient, or diluent.

Further provided is a method of treating a disease or condition that involves CK2, wherein the disease or condition is ovarian cancer, cervical cancer, breast cancer, colorectal cancer, or glioblastomas.

As used herein, the terms below have the meanings indicated.

When ranges of values are disclosed, and the notation "from $n_1 \ldots$ to $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—),(—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, Butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(=O)—NR$_2$ group with R as defined herein. The term "N-amido" as used herein, alone or in combination, refers to a RC(=O)NH— group, with R as defined herein. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4=$ derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'-group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 3 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be substituted or quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 7 membered unsaturated heteromonocyclic ring, or a fused monocyclic, bicyclic, or tricyclic ring system in which at least one of the fused rings is aromatic, which contains at least one atom selected from the group consisting of O, S, and N. In certain embodiments, said heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom may be independently selected from the group consisting of nitrogen, oxygen, and sulfur In certain embodiments, said heterocycloalkyl will comprise from 1 to 4 heteroatoms as ring members. In further embodiments, said heterocycloalkyl will comprise from 1 to 2 heteroatoms as ring members. In certain embodiments, said heterocycloalkyl will comprise from 3 to 8 ring members in each ring. In further embodiments, said heterocycloalkyl will comprise from 3 to 7 ring members in each ring. In yet further embodiments, said heterocycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems;

additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N— and not embodied in a ring.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms.

The term "lower aryl," as used herein, alone or in combination, means phenyl or naphthyl, which may be optionally substituted as provided.

The term "lower heteroaryl," as used herein, alone or in combination, means either 1) monocyclic heteroaryl comprising five or six ring members, of which between one and four said members may be heteroatoms selected from the group consisting of O, S, and N, or 2) bicyclic heteroaryl, wherein each of the fused rings comprises five or six ring members, comprising between them one to four heteroatoms selected from the group consisting of O, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms selected from the group consisting of O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently selected from the group consisting of hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethoxy" refers to a X$_3$CO— group where X is a halogen.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R″ where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N (R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"PASK inhibitor" as used herein refers to a compound that exhibits an ($IC_{50}/EC_{50}$) with respect to PASK activity of no more than about 100 μM and more typically not more than about 50 μM, as measured in the PASK assay described generally hereinbelow. $IC_{50}$ is that concentration of inhibitors which reduces the activity of PASK to half-maximal level. Certain compounds disclosed herein have been discovered to exhibit inhibition against PASK.

The phrase "therapeutically effective" is intended to qualify the amount of active ingredients used in the treatment of a disease or disorder. This amount will achieve the goal of reducing or eliminating the said disease or disorder.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means all mammals including humans. Examples of patients include humans, cows, dogs, cats, goats, sheep, pigs, and rabbits. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound.

Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of a compound as disclosed herein, and at least one other agent selected from the group comprising:

a) anti-diabetic agents such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; insulin sensitizer such as protein tyrosine phosphatase-1B (PTP-1B) inhibitors such as PTP-112; GSK3 (glycogen synthase kinase-3) inhibitors such as SB-517955, SB-4195052, SB-216763, N,N-57-05441 and N,N-57-05445; RXR ligands such as GW-0791 and AGN-194204; sodium-dependent glucose co-transporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; DPPIV (dipetidyl peptidase IV) inhibitors such as DPP728, LAF237 (vildagliptin—Example 1 of WO 00/34241), MK-0431, saxagliptin, GSK23A; an AGE breaker; a thiazolidinedione derivative (glitazone) such as pioglitazone or rosiglitazone; and a non-glitazone type PPARδ agonist e.g. GI-262570;

b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid and aspirin;

c) an anti-obesity agent or appetite regulating agent such as phentermine, leptin, bromocriptine, dexamphetamine, amphetamine, fenfluramine, dexfenfluramine, sibutramine, orlistat, dexfenfluramine, mazindol, phentermine, phendimetrazine, diethylpropion, fluoxetine, bupropion, topiramate, diethylpropion, benzphetamine, phenylpropanolamine or ecopipam, ephedrine, pseudoephedrine or cannabinoid receptor antagonists;

d) anti-hypertensive agents, e.g., loop diuretics such as ethacrynic acid, furosemide and torsemide; diuretics such as thiazide derivatives, chlorothiazide, hydrochlorothiazide, amiloride; angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutral endopeptidase (NEP) inhibitors e.g. thiorphan, terteo-thiorphan, SQ29072; ECE inhibitors e.g. SLV306; ACE/NEP inhibitors such as omapatrilat, sampatrilat and fasidotril; angiotensin n antagonists such as candesartan, eprosartan, irbesartan, losartan, tehnisartan and valsartan, in particular valsartan; renin inhibitors such as aliskiren, terlakiren, ditekiren, RO 66-1132, RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors;

e) an HDL increasing compound;

f) cholesterol absorption modulator such as etizimibe and KT6-971;

g) Apo-A1 analogues and mimetics;

h) thrombin inhibitors such as Ximelagatran;

i) aldosterone inhibitors such as anastrazole, fadrazole, and eplerenone;

j) inhibitors of platelet aggregation such as aspirin, and clopidogrel bisulfate;

k) estrogen, testosterone, a selective estrogen receptor modulator, and a selective androgen receptor modulator;

l) a chemotherapeutic agent such as aromatase inhibitors e.g. femara, anti-estrogens, topoisomerase I inhibitors, topoisomerase II inhibitors, microtubule active agents, alkylating agents, antineoplastic antimetabolites, platin compounds, and compounds decreasing the protein kinase activity such as a PDGF receptor tyrosine kinase inhibitor such as miatinib; and m) an agent interacting with a 5-HT3 receptor and/or an agent interacting with 5-HT4 receptor such as tegaserod described in the U.S. Pat. No. 5,510,353 as example 13, tegaserod hydrogen maleate, cisapride, and cilansetron.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating PASK-mediated disorders in a human or animal subject in need of such treatment comprising administering to said subject an amount of a compound disclosed herein effective to reduce or prevent said disorder in the subject, optionally in combination with at least one additional agent that is known in the art. In a related aspect, certain embodiments provide therapeutic compositions comprising at least one compound disclosed herein in combination with one or more additional agents for the treatment of PASK-mediated disorders.

Recent studies have found that elevated medium glucose concentrations caused post-translational activation of PASK. It has also been demonstrated that PASK activity is required for glucose-stimulated insulin expression, as shown by studies in PASK1 mice. It has also been demonstrated that PASK deletion results in nearly complete resistance to the phenotypes caused by a high-fat diet, including obesity, insulin resistance and hepatic fat accumulation. It has been postulated that this protection may be due to an increase in AMPK expression in each of the relevant tissues. PASK deletion abrogates nearly all of the maladaptive phenotype associated with a high-fat diet, possibly in part via maintenance of AMPK expression. Increasing AMPK signaling is a proven therapeutic strategy, as illustrated by Metformin, which acts by increasing the phosphorylation and activation of AMPK Inhibition of PASK signaling elicits similar beneficial effects, but through a distinct mechanism. This complementary therapeutic strategy, either alone or in combination, can be efficacious in the treatment of metabolic diseases. In any case, it appears that PASK inhibition can provide an effective therapeutic strategy for the treatment of diseases, for example Type 2 diabetes, insulin resistance in general, and the metabolic syndrome.

Metabolic syndrome (also known as metabolic syndrome X) is characterized by having at least three of the following symptoms: insulin resistance; abdominal fat—in men this is defined as a 40 inch waist or larger, in women 35 inches or larger; high blood sugar levels—at least 110 milligrams per deciliter (mg/dL) after fasting; high triglycerides—at least 150 mg/dL in the blood stream; low HDL-less than 40 mg/dL; pro-thrombotic state (e.g. high fibrinogen or plasminogen activator inhibitor in the blood); or blood pressure of 130/85 mmHg or higher. A connection has been found between metabolic syndrome and other conditions such as obesity, high blood pressure and high levels of LDL cholesterol, all of which are risk factors for cardiovascular diseases. For example, an increased link between metabolic syndrome and atherosclerosis has been shown. People with metabolic syndrome are also more prone to developing type 2 diabetes, as well as PCOS (polycystic ovarian syndrome) in women and prostate cancer in men.

As described above, insulin resistance can be manifested in several ways, including type 2 diabetes. Type 2 diabetes is the condition most obviously linked to insulin resistance. Compensatory hyperinsulinemia helps maintain normal glucose levels—often for decades, before overt diabetes develops. Eventually the beta cells of the pancreas are unable to overcome insulin resistance through hypersecretion. Glucose levels rise, and a diagnosis of diabetes can be made. Patients with type 2 diabetes remain hyperinsulinemic until they are in an advanced stage of disease. As described above, insulin resistance can also correlate with hypertension. One half of patients with essential hypertension are insulin resistant and hyperinsulinemic, and there is evidence that blood pressure is linked to the degree of insulin resistance. Hyperlipidemia, too, is associated with insulin resistance.

The lipid profile of patients with type 2 diabetes includes increased serum very-low-density lipoprotein cholesterol and triglyceride levels and, sometimes, a decreased low-density lipoprotein cholesterol level. Insulin resistance has been found in persons with low levels of high-density lipoprotein. Insulin levels have also been linked to very-low-density lipoprotein synthesis and plasma triglyceride levels.

Accordingly, also disclosed are methods of treating insulin resistance in a subject comprising selecting a subject in need of treatment for insulin resistance; and administering to the subject an effective amount of a compound that inhibits PAS K.

Specific diseases to be treated by the compounds, compositions, and methods disclosed herein are those mediated at least in part by PASK. Accordingly, disclosed herein are methods: for reducing glycogen accumulation in a subject; for raising HDL or HDLc, lowering LDL or LDLc, shifting LDL particle size from small dense to normal LDL, lowering VLDL, lowering triglycerides, or inhibiting cholesterol absorption in a subject; for reducing insulin resistance, enhancing glucose utilization or lowering blood pressure in a subject; for reducing visceral fat in a subject; for reducing serum transaminases in a subject; or for treating disease; all comprising the administration of a therapeutic amount of a compound as described herein, to a patient in need thereof. In further embodiments, the disease to be treated may be a metabolic disease. In further embodiment, the metabolic disease may be selected from the group consisting of: obesity, diabetes melitus, especially Type 2 diabetes, hyperinsulinemia, glucose intolerance, metabolic syndrome X, dyslipidemia, hypertriglyceridemia, hypercholesterolemia, and hepatic steatosis. In other embodiments, the disease to be treated may be selected from the group consisting of: cardiovascular diseases including vascular disease, atherosclerosis, coronary heart disease, cerebrovascular disease, heart failure and peripheral vessel disease. In preferred embodiments, the methods above do not result in the induction or maintenance of a hypoglycemic state.

Additionally, the PASK modulators disclosed herein may be used to treat proliferative disorders such as cancers. Hematological and non-hematological cancers which may be treated or prevented include but are not limited to multiple myeloma, acute and chronic leukemias including Acute Lymphocytic Leukemia (ALL), Chronic Lymphocytic Leukemia (CLL), and Chronic Myelogenous Leukemia (CLL), lymphomas, including Hodgkin's lymphoma and non-Hodgkin's lymphoma (low, intermediate, and high grade), malignancies of the brain, head and neck, breast, lung, reproductive tract, upper digestive tract, pancreas, liver, renal, bladder, prostate and colon/rectum.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

REFERENCES CITED

The following is a list of references cited herein which, while not necessarily comprehensive, is provided for the convenience of the reader. All references, patents, and patent applications cited herein are hereby incorporated by reference as if written herein in their entireties. When the teachings of these references contradict the teachings presented expressly herein, the present disclosure controls.

1. Roach, P. J. et al. (2001) in The Endocrine Pancreas and Regulation of Metabolism, eds. Chemington, A. D. & Jefferson, L. S. (Oxford Univ. Press, New York), pp. 609-647.
2. Bergstrom, J. et al. (1967) Acta Physiol. Scand. 71:, 140-150.
3. Cline, G. W. et al. (1994) J. Clin. Invest. 94:, 2369-2376.
4. Shulman, G. I. et al. G. (1990) N. Engl. J. Med. 322:, 223-228.
5. Cohen, P. (1982) Nature 296:, 613-620.
6. Roach, P. J. (1986) in The Enzymes, eds. Boyer, P. D. & Krebs, E. G. (Academic, Orlando, Fla.), Vol. 17:, pp. 499-539.
7. Cohen, P. (1986) in The Enzymes, eds. Boyer, P. D. & Krebs, E. G. (Academic, Orlando, Fla.), Vol. 17:, pp. 461-497.
8. Friedman, D. L. & Lamer, J. (1963) Biochemistry 128:, 669-675.
9. Lamer, J. (1990) Adv. Enzymol. Relat. Areas Mol. Biol. 63:, 173-231.
10. Roach, P. J. (1990) FASEB J. 4:, 2961-2968.
11. Skurat, A. V., et al. (1994) J. Biol. Chem. 269:, 25534-25542.
12. Flotow, H. & Roach, P. J. (1989) J. Biol. Chem. 264:, 9126-9128.
13. Nakielny, S., Campbell, D. G. & Cohen, P. (1991) Eur. J. Biochem. 199:, 713-722.
14. Wilson W A et al., Proc Natl Acad Sci USA. 2005 Nov. 15; 102(46):16596-601, FIG. 6
15. Skurat, A. V. & Roach, P. J. (1995) J. Biol. Chem. 270:, 12491-12497.
16. Hardy, T. A. & Roach, P. J. (1993) J. Biol. Chem. 268:, 23799-23805
17. Francois, J. & Parrou, J. L. (2001) FEMS Microbiol. Rev. 25:, 125-145.
18. Rutter, J., Probst, B. L. & McKnight, S. L. (2002) Cell 111:, 17-28.
19. Rutter, J et al. (2001) Proc. Natl. Acad. Sci. USA 98:, 8991-8996.
20. Roden M, Bemroider E: *Best Pract Res Clin Endocrinol Metab.* 2003 September; 17(3):365-83
21. Van Steenbergen W, Lanckmans S: *Int J Obes Relat Metab Disord.* 1995 September; 19 Suppl 3:S27-36.
22. Arad M et al., *Circ Res.* 2007 Mar. 2; 100(4):474-88
23. da Silva Xavier, G. et al. (2004) Proc. Natl. Acad. Sci. USA 101:, 8319-8324.
24. 33Picton, C. et al. (1982) FEBS Lett. 150:, 191-196.
25. DePaoli-Roach, A. A. et al., (1983) J. Biol. Chem. 258:, 10702-10709.
26. Elia, A. E. et al. (2003) Science 299:, 1228-1231.
27. Gao, T. et al. (1997) Neuron 19:, 185-196.
28. Wilson, W. A. et al. (1999) Mol. Cell. Biol. 19:, 7020-7030.
29. Yedovitzky, M. et al. (1997) J. Biol. Chem. 272:, 1417-1420.
30. Fernandez-Novell, J. M., et al. (2002) FEBS Lett. 531:, 222-228.

GENERAL SYNTHETIC METHODS FOR PREPARING COMPOUNDS

The following schemes can generally be used to practice the present invention.

Scheme I

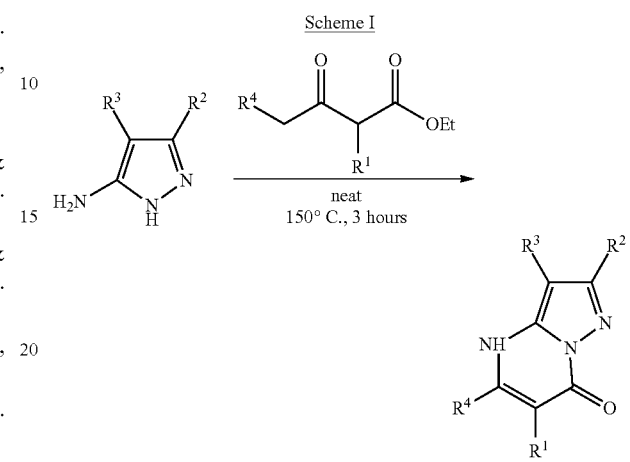

Starting materials=5-aminopyrazoles and B-ketoesters.
N. L. Nam, et. al. Chem. Het. Compounds, 39 (9), 1210 (2003)

The following intermediates were used in the preparation of some of the examples below. Their synthesis is described herein.

Intermediate 1

4-(6-Methoxypyridin-3-yl)-1H-pyrazol-5-amine

Step 1. 1-(4-Methoxybenzyl)-4-(6-methoxypyridin-3-yl)-1H-pyrazol-5-amine 1-(4-Methoxybenzyl)-4-(6-fluoropyridin-3-yl)-1H-pyrazol-5-amine (298 mg, 1.00 mmol, 1.00 equiv), sodium methoxide (108 mg, 2.00 equiv), and methanol (5 mL) were placed in a sealed tube. The reaction was stirred for 18 hr at 70° C. in an oil bath, concentrated in vacuo, and washed with 1×5 mL of H$_2$O. The resulting solid was collected by filtration resulting in 250 mg (81%) of 1-(4-methoxybenzyl)-4-(6-methoxypyridin-3-yl)-1H-pyrazol-5-amine as a yellow solid.

LC-MS (ES, m/z): 311 [M+H]$^+$ $^1$H-NMR (400 MHz, DMSO, ppm): 8.366-8.361 (s, 1H), 7.907-7.854 (m, 2H), 7.331-7.293 (m, 2H), 7.001-6.972 (m, 2H), 6.893-6.871 (d, J=6.6 Hz, 1H), 5.128-5.075 (s, 2H), 4.784 (s, 2H), 3.936-3.926 (s, 3H), 3.815-3.789 (s, 3H)

Step 2.
4-(6-Methoxypyridin-3-yl)-1H-pyrazol-5-amine

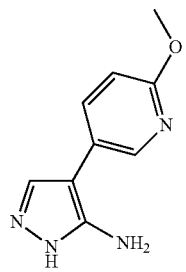

1-(4-Methoxybenzyl)-4-(6-methoxypyridin-3-yl)-1H-pyrazol-5-amine (310 mg, 1.00 mmol), CF$_3$COOH (4 mL), and (Tf)$_2$O (1 mL) were placed into a reaction tube. The tube was sealed and the reaction was stirred for 2 hr at 30° C. in an oil bath and then concentrated in vacuo. The crude product (300 mg) was purified by Flash-Prep-HPLC under the following conditions (IntelFlash-1): Column, C18 silica gel; mobile phase, CH$_3$CN/H$_2$O=5% increasing to CH$_3$CN/H$_2$O=40% within 30 min; Detector, UV 254 nm. This resulted in 200 mg of 4-(6-methoxypyridin-3-yl)-1H-pyrazol-5-amine as a yellow solid.

Intermediate 2

Methyl 3-(2,4-dimethoxyphenyl)-3-oxopropanoate

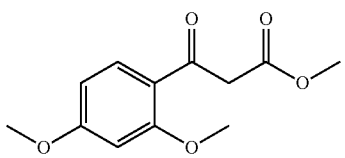

To a solution of 1-(2,4-dimethoxyphenyl)ethanone (3.6 g, 20.00 mmol, 1.00 equiv) in dimethyl carbonate (50 mL) was added sodium hydride (1.36 g, 34.00 mmol, 1.70 equiv, 60%) in several batches. The resulting solution was heated to reflux for 30 min. The resulting mixture was concentrated under vacuum. The reaction was then quenched by the addition of 20 mL of water/ice. The resulting solution was extracted with 4×30 mL of ethyl acetate and the organic layers were combined. The resulting mixture was washed with saturated aqueous sodium bicarbonate. The mixture was dried over anhydrous sodium sulfate and concentrated under vacuum. The residue was applied purified by silica gel column chromatography (ethyl acetate/petroleum ether (1:20)). This resulted in 680 mg (13%) of methyl 3-(2,4-dimethoxyphenyl)-3-oxopropanoate as a white solid.

LC-MS: (ES, m/z): 239 [M+H]$^+$

Intermediate 3

Ethyl 3-(3,5-dimethoxyphenyl)-3-oxopropanoate

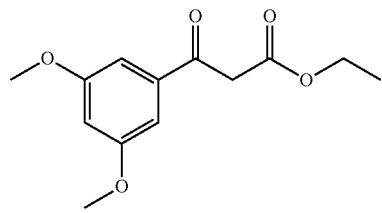 [SMILES: CCOC(=O)CC(=O)c1cc(OC)cc(OC)c1]

A solution of 3,5-dimethoxybenzoic acid (5 g, 27.47 mmol, 1.00 equiv) in thionyl chloride (40 mL) was stirred at reflux for 30 minutes, then concentrated in vacuo to afford 3,5-dimethoxybenzoyl chloride as a yellow oil. Separately, a mixture of potassium 3-ethoxy-3-oxopropanoate (9.3 g, 54.71 mmol, 1.99 equiv), MgCl$_2$ (6.5 g, 68.42 mmol, 2.49 equiv) and triethylamine (5.5 g, 54.46 mmol, 1.98 equiv) in CH$_3$CN (60 mL) was stirred at 30° C. for 30 minutes. The solution of 3,5-dimethoxybenzoyl chloride in CH$_3$CN (40 mL) was added dropwise, followed by the addition of triethylamine (550 mg, 5.45 mmol, 0.20 equiv). The resulting solution was stirred at 30° C. overnight, then diluted with 100 mL EtOAc and washed with 100 mL 1N hydrochloric acid and 100 mL brine. The organic layer was dried over Na$_2$SO$_4$ and concentrated in vacuo. The residue was purified by silica gel column chromatography (ethyl acetate/petroleum ether (1:20)). This resulted in 1.7 g (23%) of ethyl 3-(3,5-dimethoxyphenyl)-3-oxopropanoate as a red solid.

LC-MS: (ES, m/z): 253 [M+H]$^+$

Intermediate 4

Methyl 3-(benzofuran-5-yl)-3-oxopropanoate

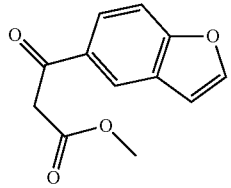 [SMILES: COC(=O)CC(=O)c1ccc2occc2c1]

Step 1. 1-Bromo-4-(2,2-diethoxyethyl)benzene)

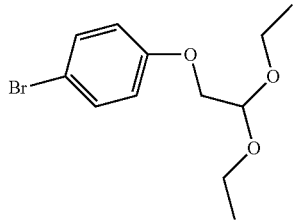 [SMILES: CCOC(COc1ccc(Br)cc1)OCC]

A solution of 4-bromophenol (17.3 g, 100.00 mmol, 1.00 equiv), N,N-dimethylformamide (200 mL), 2-bromo-1,1-diethoxyethane (19.7 g, 100.00 mmol, 1.00 equiv), and potassium carbonate (13.8 g, 100.00 mmol, 1.00 equiv) was stirred overnight at 140° C. in an oil bath. Then the reaction was quenched by the addition of 200 mL of water. The resulting solution was extracted with 3×200 mL of ethyl acetate, and the organic layers were combined and concentrated in vacuo. The residue was purified by silica gel column chromatography (ethyl acetate/petroleum ether (1:40)). This resulted in 20 g (73%) of 1-bromo-4-(2,2-diethoxyethyl)benzene as a yellow oil.

$^1$H-NMR (300 MHz, CDCl$_3$, ppm): 7.396-7.345 (d, J=15.3 Hz, 3H), 6.840-6.799 (d, J=12.3 Hz, 2H), 4.841-4.823 (m, 1H), 3.988-3.971 (d, J=5.1 Hz, 2H), 3.820-3.566 (m, 4H), 1.291-1.230 (m, 6H)

Step 2. 5-Bromobenzofuran

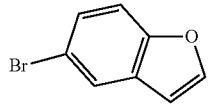

A solution of 1-bromo-4-(2,2-diethoxyethoxy)benzene (5 g, 17.29 mmol, 1.00 equiv), polyphosphoric acid (13 g, 132.65 mmol, 8.00 equiv) and toluene (50 mL) was heated to reflux for 3 hr in an oil bath. The resulting mixture was concentrated under vacuum, diluted with 50 mL of ethyl acetate, and washed with 3×50 mL of water and 2×50 mL of saturated sodium bicarbonate. The mixture was dried over anhydrous sodium sulfate and concentrated under vacuum. The residue was applied onto a silica gel column (ethyl acetate/petroleum ether (1:10)). This resulted in 2 g (59%) of 5-bromobenzofuran as a yellow oil.

$^1$H-NMR (300 MHz, CDCl$_3$, ppm): 7.759-7.751 (d, J=2.4 Hz, 1H), 7.649-7.642 (d, J=2.1 Hz, 1H), 7.442-7.381 (s, 2H), 6.748-6.741 (s, 1H)

Step 3. 1-(Benzofuran-5-yl)ethanone

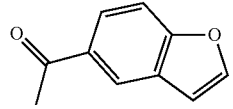

To a solution of 5-bromobenzofuran (7.9 g, 40.10 mmol, 1.00 equiv) in tetrahydrofuran (100 mL) under an inert atmosphere of nitrogen was added n-BuLi in hexane (28 mL, 1.10 equiv, 1.6M) dropwise with stirring at −78° C. The resulting solution was stirred for 1.5 hours at −78° C. in a liquid nitrogen bath. To this was added DMAC (3.48 g, 40.00 mmol, 1.00 equiv) dropwise with stirring at −78° C. The resulting solution was allowed to react, with stirring, for an additional 1 hour at −78° C. in a liquid nitrogen bath. The reaction was then quenched by the addition of aqueous NH$_4$Cl. The resulting mixture was concentrated under vacuum. The residue was applied onto a silica gel column with ethyl acetate/petroleum ether (1:10). This resulted in 5.1 g (79%) of 1-(benzofuran-5-yl)ethanone as a white solid.

$^1$H-NMR (300 MHz, CDCl$_3$, ppm): 8.285-8.280 (s, 1H), 8.011-7.969 (d, J=12.6 Hz, 1H), 7.721-7.714 (d, J=2.1 Hz, 1H), 7.584-7.555 (d, J=8.7 Hz, 1H), 6.890-6.879 (d, J=6.3 Hz, 1H), 2.689 (s, 3H)

Step 4. Methyl 3-(benzofuran-5-yl)-3-oxopropanoate

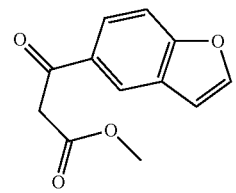 [SMILES: COC(=O)CC(=O)c1ccc2occc2c1]

To a solution of 1-(benzofuran-5-yl)ethanone (1.6 g, 9.99 mmol, 1.00 equiv) in dimethyl carbonate (20 mL) was added sodium hydride (4 g, 100.00 mmol, 10.00 equiv, 60%) in several batches at 0° C. The resulting solution was heated to reflux for 1.5 hr in an oil bath. The reaction was then quenched by the addition of 50 mL of water/ice. The pH of the solution was adjusted to 6 with HCl (1M). The resulting solution was extracted with 2×100 mL of dichloromethane, and the organic layers combined and concentrated in vacuo. The residue was applied onto a silica gel column with ethyl acetate/petroleum ether (1:10). This resulted in 1.2 g (55%) of methyl 3-(benzofuran-5-yl)-3-oxopropanoate as yellow oil.

$^1$H-NMR (300 MHz, CDCl$_3$, ppm): 8.252-8.247 (s, 1H), 8.088-8.083 (d, J=1.5 Hz, 1H), 7.740-7.707 (d, J=9.9 Hz, 1H), 7.672-7.665 (d, J=2.1 Hz, 1H), 6.878-6.873 (d, J=1.5 Hz, 1H), 4.108-4.074 (s, 2H), 3.764 (s, 3H)

Intermediate 5

5-Amino-4-(pyridin-3-yl)-1H-pyrazol-3-ol

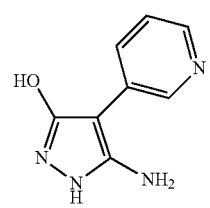 [SMILES: Nc1[nH]nc(O)c1-c1cccnc1]

Step 1. Ethyl 2-cyano-2-(pyridin-3-yl)acetate

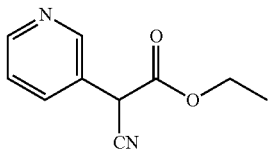

A mixture of ethyl 2-cyanoacetate (5 g, 44.25 mmol, 1.00 equiv), 3-bromopyridine (8.4 g, 53.16 mmol, 1.20 equiv), t-BuOK (12.4 g, 110.71 mmol, 2.50 equiv), and dioxane (120 mL) was stirred at 70° C. for 10 minutes. Following sequential addition of DPPF (980 mg, 1.77 mmol, 0.04 equiv) and Pd(OAc)$_2$ (198 mg, 0.88 mmol, 0.02 equivalents) in 1,4-dioxane (40 mL), the resulting solution was stirred for 3 h at 70° C. and then poured into 80 mL AcOH (1N). The combined layers were extracted with dichloromethane (100 mL×3). The organic layer was dried over anhydrous Na$_2$SO$_4$ and concentrated in vacuo. The residue was purified by silica gel column chromatography with ethyl acetate/petroleum ether (1:5). This resulted in 4.6 g (54%) of ethyl 2-cyano-2-(pyridin-3-yl)acetate as a yellow solid.

LC-MS: (ES, m/z): 191 [M+H]$^+$ $^1$H-NMR (300 MHz, CDCl$_3$, ppm) 8.74-8.68 (m, 2H), 7.91-7.86 (m, 1H), 7.45-7.40 (dd, J=5.1, 8.0 Hz, 1H), 4.33-4.26 (q, J=7.2 Hz, 2H), 1.35-1.29 (t, J=7.2 Hz, 3H)

Step 2. 5-Amino-4-(pyridin-3-yl)-1H-pyrazol-3-ol

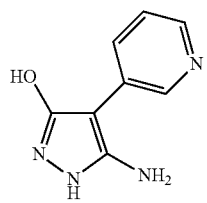 [SMILES: Nc1[nH]nc(O)c1-c1cccnc1]

A mixture of ethyl 2-cyano-2-(pyridin-3-yl)acetate (1.9 g, 10.00 mmol, 1.00 equiv) and NH$_2$NH$_2$H$_2$O (6.25 g, 100.00 mmol, 10.00 equiv, 80%), ethanol (20 mL) was stirred for 4 h at 80° C., then concentrated in vacuo. The residue was dissolved in dichloromethane and water. The aqueous layer was concentrated and cooled to room temperature. The resulting solid was collected by filtration, washed with water, and dried to afford 900 mg (51%) of 5-amino-4-(pyridin-3-yl)-1H-pyrazol-3-ol as a white solid.

LC-MS: (ES, m/z): 177 [M+H]$^+$ $^1$H-NMR (300 MHz, DMSO, ppm): 9.25 (s, 1H), 8.81-8.80 (m, 1H), 8.23-8.21 (m, 1H), 8.01-7.97 (m, 1H), 7.29-7.24 (m, 1H), 6.15 (s, 2H)

Intermediate 6

4-(4-Bromophenyl)-1H-pyrazol-5-amine

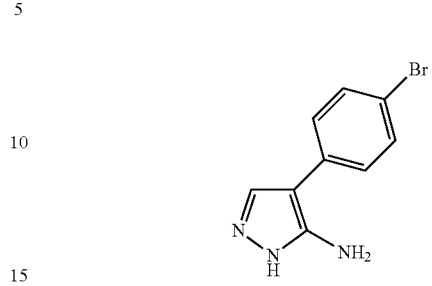

Step 1. 2-(4-Bromophenyl)-3-(dimethylamino)acrylonitrile

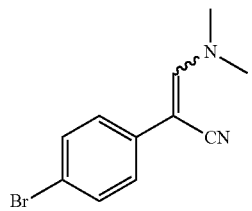

A solution of 2-(4-bromophenyl)acetonitrile (10 g, 51.02 mmol, 1.00 equiv) in DMF/DMA (50 mL) was stirred overnight at 50° C. The resulting mixture was concentrated in vacuo, and the residue was purified by silica gel column chromatography with ethyl acetate/petroleum ether (1:10). This resulted in 5.4 g (35%) of 2-(4-bromophenyl)-3-(dimethylamino)acrylonitrile as brown oil.

LC-MS: (ES, m/z): 251 [M+H]$^+$

Step 2. 4-(4-Bromophenyl)-1H-pyrazol-5-amine

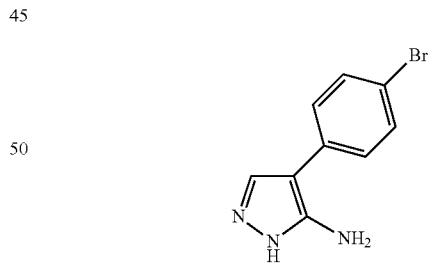

A solution of 2-(4-bromophenyl)-3-(dimethylamino)acrylonitrile (5.4 g, 18.07 mmol, 1.00 equiv, 84%) and NH$_2$NH$_2$HBr (12.2 g, 107.96 mmol, 5.97 equiv) in ethanol (60 mL) and H$_2$O (6 mL) was stirred for 3 hr at 80° C., and then concentrated in vacuo. Dichloromethane was added and the solid was filtered out and washed with dichloromethane. The filtrate was concentrated in vacuo. The resulting solid was collected by filtration and washed with EtOAc/hexane (1/10) to afford 1.32 g (25%) of 4-(4-bromophenyl)-1H-pyrazol-5-amine as a yellow solid.

LC-MS: (ES, m/z): [M+H]$^+$ 238

Intermediate 7

5-Amino-4-(pyridin-2-yl)-1H-pyrazol-3-ol

Step 1. Ethyl 2-cyano-2-(pyridin-2-yl)acetate

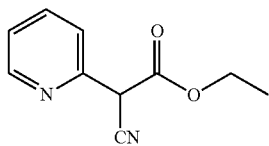

A mixture of ethyl 2-cyanoacetate (5 g, 44.25 mmol, 1.00 equiv), 2-bromopyridine (8.4 g, 53.16 mmol, 1.20 equiv), and t-BuOK (12.4 g, 110.71 mmol, 2.50 equiv) in dioxane (120 mL) was stirred at 70° C. for 10 minutes. To the resulting mixture was added a mixture of DPPF (980 mg, 1.77 mmol, 0.04 equiv) and Pd(OAc)$_2$ (198 mg, 0.88 mmol, 0.02 equiv) in 1,4-dioxane (40 mL). The resulting solution was stirred for 3 hours at 70° C., and then poured into aqueous AcOH (80 mL, 1N). The resulting aqueous solution was extracted with dichloromethane (100 mL×3). The organic layer was dried over Na$_2$SO$_4$ and concentrated in vacuo. The residue was purified by silica gel column chromatography with ethyl acetate/petroleum ether (1:5). This resulted in 2.1 g (23%) of ethyl 2-cyano-2-(pyridin-2-yl)acetate as a grey-yellow solid.

LC-MS: (ES, m/z): 191 [M+H]$^+$ $^1$H-NMR (300 MHz, CDCl$_3$, ppm): 814.11 (s, 1H), 7.65-7.57 (m, 2H), 7.37-7.33 (d, J=9.3 Hz, 1H), 6.69-6.64 (t, J=6.6 Hz, 1H), 4.31-4.23 (q, J=7.2 Hz, 2H), 1.38-1.33 (t, J=7.2 Hz, 3H)

Step 2. 5-Amino-4-(pyridin-2-yl)-1H-pyrazol-3-ol

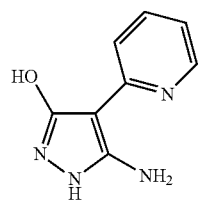 [SMILES: Nc1[nH]nc(O)c1-c1ccccn1]

A mixture of ethyl 2-cyano-2-(pyridin-2-yl)acetate (950 mg, 5.00 mmol, 1.00 equiv) and N$_2$H$_4$H$_2$O (3.2 g, 51.20 mmol, 10.24 equiv, 80%) in ethanol (50 mL) was stirred for 4 hours at 80° C. The resulting mixture was concentrated under vacuum and washed with methanol. This resulted in 450 mg (36%) of 5-amino-4-(pyridin-2-yl)-1H-pyrazol-3-ol as a yellow solid.

LC-MS: (ES, m/z): 177 [M+H]$^+$

Intermediate 8

Ethyl 5-amino-1H-pyrazole-4-carboxylate

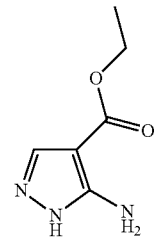

Step 1. Ethyl 2-cyano-3-ethoxyacrylate

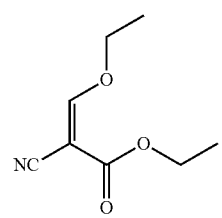

A solution of ethyl 2-cyanoacetate (22.6 g, 200.00 mmol, 1.00 equiv), triethyl orthoformate (30 g, 202.70 mmol, 1.01 equiv), and acetic anhydride (100 mL) was stirred for overnight at 140° C. The resulting mixture was concentrated under vacuum. The resulting solution was diluted with 110 mL of ether/hexane (1:10). The solids were collected by filtration. This resulted in 21 g (47%) of ethyl 2-cyano-3-ethoxyacrylate as a white solid.

LC-MS: (ES, m/z): 170 [M+H]$^+$

Step 2. Ethyl 5-amino-1H-pyrazole-4-carboxylate

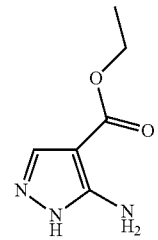

A solution of ethyl 2-cyano-3-ethoxyacrylate (21 g, 86.98 mmol, 1.00 equiv, 70%) and hydrazine hydrate (11 g, 176.00 mmol, 2.02 equiv, 80%) in ethanol (150 mL) was heated to reflux for 3 hours. The resulting mixture was concentrated under vacuum. The residue was dissolved in 100 mL of dichloromethane. The organic layer was washed with 3×50 mL of water and dried over sodium sulfate, then concentrated under vacuum. This resulted in 7.2 g (52%) of ethyl 5-amino-1H-pyrazole-4-carboxylate as a yellow solid.

LC-MS: (ES, m/z): 156 [M+H]$^+$

¹H-NMR (300 MHz, CDCl₃, ppm): 7.75 (s, 1H), 6.53 (s, 1H), 4.31-4.26 (q, J=5.4 Hz, 2H), 1.37-1.32 (t, J=5.4 Hz, 3H)

Intermediate 9

Methyl 6-methoxy-1-oxo-1,2,3,4-tetrahydronaphthalene-2-carboxylate

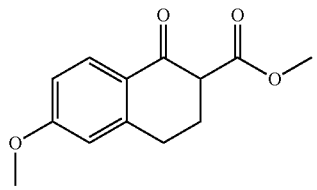 [SMILES: COC(=O)C1CCc2cc(OC)ccc2C1=O]

To a mixture of 6-methoxy-3,4-dihydronaphthalen-1(2H)-one (5 g, 28.41 mmol, 1.00 equiv), and dimethyl carbonate (50 mL) was added sodium hydride (1.46 g, 42.58 mmol, 1.50 equiv, 70%) in several batches, and the reaction was heated to reflux for 2 hours. The resulting mixture was concentrated in vacuo and diluted with 50 mL of water. The pH of the aqueous solution was adjusted to 6 with aqueous HCl (1M). The resulting solution was extracted with 3×50 mL of ethyl acetate. The organic layers were combined, dried over anhydrous Na₂SO₄, and concentrated in vacuo. The residue was purified by silica gel column chromatography with EA:PE (1:20) affording 2.4 g (36%) of methyl 6-methoxy-1-oxo-1,2,3,4-tetrahydronaphthalene-2-carboxylate as a white solid.

Intermediate 10

4-Phenyl-3-(trifluoromethyl)-1H-pyrazol-5-amine

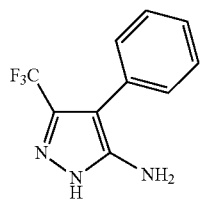 [SMILES: Nc1[nH]nc(C(F)(F)F)c1-c1ccccc1]

Step 1. 4,4,4-Trifluoro-3-oxo-2-phenylbutanenitrile

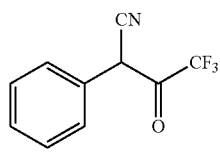 [SMILES: N#CC(C(=O)C(F)(F)F)c1ccccc1]

To a solution of Na (3.5 g, 152.17 mmol, 1.52 equiv) in ethanol (100 mL) was added a solution of 2-phenylacetonitrile (11.7 g, 100.00 mmol, 1.00 equiv) and ethyl 2,2,2-trifluoroacetate (14.2 g, 100.00 mmol, 1.00 equiv) in ethanol (50 mL) dropwise with stirring, while the temperature was maintained at reflux. The resulting solution was heated to reflux for 3 hrs. The resulting mixture was concentrated under vacuum. This resulted in 31 g (crude) of 4,4,4-trifluoro-3-oxo-2-phenylbutanenitrile as a yellow semisolid. The crude product was used for next step directly.

Step 2.
4-Phenyl-3-(trifluoromethyl)-1H-pyrazol-5-amine

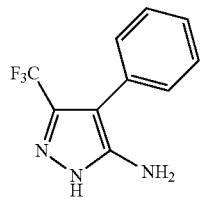 [SMILES: Nc1[nH]nc(C(F)(F)F)c1-c1ccccc1]

A solution of 4,4,4-trifluoro-3-oxo-2-phenylbutanenitrile (31 g, crude) and hydrazine hydrate (10 g, 80%) in acetic acid (100 mL) was stirred overnight at 30° C. The resulting mixture was concentrated under vacuum. The residue was dissolved in 100 mL of ethyl acetate and 100 mL of water. The resulting solution was extracted with 3×50 mL of ethyl acetate. The organic layers was combined and dried over anhydrous sodium sulfate and concentrated under vacuum. This resulted in 20 g (88%, two steps) of 4-phenyl-3-(trifluoromethyl)-1H-pyrazol-5-amine as yellow oil.

LC-MS: (ES, m/z): 228 [M+H]⁺

¹H-NMR (300 MHz, CDCl₃, ppm): 7.47-7.33 (m, 5H), 6.10 (s, 3H)

Intermediate 11

Methyl 1-oxo-1,2,3,4-tetrahydronaphthalene-2-carboxylate

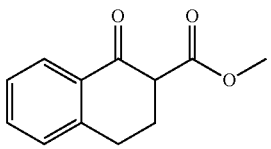

Sodium hydride (1.26 g, 36.75 mmol, 0.73 equiv, 70%) was added in several batches to a mixture of 3,4-dihydronaphthalen-1(2H)-one (7.3 g, 50.00 mmol, 1.00 equiv) and dimethyl carbonate (50 mL). The resulting solution was stirred for 20 min at 80° C. The reaction was quenched by the addition of 150 mL of water/ice, then extracted with 3×100 mL of ether. The organic layers were combined and washed with 1×50 mL of brine, dried over anhydrous sodium sulfate, and concentrated in vacuo. The residue was purified by silica gel column chromatography eluting with petroleum ether. This provided 6.5 g (64%) of methyl 1-oxo-1,2,3,4-tetrahydronaphthalene-2-carboxylate as a white solid.

LC-MS: (ES, m/z): 205 [M+H]⁺

¹H-NMR (300 MHz, CDCl₃, ppm): 12.40 (s, 0.5H), 8.07-7.16 (m, 4H), 3.83-3.78 (m, 3H), 3.66-3.61 (m, 0.5H), 3.07-2.79 (m, 2H), 2.60-2.37 (m, 2H)

Intermediate 12

Methyl 3-oxo-3-p-tolylpropanoate

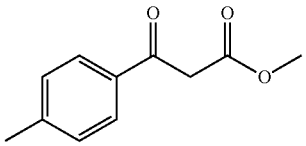

A mixture of 1-p-tolylethanone (13.4 g, 100.00 mmol, 1.00 equiv), dimethyl carbonate (80 mL), and sodium hydride (5.1 g, 148.75 mmol, 1.49 equiv, 70%) was heated to reflux for 1 hr. The resulting mixture was concentrated under vacuum, then diluted with 20 ml of water. The pH of the aqueous solution was adjusted to 6 with HCl (1M). The resulting solution was extracted with 3×100 mL of ethyl acetate, and the organic layers combined, dried over anhydrous sodium sulfate, and concentrated in vacuo. This resulted in 4 g (21%) of methyl 3-oxo-3-p-tolylpropanoate as yellow oil.

LC-MS-: (ES, m/z): 193 $[M+H]^+$ $^1$H-NMR (400 MHz, CDCl$_3$, ppm): 7.86-7.83 (d, J=8.4 Hz, 2H), 7.29-7.21 (m, 3H), 3.99 (s, 2H), 3.75 (s, 3H), 2.42 (s, 3H)

Intermediate 13

Methyl 3-(4-chloro-2-methoxyphenyl)-3-oxopropanoate

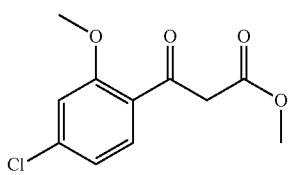 [SMILES: COC(=O)CC(=O)c1ccc(Cl)cc1OC]

Step 1. 4-Chloro-2-methoxybenzoyl chloride

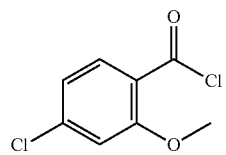

A solution of 4-chloro-2-methoxybenzoic acid (10 g, 53.48 mmol, 1.00 equiv) in thionyl chloride (74 g, 532.37 mmol, 9.96 equiv) and N,N-dimethylformamide (0.01 mL) was heated to reflux for 3 hours. Then the reaction was concentrated in vacuo affording 11 g (100%) of 4-chloro-2-methoxybenzoyl chloride as a white solid.

Step 2. 5-(4-Chloro-2-methoxybenzoyl)-2,2-dimethyl-1,3-dioxane-4,6-dione

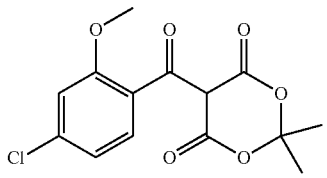 [SMILES: COc1cc(Cl)ccc1C(=O)C1C(=O)OC(C)(C)OC1=O]

To a solution of 2,2-dimethyl-1,3-dioxane-4,6-dione (7 g, 48.61 mmol, 0.91 equiv) in pyridine (9.71 g, 121.38 mmol, 2.27 equiv) and dichloromethane (30 mL) was added 4-chloro-2-methoxybenzoyl chloride (11 g, 53.40 mmol, 1.00 equiv) with stirring. The reaction was stirred for 1 h at 0° C., and then stirred at room temperature for 2 h. Then the reaction was concentrated in vacuo affording 11 g (66%) of 5-(4-chloro-2-methoxybenzoyl)-2,2-dimethyl-1,3-dioxane-4,6-dione as a brown solid.

LC-MS: (ES, m/z): 313 $[M+H]^+$

Step 3. Methyl 3-(4-chloro-2-methoxyphenyl)-3-oxopropanoate

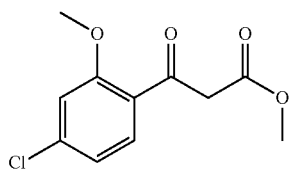

A solution of 5-(4-chloro-2-methoxybenzoyl)-2,2-dimethyl-1,3-dioxane-4,6-dione (2 g, 5.08 mmol, 1.00 equiv) in methanol (40 mL) was heated to reflux overnight. Then the reaction was concentrated in vacuo and purified by silica gel column chromatography with ethyl acetate/petroleum ether (1:20). This resulted in 300 mg (24%) of methyl 3-(4-chloro-2-methoxyphenyl)-3-oxopropanoate as colorless oil.

LC-MS: (ES, m/z): 243 $[M+H]^+$

Intermediate 14

Methyl 3-(2-methoxyphenyl)-3-oxopropanoate

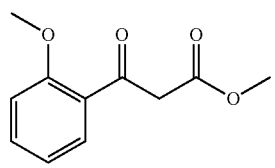

Sodium hydride (1.9 g, 55.42 mmol, 3.00 equiv, 70%) was added portionwise to a solution of 1-(2-methoxyphenyl)ethanone (4 g, 26.67 mmol, 1.00 equiv) in dimethyl carbonate (40 mL) at 0° C. The reaction was stirred for 1 h at room temperature, then for an additional 2.5 h at 50° C. Then the reaction was quenched by the addition of 50 mL of ice/water. The pH of the aqueous solution was adjusted to 2 with HCl (1N). The resulting solution was extracted with 2×20 mL of ethyl acetate. The organic layers were combined and concentrated in vacuo. The residue was purified by silica gel column chromatography with ethyl acetate/petroleum ether (1:2). This resulted in 4.8 g (87%) of methyl 3-(2-methoxyphenyl)-3-oxopropanoate as yellow green oil.

Intermediate 15

4-(Pyridin-2-yl)-1H-pyrazol-5-amine

Step 1.
3-(Dimethylamino)-2-(pyridin-2-yl)acrylonitrile

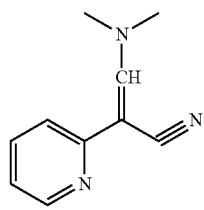

A solution of 2-(pyridin-2-yl)-acetonitrile (3.5 g, 29.91 mmol, 1.00 equiv) and DMF-DMA (15 mL) in toluene (15 mL) was heated to reflux overnight. Then the reaction was concentrated in vacuo and purified by silica gel column chromatography with ethyl acetate/petroleum ether (1:10). This resulted in 3.2 g (62%) of 3-(dimethylamino)-2-(pyridin-2-yl)acrylonitrile as yellow oil.
LC-MS: (ES, m/z): 174 [M+H]$^+$ Step 2. 4-(Pyridin-2-yl)-1H-pyrazol-5-amine

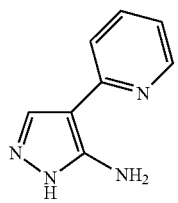 [SMILES: Nc1[nH]ncc1-c1ccccn1]

A solution of 3-(dimethylamino)-2-(pyridin-2-yl)acrylonitrile (13.5 g, 78.03 mmol, 1.00 equiv) and hydrazine hydrobromide (35 g, 312.50 mmol, 4.00 equiv) in ethanol/water (240/40 mL) was stirred overnight at 80° C., then concentrated in vacuo, and the resulting residue was dissolved in 250 mL of H$_2$O and extracted with 3×100 mL of ethyl acetate. The organic layers were combined and concentrated in vacuo. This afforded 9.8 g (78%) of 4-(pyridin-2-yl)-1H-pyrazol-5-amine as a yellow-green solid.

Intermediate 16

Methyl 3-(2,4-dichlorophenyl)-3-oxopropanoate

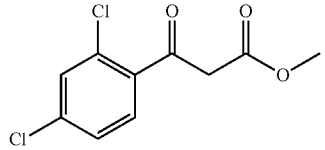

Sodium hydride (2.7 g, 78.75 mmol, 3.00 equiv, 70%) was slowly added to a solution of 1-(2,4-dichlorophenyl)ethanone (5 g, 26.46 mmol, 1.00 equiv) in dimethyl carbonate (20 mL) and cooled to 0° C. Then, the reaction was stirred for 1 h at room temperature, then warmed to 85° C. for 30 min. Then the reaction was quenched by the addition of 40 mL of water/ice. The pH of the solution was adjusted to 2 with HCl (2%). The resulting solution was extracted with 40 mL of ethyl acetate. The organic layers combined and concentrated in vacuo. The residue was purified by silica gel column chromatography with ethyl acetate/petroleum ether (1:10). The collected fractions were combined and concentrated in vacuo to afford 0.47 g of methyl 3-(2,4-dichlorophenyl)-3-oxopropanoate as a white solid.
LC-MS: (ES, m/z): 247 [M+H]$^+$ Intermediate 17

Methyl 3-(4-fluorophenyl)-3-oxopropanoate

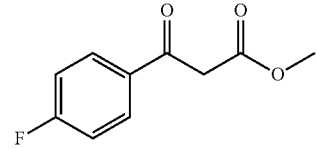

Sodium hydride (12 g, 3.00 equiv) was added portionwise to a solution of 1-(4-fluorophenyl)ethanone (13.8 g, 99.90 mmol, 1.00 equiv) in dimethyl carbonate (50 mL) cooled to 0° C. The reaction was heated to reflux for 1 h, then quenched by the addition of 100 mL of water/ice. The pH of the aqueous solution was adjusted to 4 with HCl (1M). The resulting aqueous solution was extracted with 3×200 mL of ethyl acetate. The organic layers combined and concentrated in vacuo. The residue was purified by silica gel column chromatography with ethyl acetate/petroleum ether (1:10). This resulted in 7 g (36%) of methyl 3-(4-fluorophenyl)-3-oxopropanoate as a brown oil.
LC-MS: (ES, m/z): 197 [M+H]$^+$ Intermediate 18

Methyl 3-(3,4-dichlorophenyl)-3-oxopropanoate

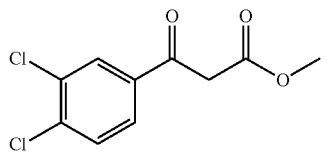

Sodium hydride (2.7 g, 78.75 mmol, 3.00 equiv, 70%) was added portion-wise to a solution of 1-(3,4-dichlorophenyl)ethanone (5 g, 26.46 mmol, 1.00 equiv) in dimethyl carbonate (40 mL) cooled to 0° C. The reaction was stirred for 3 h at room temperature, then quenched by the addition of 40 mL of water/ice. The resulting aqueous solution was extracted with 3×30 mL of ethyl acetate. The organic layers were combined and concentrated in vacuo. The residue was purified by silica gel column chromatography with ethyl acetate/petroleum ether (1:5). The collected fractions were combined and concentrated in vacuo to afford 2.7 g (41%) of methyl 3-(3,4-dichlorophenyl)-3-oxopropanoate as a white solid.

LC-MS: (ES, m/z): 247 [M+H]⁺

Intermediate 19

4-Benzyl-1H-pyrazol-5-amine

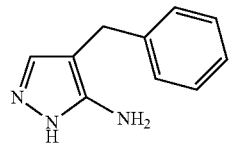

Step 1. (E)-2-Benzyl-3-(dimethylamino)acrylonitrile

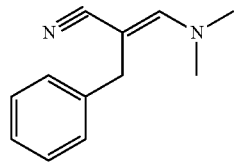

A solution of 3-phenylpropanenitrile (301 mg, 2.29 mmol, 1.00 equiv), N,N-dimethylformamide (5 mL), and 1-tert-butoxy-N,N,N',N'-tetramethylmethanediamine (600 mg, 3.44 mmol, 1.50 equiv) was stirred overnight at 140° C. The resulting mixture was concentrated in vacuo. The residue was applied onto a silica gel column with ethyl acetate/petroleum ether (1:10). This resulted in 250 mg (58%) of (E)-2-benzyl-3-(dimethylamino)acrylonitrile as a brown oil.

Step 2. 4-Benzyl-1H-pyrazol-5-amine

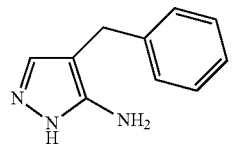 [SMILES: Nc1[nH]ncc1Cc1ccccc1]

A solution of (E)-2-benzyl-3-(dimethylamino)acrylonitrile (386 mg, 2.08 mmol, 1.00 equiv), N₂H₄Br (2.33 g, 20.80 mmol, 10.02 equiv), and ethanol/H₂O (24/3 mL) was heated to reflux overnight. The resulting mixture was concentrated in vacuo and the crude product (400 mg) was purified by Flash-Prep-HPLC under the following conditions (CombiFlash-1): Column, C18 silica gel; mobile phase, water and MeOH; Detector, UV 254 nm. This resulted in 350 mg (97%) of 4-benzyl-1H-pyrazol-5-amine as a yellow oil.

LC-MS: (ES, m/z): 174 [M+H]⁺

Intermediate 20

4-Propyl-1H-pyrazol-5-amine

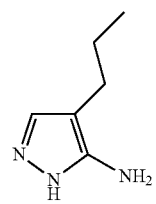

Step 1. (E)-2-((Dimethylamino)methylene)pentanenitrile

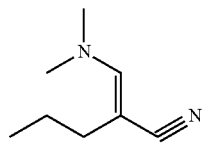

A solution of pentanenitrile (312 mg, 3.75 mmol, 1.00 equiv), N,N-dimethylformamide (2 mL), and 1-tert-butoxy-N,N,N',N'-tetramethylmethanediamine (790 mg, 4.54 mmol, 1.20 equiv) was stirred overnight at 140° C. The reaction was diluted with 30 mL of ethyl acetate and washed with 3×30 mL of brine. The organic extracts were combined and concentrated in vacuo. This resulted in 200 mg (39%) of (E)-2-((dimethylamino)methylene)pentanenitrile as brown oil.

Step 2. 4-Propyl-1H-pyrazol-5-amine

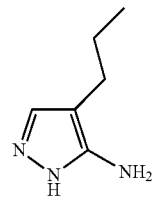

A solution of (E)-2-((dimethylamino)methylene)pentanenitrile (276 mg, 2.00 mmol, 1.00 equiv), ethanol (4 mL), hydrazine hydrobromide (1.13 g, 10.00 mmol, 10.00 equiv), and water (1 mL) was stirred overnight at 80° C., then concentrated in vacuo. The crude product (300 mg) was purified by Flash-Prep-HPLC under the following conditions (IntelFlash-1): Column, C18 silica gel; mobile phase, H₂O/MeOH=0% increasing to H₂O/MeOH=40% within 30 min; Detector, UV 254 nm. This resulted in 200 mg (80%) of 4-propyl-1H-pyrazol-5-amine as brown oil.

LC-MS: (ES, m/z): 126 [M+H]⁺

Intermediate 21

Methyl 3-(4-chlorophenyl)-3-oxopropanoate

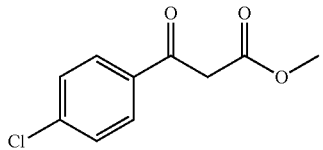

Dimethyl carbonate (5 g, 55.51 mmol) was added to a solution of 1-(4-chlorophenyl)ethan-1-one (5 g, 32.34 mmol) in tetrahydrofuran (30 mL), followed by the addition of sodium hydride (2.2 g, 91.67 mmol) at 0° C. After stirring for 3 hours at 70° C., the reaction was quenched by the dropwise addition of water (100 mL), and extracted with dichloromethane (3×30 mL). The organic layers were combined and then concentrated in vacuo to give a residue, which was purified by a silica gel column chromatography with 1%-5% ethyl acetate in petroleum ether to afford methyl 3-(4-chlorophenyl)-3-oxopropanoate as a red oil (3.5 g, 51%).

$^1$H-NMR (300 MHz, CDCl$_3$) δ 7.88-7.92 (m, 2H), 7.46-7.50 (m, 2H), 4.01 (s, 2H), 3.82 (s, 3H)

Intermediate 22

Ethyl 3-(4-(methylsulfonyl)phenyl)-3-oxopropanoate

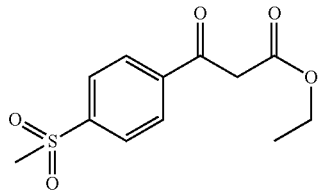 [SMILES: CCOC(=O)CC(=O)c1ccc(S(C)(=O)=O)cc1]

Step 1. 2,2-Dimethyl-5-(4-(methylsulfonyl)benzoyl)-1,3-dioxane-4,6-dione

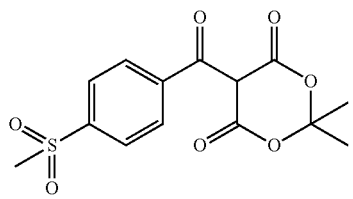 [SMILES: CC1(C)OC(=O)C(C(=O)c2ccc(S(C)(=O)=O)cc2)C(=O)O1]

A solution of 4-(methylsulfonyl)benzoic acid (2 g, 9.99 mmol, 1.00 equiv), 2,2-dimethyl-1,3-dioxane-4,6-dione (1.72 g, 11.93 mmol, 1.20 equiv), 4-dimethylaminopyridine (1.82 g, 14.92 mmol, 1.50 equiv), and 1-ethyl-3-(3-dimethylaminopropyl)carbodiimide hydrochloride (EDC HCl) (2.5 g, 13.02 mmol, 1.30 equiv) in dichloromethane (50 mL) was stirred overnight at room temperature. The resulting solution was diluted with 100 mL of DCM and washed with 3×100 mL of HCl (1N) and then 3×100 mL of brine. The resulting organic layer was concentrated in vacuo to afford 2.4 g (74%) of 2,2-dimethyl-5-(4-(methylsulfonyl)benzoyl)-1,3-dioxane-4,6-dione as yellow solid.

Step 2. Ethyl 3-(4-(methylsulfonyl)phenyl)-3-oxopropanoate

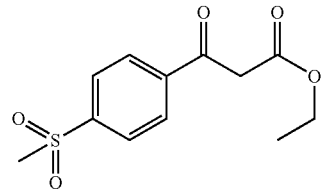 [SMILES: CCOC(=O)CC(=O)c1ccc(S(C)(=O)=O)cc1]

A solution of 2,2-dimethyl-5-(4-(methylsulfonyl)benzoyl)-1,3-dioxane-4,6-dione (1.8 g, 5.52 mmol, 1.00 equiv) in ethanol (20 mL) was heated to reflux overnight. The resulting mixture was concentrated in vacuo. The residue was purified by silica gel column chromatography with ethyl acetate/petroleum ether (1:10) which afforded 1.2 g (80%) of ethyl 3-(4-(methylsulfonyl)phenyl)-3-oxopropanoate as a yellow solid.

Intermediate 23

4-Phenyl-1H-pyrazole-3,5-diamine

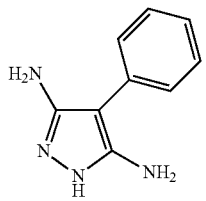

Step 1. 2-Phenylmalononitrile

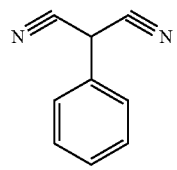 [SMILES: N#CC(C#N)c1ccccc1]

A mixture of malononitrile (3 g, 45.45 mmol, 1.00 equiv), ethylene glycol dimethyl ether (50 mL), Pd(PPh$_3$)$_2$Cl$_2$ (1.59 g, 2.27 mmol, 0.04 equiv), iodobenzene (9.2 g, 45.10 mmol, 1.00 equiv), and sodium hydride (2.7 g, 112.50 mmol, 2.50 equiv) was stirred for 2 hr at 85° C. under an inert atmosphere of nitrogen. The resulting mixture was diluted with 50 mL of H$_2$O and extracted with 2×30 mL of ethyl acetate. The organic layers were combined and concentrated in vacuo. The residue was purified by silica gel column chromatography with ethyl acetate/petroleum ether (1:5) which afforded 2.4 g (37%) of 2-phenylmalononitrile as a white solid.

¹H-NMR (300 MHz, CDCl₃, ppm) δ 7.553-7.519 (m, 5H), 5.090 (s, 1H).

Step 2. 4-Phenyl-1H-pyrazole-3,5-diamine

A mixture of 2-phenylmalononitrile (300 mg, 2.11 mmol, 1.00 equiv) and hydrazine hydrate (634 mg, 12.68 mmol, 6.00 equiv) was stirred for 30 min at 120° C. The resulting solids were collected by filtration and washed with 3×20 mL of ether. This resulted in 152 mg (41%) of 4-phenyl-1H-pyrazole-3,5-diamine as a yellow solid.

LC-MS (ES, m/z): 175 [M+H]⁺

Intermediate 24

Ethyl 5-(4-chlorophenyl)-7-oxo-4,7-dihydropyrazolo[1,5-a]pyrimidine-3-carboxylate

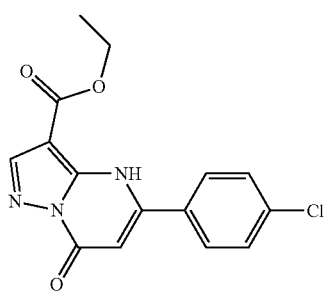 [SMILES: CCOC(=O)c1cnn2c(=O)cc(-c3ccc(Cl)cc3)[nH]c12]

A mixture of ethyl 5-amino-1H-pyrazole-4-carboxylate (1 g, 6.45 mmol, 1.00 equiv), methyl 3-(4-chlorophenyl)-3-oxopropanoate (1.5 g, 7.08 mmol, 1.10 equiv), 4-methylbenzenesulfonic acid (1.11 g, 6.45 mmol, 1.00 equiv), and toluene (10 mL) was stirred overnight at 100° C., and then concentrated in vacuo. The residue was purified by silica gel column chromatography with methanol/H₂O (79:100) to afford in 187 mg (9%) of ethyl 5-(4-chlorophenyl)-7-oxo-4,7-dihydropyrazolo[1,5-a]pyrimidine-3-carboxylate as a yellow solid.

LC-MS (ES, m/z): 318 [M+H]⁺

¹H-NMR (300 MHz, DMSO, ppm) 11.83 (s, 1H), 8.25 (s, 1H), 7.84-7.81 (d, J=9 Hz, 2H), 7.66-7.63 (d, J=9 Hz, 2H), 6.27 (s, 1H), 4.37-4.27 (m, 2H), 1.36-1.31 (t, J=7.5 Hz, 3H)

Intermediate 25

4-(Pyridin-2-yl)-1H-pyrazole-3,5-diamine

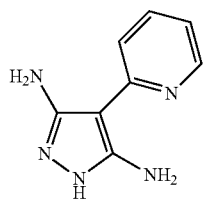

Step 1. 2-(Pyridin-2-yl)malononitrile

To a solution of malononitrile (5.50 g, 83.26 mmol) in xylene (150 mL) was added t-BuONa (21.50 g, 223.96 mmol), 2-bromopyridine (11.78 g, 74.98 mmol), and Pd(PCy₃)₂Cl₂ (1.03 g, 1.40 mmol). The reaction was stirred overnight at 140° C. under an inert atmosphere of nitrogen. Then the reaction was concentrated in vacuo. The residue was dissolved in ice water (200 mL) and adjusted to pH 8 with HCl (1N). The product was precipitated and collected by filtration to afford 2-(pyridin-2-yl)malononitrile as a yellow solid (2.10 g, 20%).

Step 2. 4-(Pyridin-2-yl)-1H-pyrazole-3,5-diamine

A solution of 2-(pyridin-2-yl)malononitrile (300 mg, 2.10 mmol) in hydrazine hydrate (150 mL) was stirred overnight at reflux, and then concentrated in vacuo to provide a residue, which was washed with dichloromethane (3×100 mL) to afford 4-(pyridin-2-yl)-1H-pyrazole-3,5-diamine as a white solid (300.0 mg, 81.7%).

LC/MS (ES, m/z): [M+H]⁺ 176.0

¹H-NMR (300 MHz, DMSO) δ 8.39-8.41 (m, 1H), 7.60-7.66 (m, 1H), 7.49 (d, J=8.1 Hz, 1H), 6.89-6.94 (m, 1H), 5.37 (s, 4H)

Intermediate 26

Ethyl 3-(benzofuran-2-yl)-3-oxopropanoate

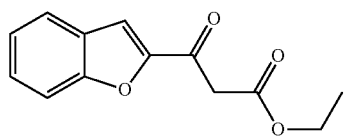 [SMILES: CCOC(=O)CC(=O)c1cc2ccccc2o1]

Step 1. 5-(Benzofuran-2-carbonyl)-2,2-dimethyl-1,3-dioxane-4,6-dione

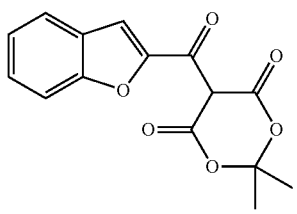 [SMILES: CC1(C)OC(=O)C(C(=O)c2cc3ccccc3o2)C(=O)O1]

To a solution of benzofuran-2-carboxylic acid (3 g, 18.52 mmol, 1.00 equiv) in dichloromethane (40 mL) was added 2,2-dimethyl-1,3-dioxane-4,6-dione (3.2 g, 22.22 mmol, 1.20 equiv), EDC HCl (4.62 g, 24.06 mmol, 1.30 equiv), and 4-dimethylaminopyridine (6.06 g, 27.80 mmol, 1.50 equiv), and the resulting mixture was stirred overnight at room temperature. The resulting solution was diluted with 50 mL of DCM, washed with 3×20 mL of HCl (1N) and then 3×50 mL of brine. The organic layers were dried over anhydrous sodium sulfate and concentrated in vacuo to afford in 3 g (56%) of 5-(benzofuran-2-carbonyl)-2,2-dimethyl-1,3-dioxane-4,6-dione as a yellow solid.

Step 2. Ethyl 3-(benzofuran-2-yl)-3-oxopropanoate

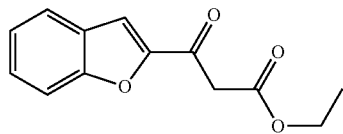 [SMILES: CCOC(=O)CC(=O)c1cc2ccccc2o1]

A solution of 5-(benzofuran-2-carbonyl)-2,2-dimethyl-1,3-dioxane-4,6-dione (3 g, 10.42 mmol, 1.00 equiv) in ethanol (40 mL) was heated to reflux for 4 hours, and then concentrated in vacuo. The residue was purified by silica gel column chromatography with ethyl acetate/petroleum ether (1:40). This resulted in 700 mg (29%) of ethyl 3-(benzofuran-2-yl)-3-oxopropanoate as a yellow oil.

Intermediate 27

4-(Pyridin-2-yl)-1H-pyrazole-3,5-diamine

Step 1. 2-(Pyridin-2-yl)malononitrile

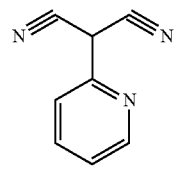 [SMILES: N#CC(C#N)c1ccccn1]

Malononitrile (12.5 g, 189.22 mmol) was added portionwise to a mixture of sodium hydride (10 g, 416.67 mmol) in tetrahydrofuran (150 mL) at 0° C., and the resulting mixture was stirred for 30 minutes. Then, 2-bromopyridine (20 g, 126.59 mmol) and Pd(PPh$_3$)$_4$ (7 g, 6.06 mmol) were added to the mixture, and it was stirred for 30 min at room temperature, then at 60° C. for 2 hours. The resulting mixture was concentrated in vacuo to provide a residue, which was dissolved in water (50 mL), adjusted pH to 8 with HCl (3N) and filtered to afford 2-(pyridin-2-yl)malononitrile as a yellow solid (10.8 g, 59%).

LC/MS (ES, m/z): [M+H]$^+$ 144.0

$^1$H-NMR (300 MHz, DMSO) δ 7.71-7.82 (m, 2H), 7.07-7.10 (d, J=8.7 Hz, 1H), 6.76-6.81 (m, 1H)

Step 2. 4-(Pyridin-2-yl)-1H-pyrazole-3,5-diamine

To a solution of 2-(pyridin-2-yl)malononitrile (12 g, 83.9 mmol) in methanol (20 mL) was added NH$_2$NH$_2$ H$_2$O (100 mL), and the resulting solution was refluxed overnight. The resulting mixture was concentrated in vacuo to afford a residue, which was dissolved in ethyl acetate (50 mL) and filtered to provide 4-(pyridin-2-yl)-1H-pyrazole-3,5-diamine as a yellow solid (10.2 g, 69%).

LC/MS (ES, m/z): [M+H]$^+$ 176.0

$^1$H-NMR (300 MHz, DMSO) δ 10.49 (s, 1H), 8.38-8.41 (m, 1H), 7.62-7.65 (m, 1H), 7.49-7.60 (m, 1H), 6.89-6.94 (m, 1H), 5.37 (s, 4H)

49

Intermediate 28

Ethyl 3-(2,2-difluorobenzo[d][1,3]dioxol-5-yl)-3-oxopropanoate

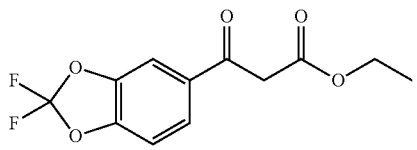 [SMILES: CCOC(=O)CC(=O)c1ccc2c(c1)OC(F)(F)O2]

Step 1. Methyl 2,2-difluorobenzo[d][1,3]dioxole-5-carboxylate

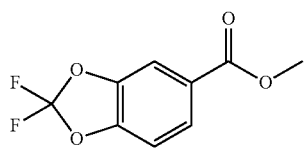

To a solution of 5-bromo-2,2-difluorobenzo[d][1,3]dioxole (3 g, 12.66 mmol) in methanol (30 ml) was added Pd(dppf)Cl$_2$ (817 mg, 1.12 mmol) and triethylamine (TEA) (2.56 g, 25.4 mmol). The resulting solution was stirred for 24 h at 100° C. under an atmosphere of CO (g), then concentrated in vacuo. It was purified by silica gel column chromagraphy with 1% ethyl acetate in petroleum ether to afford methyl 2,2-difluorobenzo[d][1,3]dioxole-5-carboxylate as a light yellow oil (1.4 g, 51%).

$^1$H-NMR (300 MHz, CDCl$_3$) δ 7.88-7.91 (m, 1H), 7.76 (d, J=1.5 Hz, 1H), 7.13 (d, J=8.4 Hz, 1H), 3.94 (s, 3H).

Step 2. 2,2-difluorobenzo[d][1,3]dioxole-5-carboxylic acid

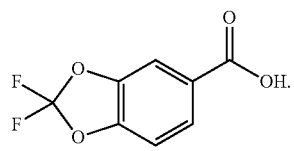 [SMILES: O=C(O)c1ccc2c(c1)OC(F)(F)O2]

A solution of methyl 2,2-difluorobenzo[d][1,3]dioxole-5-carboxylate (1.4 g, 6.48 mmol) and sodium hydroxide (830 mg, 20.75 mmol) in methanol (30 ml) was stirred overnight at room temperature. The reaction mixture was concentrated under vacuum, dissolved in water (20 ml), adjusted pH to 3 with HCl (3N) to give the precipitate, which was collected by filtration to afford 2,2-difluorobenzo[d][1,3]dioxole-5-carboxylic acid as a white solid (1.2 g, 92%).

$^1$H-NMR (300 MHz, DMSO) δ 13.23 (s, 1H), 7.85 (s, 1H), 7.53 (d, J=1.5 Hz, 1H), 7.53 (d, J=9.0 Hz, 1H)

50

Step 3. 5-(2,2-Difluorobenzo[d][1,3]dioxole-5-carbonyl)-2,2-dimethyl-1,3-dioxane-4,6-dione

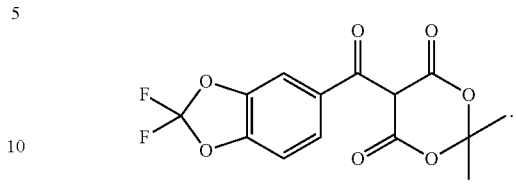

To a solution of 2,2-difluorobenzo[d][1,3]dioxole-5-carboxylic acid (1.2 g, 5.94 mmol) in dichloromethane (30 ml) was added 2,2-dimethyl-1,3-dioxane-4,6-dione (1.03 g, 7.15 mmol), 4-dimethylaminopyridine (1.09 g, 8.92 mmol) and 1-ethyl-3-(3-dimethyllaminopropyl)carbodiimide hydrochloride (EDC HCl) (1.71 g, 8.92 mmol). After stirring overnight at room temperature, the resulting solution was quenched by the addition of HCl (1N, 50 ml), washed with brine (2×50 ml), dried over anhydrous magnesium sulfate and concentrated under vacuum to afford 5-(2,2-difluorobenzo[d][1,3]dioxole-5-carbonyl)-2,2-dimethyl-1,3-dioxane-4,6-dione as an orange solid (1.74 g, crude).

Step 4. Ethyl 3-(2,2-difluorobenzo[d][1,3]dioxol-5-yl)-3-oxopropanoate

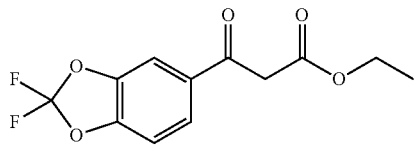 [SMILES: CCOC(=O)CC(=O)c1ccc2c(c1)OC(F)(F)O2]

A solution of 5-(2,2-difluorobenzo[d][1,3]dioxole-5-carbonyl)-2,2-dimethyl-1,3-dioxane-4,6-dione (1.74 g, crude) in ethanol (40 ml) was refluxed for 1 hour. Then the mixture was concentrated under vacuum to give a residue, which was purified by a silica gel column with 1% to 5% ethyl acetate in petroleum ether to afford ethyl 3-(2,2-difluorobenzo[d][1,3]dioxol-5-yl)-3-oxopropanoate as a light yellow oil (1.4 g).

$^1$H-NMR (300 MHz, CDCl$_3$) δ 7.77-7.80 (m, 1H), 7.71-7.76 (m, 1H), 7.18 (d, J=8.4 Hz, 1H), 4.18-4.32 (m, 2H), 4.01 (s, 2H), 1.33-1.38 (t, J=7.2 Hz, 3H)

Intermediate 29

3,5-Diamino-N-propyl-1H-pyrazole-4-carboxamide

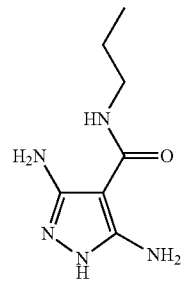

Step 1. Potassium 1,1-dicyano-2-oxo-2-(propylamino)ethan-1-ide

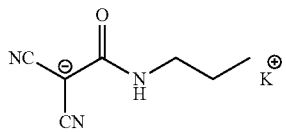

A solution of potassium hydroxide (2.9 g, 0.053 mol) in water (25 ml) was added to a solution of malononitrile (3.5 g, 0.053 mol) and 1-isocyanatopropane (4.96 g, 0.058 mol) in tetrahydrofuran (10 ml) over 10 min at 25-30° C. (water cooling). After stirring for 1 hour at 25-30° C., the reaction mixture was concentrated in vacuo to afford potassium 1,1-dicyano-2-oxo-2-(propylamino)ethan-1-ide as a light red solid (3.5 g, crude).

Step 2. 3,5-Diamino-N-propyl-1H-pyrazole-4-carboxamide

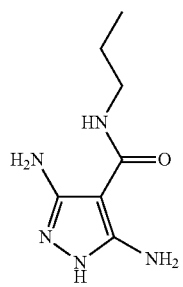

To a solution of potassium 1,1-dicyano-2-oxo-2-(propylamino)ethan-1-ide (3.5 g, crude) in water (10 ml) was added NH$_2$NH$_2$·H$_2$O (10 ml) and HCl (1.9 g, 18.5 mmol). The solution was refluxed overnight at 118° C. Then the reaction was concentrated in vacuo to give a residue, which was purified by a silica gel column chromatography with 10% dichloromethane in methanol to afford 3,5-diamino-N-propyl-1H-pyrazole-4-carboxamide as a light yellow solid (1.1 g).

LC/MS (ES, m/z): [M+H]$^+$ 184.0

Intermediate 30

Ethyl 3-(2,4-difluorophenyl)-3-oxopropanoate

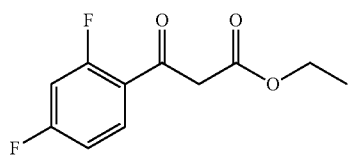

Step 1. 5-(2,4-Difluorobenzoyl)-2,2-dimethyl-1,3-dioxane-4,6-dione

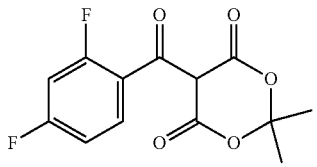 [SMILES: CC1(C)OC(=O)C(C(=O)c2ccc(F)cc2F)C(=O)O1]

To a solution of 2,4-difluorobenzoic acid (5.0 g, 31.63 mmol) in dichloromethane (250 ml) was added 2,2-dimethyl-1,3-dioxane-4,6-dione (5.5 g, 38.16 mmol), 4-dimethylaminopyridine (5.7 g, 46.66 mmol), and EDC.HCl (9.1 g, 47.40 mmol). The mixture was stirred for 24 hours at room temperature and then quenched by the addition of water (400 ml), extracted with ethyl acetate (3×250 ml). The organic layers were combined, dried over anhydrous sodium sulfate and concentrated under vacuum to afford 5-(2,4-difluorobenzoyl)-2,2-dimethyl-1,3-dioxane-4,6-dione as a red solid (7.5 g, crude).

Step 2. Ethyl 3-(2,4-difluorophenyl)-3-oxopropanoate

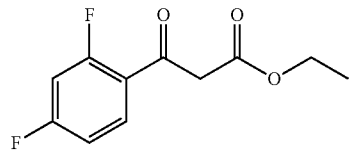 [SMILES: CCOC(=O)CC(=O)c1ccc(F)cc1F]

The solution of 5-(2,4-difluorobenzoyl)-2,2-dimethyl-1,3-dioxane-4,6-dione (7.5 g, crude) in ethanol (200 ml) was stirred overnight at 90° C. in an oil bath. Then the mixture was concentrated under vacuum to give a residue, which was purified by a silica gel column with 3% ethyl acetate in petroleum ether to afford ethyl 3-(2,4-difluorophenyl)-3-oxopropanoate as red oil (1.0 g, 14% 2 steps).

$^1$H-NMR (300 MHz, CDCl$_3$) δ 7.92-8.07 (m, 1H), 6.87-7.05 (m, 2H), 4.20-4.32 (m, 2H), 3.77-3.97 (m, 2H), 1.30-1.33 (m, 3H)

Intermediate 31

Ethyl 3-(3-fluorophenyl)-3-oxopropanoate

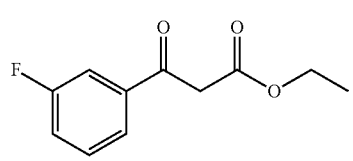

Step 1. 5-(3-fluorobenzoyl)-2,2-dimethyl-1,3-dioxane-4,6-dione

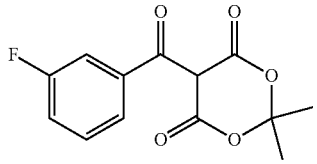 [SMILES: CC1(C)OC(=O)C(C(=O)c2cccc(F)c2)C(=O)O1]

To a solution of 3-fluorobenzoic acid (5 g, 31.6 mmol) in DCM (250 mL) was added 2,2-dimethyl-1,3-dioxane-4,6-dione (5.5 g, 38.0 mmol), DMAP (5.7 g, 47.5 mmol) and EDC HCl (9.1 g, 47.5 mmol). The resulting solution was stirred overnight at room temperature. The resulting reaction mixture was poured into water (400 mL), extracted with EA (3×250 mL), dried over anhydrous sodium sulfate and then concentrated under vacuum to afford 5-(3-fluorobenzoyl)-2,2-dimethyl-1,3-dioxane-4,6-dione as a red solid (7.5 g, crude).

Step 2. Ethyl 3-(3-fluorophenyl)-3-oxopropanoate

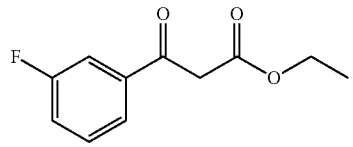

A solution of 5-(3-fluorobenzoyl)-2,2-dimethyl-1,3-dioxane-4,6-dione (7.5 g, crude) in EtOH (200 mL) was stirred overnight under reflux. The resulting reaction mixture was concentrated under vacuum to give a residue, which was purified by a silica gel column with 3% ethyl acetate in petroleum ether to afford ethyl 3-(3-fluorophenyl)-3-oxopropanoate as a red oil (5.6, 75%).

$^1$H-NMR (300 MHz, CDCl$_3$): δ 7.73-7.78 (m, 1H), 7.60-7.70 (m, 1H), 7.50-7.59 (m, 2H), 7.28-7.40 (m, 1H), 4.20-4.33 (m, 2H), 3.99 (s, 2H), 1.25-1.30 (t, J=7.2 Hz, 3H)

Intermediate 32

Ethyl 3-oxo-3-(4-(trifluoromethyl)phenyl)propanoate

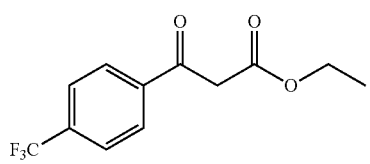 [SMILES: CCOC(=O)CC(=O)c1ccc(C(F)(F)F)cc1]

Step 1. 2,2-Dimethyl-5-(4-(trifluoromethyl)benzoyl)-1,3-dioxane-4,6-dione

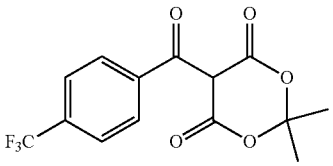 [SMILES: CC1(C)OC(=O)C(C(=O)c2ccc(C(F)(F)F)cc2)C(=O)O1]

2,2-Dimethyl-1,3-dioxane-4,6-dione (4.55 g, 31.6 mmol), DMAP (4.8 g, 39.5 mmol) and EDC HCl (7.6 g, 39.5 mmol) were added to a solution of 4-(trifluoromethyl)benzoic acid (5 g, 26.3 mmol) in DCM (250 mL). The resulting solution was stirred overnight at room temperature. The resulting reaction mixture was poured into water (500 mL), extracted with EA (3×300 mL), dried over anhydrous sodium sulfate and then concentrated in vacuo to afford 2,2-dimethyl-5-(4-(trifluoromethyl)benzoyl)-1,3-dioxane-4,6-dione as a red oil (10 g, crude).

Step 2. Ethyl 3-oxo-3-(4-(trifluoromethyl)phenyl)propanoate

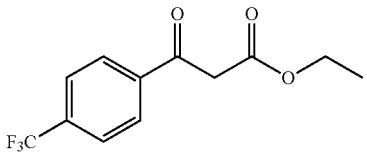 [SMILES: CCOC(=O)CC(=O)c1ccc(C(F)(F)F)cc1]

A solution of 2,2-dimethyl-5-(4-(trifluoromethyl)benzoyl)-1,3-dioxane-4,6-dione (10.0 g, crude) in EtOH (200 mL) was stirred for 5 hours under reflux and then the reaction mixture was concentrated under vacuum to give a residue, which was purified by a silica gel column with 3% ethyl acetate in petroleum ether to afford ethyl 3-oxo-3-(4-(trifluoromethyl)phenyl)propanoate as a red oil (3.1 g, 45.5%).

Intermediate 33

Ethyl 3-(4-fluorophenyl)-3-oxopropanoate

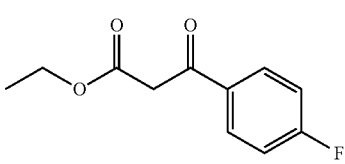

Step 1. 5-(4-Fluorobenzoyl)-2,2-dimethyl-1,3-dioxane-4,6-dione

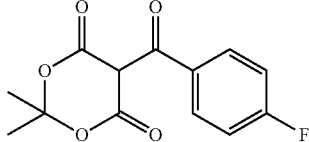 [SMILES: CC1(C)OC(=O)C(C(=O)c2ccc(F)cc2)C(=O)O1]

2,2-Dimethyl-1,3-dioxane-4,6-dione (12.3 g, 85.34 mmol), EDC HCl (16.5 g, 86.07 mmol) and 4-dimethylaminopyridine (13.9 g, 113.78 mmol) were added to a solution of 4-fluorobenzoic acid (8 g, 57.10 mmol) in dichloromethane (200 ml), and the mixture was stirred for 36 h at room temperature. The resulting mixture was washed with hydrochloric acid (3×100 mL, 3M), dried over anhydrous magnesium sulfate and concentrated in vacuo to afford 5-(4-fluorobenzoyl)-2,2-dimethyl-1,3-dioxane-4,6-dione as a yellow solid (10 g, crude).

$^1$H-NMR (300 MHz, CDCl$_3$): δ 8.12-8.17 (m, 1H), 7.72-7.77 (m, 1H), 7.12-7.20 (m, 2H), 3.63 (d, J=3.6 Hz, 1H), 1.86 (s, 3H), 1.77 (s, 3H)

Step 2. Ethyl 3-(4-fluorophenyl)-3-oxopropanoate

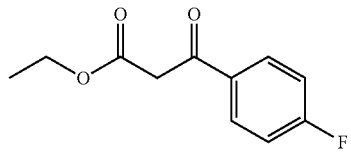

A solution of 5-(4-fluorobenzoyl)-2,2-dimethyl-1,3-dioxane-4,6-dione (10 g, 37.56 mmol) in ethanol (200 ml) was stirred for 2 hours at reflux and then concentrated in vacuo to provide a residue, which was purified by a silica gel column chromatography with 2% ethyl acetate in petroleum ether to afford ethyl 3-(4-fluorophenyl)-3-oxopropanoate as red oil (8.2 g, 67% 2 steps).

$^1$H-NMR (300 MHz, CDCl$_3$): δ 7.97-8.00 (m, 2H), 7.09-7.16 (m, 2H), 4.20-4.32 (m, 2H), 3.97 (s, 2H), 1.25-1.35 (m, 3H)

Intermediate 34

Ethyl 3-(2-methylbenzofuran-5-yl)-3-oxopropanoate

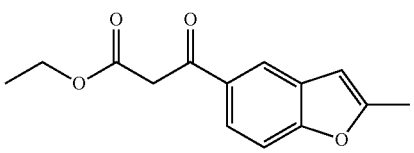 [SMILES: CCOC(=O)CC(=O)c1ccc2oc(C)cc2c1]

Step 1. Methyl 4-(allyloxy)benzoate

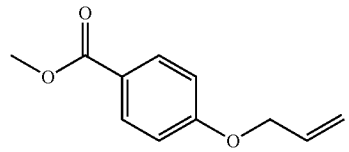

To a solution of methyl 4-hydroxybenzoate (20 g, 131.45 mmol,) in N,N-dimethylformamide (60 ml) was added sodium hydride (10.4 g, 433.33 mmol) at 0° C. The mixture was stirred for 0.5 hour at 0° C. Then 3-bromoprop-1-ene (31.8 g, 262.86 mmol) was added to this solution and stirred for 1 hour at 40° C. The reaction was then quenched by the addition of water (150 ml), extracted with ethyl acetate (3×50 ml). The organic layers were combined and dried over anhydrous magnesium sulfate and concentrated under vacuum to afford methyl 4-(allyloxy)benzoate as red oil (18 g, crude).

Step 2. Methyl 3-allyl-4-hydroxybenzoate

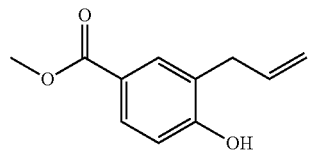

A solution of methyl 4-(allyloxy)benzoate (18 g, crude) in N-methyl-2-pyrrolidone (20 ml) was stirred for 24 hours at 200° C. The resulting solutions was applied onto a silica gel column with 2% ethyl acetate in petroleum ether to afford methyl 3-allyl-4-hydroxybenzoate as red oil (14 g).

$^1$H-NMR (300 MHz, CDCl$_3$) δ 8.48-8.50 (m, 1H), 7.98-8.05 (m, 1H), 6.80 (d, J=8.7 Hz, 1H), 6.01-6.12 (m, 1H), 5.51-5.59 (m, 1H), 5.34-5.39 (m, 1H), 4.67-4.69 (m, 2H), 3.91 (s, 3H)

Step 3. Methyl 2-methylbenzofuran-5-carboxylate

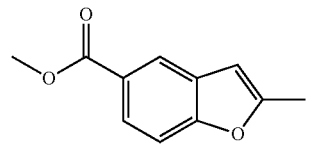

To a solution of methyl 3-allyl-4-hydroxybenzoate (14 g, 72.84 mmol) in DMF (50 ml) was added Cu(OAc)$_2$H$_2$O (43.8 g, 83.1 mmol), LiCl (21.8 mL, 10N), PdCl$_2$ (14.6 Ml, 0.1 N), and the solution was stirred for 24 h at 40° C. The reaction was then quenched by the addition of water (200 ml) and extracted with dichloromethane (3×60 mL). The organic layers were combined and dried over anhydrous magnesium sulfate then concentrated under vacuum to afford methyl 2-methylbenzofuran-5-carboxylate as a yellow solid (7.8 g, 56%).

$^1$H-NMR (300 MHz, CDCl$_3$) δ 8.22 (d, J=1.8 Hz, 1H), 7.94-7.97 (m, 1H), 7.41 (d, J=8.4 Hz, 1H), 6.43-6.47 (m, 1H), 3.94 (s, 3H), 2.49 (s, 3H)

Step 4. 2-Methylbenzofuran-5-carboxylic acid

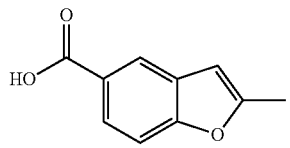

Sodium hydroxide (8 g, 200.00 mmol) was added to a solution of methyl 2-methylbenzofuran-5-carboxylate (7.8 g, 41.01 mmol) in methanol (150 ml) and water (20 ml), and the resulting solution was stirred for 2 hours at 65° C. The resulting mixture was concentrated in vacuo then diluted with water (20 ml) and adjusted to pH 3 with HCl (3N). The solids were collected by filtration to afford 2-methylbenzofuran-5-carboxylic acid as a white solid (8.3 g, crude).
LC/MS (ES, m/z): [M+H]$^+$ 177.0
$^1$H-NMR (300 MHz, DMSO) δ 12.74 (s, 1H), 8.16 (d, J=1.8 Hz, 1H), 7.82-7.86 (m, 1H), 7.56-7.67 (m, 1H), 6.70 (s, 1H), 2.50 (s, 3H)

Step 5. 2,2-Dimethyl-5-(2-methylbenzofuran-5-carbonyl)-1,3-dioxane-4,6-dione

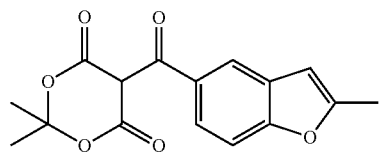

2,2-Dimethyl-1,3-dioxane-4,6-dione (4.9 g, 34.00 mmol), 4-dimethylaminopyridine (5.12 g, 41.91 mmol), and EDC HCl (8.06 g, 41.91 mmol) were added to a solution of 2-methylbenzofuran-5-carboxylic acid (5 g, 28.38 mmol) in dichloromethane (250 ml), and the reaction was stirred for 36 hours at room temperature. Then the solution was washed with HCl (1N, 100 ml) and NaCl solution (100 ml), dried over MgSO$_4$ and concentrated in vacuo to afford 2,2-dimethyl-5-(2-methylbenzofuran-5-carbonyl)-1,3-dioxane-4,6-dione as a yellow solid (6.5 g, crude).

Step 6. Ethyl 3-(2-methylbenzofuran-5-yl)-3-oxopropanoate

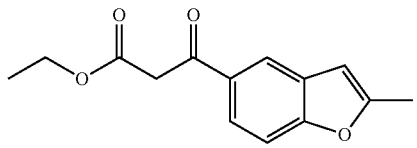 [SMILES: CCOC(=O)CC(=O)c1ccc2oc(C)cc2c1]

A solution of 2,2-dimethyl-5-(2-methylbenzofuran-5-carbonyl)-1,3-dioxane-4,6-dione (6.5 g, crude) in ethanol (50 ml) was stirred for 2 hours at 80° C. The resulting mixture was concentrated under vacuum and applied onto a silica gel column with 1.5% ethyl acetate in petroleum ether to afford ethyl 3-(2-methylbenzofuran-5-yl)-3-oxopropanoate as yellow oil (3.2 g).
$^1$H-NMR (300 MHz, CDCl$_3$) δ 8.12 (d, J=1.8 Hz, 1H), 7.86-7.95 (m, 1H), 7.41-7.48 (m, 1H), 6.48 (s, 1H), 4.27-4.32 (m 2H), 4.05 (s, 2H), 2.49 (s, 3H), 1.20-1.30 (m, 3H)

Intermediate 35

Ethyl 3-(3-methyl-1-benzofuran-5-yl)-3-oxopropanoate

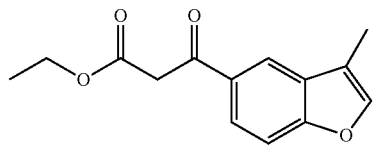 [SMILES: CCOC(=O)CC(=O)c1ccc2occ(C)c2c1]

Step 1. Methyl 4-(allyloxy)-3-iodobenzoate

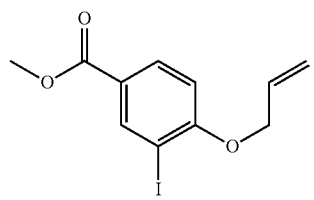

To a solution of methyl 4-hydroxy-3-iodobenzoate (20 g, 71.93 mmol) in DMF (100 ml) was added sodium hydride (6 g, 250.00 mmol) at 0° C. The mixture was stirred for 1 hour and then 3-bromoprop-1-ene (17.6 g, 145.48 mmol) was added. The resulting solution was stirred for 4 hours at room temperature, and then quenched with water (500 ml), extracted with dichloromethane (2×100 ml), and the organic layers combined and dried over MgSO$_4$ and concentrated under vacuum to afford methyl 4-(allyloxy)-3-iodobenzoate as a white solid (5.3 g, 23%).

Step 2. Methyl 3-methylbenzofuran-5-carboxylate

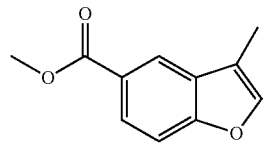

To a solution of methyl 4-(allyloxy)-3-iodobenzoate (5.3 g, 16.66 mmol) in DMF (50 ml) was added HCO$_2$Na (1.2 g, 17.65 mmol), n-Bu$_4$NCl (5.7 g, 20.50 mmol), sodium carbonate (5.3 g, 50.00 mmol), and Pd(OAc)$_2$ (500 mg, 2.23 mmol). The mixture was stirred for 2 hours at 80° C. The reaction was quenched with water (100 ml), extracted with CH$_2$Cl$_2$ (2×100 ml), and the organic layers combined and dried over MgSO$_4$, and concentrated in vacuo to provide a residue, which was purified by a silica gel column chromatography with 2% ethyl acetate in petroleum ether to afford methyl 3-methylbenzofuran-5-carboxylate as a white solid (1.5 g, 47%).

LC/MS (ES, m/z): [M+H]+ 191.0

¹H-NMR (300 MHz, CDCl₃) δ 8.30 (d, J=1.5 Hz, 1H), 8.02-8.06 (m, 1H), 7.47-7.50 (m, 2H), 3.95 (s, 3H), 2.30 (s, 3H)

Step 3. 3-Methylbenzofuran-5-carboxylic acid

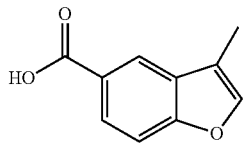

To a solution of methyl 3-methylbenzofuran-5-carboxylate (1.5 g, 7.89 mmol) in methanol (50 ml) was added sodium hydroxide (1.3 g, 32.50 mmol) and water (3 ml). The mixture was stirred overnight at room temperature then concentrated in vacuo. The residue was dissolved in water (40 ml), adjusted to pH 5 with HCl (3N). The solids were collected by filtration to afford 3-methylbenzofuran-5-carboxylic acid as a white solid (1.3 g, 94%).

LC/MS (ES, m/z): [M+H]+ 177.1

¹H-NMR (300 MHz, DMSO) δ 12.81 (s, 1H), 8.22 (s, 1H), 7.82-7.94 (m, 2H), 7.58-7.64 (m, 1H), 2.25 (s, 3H)

Step 4. 2,2-Dimethyl-5-[(3-methylbenzofuran-5-yl)carbonyl]-1,3-dioxane-4,6-dione

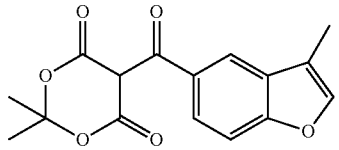 [SMILES: Cc1coc2ccc(C(=O)C3C(=O)OC(C)(C)OC3=O)cc12]

2,2-Dimethyl-1,3-dioxane-4,6-dione (1.6 g, 11.10 mmol), EDC HCl (2.1 g, 10.95 mmol,), and 4-dimethylaminopyridine (1.8 g, 14.73 mmol) were added to a solution of 3-methylbenzofuran-5-carboxylic acid (1.3 g, 7.38 mmol) in dichloromethane (50 ml). The resulting solution was stirred for 36 hours at room temperature and then quenched aqueous HCl (1N, 10 ml). The resulting solution was extracted with dichloromethane (2×50 ml) and the organic layers combined and dried over anhydrous magnesium sulfate and concentrated in vacuo to afford 2,2-dimethyl-5-[(3-methylbenzofuran-5-yl)carbonyl]-1,3-dioxane-4,6-dione as a yellow crude solid (1.8 g, crude).

Step 5. Ethyl 3-(3-methylbenzofuran-5-yl)-3-oxopropanoate

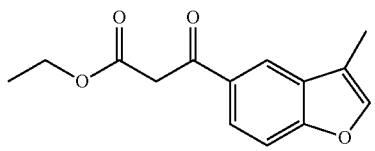 [SMILES: CCOC(=O)CC(=O)c1ccc2occ(C)c2c1]

A solution of 2,2-dimethyl-5-[(3-methylbenzofuran-5-yl)carbonyl]-1,3-dioxane-4,6-dione (1.8 g, crude) in ethanol (30 ml) was stirred for 2 h at 80° C. The residue was purified by a silica gel column chromatography with 5% ethyl acetate in petroleum ether to afford ethyl 3-(3-methylbenzofuran-5-yl)-3-oxopropanoate as off-white oil (1.3 g).

LC/MS (ES, m/z): [M+H]+ 247.0

¹H-NMR (300 MHz, CDCl₃) δ 8.20 (d, J=1.8 Hz, 1H), 7.50-7.97 (m, 1H), 7.28-7.48 (m, 2H), 4.20-4.31 (m, 2H), 4.06 (s, 2H), 2.30 (s, 3H), 1.26-1.29 (m, 3H)

Intermediate 36

Ethyl 3-(1-benzofuran-5-yl)-3-oxopropanoate

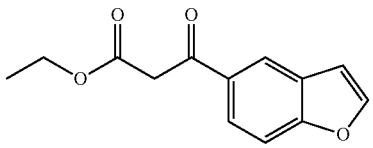 [SMILES: CCOC(=O)CC(=O)c1ccc2occc2c1]

Step 1. 5-(Benzofuran-5-carbonyl)-2,2-dimethyl-1,3-dioxane-4,6-dione

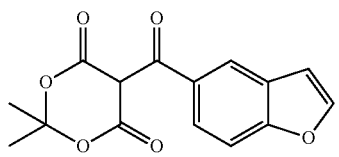 [SMILES: CC1(C)OC(=O)C(C(=O)c2ccc3occc3c2)C(=O)O1]

To a solution of benzofuran-5-carboxylic acid (2.0 g, 12.33 mmol) in dichloromethane (100 ml) was added 4-dimethylaminopyridine (2.26 g, 18.50 mmol), EDC.HCl (3.56 g, 18.49 mmol) and 2,2-dimethyl-1,3-dioxane-4,6-dione (2.13 g, 14.78 mmol) with stirring for overnight at room temperature. The reaction mixture was washed with hydrogen chloride (1N, 50 ml) and NaCl solution (100 ml), extracted with dichloromethane (3×50 ml) and the organic layers combined, dried over anhydrous magnesium sulfate and then concentrated under vacuum to afford 5-(benzofuran-5-carbonyl)-2,2-dimethyl-1,3-dioxane-4,6-dione as a yellow solid (3.43 g, crude).

Step 2. Ethyl 3-(benzofuran-5-yl)-3-oxopropanoate

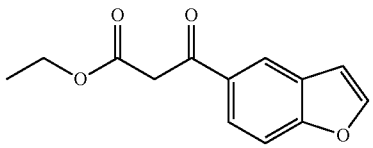 [SMILES: CCOC(=O)CC(=O)c1ccc2occc2c1]

The solution of 5-(benzofuran-5-carbonyl)-2,2-dimethyl-1,3-dioxane-4,6-dione (3.43 g, crude) in ethanol (50 ml) was stirred for 1 hour at 80° C. The reaction mixture was concentrated under vacuum to give the residue, which was applied onto a silica gel column with 2% ethyl acetate in petroleum ether to afford ethyl 3-(benzofuran-5-yl)-3-oxopropanoate as pink oil (2.18 g, 79%).

LC/MS (ES, m/z): [M+H]+ 233.0

¹H-NMR (300 MHz, CD₃OD): δ 8.35 (d, J=1.8 Hz, 1H), 7.98-8.01 (m, 1H), 7.89 (d, J=2.1 Hz, 1H), 7.61 (d, J=8.7 Hz, 1H), 7.00-7.01 (m, 1H), 4.18-4.29 (m, 2H), 1.24-1.32 (m, 3H)

Intermediate 37

4-(3-Fluoropyridin-2-yl)-1H-pyrazol-5-amine

Step 1. tert-Butyl 2-cyano-2-(3-fluoropyridin-2-yl)acetate

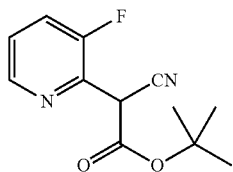 [SMILES: CC(C)(C)OC(=O)C(C#N)c1ncccc1F]

To a solution of NaH (3.8 g, 95.4 mmol) in DME (40 mL) was added tert-butyl 2-cyanoacetate (10.8 g, 76.3 mmol) at 0° C. The reaction mixture was kept at 0° C. for 40 min, and then 2-chloro-3-fluoropyridine (5.0 g, 38.2 mmol), Pd(dba)₃ (0.7 g, 0.76 mmol) and Binap (0.24 g, 0.38 mmol) were added at 0° C. The reaction mixture was stirred overnight at reflux and then poured into water (500 mL), extracted with n-BuOH (3×200 mL), dried over anhydrous sodium sulfate and then concentrated under vacuum to give a residue, which was purified by a silica gel column with 9% ethyl acetate in petroleum ether to afford tert-butyl 2-cyano-2-(3-fluoropyridin-2-yl)acetate as a light yellow solid (5.5 g, 61%).

¹H-NMR (300 MHz, CDCl₃): δ: 7.43-7.47 (m, 1H), 7.22-7.28 (m, 1H), 6.55-6.61 (m, 1H), 1.51-1.56 (s, 9H)

Step 2. 2-(3-Fluoropyridin-2-yl)acetonitrile

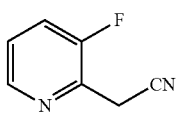

To a solution of tert-butyl 2-cyano-2-(3-fluoropyridin-2-yl)acetate (5.5 g, 23.3 mmol) in toluene (100 mL) was added TsOH (0.4 g, 2.33 mmol). The resulting solution was stirred under reflux overnight. Then the reaction mixture was poured into DCM (200 mL), washed with H₂O (3×100 mL), dried over anhydrous sodium sulfate, and then concentrated under vacuum to afford 2-(3-fluoropyridin-2-yl)acetonitrile as a light yellow solid (3 g, crude).

Step 3. (Z)-3-(dimethylamino)-2-(3-fluoropyridin-2-yl)acrylonitrile

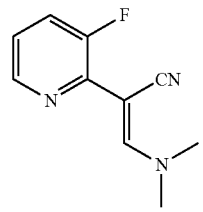

A solution of 2-(3-fluoropyridin-2-yl)acetonitrile (3.0 g, crude) in DMF/DMA (50 mL) was stirred overnight at 90° C. and then concentrated in vacuo to afford a residue, which was purified by a silica gel column chromatography with 17% ethyl acetate in petroleum ether to afford (Z)-3-(dimethylamino)-2-(3-fluoropyridin-2-yl)acrylonitrile as a light yellow solid (2.5 g, 56%, two steps).

¹H-NMR (300 MHz, CDCl₃): δ 8.22-8.25 (m, 1H), 7.72 (s, 1H), 7.28-7.35 (m, 1H), 6.99-7.05 (m, 1H), 3.33 (s, 6H)

Step 4. 4-(3-Fluoropyridin-2-yl)-1H-pyrazol-5-amine

To a solution of (Z)-3-(dimethylamino)-2-(3-fluoropyridin-2-yl)acrylonitrile (500 mg, 2.6 mmol) in AcOH (20 mL) was added NH₂NH₂H₂O (1.3 g, 26.1 mmol). The resulting solution was stirred overnight at 50° C., and then the reaction mixture was poured into H₂O (50 mL), extracted with DCM (4×30 mL), dried over anhydrous sodium sulfate and then concentrated in vacuo to afford 4-(3-fluoropyridin-2-yl)-1H-pyrazol-5-amine as a light yellow oil (277 mg, 59%).

Intermediate 38

Ethyl 3-(4-chloro-2-fluorophenyl)-3-oxopropanoate

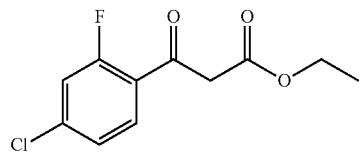 [SMILES: CCOC(=O)CC(=O)c1ccc(Cl)cc1F]

Step 1. 5-(4-chloro-2-fluorobenzoyl)-2,2-dimethyl-1,3-dioxane-4,6-dione

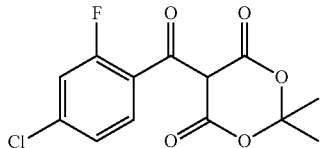 [SMILES: CC1(C)OC(=O)C(C(=O)c2ccc(Cl)cc2F)C(=O)O1]

To a solution of 4-chloro-2-fluorobenzoic acid (8 g, 46.0 mmol) in dichloromethane (100 mL) was added 2,2-dimethyl-1,3-dioxane-4,6-dione (7.9 g, 55.2 mmol), 4-dimethylaminopyridine (8.4 g, 69.0 mmol) and EDC HCl (13.2 g, 69.0 mmol). After stirring overnight at room temperature, the resulting solution was quenched by HCl (1N, 100 mL), washed with brine (2×100 mL), dried over anhydrous magnesium sulfate and concentrated under vacuum to afford 5-(4-chloro-2-fluorobenzoyl)-2,2-dimethyl-1,3-dioxane-4,6-dione as a red solid (12 g, crude).

$^1$H-NMR (300 MHz, CDCl$_3$) δ 7.53-7.59 (m, 1H), 7.30-7.33 (m, 1H), 7.17-7.25 (m, 1H), 3.64 (s, 1H), 1.80 (s, 6H)

Step 2. Ethyl 3-(4-chloro-2-fluorophenyl)-3-oxopropanoate

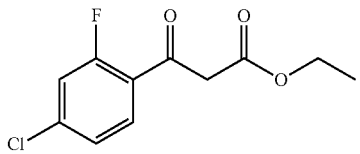 [SMILES: CCOC(=O)CC(=O)c1ccc(Cl)cc1F]

A solution of 5-(4-chloro-2-fluorobenzoyl)-2,2-dimethyl-1,3-dioxane-4,6-dione (12 g, crude) in ethanol (250 mL) was refluxed for 3 hours. Then the mixture was concentrated under vacuum to give a residue, which was purified by a silica gel column with 1% to 5% ethyl acetate in petroleum ether to afford ethyl 3-(4-chloro-2-fluorophenyl)-3-oxopropanoate as a light red oil (7.84 g).

$^1$H-NMR (300 MHz, CDCl$_3$) δ 7.82-7.96 (m, 1H), 7.15-7.27 (m, 2H), 4.25-4.32 (m, 2H), 3.97 (s, 2H), 1.25-1.30 (t, J=7.2 Hz, 3H)

Intermediate 39

3-Ethyl-4-(pyridin-2-yl)-1H-pyrazol-5-amine

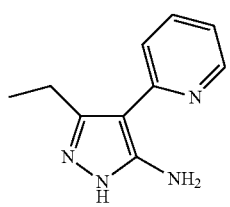

Step 1. (Z)-3-ethoxy-2-(pyridin-2-yl)pent-2-enenitrile

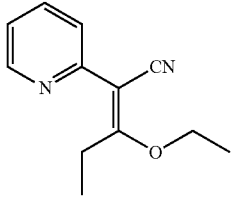

To a solution of 2-(pyridin-2-yl)acetonitrile (5 g, 42.32 mmo) in (Ac)$_2$O (8.6 g) was added 1,1,1-triethoxypropane (7.5 g, 42.55 mmol). The resulting solution was stirred overnight at 100° C. Then the reaction mixture was concentrated under vacuum to give a residue, which was purified by a silica gel column with 10% ethyl acetate in petroleum to afford (Z)-3-ethoxy-2-(pyridin-2-yl)pent-2-enenitrile as yellow oil (1.5 g, 18%).

$^1$H-NMR (300 MHz, CDCl$_3$) δ 8.56-8.58 (m, 1H), 7.66-7.72 (m 1H), 7.50-7.53 (m, 1H), 7.13-7.18 (m, 1H), 4.24-4.35 (m, 2H), 2.82-2.89 (m, 2H), 1.40-1.47 (m, 3H), 1.18-1.27 (m, 3H)

Step 2. 3-Ethyl-4-(pyridin-2-yl)-1H-pyrazol-5-amine

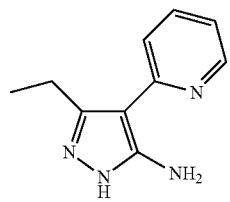

To a solution of (Z)-3-ethoxy-2-(pyridin-2-yl)pent-2-enenitrile (1.5 g, 7.42 mmol) in ethanol (6 mL) was added hydrazine hydrate (3 mL). The resulting solution was refluxed overnight. Then the reaction was concentrated under vacuum to give a residue, which was purified by a silica gel column with 5% ethyl acetate in petroleum to afford 3-ethyl-4-(pyridin-2-yl)-1H-pyrazol-5-amine as light yellow oil (800 mg, 57%).

$^1$H-NMR (300 MHz, CDCl$_3$) δ 8.54-8.57 (m, 1H), 7.62-7.68 (m, 1H), 7.33 (d, J=8.1 Hz, 1H), 7.00-7.05 (m, 1H), 5.91 (s, 3H), 2.85-2.93 (m, 2H), 1.30-1.35 (t, J=7.5 Hz, 3H)

Intermediate 40

Ethyl 3-[1-(methoxymethyl)-1H-indazol-5-yl]-3-oxopropanoate

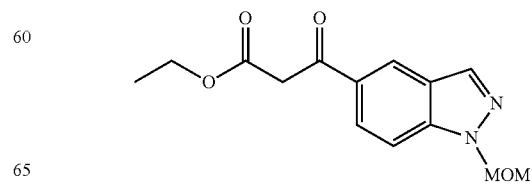

Step 1. Methyl 3-methyl-4-nitrobenzoate

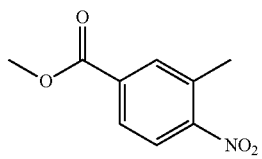

To a solution of 3-methyl-4-nitrobenzoic acid (30 g, 165.61 mmol) in methanol (300 mL), was added thionyl chloride (25 mL) dropwise with stirring at 0° C. After stirring for 1 h at 80° C., the resulting mixture was concentrated under vacuum to give residue, which was dissolved in petroleum ether (100 mL) and filtrated to give methyl 3-methyl-4-nitrobenzoate as a white solid (31 g, 96%).

LC/MS (ES, m/z): [M+H]$^+$ 196.0

$^1$H-NMR (300 MHz, CD$_3$Cl) δ 7.99-8.04 (m, 3H), 3.98 (s, 3H), 2.64 (s, 3H)

Step 2. Methyl 4-amino-3-methylbenzoate

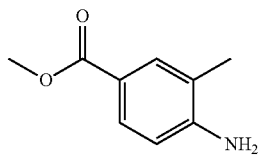

To a solution of methyl 3-methyl-4-nitrobenzoate (31 g, 158.83 mmol) in methanol (1000 mL) was added palladium on carbon (2 g), and the reaction was stirred overnight at room temperature under an atmosphere of H$_2$(g). Then the solids were filtered out and filtrate was concentrated under vacuum to afford methyl 4-amino-3-methylbenzoate as a white solid (21 g, 80%).

LC/MS (ES, m/z): [M+H]$^+$ 166.0

$^1$H-NMR (300 MHz, CD$_3$Cl) δ 7.74-7.77 (m, 2H), 6.52 (d, J=8.1 Hz, 1H), 4.09-4.11 (m, 2H), 3.87 (s, 3H), 2.20 (s, 3H)

Step 3. Methyl 1H-indazole-5-carboxylate

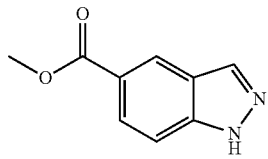

To a solution of methyl 4-amino-3-methylbenzoate (21 g, 133.18 mmol) in HCl (15 mL) and water (85 mL) was added NH$_4$BF$_4$ (20 g) and NaNO$_2$ (10 g, 144.93). The mixture was stirred for 35 minutes, and the solids were collected by filtration and added in one portion to a stirred mixture of KOAc (16 g, 163.03 mmol) and 18-crown-6 (500 mg, 1.89 mmol) in CHCl$_3$ (170 mL). After stirring for 2 hours at room temperature, the mixture was washed with water (100 mL), dried over anhydrous magnesium sulfate and concentrated under reduced pressure to afford a residue, which was purified by a silica gel column with 30% ethyl acetate in petroleum ether to afford methyl 1H-indazole-5-carboxylate as a white solid (14.5 g, 62%).

LC/MS (ES, m/z): [M+H]$^+$ 177.0

$^1$H-NMR (300 MHz, CDCl$_3$) δ 8.58-8.59 (m, 1H), 8.23 (s, 1H), 8.09-8.13 (m, 1H), 7.54 (d, J=9.0 Hz, 1H), 3.98 (s, 3H)

Step 4. Methyl 1-(methoxymethyl)-1H-indazole-5-carboxylate

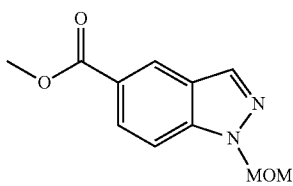

To a solution of methyl 1H-indazole-5-carboxylate (14 g, 79.5 mmol) in DMF (100 mL) was added sodium hydride (1.75 g, 72.92 mmol), and 15 minutes later, MOM-Br (3.5 mL) was added. After stirring for 2 hours at room temperature, the reaction was quenched water (100 mL), extracted with dichloromethane (3×150 mL), dried over magnesium sulfate and concentrated under reduced pressure to afford a residue, which was purified by a silica gel column with 10% ethyl acetate in petroleum ether to afford methyl 1-(methoxymethyl)-1H-indazole-5-carboxylate as a white solid (6 g, 34%).

LC/MS (ES, m/z): [M+H]$^+$ 221.0

$^1$H-NMR (300 MHz, CD$_3$Cl) δ 8.52-8.55 (m, 1H), 8.06-8.15 (m, 2H), 7.58 (d, J=8.7 Hz, 1H), 5.74 (s, 2H), 3.97 (s, 3H), 3.34 (s, 3H)

Step 5. 1-(Methoxymethyl)-1H-indazole-5-carboxylic acid

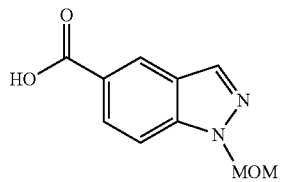

To a solution of methyl 1-(methoxymethyl)-1H-indazole-5-carboxylate (6 g, 27.3 mmol) in methanol (100 mL), was added sodium hydroxide (5 g, 125.00 mmol). After stirring overnight at room temperature, the reaction mixture was concentrated under reduced pressure to afford a residue, which was dissolved in water (50 mL), adjusted to pH 6 with HCl (3M) and filtered to give 1-(methoxymethyl)-1H-indazole-5-carboxylic acid as an off-white solid (3.9 g, 70%).

LC/MS (ES, m/z): [M+H]$^+$ 207.0

$^1$H-NMR (300 MHz, DMSO) δ 12.84 (s, 1H), 8.48-8.49 (m, 1H), 8.32 (d, J=0.9 Hz, 1H), 8.01 (d, J=1.5 Hz, 1H), 7.81 (d, J=8.7 Hz, 1H), 5.77 (s, 2H), 3.24 (s, 3H)

Step 6. 5-(1-(Methoxymethyl)-1H-indazole-5-carbonyl)-2,2-dimethyl-1,3-dioxane-4,6-dione

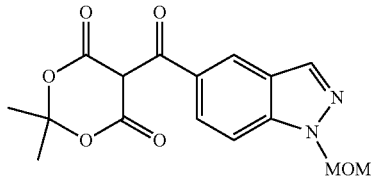

To a solution of 1-(methoxymethyl)-1H-indazole-5-carboxylic acid (3.9 g, 18.93 mmol) in dichloromethane (100 mL) was added 2,2-dimethyl-1,3-dioxane-4,6-dione (4.02 g, 27.89 mmol), EDC HCl (6.7 g, 34.95 mmol) and 4-dimethylaminopyridine (3.45 g, 28.24 mmol). After stirring overnight at room temperature, the reaction was quenched by HCl (1M, 100 mL), extracted with dichloromethane (2×150 mL), dried over anhydrous magnesium sulfate and concentrated under vacuum to give 5-(1-(methoxymethyl)-1H-indazole-5-carbonyl)-2,2-dimethyl-1,3-dioxane-4,6-dione as a yellow solid (3.5 g, crude).

Step 7. Ethyl 3-[1-(methoxymethyl)-1H-indazol-5-yl]-3-oxopropanoate

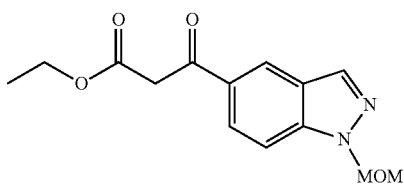

A solution of 5-(1-(methoxymethyl)-1H-indazole-5-carbonyl)-2,2-dimethyl-1,3-dioxane-4,6-dione (3.5 g, crude) in ethanol (100 mL) was stirred for 2 hours at reflux. The reaction mixture was then concentrated under vacuum to give a residue, which was purified by a silica gel column with 10% ethyl acetate in petroleum ether to afford ethyl 3-[1-(methoxymethyl)-1H-indazol-5-yl]-3-oxopropanoate as off-white oil (0.46 g).
$^1$H-NMR (300 MHz, CDCl$_3$) δ 8.43-8.44 (m, 1H), 8.19 (d, J=0.9 Hz, 1H), 8.10 (d, J=1.5 Hz, 1H), 7.62 (d, J=9.0 Hz, 1H), 5.74 (s, 2H), 4.21-4.28 (m, 2H), 4.08 (s, 2H), 3.33 (s, 3H), 1.25-1.28 (m, 3H)

Intermediate 41

3-Methoxy-4-(pyridin-2-yl)-1H-pyrazol-5-amine

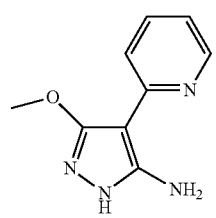

Step 1. tert-Butyl 5-amino-3-hydroxy-4-(pyridin-2-yl)-1H-pyrazole-1-carboxylate

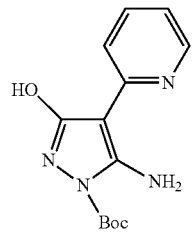

To a solution of 5-amino-4-(pyridin-2-yl)-1H-pyrazol-3-ol (600 mg, 3.40 mmol) in methanol (100 mL) was added (Boc)$_2$O (615 mg, 2.82 mmol) and sodium carbonate (300 mg, 2.83 mmol). After stirring for 3 hours at room temperature, the resulting mixture was concentrated under vacuum, dissolved in water (20 mL), extracted with dichloromethane (3×100 mL), dried over anhydrous magnesium sulfate and concentrated under vacuum to give tert-butyl 5-amino-3-hydroxy-4-(pyridin-2-yl)-1H-pyrazole-1-carboxylate as a white crude solid (700 mg, crude).

LC/MS (ES, m/z): [M+H]$^+$ 277.0

Step 2. tert-Butyl 5-amino-3-methoxy-4-(pyridin-2-yl)-1H-pyrazole-1-carboxylate

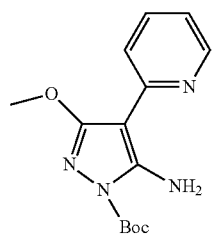 [SMILES: COc1nn(C(=O)OC(C)(C)C)c(N)c1-c1ccccn1]

To a solution of tert-butyl 5-amino-3-hydroxy-4-(pyridin-2-yl)-1H-pyrazole-1-carboxylate (700 mg, crude) in THF (30 mL) was added methanol (110 mg, 3.43 mmol), diethylazodicarboxylate (DEAD) (622 mg, 3.57 mmol) and PPh$_3$ (937 mg, 3.57 mmol). After stirring for 2 hours at room temperature, the resulting mixture was concentrated under vacuum to give a residue, which was purified by a silica gel column with 30% ethyl acetate in petroleum ether to afford tert-butyl 5-amino-3-methoxy-4-(pyridin-2-yl)-1H-pyrazole-1-carboxylate as a white solid (580 mg).

LC/MS (ES, m/z): [M+H]$^+$ 291.0
$^1$H-NMR (300 MHz, CD$_3$OD) δ 8.45-8.47 (m, 1H), 8.29-8.31 (m, 1H), 7.68-7.73 (m, 1H), 7.04-7.08 (m, 1H), 3.36 (s, 3H), 1.66 (s, 9H)

Step 3. 3-Methoxy-4-(pyridin-2-yl)-1H-pyrazol-5-amine

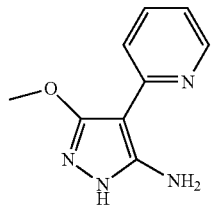

A solution of tert-butyl 5-amino-3-methoxy-4-(pyridin-2-yl)-1H-pyrazole-1-carboxylate (580 mg, 2.0 mmol), TFA (4 mL) and DCM (20 mL) was stirred for 1.5 hours at room temperature. The resulting mixture was concentrated under vacuum to give a residue, which was purified by a silica gel column with 5% methanol in dichloromethane to afford 3-methoxy-4-(pyridin-2-yl)-1H-pyrazol-5-amine as a yellow solid (320 mg, 81%).

LC/MS (ES, m/z): [M+H]$^+$ 191.0
$^1$H-NMR (300 MHz, DMSO) δ 8.48 (d, J=5.7 Hz, 1H), 8.00-8.08 (m, 2H), 7.21-7.25 (t, J=6.0 Hz, 1H), 3.12 (s, 3H)

Intermediate 42

N$^3$-Ethyl-4-(pyridin-2-yl)-1H-pyrazole-3,5-diamine

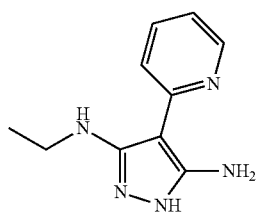

Step 1.
3,3-Bis(methylthio)-2-(pyridin-2-yl)acrylonitrile

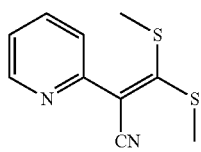

Sodium hydride (370 mg, 15.42 mmol) and CS$_2$ (710 mg, 9.34 mmol) was added to a solution of 2-(pyridin-2-yl)acetonitrile (1 g, 8.46 mmol) in DMF (15 mL) at 0° C. After stirring for 5 hours at room temperature, MeI (3.6 g, 25.35 mmol) was added. After 1 hour, the reaction was quenched by water (40 mL), extracted with dichloromethane (3×50 mL), dried over anhydrous magnesium sulfate, and concentrated in vacuo to afford a residue, which was purified by a silica gel column chromatography with 5% ethyl acetate in petroleum ether to afford 3,3-bis(methylthio)-2-(pyridin-2-yl)acrylonitrile as a yellow solid (31.4 g, 74%).

LC/MS (ES, m/z): [M+H]$^+$ 223.0.

$^1$H-NMR (300 MHz, CDCl$_3$) δ 8.67-8.69 (m, 1H), 7.74-7.80 (m, 1H), 7.64-7.67 (m, 1H), 7.23-7.28 (m, 1H), 2.65 (s, 3H), 2.42 (s, 3H)

Step 2. (Z)-3-(ethylamino)-3-(methylthio)-2-(pyridin-2-yl)acrylonitrile

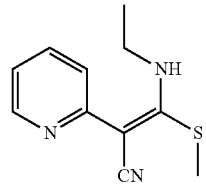

Ethanamine hydrate (540 mg, 8.56 mmol) was added to a solution of 3,3-bis(methylthio)-2-(pyridin-2-yl)acrylonitrile (1.23 g, 5.53 mmol,) in ethanol (50 mL). After stirring for 5 hours at 60° C., the resulting mixture was concentrated in vacuo to give (Z)-3-(ethylamino)-3-(methylthio)-2-(pyridin-2-yl)acrylonitrile as a solid (1.2 g, crude).

LC/MS (ES, m/z): [M+H]$^+$ 220.0.
$^1$H-NMR (300 MHz, CDCl$_3$) δ 8.35 (d, J=4.5 Hz, 1H), 7.63-7.69 (m, 1H), 7.53 (d, J=8.4 Hz, 1H), 6.97-6.99 (m, 1H), 3.65-3.74 (m, 2H), 3.08-3.17 (m, 2H), 1.20-1.46 (m, 6H)

Step 3. N$^3$-Ethyl-4-(pyridin-2-yl)-1H-pyrazole-3,5-diamine

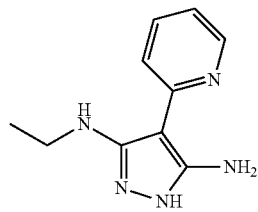

Hydrazine hydrate (30 mL) was added to a solution of (Z)-3-(ethylamino)-3-(methylthio)-2-(pyridin-2-yl)acrylonitrile (1.2 g, crude). After refluxing for 1.5 hours, the resulting mixture was concentrated in vacuo to give a residue, which was dissolved in petroleum ether (10 mL) and filtered to provide N$^3$-ethyl-4-(pyridin-2-yl)-1H-pyrazole-3,5-diamine as an off-white solid (1.1 g).

LC/MS (ES, m/z): [M+H]$^+$ 204.0
$^1$H-NMR (300 MHz, DMSO) δ 8.38-8.39 (m, 1H), 7.59-7.65 (m, 1H), 7.48 (d, J=8.1 Hz, 1H), 6.88-6.92 (m, 1H), 6.33 (s, 1H), 5.33 (s, 2H), 3.12-3.20 (m, 2H), 1.14-1.19 (t, J=7.2 Hz, 3H)

Intermediate 43

4-Benzyl-1H-pyrazol-5-amine

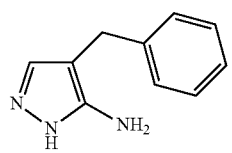

Step 1. 2-Benzyl-3-oxopropanenitrile

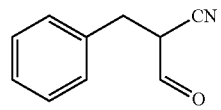 [SMILES: N#CC(C=O)Cc1ccccc1]

To a solution of 3-phenylpropanenitrile (10 g, 76.23 mmol) in THF (70 mL) was added sodium hydride (6 g, 250.00 mmol) and then ethyl formate (17.7 g, 238.94 mmol), and the resulting mixture was stirred overnight at room temperature. The reaction was then quenched by the addition of ice water (300 mL), extracted with ethyl acetate (3×80 mL), and concentrated in vacuo to get a residue, which was purified via a silica gel column chromatography with 5%-20% ethyl acetate in petroleum ether to afford 2-benzyl-3-oxopropanenitrile as a yellow oil solid (4.4 g, 36%).

LC/MS (ES, m/z): [M+H]$^+$ 160.1

Step 2. 4-Benzyl-1H-pyrazol-5-amine

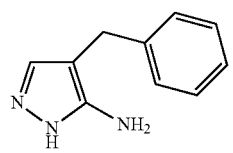 [SMILES: Nc1[nH]ncc1Cc1ccccc1]

To a solution of 2-benzyl-3-oxopropanenitrile (4.4 g, 27.64 mmol) in ethanol (60 mL) and water (5 mL) was added N$_2$H$_4$ HBr (4.3 g, 38.21 mmol), and the resulting mixture was stirred for 3 hours at 85° C. The resulting solution was concentrated in vacuo, diluted with water (100 mL), adjusted to pH 8 with NaHCO$_3$ solution, extracted with ethyl acetate (4×50 mL), and concentrated in vacuo to afford 4-benzyl-1H-pyrazol-5-amine as a red solid (4 g, 84%).

LC/MS (ES, m/z): [M+H]$^+$ 174.1
$^1$H-NMR (300 MHz, CDCl$_3$) δ 7.28-7.35 (m, 2H), 7.21-7.26 (m, 4H), 5.62 (s, 2H), 3.80 (s, 2H)

Intermediate 44

3-Ethyl-4-phenyl-1H-pyrazol-5-amine

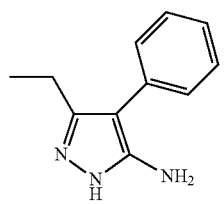

Step 1. 3-Oxo-2-phenylpentanenitrile

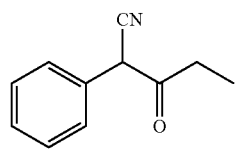

To a solution of 2-phenylacetonitrile (10 g, 85.36 mmol) in THF (100 ml) was added potassium t-amylate (1N, 56 mL) and ethyl propanoate (34.87 g, 341.42 mmol) dropwise, with stirring. After stirring 30 minutes at room temperature, the reaction was quenched by the addition of HCl (3N), extracted with ethyl acetate (300 mL), washed with water (3×100 mL), dried over anhydrous magnesium sulfate, and concentrated in vacuo to give a residue, which was purified by a silica gel column chromatography with 10% ethyl acetate in petroleum ether to afford 3-oxo-2-phenylpentanenitrile as a brown solid (4.2 g, 28%).

$^1$H-NMR (300 MHz, DMSO) δ 7.36-7.53 (m, 5H), 4.71 (s, 1H), 2.53-2.64 (m, 2H), 1.00-1.06 (m, 3H)

Step 2. 3-Ethyl-4-phenyl-1H-pyrazol-5-amine

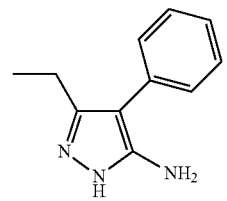

To a solution of 3-oxo-2-phenylpentanenitrile (2.26 g, 13.05 mmol) in ethanol (70 mL) was added a solution of N$_2$H$_4$HBr (4.43 g, 39.18 mmol) in water (10 mL). After stirring 2.5 hours at 80° C., the pH of the solution was adjusted to 8 with saturated aqueous sodium bicarbonate, extracted with ethyl acetate (3×100 mL), dried over anhydrous magnesium sulfate, and concentrated in vacuo to afford 3-ethyl-4-phenyl-1H-pyrazol-5-amine as a white solid (1.9 g, 78%).

LC/MS (ES, m/z): [M+H]$^+$ 188.1
$^1$H-NMR (300 MHz, CDCl$_3$) δ 7.27-7.46 (m, 5H), 4.79 (s, 2H), 2.67-2.74 (m, 2H), 1.21-1.31 (m, 3H)

Intermediate 45

Ethyl 3-(1-methyl-1H-indazol-5-yl)-3-oxopropanoate

Step 1. Methyl 1-methyl-1H-indazole-5-carboxylate

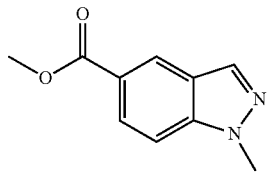

To a solution of 5-bromo-1-methyl-1H-indazole (5 g, 23.81 mmol) in methanol (40 ml) was added Pd(dppf)Cl$_2$ (870 mg, 1.19 mmol), TEA (4.8 g, 47.52 mmol), and the resulting mixture was stirred for 24 hours at 100° C. under an atmosphere of CO(g). The reaction mixture was then concentrated in vacuo and purified by silica gel column chromatography with 3% ethyl acetate in petroleum ether to afford methyl 1-methyl-1H-indazole-5-carboxylate as a white solid (3.7 g, 82%).

LC/MS (ES, m/z): [M+H]$^+$ 191.1
$^1$H-NMR (300 MHz, CDCl$_3$) δ 8.54 (s, 1H), 8.11 (s, 1H), 8.08 (d, J=1.5 Hz, 2H), 7.42 (d, J=8.7 Hz, 1H), 4.13 (s, 3H), 3.97 (s, 3H)

Step 2. 1-Methyl-1H-indazole-5-carboxylic acid

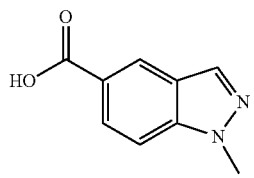

A solution of methyl 1-methyl-1H-indazole-5-carboxylate (3.7 g, 19.47 mmol) and sodium hydroxide (3.9 g, 97.50 mmol) in methanol (30 mL) was stirred for 2 hours at 65° C., and then concentrated in vacuo. The residue was dissolved in water (30 mL) and adjusted to pH 3 with HCl (3N). The product formed a precipitate and was collected by filtration to afford 1-methyl-1H-indazole-5-carboxylic acid as a white solid (3.2 g, 93%).

LC/MS (ES, m/z): [M+H]$^+$ 177.0
$^1$H-NMR (300 MHz, DMSO) δ 12.79 (s, 1H), 8.45 (d, J=0.6 Hz, 1H), 8.22 (d, J=0.6 Hz, 1H), 7.93-7.96 (m, 1H), 7.70 (d, J=8.7 Hz, 1H), 4.08 (s, 3H)

Step 3. 2,2-Dimethyl-5-(1-methyl-1H-indazole-5-carbonyl)-1,3-dioxane-4,6-dione

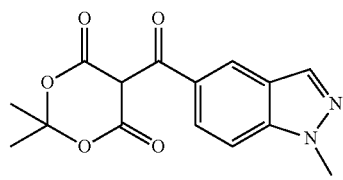 [SMILES: Cn1ncc2cc(C(=O)C3C(=O)OC(C)(C)OC3=O)ccc21]

A solution of 1-methyl-1H-indazole-5-carboxylic acid (3.2 g, 18.18 mmol), 2,2-dimethyl-1,3-dioxane-4,6-dione (3.5 g, 20.30 mmol), 4-dimethylaminopyridine (3.66 g, 30.00 mmol), and EDC HCl (5.76 g, 30.00 mmol) in DCM (100 mL) was stirred overnight at room temperature. The reaction mixture was then washed with HCl (3N, 50 mL) and saturated sodium chloride (50 mL), dried over anhydrous magnesium sulfate, and concentrated in vacuo to afford 2,2-dimethyl-5-(1-methyl-1H-indazole-5-carbonyl)-1,3-dioxane-4,6-dione as a yellow crude solid (4.0 g, crude).

LC/MS (ES, m/z): [M+H]$^+$ 303.0

Step 4. Ethyl 3-(1-methyl-1H-indazol-5-yl)-3-oxopropanoate

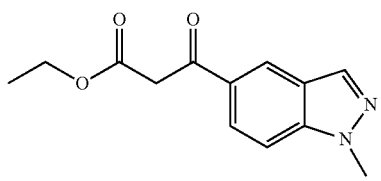 [SMILES: CCOC(=O)CC(=O)c1ccc2c(cnn2C)c1]

A solution of 2,2-dimethyl-5-(1-methyl-1H-indazole-5-carbonyl)-1,3-dioxane-4,6-dione (4.0 g, crude) in ethanol (50 mL) was stirred for 2 hours at 80° C. The resulting mixture was concentrated in vacuo to provide a residue, which was purified by a silica gel column chromatography with 6% ethyl acetate in petroleum ether to afford ethyl 3-(1-methyl-1H-indazol-5-yl)-3-oxopropanoate as light yellow oil (2.6 g, 47% 2 steps).

LC/MS (ES, m/z): [M+H]$^+$ 247.0
$^1$H-NMR (300 MHz, CDCl$_3$) δ 8.40-8.42 (t, J=0.6 Hz, 1H), 8.14 (d, J=3.9 Hz, 1H), 8.04-8.08 (m, 1H), 7.44-7.47 (t, J=4.5 Hz, 1H), 4.26-4.36 (m, 2H), 4.13 (s, 3H), 4.08 (s, 2H), 1.25-1.30 (m, 3H)

Intermediate 46

4-Phenyl-1H-pyrazole-3,5-diamine

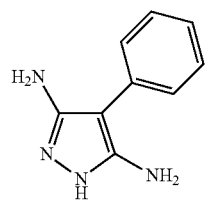

Step 1. 2-Phenylmalononitrile

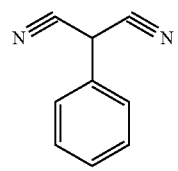 [SMILES: N#CC(C#N)c1ccccc1]

To a solution of sodium hydride (5 g, 208.33 mmol) in ethylene glycol dimethyl ether (100 mL) was added malononitrile (5 g, 75.69 mmol) in DME over 10 minutes with stirring at 20-35° C. under an inert atmosphere of nitrogen, and the resulting mixture was stirred for 1 hour at room temperature. Then, iodobenzene (12.88 g, 63.13 mmol) and Pd(PPh₃)₂Cl₂ (2.2 g, 3.13 mmol) were added, and the reaction mixture was stirred for 3 hours at 90° C. The resulting solution was diluted with water (500 ml) and adjusted to pH 6 with HCl (3N), extracted with ethyl acetate (4×80 mL), and the organic layers combined and concentrated in vacuo to provide a residue, which was purified via silica gel column chromatography with 1%-5% ethyl acetate in petroleum ether to afford 2-phenylmalononitrile as a white solid (7.3 g, 81%).

¹H-NMR (300 MHz, CDCl₃): δ 7.55 (s, 5H), 6.51 (s, 1H)

Step 2. 4-Phenyl-1H-pyrazole-3,5-diamine

To a solution of 2-phenylmalononitrile (7 g, 49.24 mmol) in ethanol (15 mL) was added N₂H₄H₂O (15 g, 80% aq.), and the reaction was stirred overnight at 120° C. The resulting mixture was concentrated in vacuo and precipitated from water (30 mL) to afford 4-phenyl-1H-pyrazole-3,5-diamine as a yellow solid (5.49 g, 64%).

LC/MS (ES, m/z): [M+H]⁺ 175.1
¹H-NMR (300 MHz, DMSO): δ 7.30-7.39 (m, 4H), 7.06-7.11 (m, 1H), 4.52 (s, 2H)

Intermediate 47

Ethyl 3-(1-acetyl-1H-indazol-5-yl)-3-oxopropanoate

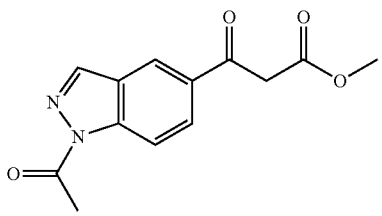 [SMILES: COC(=O)CC(=O)c1ccc2c(cnn2C(C)=O)c1]

Step 1. Methyl 4-amino-3-methylbenzoate

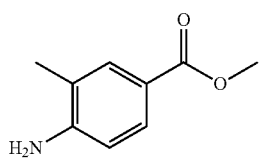

A solution of 4-amino-3-methylbenzoic acid (60 g, 396.92 mmol) and SOCl₂ (141.9 g, 1.19 mol) in methanol (700 mL) was stirred 3 hours at 80° C. The resulting solution was concentrated in vacuo to afford a residue, which was dissolved in dichloromethane (500 mL) and washed with saturated aqueous sodium bicarbonate, dried over anhydrous magnesium sulfate and concentrated in vacuo to afford methyl 4-amino-3-methylbenzoate (62 g, 95%) as a pink solid.

LC/MS (ES, m/z): [M+H]⁺ 152.1
¹H-NMR (300 MHz, CDCl₃) δ 7.78 (d, J=0.6 Hz, 1H), 7.74 (d, J=2.1 Hz, 1H), 6.65 (d, J=8.1 Hz, 1H), 4.11 (s, 2H), 3.87 (s, 3H), 2.20 (s, 3H)

Step 2. Methyl 1H-indazole-5-carboxylate

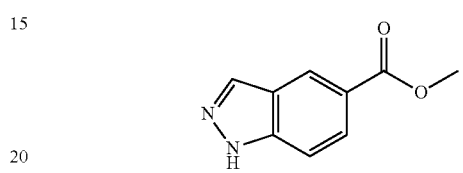

To a solution of methyl 4-amino-3-methylbenzoate (17 g, 102.91 mmol) in HBF₄ (125 ml, 50% aq.) was added a solution of sodium nitrite (7.8 g, 113.05 mmol) in water (12 ml) at 0° C.~5° C. The reaction was stirred for 3 hours at 10° C. in a water/ice bath, the solids were collected by filtration to afford crude 4-(methoxycarbonyl)-2-methylbenzenediazonium tetrafluoroborate (26 g) as a white solid, which was added to a solution of potassium acetate (18.97 g, 193.29 mmol) and 18-Crown-6 (1.82 g, 6.89 mmol) in chloroform (600 ml). After stirring 2 hours at 10° C. in an ice-water bath, the resulting solution was quenched by the addition of water (400 ml). The organic layers were separated from the mixture, and the aqueous layers were further extracted with chloroform (3×200 ml). The combined organic layers were dried over anhydrous magnesium sulfate and concentrated in vacuo to afford a residue, which was purified by silica gel column chromatography with 10% ethyl acetate in petroleum ether to afford methyl 1H-indazole-5-carboxylate (6.7 g, 28%) as a gray solid.

LC/MS (ES, m/z): [M+H]⁺ 177.1
¹H-NMR (300 MHz, CDCl₃) δ 8.59 (d, J=0.6 Hz, 1H), 8.31 (s, 1H), 8.12 (d, J=8.4 Hz, 1H), 7.54 (d, J=8.7 Hz, 1H), 3.98 (s, 3H)

Step 3. 1H-Indazole-5-carboxylic acid

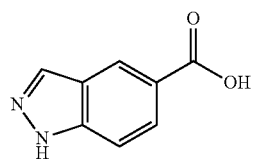 [SMILES: O=C(O)c1ccc2[nH]ncc2c1]

A solution of methyl 1H-indazole-5-carboxylate (6.2 g, 35.19 mmol) and NaOH (5.6 g, 140.01 mmol) in methanol (100 mL) and water (10 mL) was stirred 14 hours at 60° C., the resulting mixture was concentrated in vacuo to provide a residue, which was dissolved in water (80 mL) and adjusted to pH 6 with HCl (3N). The solids were collected by filtration to afford 1H-indazole-5-carboxylic acid (5.3 g, 93%) as a yellow solid.

LC/MS (ES, m/z): [M+H]⁺ 163.2

¹H-NMR (300 MHz, DMSO) δ 13.33 (s, 1H), 12.73-12.88 (m, 1H), 8.46 (d, J=0.6 Hz, 1H), 8.25 (s, 1H), 7.90-7.94 (m, 1H), 7.59 (d, J=8.7 Hz, 1H)

Step 4. 1-Acetyl-1H-indazole-5-carboxylic acid

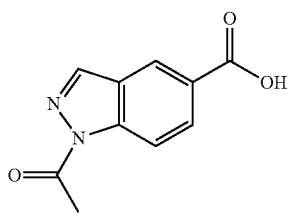

A solution of 1H-indazole-5-carboxylic acid (1.47 g, 9.07 mmol) and acetic anhydride (2.78 g, 27.23 mmol) in acetic acid (60 mL) was stirred 2.5 hours at 80° C. The resulting solution was concentrated in vacuo, precipitated from petroleum ether (50 mL) and filtered to afford 1-acetyl-1H-indazole-5-carboxylic acid as a yellow solid (1.53 g, 83%).
LC/MS (ES, m/z): [M+H]⁺ 205.3
¹H-NMR (300 MHz, DMSO) δ 8.45 (s, 1H), 8.30 (s, 1H), 8.16 (s, 2H), 2.72-2.74 (t, J=3.0 Hz, 3H)

Step 5. 5-(1-Acetyl-1H-indazole-5-carbonyl)-2,2-dimethyl-1,3-dioxane-4,6-dione

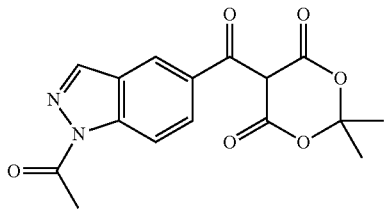 [SMILES: CC(=O)n1ncc2cc(C(=O)C3C(=O)OC(C)(C)OC3=O)ccc21]

A solution of 1-acetyl-1H-indazole-5-carboxylic acid (1.5 g, 7.35 mmol), 2,2-dimethyl-1,3-dioxane-4,6-dione (1.27 g, 8.81 mmol,), EDC HCl (2.12 g, 11.06 mmol) and 4-dimethylaminopyridine (1.34 g, 10.97 mmol) in dichloromethane (100 mL) was stirred overnight at room temperature. The resulting solution was washed with 10% aqueous acetic acid (100 mL) and NaCl solution (50 mL), dried over anhydrous sodium sulfate, and concentrated in vacuo to afford a crude 5-(1-acetyl-1H-indazole-5-carbonyl)-2,2-dimethyl-1,3-dioxane-4,6-dione as a solid (1.53 g, crude).

Step 6. Methyl 3-(1-acetyl-1H-indazol-5-yl)-3-oxopropanoate

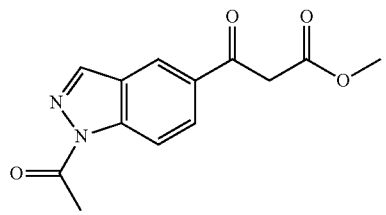 [SMILES: COC(=O)CC(=O)c1ccc2c(cnn2C(C)=O)c1]

The solution of 5-(1-acetyl-1H-indazole-5-carbonyl)-1,3-dioxane-4,6-dione (1.53 g, crude) in ethanol (30 mL) was stirred for 3 hours at 90° C. The resulting mixture was concentrated in vacuo to provide a residue which was purified by silica gel column chromatography with ethyl acetate:petroleum ether:dichloromethane (0.1:1:1) to afford methyl 3-(1-acetyl-1H-indazol-5-yl)-3-oxopropanoate as a yellow solid (1.33 g).
LC/MS (ES, m/z): [M+H]⁺ 261.1
¹H-NMR (300 MHz, CDCl₃) δ 8.53 (d, J=8.7 Hz, 1H), 8.41 (d, J=0.9 Hz, 1H), 8.27 (d, J=0.6 Hz, 1H), 8.17-8.20 (m, 1H), 4.21-4.35 (m, 2H), 4.09 (s, 2H), 2.84 (s, 3H), 1.26-1.31 (t, J=7.4 Hz, 3H)

Intermediate 48

Ethyl 3-(1-methyl-1H-benzo[d][1,2,3]triazol-5-yl)-3-oxopropanoate

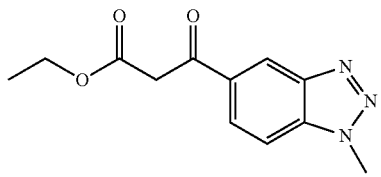 [SMILES: CCOC(=O)CC(=O)c1ccc2c(c1)nnn2C]

Step 1. 4-(Methylamino)-3-nitrobenzoic acid

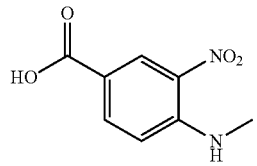

A solution of 4-fluoro-3-nitrobenzoic acid (1.85 g, 9.99 mmol) and methylamine (5 ml, 33% aq) in DMF (10 ml) was stirred for 1 hour at room temperature, and then diluted with water (20 ml). The solids precipitated and were collected by filtration, and the filter cake was washed with ether (20 ml) to afford 4-(methylamino)-3-nitrobenzoic acid as a yellow solid (1.7 g, 87%).
LC/MS (ES, m/z): [M+H]⁺. 197.1
¹H-NMR (300 MHz, DMSO) δ 12.84 (s, 1H), 8.61 (s, 1H), 8.54 (d, J=4.8 Hz, 1H), 7.97-8.00 (m, 1H), 7.04 (d, J=9.3 Hz, 1H), 3.00 (s, 3H)

Step 2. 3-Amino-4-(methylamino)benzoic acid

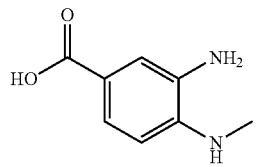

A mixture of 4-(methylamino)-3-nitrobenzoic acid (9.8 g, 49.96 mmol) and palladium on carbon (1 g) in methanol (200 ml) under an atmosphere of H₂(g) was stirred for 2 hours at room temperature and the solids were filtered out. The filtrate was concentrated in vacuo to afford 3-amino-4-(methylamino)benzoic acid as a white solid (8.2 g, 99%).

LC/MS (ES, m/z): [M+H]⁺. 167.1

¹H-NMR (300 MHz, DMSO) δ 7.47-7.51 (m, 1H), 7.37 (d, J=2.1 Hz, 1H), 6.53 (d, J=8.4 Hz, 1H), 2.90 (s, 3H)

Step 3. 1-Methyl-1H-benzo[d][1,2,3]triazole-5-carboxylic acid

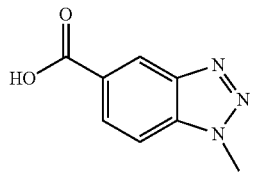

To a solution of 3-amino-4-(methylamino)benzoic acid (8 g, 48.1 mmol) in 5% AcOH (300 ml) was added a solution of sodium nitrite (3.9 g, 56.93 mmol) in water, dropwise with stirring at 0° C. The resulting solution was stirred for 24 hours at 0° C. The solids were collected by filtration to afford 1-methyl-1H-benzo[d][1,2,3]triazole-5-carboxylic acid as a white solid (6.7 g, 79%).

LC/MS (ES, m/z): [M+H]⁺. 178.1

¹H-NMR (300 MHz, DMSO) δ 13.16 (s, 1H), 8.60 (s, 1H), 8.09-8.12 (m, 1H), 7.93 (d, J=8.7 Hz, 1H), 4.35 (s, 3H)

Step 4. 2,2-Dimethyl-5-(1-methyl-1H-1,2,3-benzotriazole-5-carbonyl)-1,3-dioxane-4,6-dione

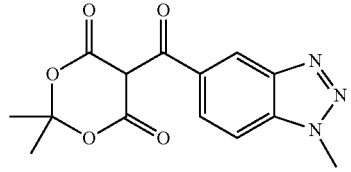 [SMILES: Cn1nnc2cc(C(=O)C3C(=O)OC(C)(C)OC3=O)ccc21]

A solution of 1-methyl-1H-benzo[d][1,2,3]triazole-5-carboxylic acid (1 g, 5.64 mmol), EDC HCl (1.61 g, 10.37 mmol), 4-dimethylaminopyridine (1.44 g, 11.79 mmol), and 2,2-dimethyl-1,3-dioxane-4,6-dione (970 mg, 6.73 mmol) in dichloromethane (30 ml) was stirred for 24 hours at room temperature. The resulting solution was washed with HCl (3N), dried over anhydrous magnesium sulfate, and concentrated in vacuo to afford 2,2-dimethyl-5-(1-methyl-1H-1,2,3-benzotriazole-5-carbonyl)-1,3-dioxane-4,6-dione as a white solid (1.4 g, crude).

Step 5. Ethyl 3-(1-methyl-1H-benzo[d][1,2,3]triazol-5-yl)-3-oxopropanoate

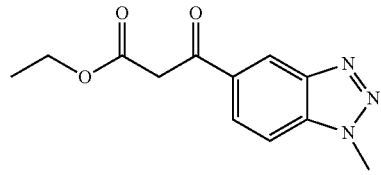 [SMILES: CCOC(=O)CC(=O)c1ccc2c(c1)nnn2C]

A solution of 2,2-dimethyl-5-(1-methyl-1H-1,2,3-benzotriazole-5-carbonyl)-1,3-dioxane-4,6-dione (1.4 g, crude) in ethanol (20 ml) was stirred for 4 hours at reflux, and then concentrated in vacuo to provide a residue, which was purified via silica gel column chromatography with 50% dichloromethane in petroleum ether to afford ethyl 3-(1-methyl-1H-benzo[d][1,2,3]triazol-5-yl)-3-oxopropanoate as a red solid (0.9 g).

LC/MS (ES, m/z): [M+H]⁺. 248.1

¹H-NMR (300 MHz, CDCl₃) δ 8.66 (d, J=0.6 Hz, 1H), 8.06-8.20 (m, 1H), 7.62 (d, J=0.6 Hz, 1H), 4.35 (s, 3H), 4.20-4.31 (m, 2H), 4.11 (s, 2H), 1.30-1.36 (m, 3H)

Intermediate 49

Ethyl 3-(1-acetyl-3-methyl-1H-indazol-5-yl)-3-oxopropanoate

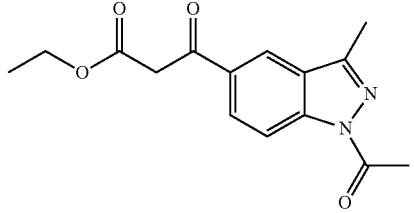 [SMILES: CCOC(=O)CC(=O)c1ccc2c(c1)c(C)nn2C(C)=O]

Step 1. Methyl 3-methyl-1H-indazole-5-carboxylate

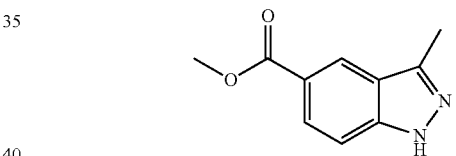

A mixture of 5-bromo-3-methyl-1H-indazole (11.0 g, 52.12 mmol), Pd(dppf)Cl₂ (1.9 g, 2.60 mmol) and TEA (10.53 g, 104.06 mmol) in methanol (40 ml) was stirred for 24 hours at 100° C. under an atmosphere of CO (g). The resulting mixture was concentrated in vacuo to provide a residue, which was purified by a silica gel column chromatography with 3% ethyl acetate in petroleum ether to afford methyl 3-methyl-1H-indazole-5-carboxylate as a gray solid (5.0 g, 50%).

LC/MS (ES, m/z): [M+H]⁺ 191.0

¹H-NMR (300 MHz, DMSO) δ 12.99 (s, 1H), 8.41 (s, 1H), 7.89-7.93 (m, 1H), 7.52-7.55 (m, 1H), 4.08 (s, 3H), 2.55 (s, 3H)

Step 2. 3-Methyl-1H-indazole-5-carboxylic acid

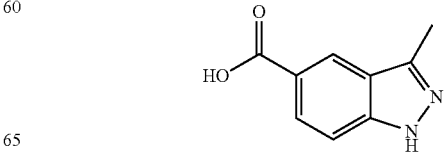

A solution of methyl 3-methyl-1H-indazole-5-carboxylate (5.0 g, 26.29 mmol) and sodium hydroxide (4.2 g, 105.00 mmol) in methanol (30 ml) and water (2 ml) was stirred for 2 hours at 65° C. The reaction mixture was concentrated in vacuo, dissolved in water (30 ml), adjusted to pH 5 with HCl (3N) to provide a precipitate, which was collected by filtration to afford 3-methyl-1H-indazole-5-carboxylic acid as a white solid (4.40 g, 95%).

$^1$H-NMR (300 MHz, DMSO) δ 12.93 (s, 1H), 12.68 (s, 1H), 8.37-8.38 (t, J=0.6 Hz, 1H), 7.88-7.92 (m, 1H), 7.49-7.53 (m, 1H), 2.55 (s, 3H)

Step 3. 1-Acetyl-3-methyl-1H-indazole-5-carboxylic acid

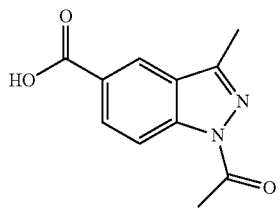 [SMILES: CC(=O)n1nc(C)c2cc(C(=O)O)ccc21]

A solution of 3-methyl-1H-indazole-5-carboxylic acid (4.4 g, 24.98 mmol) and acetic anhydride (3.83 g, 37.55 mmol) in AcOH (80 ml) was stirred for 3 hours at 85° C. The reaction mixture was concentrated in vacuo to afford 1-acetyl-3-methyl-1H-indazole-5-carboxylic acid as a gray solid (4.8 g, 88%).

$^1$H-NMR (300 MHz, DMSO) δ 8.46 (d, J=0.6 Hz, 1H), 8.46 (d, J=8.7 Hz, 1H), 8.17-8.20 (m, 1H), 2.70 (s, 3H), 2.62 (s, 3H)

Step 4. 5-(1-Acetyl-3-methyl-1H-indazole-5-carbonyl)-2,2-dimethyl-1,3-dioxane-4,6-dione

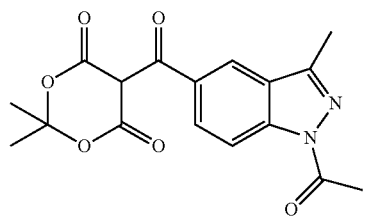 [SMILES: CC(=O)n1nc(C)c2cc(C(=O)C3C(=O)OC(C)(C)OC3=O)ccc21]

A mixture of 1-acetyl-3-methyl-1H-indazole-5-carboxylic acid (1.2 g, 5.50 mmol), 2,2-dimethyl-1,3-dioxane-4,6-dione (950 mg, 6.59 mmol), 4-dimethylaminopyridine (1.01 g, 8.27 mmol) and EDC HCl (1.58 g, 8.24 mmol) in dichloromethane (80 mL) was stirred overnight at room temperature. The reaction mixture was washed with HCl (3N) (30 mL×3), and the organic layers were dried over anhydrous magnesium sulfate and concentrated in vacuo to afford 5-(1-acetyl-3-methyl-1H-indazole-5carbonyl)-2,2-dimethyl-1,3-dioxane-4,6-dione as a yellow crude solid (1.30 g, crude).

Step 5. Ethyl 3-(1-acetyl-3-methyl-1H-indazol-5-yl)-3-oxopropanoate

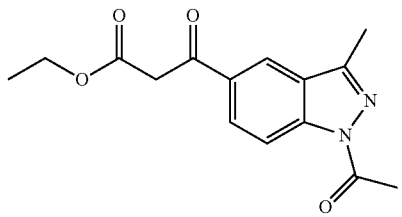 [SMILES: CCOC(=O)CC(=O)c1ccc2c(c1)c(C)nn2C(C)=O]

A solution of 5-(1-acetyl-3-methyl-1H-indazole-5-carbonyl)-2,2-dimethyl-1,3-dioxane-4,6-dione (1.30 g, 3.78 mmol) in ethanol (30 ml) was stirred for 3 hours at 85° C. The reaction mixture was concentrated in vacuo and purified by silica gel column chromatography with 6% ethyl acetate in petroleum ether to afford ethyl 3-(1-acetyl-3-methyl-1H-indazol-5-yl)-3-oxopropanoate as light yellow oil (1.20 g).

$^1$H-NMR (300 MHz, CDCl$_3$) δ 8.48-8.51 (m, 1H), 8.32-8.33 (m, 1H), 8.13-8.16 (m, 1H), 4.26-4.33 (m, 2H), 4.09 (s, 2H), 2.79 (s, 3H), 2.65 (s, 3H), 1.26-1.31 (m, 3H)

Intermediate 50

Ethyl 3-(1H-benzo[d][1,2,3]triazol-5-yl)-3-oxopropanoate

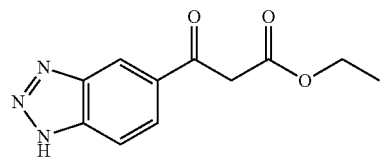 [SMILES: CCOC(=O)CC(=O)c1ccc2[nH]nnc2c1]

Step 1. 1H-Benzo[d][1,2,3]triazole-5-carboxylic acid

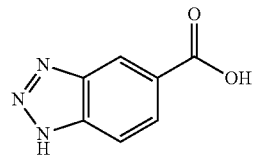 [SMILES: O=C(O)c1ccc2[nH]nnc2c1]

To a solution of 3,4-diaminobenzoic acid (10 g, 65.72 mmol) in AcOH (aq) (150 ml) was added sodium nitrite (5 g, 72.47 mmol) with stirring, and the reaction mixture was stirred overnight at 0-5° C. in an ice/salt bath. The solids were collected by filtration to afford 1H-benzo[d][1,2,3]triazole-5-carboxylic acid as a solid (9.8 g, 91%).

LC/MS (ES, m/z):[M+H]$^+$ 153.1

$^1$H-NMR (300 MHz, DMSO) δ 8.53 (s, 1H), 8.01-8.04 (m, 1H), 7.93 (d, J=8.4 Hz, 1H)

Step 2. 5-(1H-benzo[d][1,2,3]triazole-5-carbonyl)-2,2-dimethyl-1,3-dioxane-4,6-dione

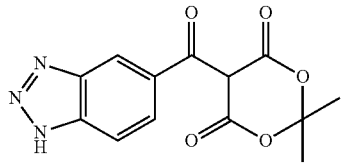 [SMILES: CC1(C)OC(=O)C(C(=O)c2ccc3[nH]nnc3c2)C(=O)O1]

A solution of 1H-benzo[d][1,2,3]triazole-5-carboxylic acid (5 g, 30.65 mmol), 4-dimethylaminopyridine (5.6 g, 45.84 mmol), EDC HCl (8.8 g, 45.9 mmol), and 2,2-dimethyl-1,3-dioxane-4,6-dione (5.3 g, 36.77 mmol) in dichloromethane (100 ml) was stirred for 36 hours at room temperature. The resulting mixture was washed with of HCl (150 ml, 1N), extracted with dichloromethane (5×30 ml), dried over anhydrous magnesium sulfate, and concentrated in vacuo to provide 5-(1H-benzo[d][1,2,3]triazole-5-carbonyl)-2,2-dimethyl-1,3-dioxane-4,6-dione as a solid (8 g, crude).

Step 3. Ethyl 3-(1H-benzo[d][1,2,3]triazol-5-yl)-3-oxopropanoate

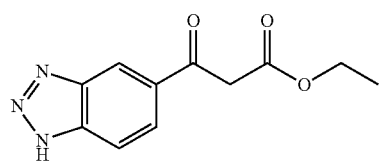 [SMILES: CCOC(=O)CC(=O)c1ccc2[nH]nnc2c1]

A solution of 5-(1H-benzo[d][1,2,3]triazole-5-carbonyl)-2,2-dimethyl-1,3-dioxane-4,6-dione (3.2 g, crude) in ethanol (80 ml) was stirred overnight at 80° C. The resulting mixture was concentrated in vacuo to provide a residue which was purified via silica gel column chromatography with 5% ethyl acetate in petroleum ether to afford ethyl 3-(1H-benzo[d][1,2,3]triazol-5-yl)-3-oxopropanoate as a solid (500 mg).
LC/MS (ES, m/z):[M+H]⁺ 234.1

Intermediate 51

4-Benzyl-3-methyl-1H-pyrazol-5-amine

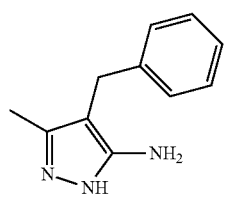

Step 1. (Z)-3-Aminobut-2-enenitrile

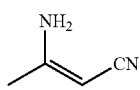

Acetonitrile (100 g, 2.43 mol) was added dropwise to a solution of sodium (30.8 g, 1.34 mol) in toluene (200 mL) cooled below 30° C. The resulting solution was stirred for 3 hours at 80° C. and then the solids were collected by filtration. The filter cake was washed with ether (100 mL), diluted with water (300 mL), and extracted with ethyl acetate (2×200 mL). The organic layers were dried over anhydrous magnesium sulfate and concentrated in vacuo to afford (Z)-3-aminobut-2-enenitrile as a red oil (35 g, 17%).

Step 2. 3-Oxobutanenitrile

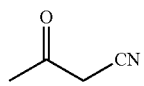

A solution of (Z)-3-aminobut-2-enenitrile (35 g, 0.43 mol) in HCl (100 mL, 6N) was stirred for 3 hours at 80° C. and then extracted with dichloromethane (6×60 mL). The organic layers were combined, dried over anhydrous magnesium and concentrated in vacuo to provide 3-oxobutanenitrile as a colorless oil (17 g, 48%).
¹H-NMR (300 MHz, CDCl₃): δ 3.48 (d, J=4.8 Hz, 2H), 2.38 (s, 3H)

Step 3. 2-Benzyl-3-oxobutanenitrile

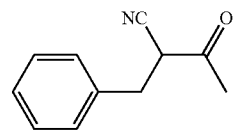

To a solution of Na (1.17 g, 50.87 mmol) in EtOH (20 mL) was added 3-oxobutanenitrile (2.5 g, 30.09 mmol) and (bromomethyl)benzene (5 g, 29.23 mmol), and the reaction mixture was stirred for 2 hours at 80° C. The resulting mixture was concentrated in vacuo, diluted with water (200 mL), adjusted to pH 6 with HCl (3N), extracted with ethyl acetate (3×100 mL), dried over anhydrous magnesium and concentrated in vacuo to provide a residue, which was purified via silica gel column chromatography with 1.25% to 5% ethyl acetate in petroleum ether to afford 2-benzyl-3-oxobutanenitrile as a brown solid (2 g, 39%).
LC/MS (ES, m/z):[M+H]⁺ 174.1

Step 4. 4-Benzyl-3-methyl-1H-pyrazol-5-amine

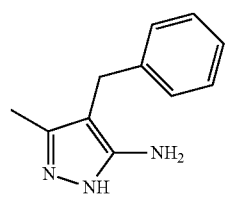

A solution of 2-benzyl-3-oxobutanenitrile (2 g, 11.55 mmol), N₂H₄Br (1.96 g, 17.35 mmol), and triethylamine (1 g, 9.88 mmol) in EtOH (50 mL) was stirred for 3 hours at 85° C. The resulting solution was concentrated in vacuo, diluted with water (200 mL), and extracted with ethyl acetate (3×80 mL). The organic layers were dried over anhydrous magnesium sulfate and concentrated in vacuo to afford 4-benzyl-3-methyl-1H-pyrazol-5-amine as yellow oil (878 mg, 41%).

LC/MS (ES, m/z):[M+H]⁺ 188.1

¹H-NMR (300 MHz, CDCl₃): δ 7.27-7.40 (m, 5H), 3.22-3.28 (m, 1H), 3.08-3.15 (m, 1H), 2.36 (s, 3H)

Intermediate 52

Ethyl 3-(1-methyl-1H-indazol-5-yl)-3-oxopropanoate

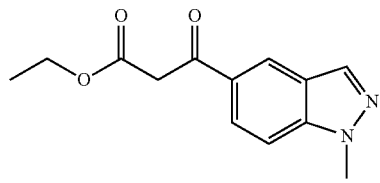 [SMILES: CCOC(=O)CC(=O)c1ccc2c(cnn2C)c1]

Step 1. Methyl 1-methyl-1H-indazole-5-carboxylate

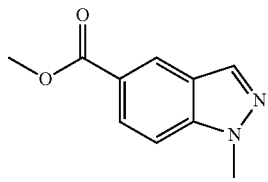

A solution of 5-bromo-1-methyl-1H-indazole (4 g, 18.95 mmol), Pd(dppf)Cl₂ (700 mg, 0.96 mmol), and TEA (3.8 g, 37.55 mmol) in methanol (40 ml) was stirred for 24 hours at 100° C. under an atmosphere of CO(g). The resulting mixture was concentrated in vacuo and purified by silica gel column chromatography with 3% ethyl acetate in petroleum ether to afford methyl 1-methyl-1H-indazole-5-carboxylate as a white solid (2.6 g, 72%).

LC/MS (ES, m/z): [M+H]⁺ 191.0

¹H NMR (300 MHz, CDCl₃) δ 8.54 (s, 1H), 8.07-8.11 (m, 2H), 7.41 (d, J=8.7 Hz, 1H), 4.33 (s, 3H), 3.97 (s, 3H)

Step 2. 1-Methyl-1H-indazole-5-carboxylic acid

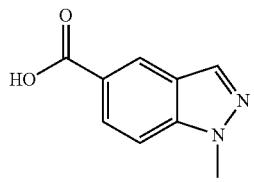

A solution of methyl 1-methyl-1H-indazole-5-carboxylate (2.6 g, 13.67 mmol) and sodium hydroxide (2.7 g, 67.50 mmol) in methanol (30 ml) was stirred for 2 hours at 65° C. and then concentrated in vacuo. The reaction was then quenched water (20 ml) and adjusted to pH 3 with HCl (3N). The solids were collected by filtration to afford 1-methyl-1H-indazole-5-carboxylic acid as a white solid (1.9 g, 79%).

LC/MS (ES, m/z): [M+H]⁺ 177.0

¹H-NMR (300 MHz, DMSO) δ 12.76 (s, 1H), 8.45 (s, 1H), 8.22 (s, 1H), 7.72-7.97 (m, 1H), 7.70 (d, J=6 Hz, 1H), 4.08 (s, 3H)

Step 3. 2,2-Dimethyl-5-(1-methyl-1H-indazole-5-carbonyl)-1,3-dioxane-4,6-dione

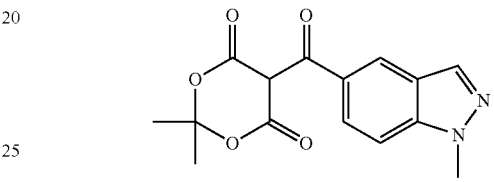

A solution of 1-methyl-1H-indazole-5-carboxylic acid (1.9 g, 10.78 mmol), 2,2-dimethyl-1,3-dioxane-4,6-dione (1.865 g, 12.94 mmol), 4-dimethylaminopyridine (1.98 g, 16.21 mmol), and EDC HCl (3.1 g, 16.17 mmol) in dichloromethane (30 mL) was stirred overnight at room temperature, then quenched with water (30 ml). The resulting mixture was washed with HCl (3M, 30 mL) and saturated sodium chloride (30 mL). The organic layers were dried over anhydrous magnesium sulfate and concentrated in vacuo to afford 2,2-dimethyl-5-(1-methyl-1H-indazole-5-carbonyl)-1,3-dioxane-4,6-dione as a yellow crude solid (2.3 g, crude).

Step 4. Ethyl 3-(1-methyl-1H-indazol-5-yl)-3-oxopropanoate

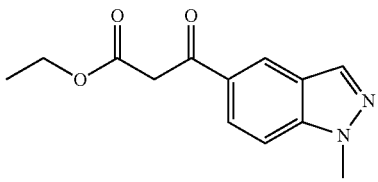 [SMILES: CCOC(=O)CC(=O)c1ccc2c(cnn2C)c1]

A solution of 2,2-dimethyl-5-(1-methyl-1H-indazol-5-carbonyl)-1,3-dioxane-4,6-dione (2.3 g, crude) in ethanol (30 ml) was stirred for 2 hours at 80° C. The resulting mixture was concentrated in vacuo and purified by silica gel column chromatography with 6% ethyl acetate in petroleum ether to afford ethyl 3-(1-methyl-1H-indazol-5-yl)-3-oxopropanoate as light yellow oil (1.6 g).

LC/MS (ES, m/z): [M+H]⁺ 247.1

¹H-NMR (300 MHz, CDCl₃) δ 8.41 (s, 1H), 8.04-8.15 (m, 2H), 7.44-7.47 (m, 1H), 4.26-4.36 (m, 2H), 4.13-4.25 (m, 5H), 1.25-1.30 (m, 3H)

Intermediate 53

Methyl 3-(4-methoxybenzo[d][1,3]dioxol-5-yl)-3-oxopropanoate

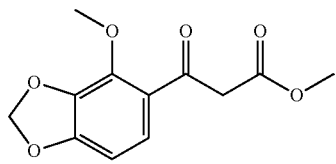 [SMILES: COC(=O)CC(=O)c1ccc2c(c1OC)OCO2]

Step 1. 1-(2,3,4-Trihydroxyphenyl)ethanone

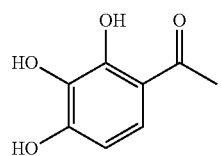

To a solution of benzene-1,2,3-triol (30 g, 237.89 mmol) in $BF_3Et_2O$ (240 ml) was added AcOH (30 g, 499.58 mmol), and the resulting mixture was stirred for 18 hours at 45° C. The solids were collected by filtration, diluted with water (20 ml), and the pH was adjusted to 7 with sodium bicarbonate solution. The solids were collected by filtration and washed with water (3×10 ml) and dried in an oven under reduced pressure to afford 1-(2,3,4-trihydroxyphenyl)ethanone as a red solid (17 g, 43%).

LC/MS (ES, m/z): $[M+H]^+$ 169.0

$^1$H-NMR (300 MHz, DMSO): δ 7.29 (d, J=8.7 Hz, 1H), 6.38 (d, J=8.7 Hz, 1H), 2.52 (s, 3H)

Step 2. 1-(4-Hydroxybenzo[d][1,3]dioxol-5-yl)ethanone

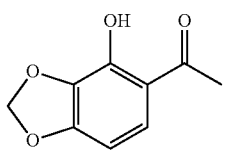

A solution of 1-(2,3,4-trihydroxyphenyl)ethanone (15 g, 89.21 mmol), bromo(chloro)methane (10.2 g, 78.84 mmol) and potassium carbonate (11 g, 79.59 mmol) in DMF (140 ml) was stirred for 3 hours at 150° C. The reaction was monitored by TLC (PE:EA=5:1) and then quenched with water (700 ml), extracted with ethyl acetate (4×100 ml) and the organic layers combined, dried over anhydrous sodium sulfate and concentrated in vacuo to give the residue, which was purified by silica gel column chromatography with 5% ethyl acetate in petroleum ether to afford 1-(4-hydroxybenzo[d][1,3]dioxol-5-yl)ethanone as a light yellow solid (5.7 g, 35%).

LC/MS (ES, m/z): $[M+H]^+$ 181.0

$^1$H-NMR (300 MHz, DMSO): δ 12.22 (s, 1H), 7.59 (d, J=8.7 Hz, 1H), 6.64 (d, J=8.7 Hz, 1H), 6.14 (s, 2H), 2.59 (s, 3H)

Step 3. 1-(4-Methoxybenzo[d][1,3]dioxol-5-yl)ethanone

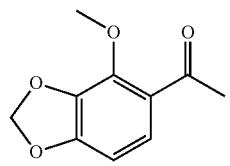

A solution of 1-(4-hydroxy-2H-1,3-benzodioxol-5-yl)ethan-1-one (7.7 g, 42.74 mmol), $CH_3I$ (12 g, 84.54 mmol) and potassium carbonate (7 g, 50.65 mmol) in acetone (40 ml) was stirred for 48 hours at 70° C. The reaction was then quenched by the addition of water (300 ml), extracted with ethyl acetate (4×80 ml), and the organic layers were combined, dried over anhydrous sodium sulfate and concentrated in vacuo to afford 1-(4-methoxybenzo[d][1,3]dioxol-5-yl)ethanone as a yellow crude solid (7.4 g, 89%).

LC/MS (ES, m/z): [M+H]+ 195.0

$^1$H-NMR (300 MHz, DMSO): δ 7.23 (d, J=8.4 Hz, 1H), 6.72 (d, J=8.1 Hz, 1H), 6.12 (s, 2H), 4.00 (s, 3H), 2.59 (s, 3H)

Step 4. Methyl 3-(4-methoxybenzo[d][1,3]dioxol-5-yl)-3-oxopropanoate

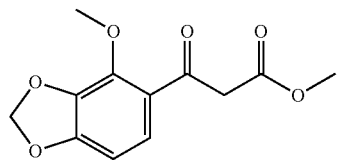 [SMILES: COC(=O)CC(=O)c1ccc2c(c1OC)OCO2]

To a solution of sodium hydride (6.1 g, 254.17 mmol) in dimethyl carbonate (25 ml) was added a solution of 1-(4-methoxybenzo[d][1,3]dioxol-5-yl)ethanone (7.4 g, 38.11 mmol) in dimethyl carbonate (25 ml) dropwise with stirring at 90° C. The resulting solution was stirred for 1 hour under reflux. The reaction was monitored by TLC (PE/EA=8/1). The reaction was then quenched by the addition of water/ice (500 ml). The pH was adjusted to 7 with HCl (3N), then the reaction mixture was extracted with ethyl acetate (5×100 ml), and the organic layers combined and dried over anhydrous sodium sulfate and concentrated in vacuo to give a residue, which was purified by silica gel column chromatography with ethyl acetate/petroleum ether/dichloromethane (1:100:10) to afford methyl 3-(4-methoxybenzo[d][1,3]dioxol-5-yl)-3-oxopropanoate as a light yellow solid (7.9 g, 82%).

LC/MS (ES, m/z): $[M+H]^+$ 253.0

$^1$H-NMR (300 MHz, DMSO): δ 7.36 (d, J=8.4 Hz, 1H), 6.74 (d, J=8.4 Hz, 1H), 6.14 (d, J=9.0 Hz, 2H), 3.96 (s, 3H), 3.91 (s, 2H), 3.64 (s, 3H)

Intermediate 54

Ethyl 3-(4-methylbenzo[d][1,3]dioxol-5-yl)-3-oxopropanoate

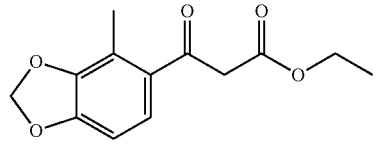 [SMILES: CCOC(=O)CC(=O)c1ccc2c(c1C)OCO2]

Step 1. 4-Methylbenzo[d][1,3]dioxole-5-carboxylic acid

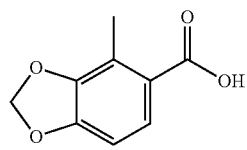

To a solution of benzo[d][1,3]dioxole-5-carboxylic acid (3.0 g, 18.06 mmol) in THF (35 ml) was added n-BuLi (16 ml, 2.5N) dropwise at or below −78° C. under an atmosphere of nitrogen. When the addition was complete the cooling bath was removed, and the reaction was allowed to warm to −20° C. The reaction was returned to the bath and cooled to −75° C. at which time CH$_3$I (5.1 g, 35.93 mmol) was added dropwise. The resulting solution was stirred for 45 min at 0° C. and then quenched with water (200 ml), adjusted to pH 4 with HCl (2N), extracted with ethyl acetate (3×100 ml), and the organic layers were combined and dried over anhydrous magnesium sulfate. The solids were collected by filtration to afford 4-methylbenzo[d][1,3]dioxole-5-carboxylic acid as a light yellow solid (2.9 g, 89%).

LC/MS (ES, m/z): [M+H]$^+$ 181.0

$^1$H-NMR (300 MHz, DMSO): δ 12.57 (s, 1H), 7.49 (d, J=8.4 Hz, 1H), 6.81 (d, J=8.4 Hz, 1H), 6.09 (s, 2H), 2.38 (s, 3H)

Step 2. 2,2-Dimethyl-5-(4-methylbenzo[d][1,3]dioxole-5-carbonyl)-1,3-dioxane-4,6-dione

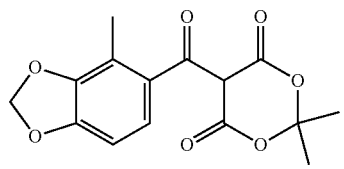 [SMILES: Cc1c(C(=O)C2C(=O)OC(C)(C)OC2=O)ccc2c1OCO2]

A solution of 4-methylbenzo[d][1,3]dioxole-5-carboxylic acid (2.9 g, 16.10 mmol), 2,2-dimethyl-1,3-dioxane-4,6-dione (2.78 g, 19.29 mmol), 4-dimethylaminopyridine (2.95 g, 24.15 mmol) and EDC HCl (6.19 g, 32.20 mmol) in dichloromethane (100 ml) was stirred overnight at room temperature. The reaction mixture was then washed with HCl (aq) (2×60 ml) and NaCl solution (100 ml). The aqueous layers were extracted with dichloromethane (3×60 ml), and the organic layers combined and dried over anhydrous magnesium sulfate, and concentrated in vacuo to afford 2,2-dimethyl-5-(4-methylbenzo[d][1,3]dioxole-5-carbonyl)-1,3-dioxane-4,6-dione as a red brown solid (3.1 g, crude), which was used to the next step directly.

Step 3. Ethyl 3-(4-methylbenzo[d][1,3]dioxol-5-yl)-3-oxopropanoate

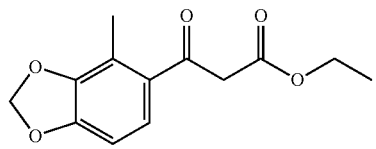 [SMILES: CCOC(=O)CC(=O)c1ccc2c(c1C)OCO2]

A solution of 2,2-dimethyl-5-(4-methylbenzo[d][1,3]dioxole-5-carbonyl)-1,3-dioxane-4,6-dione (3.1 g, crude) in ethanol (70 ml) was stirred for 3 hours at reflux and then concentrated in vacuo to give the residue, which was purified by silica gel column chromatography eluting with 1% ethyl acetate in petroleum ether to afford ethyl 3-(4-methylbenzo[d][1,3]dioxol-5-yl)-3-oxopropanoate as a white solid (1.3 g).

LC/MS (ES, m/z): [M+H]$^+$ 251.0

$^1$H-NMR (300 MHz, CDCl$_3$): δ 7.35 (d, J=8.1 Hz, 1H), 6.68-6.74 (m, 1H), 6.05 (s, 2H), 4.18-4.28 (m, 2H), 3.93 (s, 3H), 2.46 (s, 3H), 1.25-1.30 (t, J=7.2 Hz, 3H)

Intermediate 55

5-Amino-3-hydroxy-N-propyl-1H-pyrazole-4-carboxamide

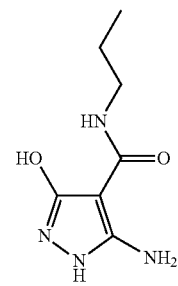

Step 1. Ethyl 2-cyano-3-oxo-3-(propylamino)propanoate

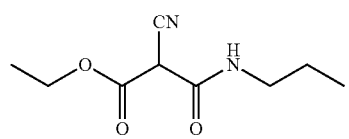

A solution of ethyl 2-cyanoacetate (3 g, 26.52 mmol), 1-isocyanatopropane (2.3 g, 27.03 mmol), and triethylamine (5.4 g, 53.36 mmol) in DMF (8 ml) was stirred for 1.5 days at room temperature. The resulting mixture was diluted with water (250 ml), extracted with dichloromethane (8×50 ml), and concentrated in vacuo to afford ethyl 2-cyano-3-oxo-3-(propylamino)propanoate as yellow crude oil (4.9 g, crude).

Step 2. 5-Amino-3-hydroxy-N-propyl-1H-pyrazole-4-carboxamide

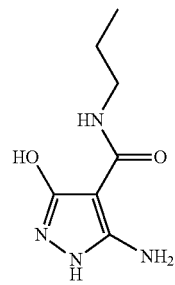

A solution of ethyl 2-cyano-3-oxo-3-(propylamino)propanoate (4.9 g, crude) and $N_2H_4H_2O$ (10 ml, 80%) in ethanol (30 ml) was stirred for 3 days at reflux. The resulting mixture was concentrated in vacuo to get a residue, which was purified by silica gel column chromatography with 5% to 10% methanol in dichloromethane to afford 5-amino-3-hydroxy-N-propyl-1H-pyrazole-4-carboxamide as an off-white solid (2 g, 41% 2 steps).

LC/MS (ES, m/z): [M+H]$^+$ 185.1

$^1$H-NMR (300 MHz, DMSO) δ 9.57 (s, 1H), 4.08 (s, 2H), 3.10-3.17 (m, 2H), 1.37-1.49 (m, 2H), 0.83-0.88 (m, 3H)

Intermediate 56

Ethyl 3-(2,3-dihydrobenzo[b][1,4]dioxin-6-yl)-3-oxopropanoate

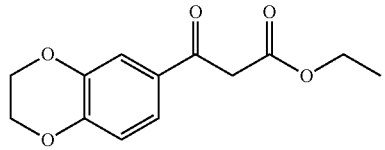 [SMILES: CCOC(=O)CC(=O)c1ccc2c(c1)OCCO2]

Step 1. 5-(2,3-Dihydrobenzo[b][1,4]dioxine-6-carbonyl)-2,2-dimethyl-1,3-dioxane-4,6-dione

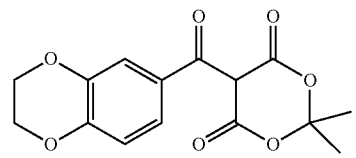 [SMILES: CC1(C)OC(=O)C(C(=O)c2ccc3c(c2)OCCO3)C(=O)O1]

A solution of 2,3-dihydrobenzo[b][1,4]dioxine-6-carboxylic acid (5 g, 27.8 mmol), 2,2-dimethyl-1,3-dioxane-4,6-dione (4.41 g, 30.6 mmol), 4-dimethylaminopyridine (5.1 g, 41.7 mmol) and EDC HCl (8.0 g, 41.7 mmol) in dichloromethane (125 mL) was stirred overnight at room temperature, and then quenched by the addition of HCl (1 N, 100 mL) and NaCl solution (100 mL). The organic layers were dried over sodium sulfate and concentrated in vacuo to afford 5-(2,3-dihydrobenzo[b][1,4]dioxine-6-carbonyl)-2,2-dimethyl-1,3-dioxane-4,6-dione as a yellow solid (8 g, crude). It was used for next step without further purification.

Step 2. Ethyl 3-(2,3-dihydrobenzo[b][1,4]dioxin-6-yl)-3-oxopropanoate

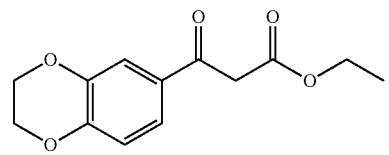 [SMILES: CCOC(=O)CC(=O)c1ccc2c(c1)OCCO2]

A solution of 5-(2,3-dihydrobenzo[b][1,4]dioxine-6-carbonyl)-2,2-dimethyl-1,3-dioxane-4,6-dione (8 g, crude) in ethanol (150 mL) was stirred overnight at reflux. The resulting mixture was concentrated in vacuo to give a residue, which was purified by silica gel column chromatography with 5% ethyl acetate in petroleum ether to afford ethyl 3-(2,3-dihydrobenzo[b][1,4]dioxin-6-yl)-3-oxopropanoate as light-yellow solid (2.4 g, 35% 2 steps).

LC/MS (ES, m/z): [M+H]$^+$ 251.0

Intermediate 57

3,5-Diamino-N-propyl-1H-pyrazole-4-carboxamide

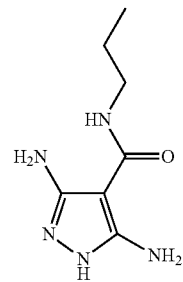

Step 1. Potassium 1,1-dicyano-2-oxo-2-(propylamino)ethan-1-ide

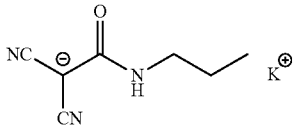

A solution of potassium hydroxide (3.6 g, 64 mmol) in water (15 mL) was added to a solution of malononitrile (3.9 g, 59 mmol) and 1-isocyanatopropane (5 g, 59 mmol) in THF (20 mL) over 10 mins at 25-30° C. (water cooling). After stirring for 3 hours at 25-30° C., the reaction was concentrated in vacuo to afford potassium 1,1-dicyano-2-oxo-2-(propylamino)ethan-1-ide as a light red solid (4 g, crude).

Step 2. 3,5-Diamino-N-propyl-1H-pyrazole-4-carboxamide

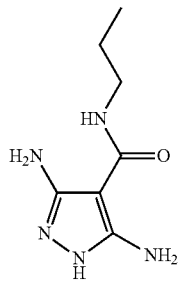

A solution of potassium 1,1-dicyano-2-oxo-2-(propylamino)ethan-1-ide (4 g, crude), NH$_2$NH$_2$ H$_2$O (10 mL) and concentrated HCl (2 mL) in water (10 mL) was heated under reflux overnight. Then the reaction was concentrated in vacuo to give a residue, which was purified by silica gel column chromatography with 10% dichloromethane in methanol to afford 3,5-diamino-N-propyl-1H-pyrazole-4-carboxamide as a light yellow solid (1.1 g, 10% 2 steps).

LC/MS (ES, m/z): [M+H]$^+$ 184.0

Intermediate 58

Ethyl 3-(1H-benzo[d][1,2,3]triazol-5-yl)-3-oxopropanoate

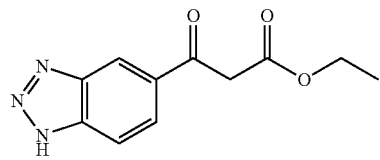 [SMILES: CCOC(=O)CC(=O)c1ccc2[nH]nnc2c1]

Step 1. 1H-Benzo[d][1,2,3]triazole-5-carboxylic acid

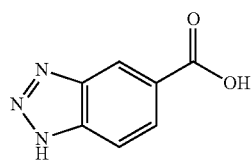 [SMILES: O=C(O)c1ccc2[nH]nnc2c1]

Sodium nitrite (10 g, 145 mmol) was added to a solution of 3,4-diaminobenzoic acid (20 g, 131.5 mmol) in AcOH (aq) (150 mL). The reaction was stirred overnight at 0-5° C. in an ice/salt bath. The solids were collected by filtration to afford 1H-benzo[d][1,2,3]triazole-5-carboxylic acid as a solid (12.6 g, 59%).

LC/MS (ES, m/z):[M+H]$^+$ 153.1

$^1$H-NMR (300 MHz, DMSO) δ 8.53 (s, 1H), 8.01-8.04 (m, 1H), 7.93 (d, J=8.4 Hz, 1H)

Step 2. 5-(1H-Benzo[d][1,2,3]triazole-5-carbonyl)-2,2-dimethyl-1,3-dioxane-4,6-dione

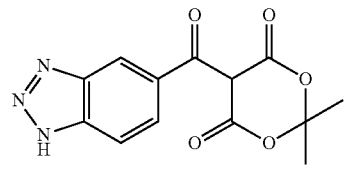 [SMILES: CC1(C)OC(=O)C(C(=O)c2ccc3[nH]nnc3c2)C(=O)O1]

A solution of 1H-benzo[d][1,2,3]triazole-5-carboxylic acid (12.6 g, 77.3 mmol), 4-dimethylaminopyridine (14.1 g, 115.6 mmol), EDC HCl (22.1 g, 115.6 mmol), and 2,2-dimethyl-1,3-dioxane-4,6-dione (13.3 g, 87.4 mmol) in dichloromethane (200 mL) was stirred for 36 hours at room temperature. The resulting mixture was washed with HCl (150 mL, 1N), extracted with dichloromethane (5×30 mL), and the organic layers were dried over anhydrous magnesium sulfate and concentrated in vacuo to afford 5-(1H-benzo[d][1,2,3]triazole-5-carbonyl)-2,2-dimethyl-1,3-dioxane-4,6-dione as a yellow solid (20 g, crude).

Step 3. Ethyl 3-(1H-benzo[d][1,2,3]triazol-5-yl)-3-oxopropanoate

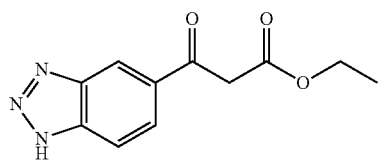 [SMILES: CCOC(=O)CC(=O)c1ccc2[nH]nnc2c1]

A solution of 5-(1H-benzo[d][1,2,3]triazole-5-carbonyl)-2,2-dimethyl-1,3-dioxane-4,6-dione (20 g, crude) in ethanol (150 ml) was stirred overnight at 80° C., and then concentrated in vacuo to give a residue, which was purified by silica gel column chromatography with 5% ethyl acetate in petroleum ether to afford ethyl 3-(1H-benzo[d][1,2,3]triazol-5-yl)-3-oxopropanoate as a solid (5.3 g).

LC/MS (ES, m/z):[M+H]$^+$ 234.1

Intermediate 59

5-Amino-4-(4-chlorophenyl)-1H-pyrazol-3-ol

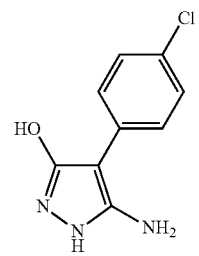 [SMILES: Nc1[nH]nc(O)c1-c1ccc(Cl)cc1]

Step 1. Methyl 2-(4-chlorophenyl)-2-cyanoacetate

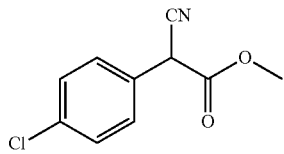

To a solution of 2-(4-chlorophenyl)acetonitrile (10 g, 66.22 mmol) in dimethyl carbonate (150 ml) was added sodium ethoxide (5.4 g, 79.5 mmol). After stirring overnight at reflux, the resulting solution was concentrated in vacuo and the residue was dissolved in water (50 ml), adjusted to pH 5 with HCl (3N), extracted with ethyl acetate (3×60 ml) and concentrated in vacuo to afford methyl 2-(4-chlorophenyl)-2-cyanoacetate as black oil (8 g, 57%).

Step 2. 5-Amino-4-(4-chlorophenyl)-1H-pyrazol-3-ol

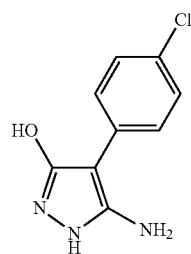 [SMILES: Nc1[nH]nc(O)c1-c1ccc(Cl)cc1]

To a solution of methyl 2-(4-chlorophenyl)-2-cyanoacetate (8 g, 38.28 mmol) in ethanol (60 ml) was added $N_2H_4H_2O$ (9.1 g, 181.96 mmol). After stirring overnight at reflux, the reaction mixture was cooled to room temperature and the solids were collected by filtration. The solids were washed with EtOH (30 ml) and dried to afford 5-amino-4-(4-chlorophenyl)-1H-pyrazol-3-ol as a white solid (4.8 g, 60%).

LC/MS (ES, m/z): [M+H]$^+$ 210.1

$^1$H NMR (300 MHz, DMSO) δ 7.60-7.70 (m, 2H), 7.26-7.32 (m, 2H), 6.07 (s, 2H)

Intermediate 60

Methyl 3-(1-acetyl-1H-indazol-5-yl)-3-oxopropanoate

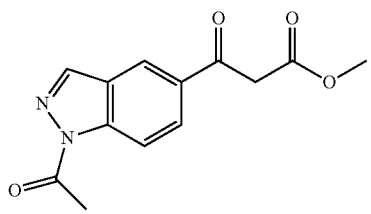 [SMILES: COC(=O)CC(=O)c1ccc2c(cnn2C(C)=O)c1]

Step 1. 1-Acetyl-1H-indazole-5-carboxylic acid

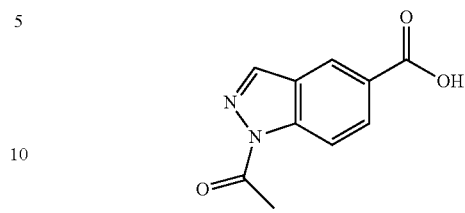

Acetic anhydride (5.7 g, 55.5 mmol) was added to a solution of 1H-indazole-5-carboxylic acid (3 g, 18.5 mmol) in acetic acid (60 ml). After stirring 2.5 hours at 80° C., the solution was concentrated in vacuo, precipitated from petroleum ether (50 ml), and filtered to afford 1-acetyl-1H-indazole-5-carboxylic acid as a yellow solid (3.4 g, 90%).

LC/MS (ES, m/z): [M+H]+ 205.3

$^1$H-NMR (300 MHz, DMSO) δ 8.45 (s, 1H), 8.30 (s, 1H), 8.16 (s, 2H), 2.72-2.74 (t, J=3.0 Hz, 3H)

Step 2. 5-(1-Acetyl-1H-indazole-5-carbonyl)-2,2-dimethyl-1,3-dioxane-4,6-dione

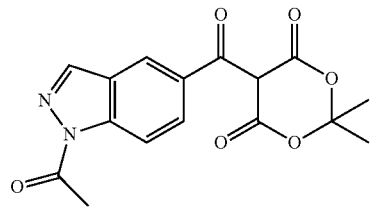 [SMILES: CC(=O)n1ncc2cc(C(=O)C3C(=O)OC(C)(C)OC3=O)ccc21]

A solution of 1-acetyl-1H-indazole-5-carboxylic acid (3.4 g, 16.7 mmol), 2,2-dimethyl-1,3-dioxane-4,6-dione (2.88 g, 20 mmol,), EDC HCl (4.8 g, 25 mmol) and 4-dimethylaminopyridine (3.0 g, 25 mmol) in dichloromethane (150 ml) was stirred overnight at room temperature. The reaction was then washed with acetic acid (10% aq, 100 ml), brine (50 ml), and the organic layers were dried over anhydrous sodium sulfate and concentrated in vacuo to afford a crude 5-(1-acetyl-1H-indazole-5-carbonyl)-2,2-dimethyl-1,3-dioxane-4,6-dione as a solid (5.5 g, crude).

Step 3. Methyl 3-(1-acetyl-1H-indazol-5-yl)-3-oxopropanoate

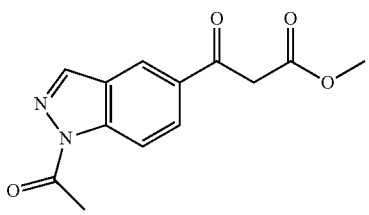 [SMILES: COC(=O)CC(=O)c1ccc2c(cnn2C(C)=O)c1]

A solution of 5-(1-acetyl-1H-indazole-5-carbonyl)-1,3-dioxane-4,6-dione (5.5 g, crude) in ethanol (100 ml) was stirred for 3 hours at 90° C., then concentrated in vacuo to afford a residue, which was purified by silica gel column chromatography with ethyl acetate:petroleum ether:dichloromethane (0.1:1:1) to afford methyl 3-(1-acetyl-1H-indazol-5-yl)-3-oxopropanoate as a yellow solid (2.5 g).

LC/MS (ES, m/z): [M+H]+ 261.1

$^1$H-NMR (300 MHz, CDCl$_3$) δ 8.53 (d, J=8.7 Hz, 1H), 8.41 (d, J=0.9 Hz, 1H), 8.27 (d, J=0.6 Hz, 1H), 8.17-8.20 (m, 1H), 4.21-4.35 (m, 2H), 4.09 (s, 2H), 2.84 (s, 3H), 1.26-1.31 (t, J=7.4 Hz, 3H)

Intermediate 61

4-(4-Chlorophenyl)-1H-pyrazol-5-amine

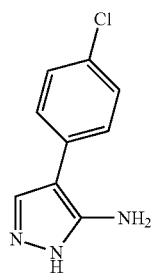 [SMILES: Nc1[nH]ncc1-c1ccc(Cl)cc1]

Step 1. 2-(4-Chlorophenyl)-3-oxopropanenitrile

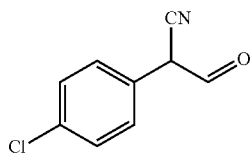 [SMILES: N#CC(C=O)c1ccc(Cl)cc1]

To a solution of Na (1.5 g, 66 mmol) in ethanol (80 ml) was added a solution of 2-(4-chlorophenyl)acetonitrile (5 g, 33.1 mmol) and ethyl formate (3.7 g, 50.00 mmol) in ethanol (20 mL), while the temperature was maintained at reflux. The resulting solution was heated at reflux overnight, and then concentrated in vacuo to afford a residue, which was dissolved in water (150 ml), and extracted with ether (2×100 mL). The aqueous layer was acidified with HCl (3N) to pH<5. The resulting solution was extracted with ethyl acetate (4×100 mL) and the organic layers combined and dried over anhydrous sodium sulfate and concentrated in vacuo to afford 2-(4-chlorophenyl)-3-oxopropanenitrile as a white solid (4 g, 67%).

Step 2. 4-(4-Chlorophenyl)-1H-pyrazol-5-amine

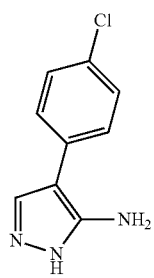 [SMILES: Nc1[nH]ncc1-c1ccc(Cl)cc1]

To a solution of 2-(4-chlorophenyl)-3-oxopropanenitrile (0.4 g, 2.27 mmol) in ethanol (20 mL) was added N$_2$H$_4$ H$_2$O (0.25 g, 5 mmol). The resulting solution was stirred overnight at reflux and then concentrated in vacuo to afford a residue, which was purified by silica gel column chromatography eluting with 20% ethyl acetate in petroleum ether to afford 4-(4-chlorophenyl)-1H-pyrazol-5-amine as red oil (0.3 g, 81%).

LC/MS (ES, m/z): [M+H]+. 194.1

$^1$H-NMR (300 MHz, DMSO) δ 7.34-7.54 (m, 5H), 4.06 (s, 2H)

Intermediate 62

4-(4-Chlorophenyl)-1H-pyrazole-3,5-diamine

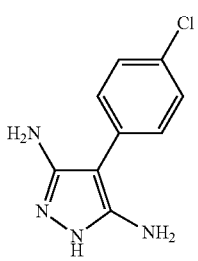 [SMILES: Nc1n[nH]c(N)c1-c1ccc(Cl)cc1]

Step 1. 2-(4-Chlorophenyl)malononitrile

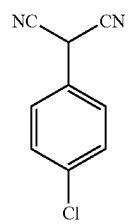

To a solution of sodium hydride (1.26 g, 30.00 mol) in ethylene glycol dimethyl ether (40 mL) was added dropwise a solution of malononitrile (1.66 g, 25.13 mmol) in ethylene glycol dimethyl ether (5.0 mL) at 18° C., and the resulting mixture was stirred for 30 minutes. Then, 1-chloro-4-iodobenzene (5.0 g, 20.97 mmol) in ethylene glycol dimethyl ether (40 mL) and Pd(PPh$_3$)$_2$Cl$_2$ (740 mg, 2 mmol) was added, and the reaction was stirred overnight at 85° C. Then the reaction was quenched with ice-water (80 mL), adjusted to pH 6 with HCl (3N), and extracted with ethyl acetate (3×50 mL). The organic layers were combined, dried over anhydrous sodium sulfate, and concentrated in vacuo to afford a residue, which was purified by silica gel column chromatography with 20% dichloromethane in petroleum ether to afford 2-(4-chlorophenyl)malononitrile as a red solid (1.7 g, 46%).

LC/MS (ES, m/z): [M+H]+ 177.0

$^1$H-NMR (300 MHz, CDCl$_3$): δ 7.46-7.54 (m, 4H), 5.08 (s, 1H)

Step 2.
4-(4-Chlorophenyl)-1H-pyrazole-3,5-diamine

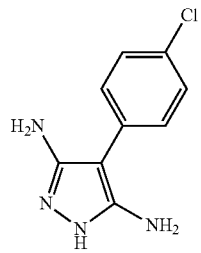 [SMILES: Nc1n[nH]c(N)c1-c1ccc(Cl)cc1]

To a solution of 2-(4-chlorophenyl)malononitrile (1.86 g, 10.53 mmol) in ethanol (50 mL) was added N₂H₄H₂O (3.16 mL), and the reaction was stirred overnight at reflux. The reaction mixture was concentrated in vacuo and precipitated from water (10 mL) to afford 4-(4-chlorophenyl)-1H-pyrazole-3,5-diamine as a greenish solid (740 mg, 34%).

LC/MS (ES, m/z): [M+H]⁺ 209.0

¹H-NMR (300 MHz, DMSO): δ 7.34-7.41 (m, 4H)

Intermediate 63

4-(4-chlorophenyl)-3-methyl-1H-pyrazol-5-amine

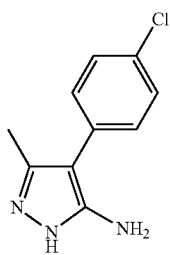

Step 1. 2-(4-Chlorophenyl)-3-oxobutanenitrile

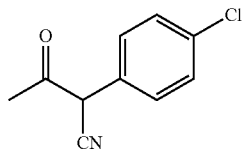

To a solution of 2-(4-chlorophenyl)acetonitrile (15 g, 99.3 mmol) in ethyl acetate (400 ml) was added sodium (2.7 g, 117.4 mmol). After stirring 14 hours at 80° C., the solids were collected by filtration and dissolved in water (150 ml), adjusted to pH 5 with HCl (3N), extracted with ethyl acetate (3×100 ml), dried over anhydrous magnesium sulfate and concentrated in vacuo to afford 2-(4-chlorophenyl)-3-oxobutanenitrile as a light yellow solid (13.1 g, 68%).

¹H-NMR (300 MHz, CDCl₃) δ 7.34-7.46 (m, 4H), 4.67 (s, 1H), 2.33 (s, 3H)

Step 2.
4-(4-Chlorophenyl)-3-methyl-1H-pyrazol-5-amine

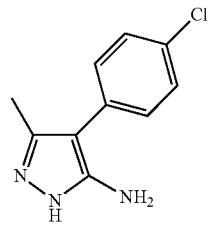

To a solution of 2-(4-chlorophenyl)-3-oxobutanenitrile (12.6 g, 65.07 mmol) in toluene (200 ml) was added N₂H₄H₂O (10.2 g, 203.96 mmol) and AcOH (13.7 g, 228.14 mmol). After stirring 14 hours at 105° C., the resulting mixture was concentrated in vacuo and then diluted with water (100 ml), adjusted to pH 5 with HCl (3N). The solids were collected by filtration to afford 4-(4-chlorophenyl)-3-methyl-1H-pyrazol-5-amine as a light yellow solid (11.8 g, 87%).

LC/MS (ES, m/z): [M+H]⁺ 208.0

¹H-NMR (300 MHz, DMSO) δ 7.34-7.48 (m, 4H), 2.13-2.18 (m, 3H)

Intermediate 64

5-Amino-4-phenyl-1H-pyrazol-3-ol

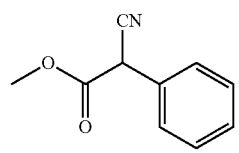

Step 1. Methyl 2-cyano-2-phenylacetate

To a solution of 2-phenylacetonitrile (10 g, 85.5 mmol) in dimethyl carbonate (100 mL) was added EtONa (12.1 g, 170.72 mmol) in portions. The resulting solution was stirred overnight at 90° C. and then concentrated in vacuo. The residue was diluted with water (500 mL) and extracted with dichloromethane (3×500 mL). The organic layers were combined, dried over anhydrous magnesium sulfate and concentrated in vacuo to afford methyl 2-cyano-2-phenylacetate as red oil (15 g, crude).

LC/MS (ES, m/z): [M+H]+. 176.1

Step 2. 5-Amino-4-phenyl-1H-pyrazol-3-ol

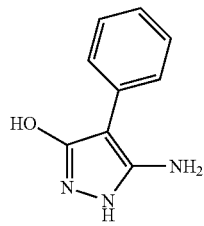 [SMILES: Nc1[nH]nc(O)c1-c1ccccc1]

To a solution of methyl 2-cyano-2-phenylacetate (5 g, 28.54 mmol) in ethanol (30 mL) was added N₂H₄H₂O (3 g, 56 mmol). The resulting solution was stirred for 3 hours at 80° C. and then concentrated in vacuo. The product was precipitated from water (15 mL) and collected by filtration to afford 5-amino-4-phenyl-1H-pyrazol-3-ol as a white solid (3 g, 60%).

LC/MS (ES, m/z): [M+H]+. 176.1

$^1$H-NMR (300 MHz, DMSO) δ 9.08 (s, 1H), 7.59-7.61 (t, J=1.2 Hz, 2H), 7.24-7.29 (m, 2H), 7.00-7.05 (m, 1H), 5.95 (s, 2H)

Intermediate 65

5-Amino-N-propyl-1H-pyrazole-4-carboxamide

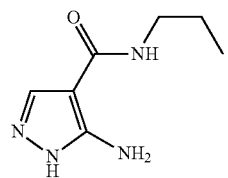

Step 1. 2-Cyano-N-propylacetamide

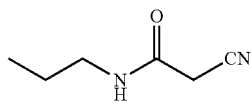

A solution of ethyl 2-cyanoacetate (10 g, 88.5 mmol) in propan-1-amine (30 ml) was stirred overnight at room temperature and then concentrated in vacuo. The solid was precipitated from water (50 mL) and collected by filtration to afford 2-cyano-N-propylacetamide as a white solid (11 g, 98%).

LC/MS (ES, m/z): [M+H]+. 127.1

$^1$H-NMR (300 MHz, CDCl₃) δ 6.16 (s, 1H), 3.47 (s, 2H), 3.26-3.39 (m, 2H), 1.53-1.66 (m, 2H), 0.94-0.99 (t, J=7.5 Hz, 3H)

Step 2.
(E)-2-Cyano-3-(dimethylamino)-N-propylacrylamide

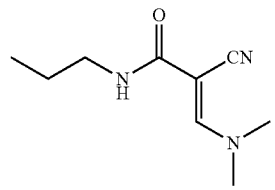

A solution of 2-cyano-N-propylacetamide (3 g, 23.78 mmol) in DMF-DMA (10 mL) was stirred for 3 hours at reflux and then concentrated in vacuo. The solids were precipitated from ether (50 mL) and collected by filtration to afford (E)-2-cyano-3-(dimethylamino)-N-propylacrylamide as a yellow solid (3.5 g, 81%).

LC/MS (ES, m/z): [M+H]+. 182.1

$^1$H-NMR (300 MHz, CDCl₃) δ 7.80 (s, 1H), 5.92 (s, 1H), 3.24-3.39 (m, 5H), 3.10-3.19 (m, 3H), 1.50-1.66 (m, 2H), 0.92-1.03 (m, 3H)

Step 3.
5-Amino-N-propyl-1H-pyrazole-4-carboxamide

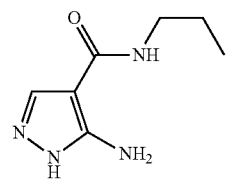

To a solution of (E)-2-cyano-3-(dimethylamino)-N-propylacrylamide (500 mg, 2.76 mmol) in ethanol (15 mL) was added N₂H₄H₂O (1 mL). The resulting solution was heated to reflux for 4 hours and then concentrated in vacuo. The product was precipitated from ether (10 mL) and collected by filtration to afford 5-amino-N-propyl-1H-pyrazole-4-carboxamide as a white solid (0.3 g, 65%).

LC/MS (ES, m/z): [M+H]+. 169.1

$^1$H-NMR (300 MHz, DMSO) δ 11.7 (s, 1H), 7.74 (s, 1H), 7.62-7.66 (t, J=5.1 Hz, 1H), 5.63 (s, 2H), 3.08-3.14 (m, 2H), 1.41-1.53 (m, 2H), 0.81-0.89 (m, 3H)

Intermediate 66

4-(pyridin-3-yl)-1H-pyrazol-5-amine

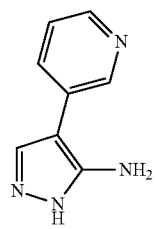 [SMILES: Nc1[nH]ncc1-c1cccnc1]

Step 1.
3-(Dimethylamino)-2-(pyridin-3-yl)acrylonitrile

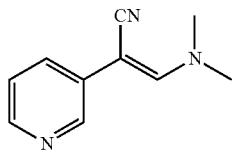

The solution of 2-(pyridin-3-yl)acetonitrile (2.3 g, 19.47 mmol) in DMF-DMA (8 mL) was stirred overnight at reflux. The resulting mixture was concentrated in vacuo and then precipitated from ether (20 mL). The solids were collected by filtration to afford 3-(dimethylamino)-2-(pyridin-3-yl)acrylonitrile as a brown solid (2.27 g, 67%).

$^1$H-NMR (300 MHz, CDCl$_3$) δ 8.54 (d, J=2.1 Hz, 1H), 8.35-8.37 (m, 1H), 7.61-7.65 (m, 1H), 7.19-7.24 (m, 1H), 6.93 (s, 1H), 3.27 (s, 6H)

Step 2. 4-(Pyridin-3-yl)-1H-pyrazol-5-amine

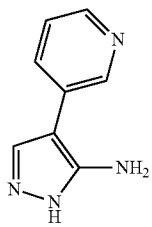 [SMILES: Nc1[nH]ncc1-c1cccnc1]

To a solution of 3-(dimethylamino)-2-(pyridin-3-yl)acrylonitrile (1.2 g, 6.93 mmol) in ethanol (10 mL) was added N$_2$H$_4$H$_2$O (1.3 mL, 80%). The resulting solution was stirred overnight at reflux, and then concentrated in vacuo to give a residue, which was purified by silica gel column chromatography with 2% methanol in dichloromethane to afford 4-(pyridin-3-yl)-1H-pyrazol-5-amine as red oil (0.9 g, 82%).

LC/MS (ES, m/z):[M+H]$^+$ 161.1

Intermediate 67

3-Methyl-4-phenyl-1H-pyrazol-5-amine

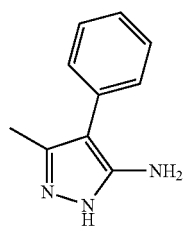

Step 1. 3-Oxo-2-phenylbutanenitrile

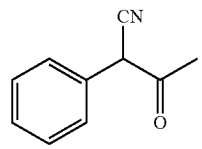

To a solution of 2-phenylacetonitrile (20.4 g, 174.14 mmol) in ethyl acetate (400 mL) was added sodium (5.6 g, 243.59 mmol). After stirring 14 hours at 80° C., the solids were collected by filtration and dissolved in water (150 mL), the pH was adjusted to 5 with HCl (3N), extracted with ethyl acetate (2×200 mL), and the organic layers were dried over anhydrous magnesium sulfate and concentrated in vacuo to afford 3-oxo-2-phenylbutanenitrile as a light yellow solid (24.2 g, 87%).

$^1$H-NMR (300 MHz, CDCl$_3$) δ 7.40-7.50 (m, 5H), 4.70 (s, 1H), 2.29 (s, 3H)

Step 2. 3-Methyl-4-phenyl-1H-pyrazol-5-amine

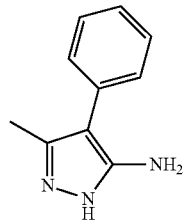

To a solution of 3-oxo-2-phenylbutanenitrile (15 g, 94.23 mmol) in toluene (200 mL), was added hydrazine hydrate (13.98 g, 279.54 mmol) and acetic acid (19.57 g, 325.88 mmol). After stirring 16 hours at 90° C., the resulting mixture was concentrated in vacuo and filtered. The solids were washed with ether (100 mL) to afford 3-methyl-4-phenyl-1H-pyrazol-5-amine as a light yellow solid (13.21 g, 81%).

LC/MS (ES, m/z): [M+H]$^+$ 174.1

$^1$H-NMR (300 MHz, CDCl$_3$) δ 7.37-7.47 (m, 4H), 7.26-7.32 (m, 1H), 2.31 (s, 3H)

Intermediate 68

4-(Pyridin-2-ylmethyl)-1H-pyrazol-5-amine

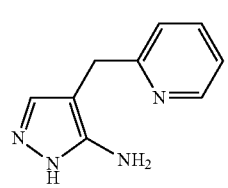

Step 1. 2-(2-Bromoethyl)pyridine

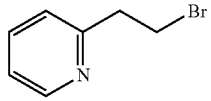

To a solution of 2-(pyridin-2-yl)ethanol (10 g, 81.20 mmol) in THF (100 mL) was added triphenylphosphine (32 g, 122.00 mmol), and carbon tetrabromide (40 g, 120.62 mmol) at 0° C. under an inert atmosphere of nitrogen. The solution was stirred overnight at room temperature, and then diluted with ether (200 mL). The solids were filtered and the filtrate was concentrated in vacuo to afford a residue, which was purified by silica gel column chromatography with 5%-10% ethyl acetate in petroleum ether to afford 2-(2-bromoethyl)pyridine as a yellow oil (12.2 g, 81%).

LC/MS (ES, m/z): [M+H]$^+$ 186.0

$^1$H-NMR (300 MHz, CDCl$_3$) δ 8.56-8.57 (m, 1H), 7.60-7.65 (m, 1H), 7.15-7.20 (m, 2H), 3.75-3.80 (t, J=6.9 Hz, 2H), 3.04-3.35 (t, J=6.9 Hz, 2H)

Step 2. 3-(Pyridin-2-yl)propanenitrile

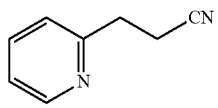

To a solution of 2-(2-bromoethyl)pyridine (6.2 g, 33.32 mmol) in DMF (20 mL) was added Zn(CN)$_2$ (4.34 g, 37.09 mmol), and Pd(PPh$_3$)$_4$ (2 g, 1.73 mmol) under an inert atmosphere of nitrogen. The resulting solution was stirred overnight at 85° C. Then the reaction was diluted with water (200 mL), extracted with dichloromethane (3×40 mL), and the organic layers combined and dried over anhydrous sodium sulfate and concentrated in vacuo to give a residue, which was purified by silica gel column chromatography with 5%-15% ethyl acetate in petroleum ether to afford 3-(pyridin-2-yl)propanenitrile as a yellow oil (1.45 g, 33%).

LC/MS (ES, m/z): [M+H]$^+$ 133.0

$^1$H-NMR (300 MHz, CDCl$_3$) δ 8.56 (d, J=4.8 Hz, 1H), 7.60-7.68 (m, 1H), 7.15-7.28 (m, 2H), 3.08-3.34 (m, 2H), 2.83-2.95 (m, 2H)

Step 3. Sodium (Z)-2-cyano-3-(pyridin-2-yl)prop-1-en-1-olate

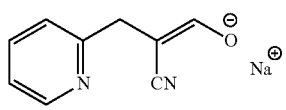 [SMILES: N#C/C(=C\[O-])Cc1ccccn1 ; [Na+]]

To a solution of sodium hydride (1.44 g, 60.00 mmol) in THF was added a solution of 3-(pyridin-2-yl)propanenitrile (1.6 g, 12.11 mmol) and ethyl formate (6.28 g, 84.77 mmol) in THF at 0° C. The reaction was stirred for 48 hours at room temperature. The resulting mixture was concentrated in vacuo to afford sodium (Z)-2-cyano-3-(pyridin-2-yl)prop-1-en-1-olate as red oil (3.2 g, crude).

LC/MS (ES, m/z): [M+H]$^+$ 161.0

Step 4. 4-(Pyridin-2-ylmethyl)-1H-pyrazol-5-amine

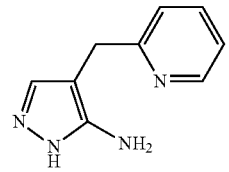 [SMILES: Nc1[nH]ncc1Cc1ccccn1]

To a solution of sodium (Z)-2-cyano-3-(pyridin-2-yl)prop-1-en-1-olate (3.2 g, 17.57 mmol) in water (10 mL) was added concentrated HCl (1.3 mL), and N$_2$H$_4$H$_2$O (5 mL). The resulting solution was stirred for 3 hours at 120° C. The reaction was concentrated in vacuo to afford a residue, which was purified by silica gel column chromatography with 5% methanol in dichloromethane to afford 4-(pyridin-2-ylmethyl)-1H-pyrazol-5-amine as yellow oil (0.4 g, 13% 2 steps).

LC/MS (ES, m/z): [M+H]$^+$ 175.0

$^1$H-NMR (300 MHz, DMSO) δ 8.44-8.47 (m, 1H), 7.65-7.71 (m, 1H), 7.14-7.26 (m, 3H), 3.74 (s, 2H)

Intermediate 69

3-Methyl-4-(pyridin-2-ylmethyl)-1H-pyrazol-5-amine

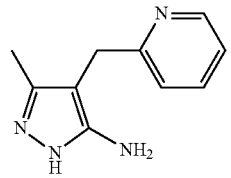

Step 1. 3-Oxo-2-(pyridin-2-ylmethyl)butanenitrile

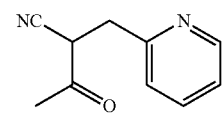

To a solution of benzene-1,2-diamine (1.1 g, 10.17 mmol) in ethanol (20 mL) was added proline (0.23 g), 3-oxobutanenitrile (830 mg, 9.99 mmol), and picolinaldehyde (2.2 g, 20.54 mmol). The resulting solution was stirred for 3 hours at 25° C., and then concentrated in vacuo to provide 3-oxo-2-(pyridin-2-ylmethyl)butanenitrile as a red oil (1.5 g, crude), which was reacted directly in the next step.

LC/MS (ES, m/z):[M+H]$^+$ 175.1

Step 2. 3-Methyl-4-(pyridin-2-ylmethyl)-1H-pyrazol-5-amine

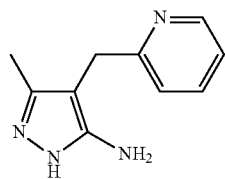

To a solution of 3-oxo-2-(pyridin-2-ylmethyl)butanenitrile (1.5 g, crude) in ethanol (20 mL) was added N₂H₄H₂O (3 mL). After stirring 3 hours at 85° C., the resulting mixture was concentrated in vacuo to give a residue, which was purified by silica gel column chromatography with 5% methanol in dichloromethane to afford 3-methyl-4-(pyridin-2-ylmethyl)-1H-pyrazol-5-amine as a red solid (350 mg, 18%, 2 steps).

LC/MS (ES, m/z): [M+H]⁺ 189.1

¹H-NMR (300 MHz, DMSO) δ 8.43-8.46 (m, 1H), 7.64-7.69 (m, 1H), 7.15-7.24 (m, 2H), 3.69 (s, 2H), 2.02 (s, 3H)

Intermediate 70

5-Amino-4-benzyl-1H-pyrazol-3-ol

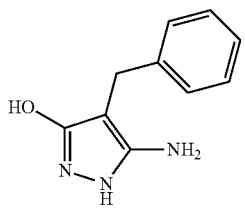 [SMILES: Nc1[nH]nc(O)c1Cc1ccccc1]

Step 1. Ethyl 2-cyano-3-phenylpropanoate

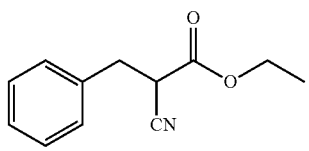

To a solution of benzaldehyde (10.6 g, 102.79 mmol) in ethanol (50 mL) was added DL-proline (1.15 g, 9.99 mmol), ethyl 2-cyanoacetate (5.65 g, 49.95 mmol), and benzene-1,2-diamine (5.4 g, 49.93 mmol). After stirring 1.5 hours at room temperature, the resulting mixture was concentrated in vacuo to afford a residue, which was purified by silica gel column chromatography with 2% ethyl acetate in petroleum ether to afford ethyl 2-cyano-3-phenylpropanoate as colorless oil (2.23 g, 22%).

LC/MS (ES, m/z): [M+H]⁺ 204.0

¹H-NMR (300 MHz, CDCl₃) δ 7.31-7.40 (m, 5H), 4.12-4.35 (m, 2H), 3.72-3.77 (m, 1H), 3.18-3.34 (m, 2H), 1.26-1.32 (m, 3H)

Step 2. 5-Amino-4-benzyl-1H-pyrazol-3-ol

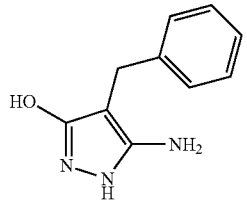 [SMILES: Nc1[nH]nc(O)c1Cc1ccccc1]

To a solution of ethyl 2-cyano-3-phenylpropanoate (1.22 g, 5.99 mmol) in ethanol (15 mL) was added N₂H₄H₂O (1.13 g, 22.50 mmol). After stirring 3 hours at 80° C., the resulting mixture was concentrated in vacuo to afford a residue, which was purified by silica gel column chromatography with 3% methanol in dichloromethane to afford 5-amino-4-benzyl-1H-pyrazol-3-ol as a white solid (0.82 g, 72%).

LC/MS (ES, m/z): [M+H]⁺ 190.1

¹H-NMR (300 MHz, DMSO) δ 9.43 (s, 1H), 7.21-7.36 (m, 5H), 2.96-3.12 (m, 2H)

Intermediate 71

4-Benzyl-1H-pyrazole-3,5-diamine

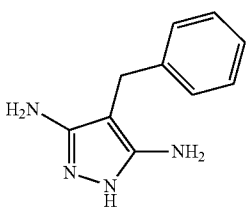 [SMILES: Nc1n[nH]c(N)c1Cc1ccccc1]

Step 1. 2-Benzylmalononitrile

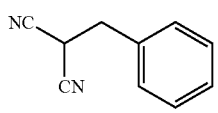 [SMILES: N#CC(C#N)Cc1ccccc1]

A solution of benzaldehyde (10 g, 94.23 mmol), malononitrile (3.1 g, 46.93 mmol), benzene-1,2-diamine (5.08 g, 46.98 mmol), and pyrrolidine-2-carboxylic acid (1.08 g, 9.38 mmol) in ethanol (30 mL) was stirred overnight at room temperature. Then the resulting mixture was concentrated in vacuo and purified by silica gel column chromatography with 1%-3% ethyl acetate in petroleum ether to afford 2-benzylmalononitrile as a solid (1.73 g, 24%).

LC/MS (ES, m/z): [M+H]⁺ 157.0

¹H-NMR (300 MHz, CDCl₃) δ 7.33-6.53 (m, 5H), 3.91-3.95 (t, J=6.9 Hz, 1H), 3.31 (d, J=6.9 Hz, 2H)

Step 2. 4-Benzyl-1H-pyrazole-3,5-diamine

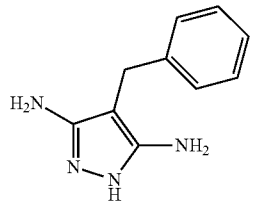 [SMILES: Nc1n[nH]c(N)c1Cc1ccccc1]

A solution of 2-benzylmalononitrile (1.28 g, 8.20 mmol) N$_2$H$_4$HBr (1.39 g, 12.3 mmol) and triethylamine (830 mg, 8.20 mmol) in ethanol (30 mL) was stirred for 3 hours at 110° C. Then the reaction mixture was concentrated in vacuo, and the resulting residue purified by silica gel column chromatography with 10% methanol in dichloromethane to afford 4-benzyl-1H-pyrazole-3,5-diamine as a dark solid (0.4 g, 26%).

LC/MS (ES, m/z): [M+H]$^+$ 189.0

$^1$H-NMR (300 MHz, DMSO) δ 7.08-7.24 (m, 5H), 4.34 (s, 4H), 3.50 (s, 2H)

Intermediate 72

Ethyl 3-(4-cyanophenyl)-3-oxopropanoate

A solution of 4-cyanobenzoic acid (5 g, 0.03 mol) and 1,1'-carbonyldiimidazole (6.6 g, 0.04 mol) in THF (80 ml) was stirred overnight at room temperature. Then a solution of the magnesium salt of malonic acid monoethyl ester (prepared via the dropwise addition of Et$_3$N (8.6 g, 0.085 mol) and MgCl$_2$ (10.5 g, 0.11 mol) to a solution of potassium 3-ethoxy-3-oxopropanoate (11 g, 0.065 mol) in acetonitrile (80 mL) was added to the reaction mixture, followed by stirring at room temperature for 2 h at 0° C. The reaction mixture was stirred overnight at reflux, quenched by the addition of water (300 mL), adjusted to pH 7 with HCl (3N), extracted with ethyl acetate (3×100 mL), and the organic layers were combined and dried over anhydrous magnesium sulfate and concentrated in vacuo to provide a residue, which was purified by silica gel column chromatography with 5% ethyl acetate in petroleum ether to afford ethyl 3-(4-cyanophenyl)-3-oxopropanoate as an orange solid (2.5 g, 34%).

LC/MS (ES, m/z): [M+H]$^+$ 218.0

$^1$H-NMR (300 MHz, CDCl$_3$) δ 12.57 (s, 1H), 7.88-7.90 (m, 2H), 7.72-7.75 (m, 2H), 5.74 (s, 1H), 4.27-4.35 (m, 2H), 1.33-1.39 (m, 3H)

Intermediate 73

Ethyl 3-(4-(oxazol-2-yl)phenyl)-3-oxopropanoate

Step 1. 4-Carbamoylbenzoic acid

A solution of 4-cyanobenzoic acid (10 g, 688 mmol) in concentrated sulfuric acid (100 mL) was stirred for 1 h at 40° C. in an oil bath and then diluted with ice-water (300 mL). The solids were collected by filtration, washed with water (100 mL), and dried in an oven under reduced pressure to afford 4-carbamoylbenzoic acid as an off-white solid (10 g, 85%).

$^1$H-NMR (300 MHz, DMSO) δ 8.12-8.21 (m, 1H), 7.94-8.01 (m, 3H), 7.54 (m, 1H)

Step 2. 4-(Oxazol-2-yl)benzoic acid

A solution of 4-carbamoylbenzoic acid (8.0 g, 48.44 mmol) and 2-bromo-1,1-diethoxyethane (19.0 g, 96.41 mmol) in dioxane (100 mL) was stirred for 4 hours at 125° C. The solids were filtered out and the filtrate was concentrated in vacuo to afford the residue, which was purified by silica gel column with 5% ethyl acetate in petroleum to afford 4-(oxazol-2-yl)benzoic acid (600 mg, crude) as yellow oil.

LC/MS (ES, m/z): [M+H]$^+$ 190.0

Step 3. Ethyl 3-(4-(oxazol-2-yl)phenyl)-3-oxopropanoate

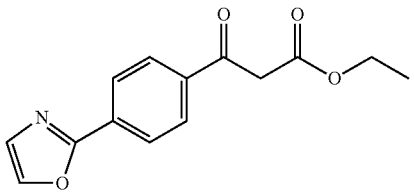 [SMILES: CCOC(=O)CC(=O)c1ccc(-c2ncco2)cc1]

A solution of 4-(oxazol-2-yl)benzoic acid (600 mg, crude) and 1,1'-carbonyldiimidazole (771 mg, 4.75 mmol) in THF (50 mL) was stirred at room temperature for 3 hours. Then a solution of the magnesium salt of malonic acid monoethyl ester (prepared via the addition of Et$_3$N (960 mg, 9.51 mmol) and MgCl$_2$ (1.35 g, 14.26 mmol) to a solution of potassium 3-ethoxy-3-oxopropanoate (1.6 g, 9.51 mmol) in acetonitrile (80 mL)) was added dropwise at 0° C. to the reaction mixture, and it was stirred at room temperature for 2 hours. The reaction mixture was then stirred overnight at 80° C., quenched by the addition of water (250 mL) and adjusted to pH 2 with HCl (3N). The mixture was extracted with ethyl acetate (3×100 mL), and the organic layers were combined, dried over anhydrous magnesium sulfate and concentrated under vacuum to give a residue, which was purified by silica gel column with 50% ethyl acetate in petroleum ether to afford ethyl 3-(4-(oxazol-2-yl)phenyl)-3-oxopropanoate as a light yellow oil (300 mg, crude).

LC/MS (ES, m/z): [M+H]$^+$ 260.0

Intermediate 74

Methyl 4-(3-ethoxy-3-oxopropanoyl)benzoate

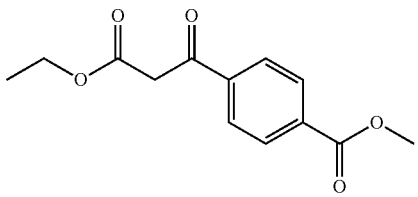 [SMILES: CCOC(=O)CC(=O)c1ccc(C(=O)OC)cc1]

A solution of 4-(methoxycarbonyl)benzoic acid (3 g, 16.65 mmol) and 1,1'-carbonyldiimidazole (3.2 g, 19.73 mmol) in THF (50 ml) was stirred for 3 hours at 50° C. Then, a solution of the magnesium salt of malonic acid monoethyl ester (prepared via the addition of Et$_3$N (4.3 g, 42.49 mmol) and MgCl$_2$ (5.2 g, 58.51 mmol) to a solution of potassium 3-ethoxy-3-oxopropanoate (7.8 g, 45.88 mmol) in acetonitrile (100 ml) stirred at room temperature for 2.5 h) was added at 0° C. The resulting solution was stirred overnight at 85° C., quenched by the addition of water (100 ml) and adjusted to pH 7 with HCl (3N). The resulting solution was extracted with ethyl acetate (3×100 ml), and the organic layers were combined, dried over anhydrous magnesium sulfate, and concentrated in vacuo to give a residue, which was purified by silica gel column chromatography with 2%-10% ethyl acetate in petroleum ether to afford methyl 4-(3-ethoxy-3-oxopropanoyl)benzoate as a white solid (2.6 g, 62%).

LC/MS (ES, m/z): [M+H]$^+$ 251.0

$^1$H-NMR (300 MHz, CDCl$_3$): δ 12.56 (s, 1H), 7.99-8.16 (m, 6H), 7.83-7.90 (m, 2H), 5.74 (s, 1H), 4.25-4.32 (m, 4H), 4.02-4.23 (m, 2H), 3.97 (s, 6H), 1.26-1.37 (m, 6H).

Intermediate 75

Methyl 3-(4-hydroxyphenyl)-3-oxopropanoate

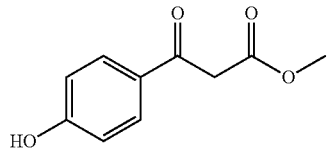

To a solution of methyl 3-(4-methoxyphenyl)-3-oxopropanoate (4 g, 19.23 mmol) in dichloromethane (60 mL) was added a solution of BBr$_3$ (14.3 g, 57.7 mmol) in dichloromethane (3 mL). The resulting solution was stirred for 1 hour at 0° C. and then concentrated under vacuum. Two batches of the reaction mixture were combined, dissolved in water (200 mL), and extracted with ethyl acetate (5×50 mL), and the organic layers were combined, dried over anhydrous magnesium sulfate and concentrated in vacuo. This resulted in 3 g (80%) of methyl 3-(4-hydroxyphenyl)-3-oxopropanoate as a red liquid.

LC/MS (ES, m/z): [M+H]$^+$ 195.0

Intermediate 76

Methyl 3-(4-isopropoxybenzo[d][1,3]dioxol-5-yl)-3-oxopropanoate

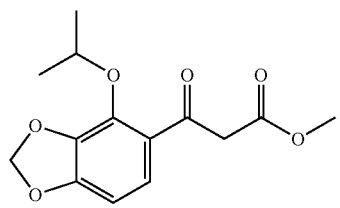 [SMILES: COC(=O)CC(=O)c1ccc2c(c1OC(C)C)OCO2]

Step 1. 1-(4-Isopropoxybenzo[d][1,3]dioxol-5-yl)ethanone

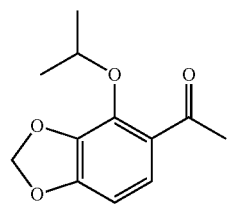 [SMILES: CC(=O)c1ccc2c(c1OC(C)C)OCO2]

A solution of 1-(4-hydroxybenzo[d][1,3]dioxol-5-yl)ethanone (5.6 g, 31.08 mmol), 2-iodopropane (10 g, 58.83 mmol) and potassium carbonate (5 g, 36.18 mmol) in acetone (280 ml) was stirred for 3 days at 70° C. The reaction was then evaporated in vacuo to give a residue and diluted with water (200 ml), adjusted to pH 7 with HCl (3N), and extracted with ethyl acetate (3×100 ml). The organic layers were combined and dried over anhydrous sodium sulfate, and concentrated in vacuo to afford 1-(4-isopropoxybenzo[d][1,3]dioxol-5-yl)ethanone as a light yellow crude oil (9.0 g, crude).

Step 2. Methyl 3-(4-isopropoxybenzo[d][1,3]dioxol-5-yl)-3-oxopropanoate

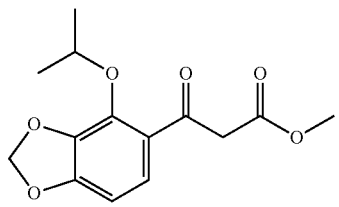 [SMILES: COC(=O)CC(=O)c1ccc2c(c1OC(C)C)OCO2]

To a solution of sodium hydride (6.5 g, 60%) in dimethyl carbonate (15 ml) was added a solution of 1-(4-isopropoxybenzo[d][1,3]dioxol-5-yl)ethanone (9 g, crude) in dimethyl carbonate (10 mL) dropwise with stirring for 40 minutes at 115° C. The reaction mixture was cooled to room temperature, adjusted to pH 7 with HCl (3N). The resulting solution was extracted with ethyl acetate (3×80 ml), and the organic layers were combined, dried over anhydrous sodium sulfate and concentrated in vacuo to give the residue, which was purified by a gel silica column chromatography with 5% ethyl acetate in petroleum ether to afford methyl 3-(4-isopropoxybenzo[d][1,3]dioxol-5-yl)-3-oxopropanoate as light yellow oil (6 g, 69% 2 steps).

LC/MS (ES, m/z): [M+H]$^+$ 281.0

$^1$H-NMR (300 MHz, DMSO): δ 7.33-7.37 (m, 1H), 6.72-6.78 (t, J=8.7 Hz, 1H), 6.10 (d, J=1.8 Hz, 2H), 4.91-4.99 (m, 1H), 3.96 (s, 2H), 3.63 (s, 3H), 1.27 (t, J=6.3 Hz, 6H)

Intermediate 77

Ethyl 3-(4-methoxy-1H-benzo[d][1,2,3]triazol-5-yl)-3-oxopropanoate

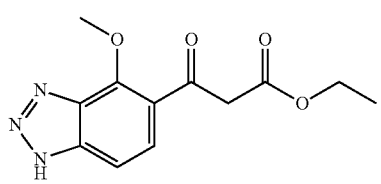

Step 1. Methyl 4-amino-5-chloro-2-methoxybenzoate

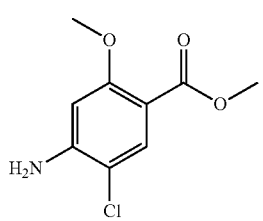

A solution of 4-amino-5-chloro-2-methoxybenzoic acid (30 g, 148.80 mmol) and thionyl chloride (35.1 g, 296.95 mmol) in methanol (400 mL) was stirred 5 hours at 80° C. The reaction mixture was concentrated in vacuo, diluted with water (200 mL), extracted with ethyl acetate (2×200 mL), dried over anhydrous magnesium sulfate, and concentrated in vacuo to afford methyl 4-amino-5-chloro-2-methoxybenzoate as a pink solid (31.3 g, 97%).

LC/MS (ES, m/z): [M+H]$^+$ 216.0

$^1$H-NMR (300 MHz, CDCl$_3$) δ 7.84 (s, 1H), 6.30 (s, 1H), 3.85 (s, 3H), 3.84 (s, 3H)

Step 2. Methyl 4-acetamido-5-chloro-2-methoxybenzoate

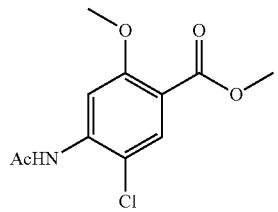 [SMILES: COC(=O)c1cc(Cl)c(NC(C)=O)cc1OC]

A solution of methyl 4-amino-5-chloro-2-methoxybenzoate (28 g, 129.85 mmol) and acetic anhydride (16 g, 156.73 mmol) in AcOH (150 mL) was stirred for 5 hours at 50° C. The reaction was concentrated in vacuo, diluted with water (150 mL), adjusted to pH 8 with aqueous sodium bicarbonate (3N), and extracted with ethyl acetate (2×200 mL). The organic layers were combined and dried over anhydrous magnesium sulfate and concentrated in vacuo to afford methyl 4-acetamido-5-chloro-2-methoxybenzoate as a light yellow solid (27 g, 80%).

LC/MS (ES, m/z): [M+H]$^+$ 258.0

$^1$H-NMR (300 MHz, CDCl$_3$) δ 8.31 (s, 1H), 7.88 (s, 1H), 7.79 (s, 1H), 3.93 (s, 3H), 3.88 (d, J=8.4 Hz, 3H), 2.28 (s, 3H)

Step 3. Methyl 4-acetamido-5-chloro-2-methoxy-3-nitrobenzoate

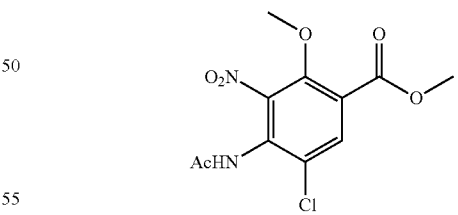

Fuming nitric acid (30 mL) was added dropwise at 20° C. to methyl 4-acetamido-5-chloro-2-methoxybenzoate (19 g, 73.92 mmol) over 15 minutes. After stirring for an additional 10 minutes at 20° C., the mixture was poured into ice water and extracted with ethyl acetate (500 mL). The combined organic phases were washed with brine (2×100 mL), dried over MgSO$_4$ and concentrated in vacuo to afford methyl 4-acetamido-5-chloro-2-methoxy-3-nitrobenzoate as a light yellow solid (18 g, 80%).

LC/MS (ES, m/z): [M+H]$^+$ 303.0

$^1$H-NMR (300 MHz, DMSO) δ 10.33 (s, 1H), 8.15 (s, 1H), 3.94 (s, 3H), 3.88 (d, J=8.4 Hz, 3H), 2.04 (s, 3H)

Step 4. Methyl 4-acetamido-3-amino-2-methoxybenzoate

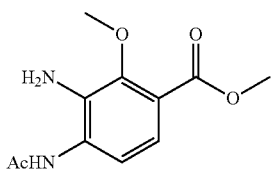 [SMILES: COC(=O)c1ccc(NC(C)=O)c(N)c1OC]

A solution of methyl 4-acetamido-5-chloro-2-methoxy-3-nitrobenzoate (15 g, 49.66 mmol), triethylamine (75 mL), and palladium on carbon (1.5 g) in methanol (150 mL) was stirred for 6 hours at 25° C. under an atmosphere of H$_2$(g). The solids were filtered off and the filtrate was concentrated in vacuo to afford methyl 4-acetamido-3-amino-2-methoxybenzoate as brown oil (9.5 g, 80%).

LC/MS (ES, m/z): [M+H]$^+$ 239.0

Step 5. Methyl 1-acetyl-4-methoxy-1H-benzo[d][1,2,3]triazole-5-carboxylate

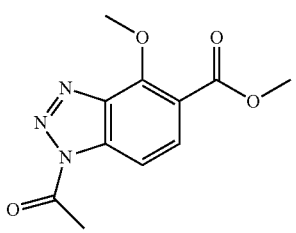 [SMILES: COC(=O)c1ccc2c(nnn2C(C)=O)c1OC]

To a solution of methyl 4-acetamido-3-amino-2-methoxybenzoate (9.9 g, 41.58) in acetic acid (40 ml, 5% aq.) was added a solution of sodium nitrite (3.2 g, 46.4 mmol) in H$_2$O (5 mL). After stirring 4 hours at 5° C., the solids were collected by filtration, washed with water (2×30 mL), and dried to afford methyl 1-acetyl-4-methoxy-1H-benzo[d][1,2,3]triazole-5-carboxylate as a light yellow solid (8 g, 820%).

LC/MS (ES, m/z): [M+H]$^+$ 234.1

$^1$H-NMR (300 MHz, DMSO) δ 7.99 (d, J=8.4 Hz, 1H), 7.82 (d, J=8.7 Hz, 1H), 4.55 (s, 3H), 3.88 (s, 3H), 2.94 (s, 3H)

Step 6. 4-Methoxy-1H-benzo[d][1,2,3]triazole-5-carboxylic acid

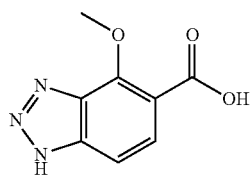

To a solution of methyl 1-acetyl-4-methoxy-1H-benzo[d][1,2,3]triazole-5-carboxylate (8 g, 32.1 mmol) in methanol (100 mL) was added a solution of NaOH (5 g, 128 mmol) in water (5 mL). After stirring overnight at 60° C., the resulting mixture was concentrated in vacuo, diluted with water (60 mL), adjusted to pH 5 with HCl (3N), and filtered to collect the solids, which provided 4-methoxy-1H-benzo[d][1,2,3]triazole-5-carboxylic acid as an off-white solid (6 g, 80%).

LC/MS (ES, m/z): [M+H]$^+$ 194.1

$^1$H-NMR (300 MHz, DMSO) δ 7.74 (d, J=8.7 Hz, 1H), 7.40 (s, 1H), 4.63 (s, 3H)

Step 7. Ethyl 3-(4-methoxy-1H-benzo[d][1,2,3]triazol-5-yl)-3-oxopropanoate

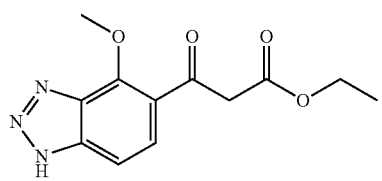 [SMILES: CCOC(=O)CC(=O)c1ccc2[nH]nnc2c1OC]

A solution of 4-methoxy-1H-benzo[d][1,2,3]triazole-5-carboxylic acid (500 mg, 2.59 mmol) and 1,1'-carbonyldiimidazole (460 mg, 2.84 mmol) in THF (20 mL) was stirred for 2.5 hours at 50° C. and then added dropwise to a solution of the magnesium salt of malonic acid monoethyl ester (prepared via the addition of Et$_3$N (1.52 g, 15.02 mmol) and MgCl$_2$ (1.77 g, 18.59 mmol) to a solution of potassium 3-ethoxy-3-oxopropanoate (2.64 g, 15.51 mmol) in acetonitrile (30 mL) followed by stirring at 30° C. for 3 hours) at 0° C. The resulting mixture was warmed slowly to 80° C. and stirred for 20 hours. The reaction was quenched by the addition of water (200 mL), adjusted to pH 4 with HCl (6N), extracted with ethyl acetate (3×60 mL), washed with brine (2×50 mL), dried over anhydrous magnesium sulfate, and concentrated in vacuo to afford ethyl 3-(4-methoxy-1H-benzo[d][1,2,3]triazol-5-yl)-3-oxopropanoate as a light yellow solid (520 mg, 76%).

LC/MS (ES, m/z): [M+H]$^+$ 263.1

$^1$H-NMR (300 MHz, DMSO) δ 16.07 (s, 1H), 7.83 (d, J=8.7 Hz, 1H), 7.40 (s, 1H), 4.59 (s, 3H), 4.09-4.16 (m, 2H), 4.00 (s, 2H), 1.16-1.21 (t, J=7.2 Hz, 3H)

Intermediate 78

Ethyl 3-(6-methyl-1H-benzo[d][1,2,3]triazol-5-yl)-3-oxopropanoate

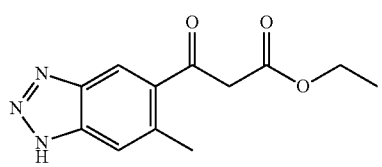 [SMILES: CCOC(=O)CC(=O)c1cc2nn[nH]c2cc1C]

Step 1. Methyl 4-fluoro-2-methylbenzoate

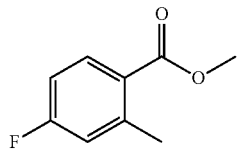

A solution of 4-fluoro-2-methylbenzoic acid (50 g, 324.38 mmol) and SOCl$_2$ (77 g, 648.76 mmol) in methanol (200 mL) was heated to reflux for 3 hours at 80° C. Then, the mixture was concentrated in vacuo to afford methyl 4-fluoro-2-methylbenzoate as brown oil (52 g, 95%).

$^1$H-NMR (300 MHz, CDCl$_3$): δ 7.92-7.98 (m, 1H), 6.88-6.95 (m, 2H), 3.90 (s, 3H), 2.61 (s, 3H)

Step 2. Methyl 4-fluoro-2-methyl-5-nitrobenzoate

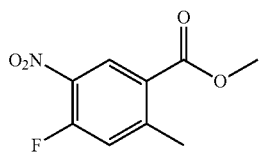

To a solution of methyl 4-fluoro-2-methylbenzoate (52 g, 309.22 mmol) in sulfuric acid (400 mL, conc) was added a solution of potassium nitrate (31.3 g, 309.9 mmol) in sulfuric acid (50 mL, conc) dropwise at −20~−1-10° C. The resulting solution was stirred for 40 min at −20~−10° C. Then the mixture quenched water/ice (400 mL). The solids were collected by filtration to afford methyl 4-fluoro-2-methyl-5-nitrobenzoate as a light red solid (50 g, 76%).

$^1$H-NMR (300 MHz, CDCl$_3$) δ 8.70 (d, J=7.8 Hz, 1H), 7.14-7.22 (m, 1H), 3.94 (s, 3H), 2.74 (s, 3H)

Step 3. Methyl 4-amino-2-methyl-5-nitrobenzoate

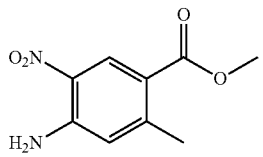

Ammonia (g) was bubbled into the solution of methyl 4-fluoro-2-methyl-5-nitrobenzoate (30 g, 140.74 mmol) in THF (180 mL) for 5 hours at room temperature, and then quenched water (500 mL). The solids were collected by filtration to afford methyl 4-amino-2-methyl-5-nitrobenzoate as a yellow solid (24.5 g, 83%).

LC/MS (ES, m/z): [M+H]$^+$ 211.0

$^1$H-NMR (300 MHz, CDCl$_3$): δ 8.85 (s, 1H), 6.64 (s, 1H), 3.88 (s, 3H), 2.61 (s, 3H)

Step 4. Methyl 4,5-diamino-2-methylbenzoate

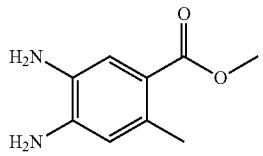

A solution of methyl 4-amino-2-methyl-5-nitrobenzoate (24.5 g, 116.56 mmol) and palladium on carbon (1.23 g) in methanol (500 mL) was stirred 3.5 hours at room temperature under an atmosphere of H$_2$ (g). The solids were filtered off, and the filtrate was concentrated in vacuo to provide a residue, which was purified by silica gel column chromatography with 1%-10% ethyl acetate in petroleum ether to afford methyl 4,5-diamino-2-methylbenzoate as a red solid (16 g, 76%).

LC/MS (ES, m/z): [M+H]$^+$ 181.0

$^1$H-NMR (300 MHz, CDCl$_3$): δ 7.41 (s, 1H), 6.53 (s, 1H), 3.84 (s, 3H), 2.50 (s, 3H)

Step 5. Methyl 6-methyl-1H-benzo[d][1,2,3]triazole-5-carboxylate

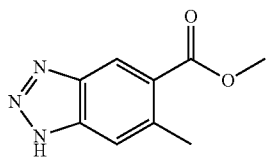

To a solution of methyl 4,5-diamino-2-methylbenzoate (16 g, 88.79 mmol) in acetic acid (120 ml, 5% aq.) was added a solution of sodium nitrite (6.75 g, 97.83 mmol) in water (15 ml) dropwise at 0-5° C. The resulting solution was stirred for 1.5 hours at 0-5° C. The solids were collected by filtration to afford methyl 6-methyl-1H-benzo[d][1,2,3]triazole-5-carboxylate as a light yellow solid (13.6 g, 80%).

LC/MS (ES, m/z): [M+H]$^+$ 192.0

$^1$H-NMR (300 MHz, CDCl$_3$): δ 8.65 (s, 1H), 7.66 (s, 1H), 3.98 (s, 3H), 2.77 (s, 3H)

Step 6. 6-Methyl-1H-benzo[d][1,2,3]triazole-5-carboxylic acid

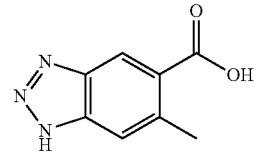

A solution of methyl 6-methyl-1H-benzo[d][1,2,3]triazole-5-carboxylate (15 g, 78.46 mmol) and sodium hydroxide (9.4 g, 235.00 mmol) in methanol (180 mL) and water (5 mL) was stirred overnight at 60° C. The resulting mixture was concentrated in vacuo, diluted with water (100 mL), adjusted to pH 4 with HCl (2N). The solids were collected by filtration to afford 6-methyl-1H-benzo[d][1,2,3]triazole-5-carboxylic acid as a light red solid (12 g, 86%).

LC/MS (ES, m/z): [M+H]+ 178.0

1H-NMR (300 MHz, DMSO): δ 8.40 (s, 1H), 7.73 (s, 1H), 2.65 (s, 3H)

Step 7. Ethyl 3-(6-methyl-1H-benzo[d][1,2,3]triazol-5-yl)-3-oxopropanoate

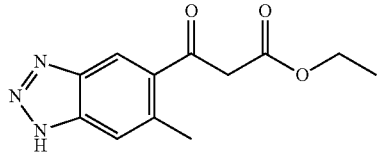 [SMILES: CCOC(=O)CC(=O)c1cc2nn[nH]c2cc1C]

To a solution of 6-methyl-1H-benzo[d][1,2,3]triazole-5-carboxylic acid (5 g, 28.22 mmol) in THF (100 mL) was added 1,1'-carbonyldiimidazole (5.5 g, 33.92 mmol). The resulting solution was stirred for 2 hours at 50° C. To a solution of potassium 3-ethoxy-3-oxopropanoate (13 g, 34 mmol) in CH3CN (100 mL) was added MgCl2 (8.5 g, 90 mmol), and TEA (7 g, 69.18 mmol). This second resulting solution was stirring 2.5 hours at room temperature. Then the two resulting solutions were combined and reacted for an additional 18 hours at 80° C. The reaction was quenched with water (200 mL), adjusted to pH 7 with HCl (3N), extracted with ethyl acetate (3×200 mL) and the organic layers were combined. The solids were filtered off and concentrated in vacuo to provide a residue, which was purified by silica gel column chromatography with 5%-20% ethyl acetate in petroleum ether to afford ethyl 3-(6-methyl-1H-benzo[d][1,2,3]triazol-5-yl)-3-oxopropanoate as a white solid (5.5 g, 79%).

LC/MS (ES, m/z): [M+H]+ 248.0

1H-NMR (300 MHz, DMSO): δ 8.66 (s, 1H), 7.68 (s, 1H), 4.24 (s, 2H), 4.02-4.06 (m, 2H), 2.51 (s, 3H), 1.14-1.20 (m, 3H)

The invention is further illustrated by the following examples, which can be made by the methods above or by one skilled in the art without undue experimentation, or can be purchased from commercial sources.

Example 1

3-(4-Chloro-phenyl)-2-methyl-5-(4-nitro-phenyl)-4H-pyrazolo[1,5-a]pyrimidin-7-one

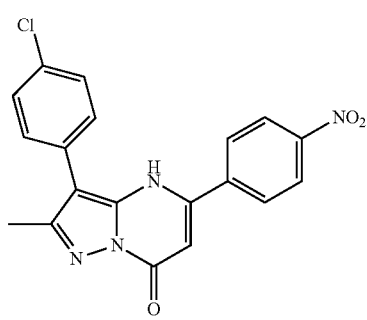 [SMILES: Cc1nn2c(=O)cc(-c3ccc([N+](=O)[O-])cc3)[nH]c2c1-c1ccc(Cl)cc1]

Example 2

2-(4-Chloro-phenyl)-5-methyl-4H-pyrazolo[1,5-a]pyrimidin-7-one

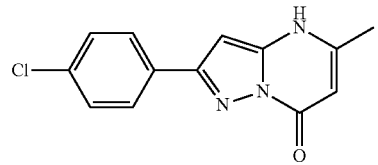 [SMILES: Cc1cc(=O)n2nc(-c3ccc(Cl)cc3)cc2[nH]1]

Example 3

6-Benzyl-3-(4-chloro-phenyl)-5-methyl-4H-pyrazolo[1,5-a]pyrimidin-7-one

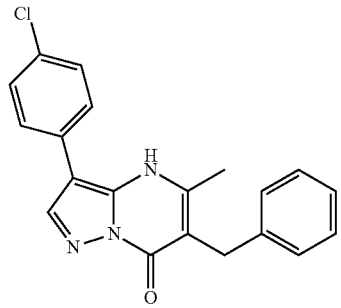 [SMILES: Cc1[nH]c2c(-c3ccc(Cl)cc3)cnn2c(=O)c1Cc1ccccc1]

Example 4

2-(3-Bromo-phenyl)-5-methyl-4H-pyrazolo[1,5-a]pyrimidin-7-one

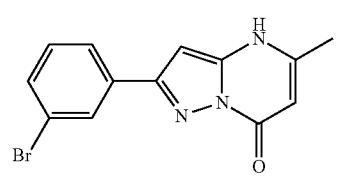 [SMILES: Cc1cc(=O)n2nc(-c3cccc(Br)c3)cc2[nH]1]

Example 5

2-Benzyl-3-(4-methoxy-phenyl)-5-phenyl-4H-pyrazolo[1,5-a]pyrimidin-7-one

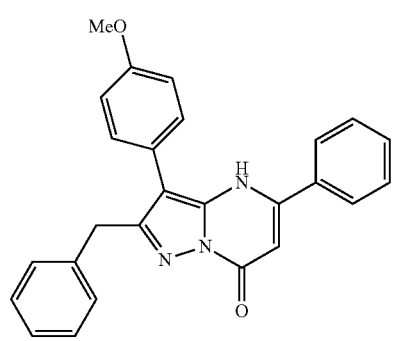 [SMILES: COc1ccc(-c2c(Cc3ccccc3)nn3c(=O)cc(-c4ccccc4)[nH]c23)cc1]

Example 6

3-(4-Methoxy-phenyl)-2-methyl-5-phenyl-4H-pyrazolo[1,5-a]pyrimidin-7-one

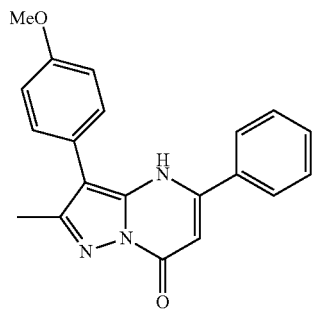 [SMILES: COc1ccc(-c2c(C)nn3c(=O)cc(-c4ccccc4)[nH]c23)cc1]

Example 7

2-Benzyl-3,5-diphenyl-4H-pyrazolo[1,5-a]pyrimidin-7-one

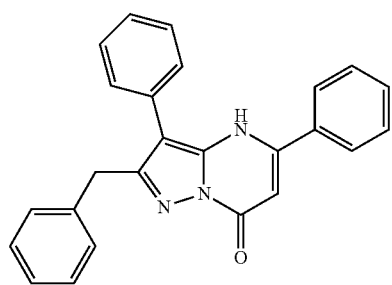 [SMILES: O=c1cc(-c2ccccc2)[nH]c2c(-c3ccccc3)c(Cc3ccccc3)nn12]

Example 8

3-(4-Chloro-phenyl)-2-methyl-5-phenyl-4H-pyrazolo[1,5-a]pyrimidin-7-one

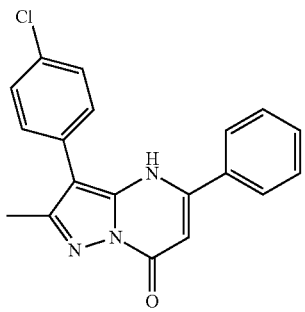

Example 9

2-Benzyl-3-(4-chloro-phenyl)-5-(4-nitro-phenyl)-4H-pyrazolo[1,5-a]pyrimidin-7-one

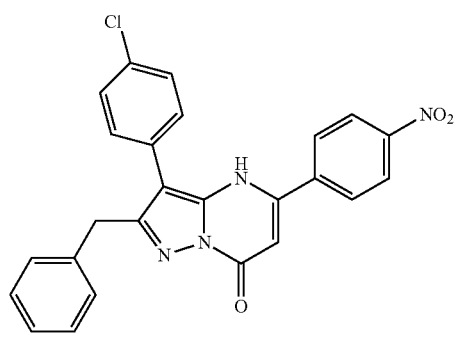 [SMILES: O=c1cc(-c2ccc([N+](=O)[O-])cc2)[nH]c2c(-c3ccc(Cl)cc3)c(Cc3ccccc3)nn12]

Example 10

2-Benzyl-3-(4-chloro-phenyl)-5-phenyl-4H-pyrazolo[1,5-a]pyrimidin-7-one

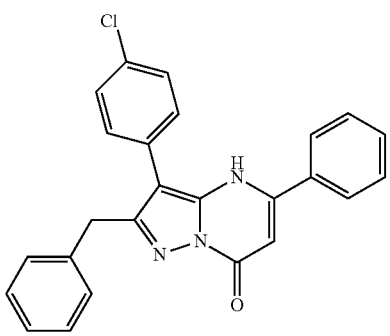 [SMILES: O=c1cc(-c2ccccc2)[nH]c2c(-c3ccc(Cl)cc3)c(Cc3ccccc3)nn12]

Example 11

2-Benzyl-3-naphthalen-1-yl-5-phenyl-4H-pyrazolo[1,5-a]pyrimidin-7-one

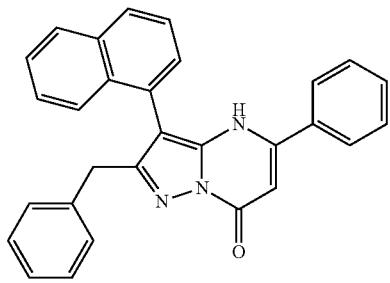 [SMILES: O=c1cc(-c2ccccc2)[nH]c2c(-c3cccc4ccccc34)c(Cc3ccccc3)nn12]

Example 12

2-(4-Methoxy-benzyl)-3,5-diphenyl-4H-pyrazolo[1,5-a]pyrimidin-7-one

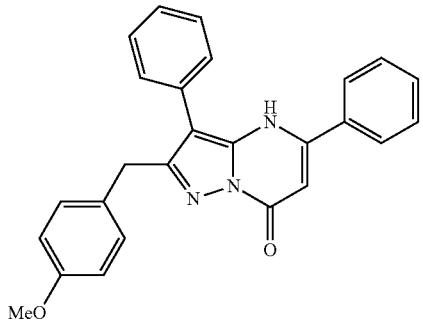 [SMILES: COc1ccc(Cc2nn3c(=O)cc(-c4ccccc4)[nH]c3c2-c2ccccc2)cc1]

Example 13

2-Methyl-7-oxo-3,5-diphenyl-4,7-dihydro-pyrazolo[1,5-a]pyrimidine-6-carbonitrile

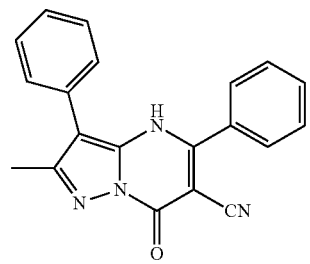 [SMILES: Cc1nn2c(=O)c(C#N)c(-c3ccccc3)[nH]c2c1-c1ccccc1]

Example 14

5-(4-Methoxy-phenyl)-2-methyl-3-phenyl-4H-pyrazolo[1,5-a]pyrimidin-7-one

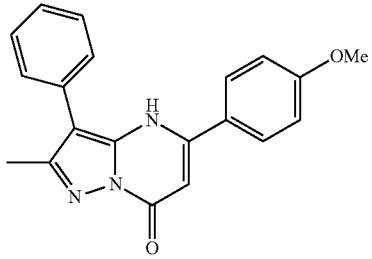 [SMILES: COc1ccc(-c2cc(=O)n3nc(C)c(-c4ccccc4)c3[nH]2)cc1]

Example 15

3-(4-Fluoro-phenyl)-2-methyl-5-phenyl-4H-pyrazolo[1,5-a]pyrimidin-7-one

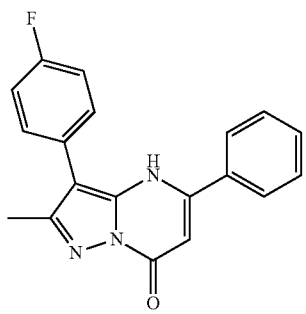 [SMILES: Cc1nn2c(=O)cc(-c3ccccc3)[nH]c2c1-c1ccc(F)cc1]

Example 16

5-(2-Methoxy-phenyl)-2-methyl-3-phenyl-4H-pyrazolo[1,5-a]pyrimidin-7-one

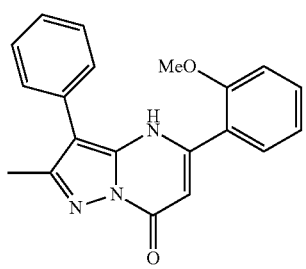 [SMILES: COc1ccccc1-c1cc(=O)n2nc(C)c(-c3ccccc3)c2[nH]1]

Example 17

5-(4-Chloro-phenyl)-2-methyl-3-phenyl-4H-pyrazolo[1,5-a]pyrimidin-7-one

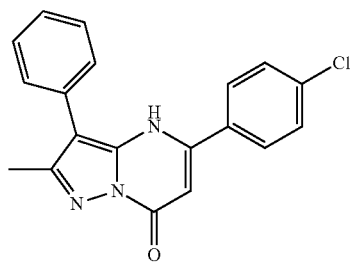 [SMILES: Cc1nn2c(=O)cc(-c3ccc(Cl)cc3)[nH]c2c1-c1ccccc1]

Example 18

2-Benzyl-3-(4-chloro-phenyl)-5-propyl-4H-pyrazolo[1,5-a]pyrimidin-7-one

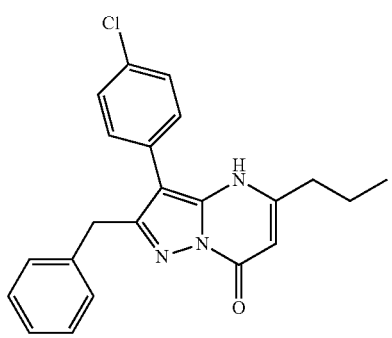 [SMILES: CCCc1cc(=O)n2nc(Cc3ccccc3)c(-c3ccc(Cl)cc3)c2[nH]1]

Example 19

2-Benzyl-5-methoxymethyl-3-(4-methoxy-phenyl)-4H-pyrazolo[1,5-a]pyrimidin-7-one

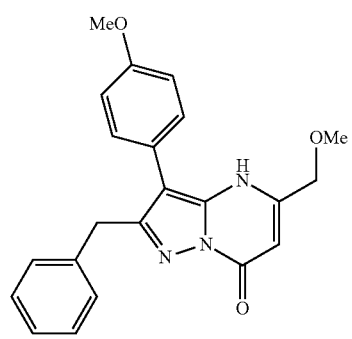 [SMILES: COCc1cc(=O)n2nc(Cc3ccccc3)c(-c3ccc(OC)cc3)c2[nH]1]

Example 20

3-(4-Methoxy-phenyl)-2-methyl-5-phenyl-4H-pyrazolo[1,5-a]pyrimidin-7-one

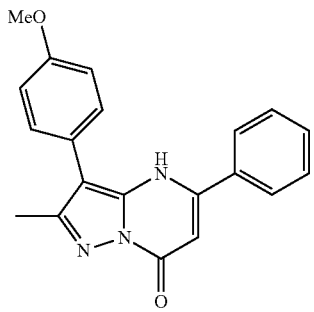 [SMILES: COc1ccc(-c2c(C)nn3c(=O)cc(-c4ccccc4)[nH]c23)cc1]

Example 21

2,5-Dibenzyl-3-phenyl-4H-pyrazolo[1,5-a]pyrimidin-7-one

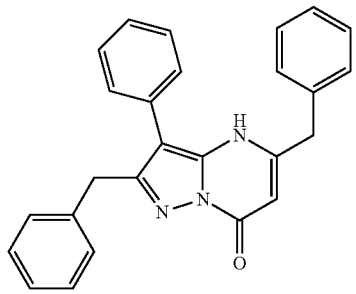 [SMILES: O=c1cc(Cc2ccccc2)[nH]c2c(-c3ccccc3)c(Cc3ccccc3)nn12]

Example 22

3-(4-Chloro-phenyl)-2-methyl-5-propyl-4H-pyrazolo[1,5-a]pyrimidin-7-one

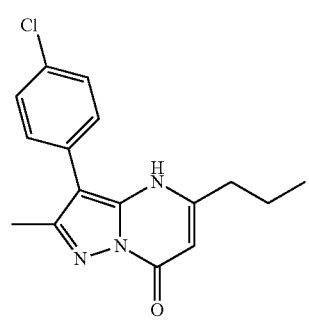 [SMILES: CCCc1cc(=O)n2nc(C)c(-c3ccc(Cl)cc3)c2[nH]1]

Example 23

5-Benzyl-3-(4-methoxy-phenyl)-2-methyl-4H-pyrazolo[1,5-a]pyrimidin-7-one

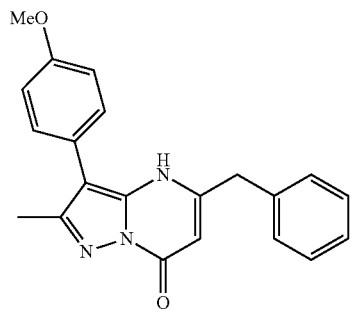 [SMILES: COc1ccc(-c2c(C)nn3c(=O)cc(Cc4ccccc4)[nH]c23)cc1]

Example 24

2-Benzyl-3-(4-chloro-phenyl)-5-methoxymethyl-4H-pyrazolo[1,5-a]pyrimidin-7-one

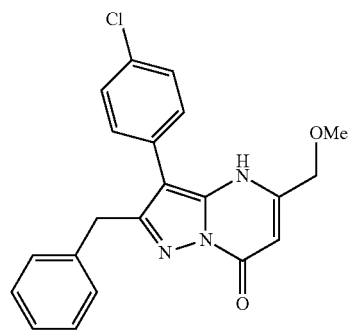 [SMILES: COCc1cc(=O)n2nc(Cc3ccccc3)c(-c3ccc(Cl)cc3)c2[nH]1]

Example 25

2-Benzyl-3-(4-chloro-phenyl)-5-phenyl-4H-pyrazolo[1,5-a]pyrimidin-7-one

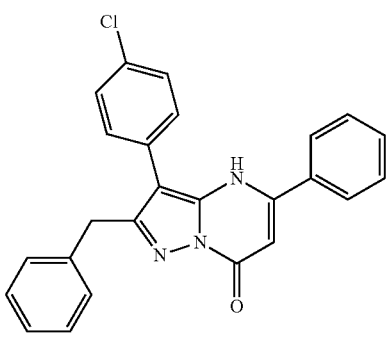 [SMILES: O=c1cc(-c2ccccc2)[nH]c2c(-c3ccc(Cl)cc3)c(Cc3ccccc3)nn12]

Example 26

2-Benzyl-3-(4-chlorophenyl)-6,7-dihydro-4H-cyclopenta[d]pyrazolo[1,5-a]pyrimidin-8(5H)-one

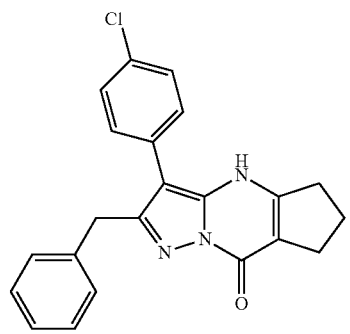 [SMILES: O=c1c2c([nH]c3c(-c4ccc(Cl)cc4)c(Cc4ccccc4)nn13)CCC2]

Example 27

3-(4-Chlorophenyl)-2-methyl-6,7-dihydro-4H-cyclopenta[d]pyrazolo[1,5-a]pyrimidin-8(5H)-one

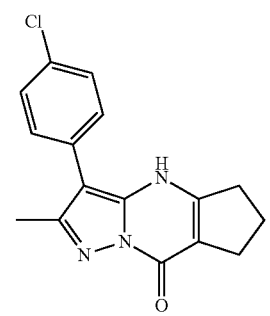 [SMILES: Cc1nn2c(=O)c3c([nH]c2c1-c1ccc(Cl)cc1)CCC3]

Example 28

3-(4-Chloro-phenyl)-2,5-dimethyl-4H-pyrazolo[1,5-a]pyrimidin-7-one

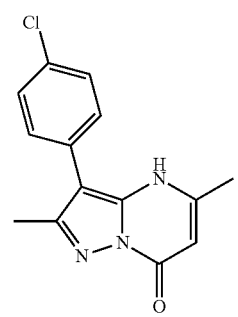

Example 29

2-(4-Chloro-phenyl)-5-methoxymethyl-4H-pyrazolo[1,5-a]pyrimidin-7-one

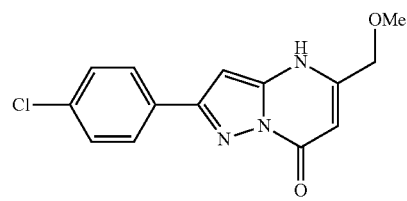 [SMILES: COCc1cc(=O)n2nc(-c3ccc(Cl)cc3)cc2[nH]1]

Example 30

5-Isopropyl-2-(4-methoxy-phenyl)-3-phenyl-4H-pyrazolo[1,5-a]pyrimidin-7-one

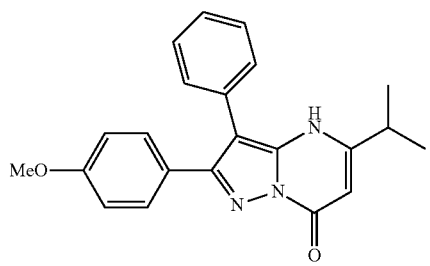 [SMILES: COc1ccc(-c2nn3c(=O)cc(C(C)C)[nH]c3c2-c2ccccc2)cc1]

Example 31

2-(4-Methoxy-benzyl)-5-methyl-3-phenyl-4H-pyrazolo[1,5-a]pyrimidin-7-one

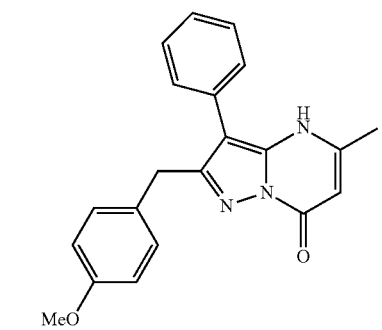 [SMILES: COc1ccc(Cc2nn3c(=O)cc(C)[nH]c3c2-c2ccccc2)cc1]

Example 32

6-Ethyl-2-(4-methoxy-benzyl)-5-methyl-3-phenyl-4H-pyrazolo[1,5-a]pyrimidin-7-one

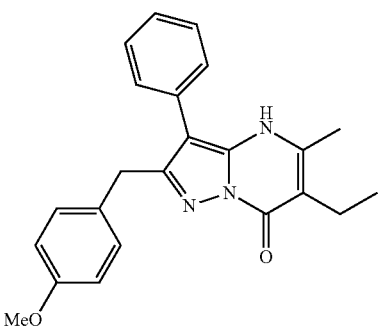 [SMILES: CCc1c(C)[nH]c2c(-c3ccccc3)c(Cc3ccc(OC)cc3)nn2c1=O]

Example 33

3-(4-Chloro-phenyl)-6-ethyl-2,5-dimethyl-4H-pyrazolo[1,5-a]pyrimidin-7-one

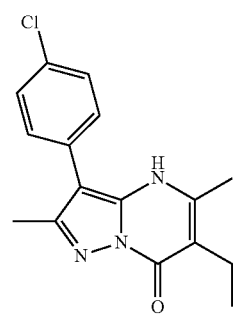 [SMILES: CCc1c(C)[nH]c2c(-c3ccc(Cl)cc3)c(C)nn2c1=O]

Example 34

5-Benzyl-2,3-diphenyl-4H-pyrazolo[1,5-a]pyrimidin-7-one

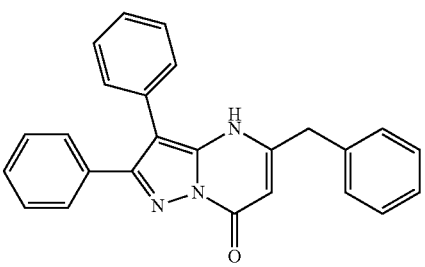 [SMILES: O=c1cc(Cc2ccccc2)[nH]c2c(-c3ccccc3)c(-c3ccccc3)nn12]

Example 35

2,3-Diphenyl-6,7-dihydro-4H-cyclopenta[d]pyrazolo[1,5-a]pyrimidin-8(5H)-one

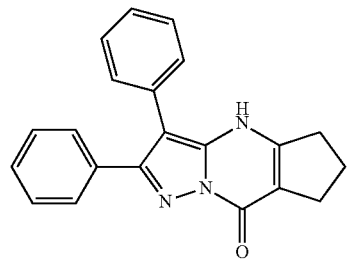 [SMILES: O=c1c2c([nH]c3c(-c4ccccc4)c(-c4ccccc4)nn13)CCC2]

Example 36

(7-oxo-2,3-diphenyl-4,7-dihydro-pyrazolo[1,5-a]pyrimidin-5-yl)-acetic acid ethyl ester

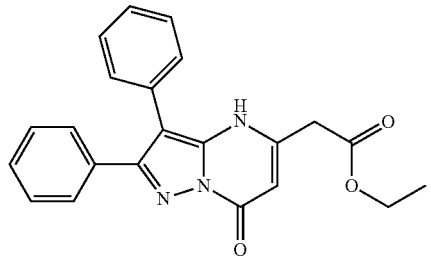 [SMILES: CCOC(=O)Cc1cc(=O)n2nc(-c3ccccc3)c(-c3ccccc3)c2[nH]1]

Example 37

2-Methyl-3-phenyl-5-p-tolyl-4H-pyrazolo[1,5-a]pyrimidin-7-one

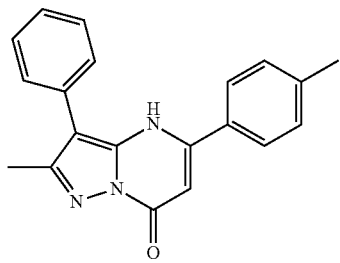

Example 38

3-(4-Fluoro-phenyl)-5-(4-methoxy-phenyl)-2-methyl-4H-pyrazolo[1,5-a]pyrimidin-7-one

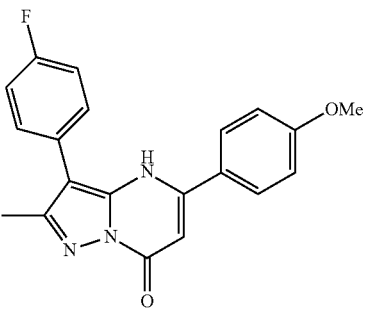 [SMILES: COc1ccc(-c2cc(=O)n3nc(C)c(-c4ccc(F)cc4)c3[nH]2)cc1]

Example 39

2-(3-Bromo-phenyl)-5-methyl-4H-pyrazolo[1,5-a]pyrimidin-7-one

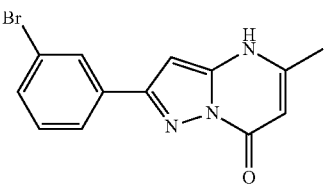 [SMILES: Cc1cc(=O)n2nc(-c3cccc(Br)c3)cc2[nH]1]

Example 40

5-(2,3-Dihydrobenzo[b][1,4]dioxin-6-yl)-3-phenylpyrazolo[1,5-a]pyrimidin-7(4H)-one

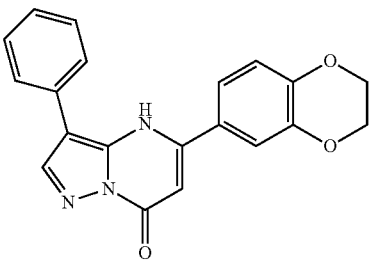

A solution of 4-phenyl-1H-pyrazol-5-amine (159 mg, 1.00 mmol, 1.00 equiv) and ethyl 3-(2,3-dihydrobenzo[b][1,4]dioxin-6-yl)-3-oxopropanoate (250 mg, 1.00 mmol, 1.00 equiv) in acetic acid (2 mL) was placed in an 8-mL sealed tube and stirred overnight at 110° C. The resulting solution was concentrated to dryness, then diluted with 5 mL methanol and filtered. The solids obtained were washed with methanol and concentrated to afford 187 mg (54%) of 5-(2,3-dihydrobenzo[b][1,4]dioxin-6-yl)-3-phenylpyrazolo[1,5-a]pyrimidin-7(4H)-one as a light pink solid.
LC-MS (ES, m/z): 346 [M+H]$^+$ ¹H-NMR (300 MHz, DMSO, ppm): 12.07 (s, 1H), 8.17-7.01 (m, 9H), 5.99 (s, 1H), 4.32 (s, 4H)

Example 41

5-(2,3-Dihydrobenzo[b][1,4]dioxin-6-yl)-2-methyl-3-phenylpyrazolo[1,5-a]pyrimidin-7(4H)-one

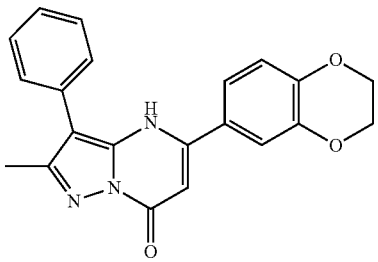

A solution of 3-methyl-4-phenyl-1H-pyrazol-5-amine (173 mg, 1.00 mmol, 1.00 equiv) and ethyl 3-(2,3-dihydrobenzo[b][1,4]dioxin-6-yl)-3-oxopropanoate (250 mg, 1.00 mmol, 1.00 equiv) in acetic acid (2 mL) was placed in an 8-mL sealed tube and stirred overnight at 110° C. The resulting solution was concentrated to dryness, diluted with 5 mL methanol, and filtered. The solids obtained were washed with methanol, and concentrated to afford in 210 mg (58%) of 5-(2,3-dihydrobenzo[b][1,4]dioxin-6-yl)-2-methyl-3-phenylpyrazolo[1,5-a]pyrimidin-7(4H)-one as a yellow solid.

LC-MS (ES, m/z): 360 [M+H]⁺

¹H-NMR (300 MHz, DMSO, ppm) 11.95 (s, 1H), 7.50-6.98 (m, 8H), 5.90 (s, 1H), 4.30 (s, 4H), 2.3 (s, 3H)

Example 42

5-(Benzo[d][1,3]dioxol-5-yl)-3-phenylpyrazolo[1,5-a]pyrimidin-7(4H)-one

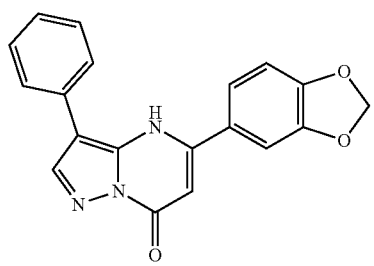 [SMILES: O=c1cc(-c2ccc3c(c2)OCO3)[nH]c2c(-c3ccccc3)cnn12]

A solution of 4-phenyl-1H-pyrazol-5-amine (220 mg, 1.38 mmol, 1.00 equiv), ethyl 3-(benzo[d][1,3]dioxol-5-yl)-3-oxopropanoate (370 mg, 1.57 mmol, 1.13 equiv) and acetic acid (2 mL) was placed in an 8-mL sealed tube and stirred overnight at 110° C. The resulting mixture was concentrated under vacuum. The solids obtained were washed with 3×5 mL of methanol and dried in vacuo, resulting in 0.25 g (55%) of 5-(benzo[d][1,3]dioxol-5-yl)-3-phenylpyrazolo[1,5-a]pyrimidin-7(4H)-one as a yellow solid.

LC-MS (ES, m/z): 332 [M+H]+

¹H-NMR (300 MHz, DMSO, ppm) δ 12.09 (s, 1H), 8.18-7.09 (m, 9H), 6.15 (s, 2H), 6.00 (s, 1H)

Example 43

5-(Benzo[d][1,3]dioxol-5-yl)-2-methyl-3-phenylpyrazolo[1,5-a]pyrimidin-7(4H)-one

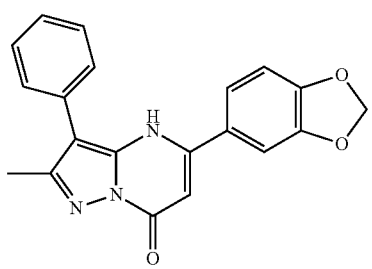 [SMILES: Cc1nn2c(=O)cc(-c3ccc4c(c3)OCO4)[nH]c2c1-c1ccccc1]

A solution of 3-methyl-4-phenyl-1H-pyrazol-5-amine (190 mg, 1.10 mmol, 1.00 equiv), ethyl 3-(benzo[d][1,3]dioxol-5-yl)-3-oxopropanoate (350 mg, 1.48 mmol, 1.35 equiv), and acetic acid (2 mL) was placed in an 8-mL sealed tube and stirred overnight at 110° C. The resulting mixture was concentrated under vacuum. The resulting solids were washed with 3×5 mL of methanol and dried in vacuo, resulting in 0.17 g (45%) of 5-(benzo[d][1,3]dioxol-5-yl)-2-methyl-3-phenylpyrazolo[1,5-a]pyrimidin-7(4H)-one as a yellow solid.

LC-MS (ES, m/z): 346 [M+H]+

¹H-NMR (300 MHZ, DMSO, ppm) δ 11.97 (s, 1H), 7.53-7.06 (m, 8H), 6.13 (s, 2H), 5.91 (s, 1H), 2.31 (s, 3H)

Example 44

5-(2,3-Dihydrobenzo[b][1,4]dioxin-6-yl)-3-(pyridin-2-yl)pyrazolo[1,5-a]pyrimidin-7(4H)-one

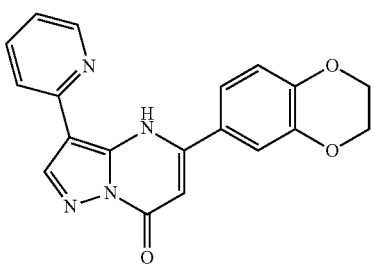 [SMILES: O=c1cc(-c2ccc3c(c2)OCCO3)[nH]c2c(-c3ccccn3)cnn12]

Example 45

5-(2,3-Dihydrobenzo[b][1,4]dioxin-6-yl)-3-(pyridin-3-yl)pyrazolo[1,5-a]pyrimidin-7(4H)-one

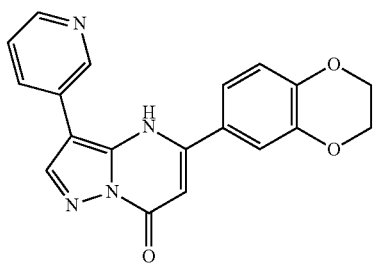 [SMILES: O=c1cc(-c2ccc3c(c2)OCCO3)[nH]c2c(-c3cccnc3)cnn12]

Example 46

5-(Benzo[d][1,3]dioxol-5-yl)-3-(pyridin-3-yl)pyrazolo[1,5-a]pyrimidin-7(4H)-one

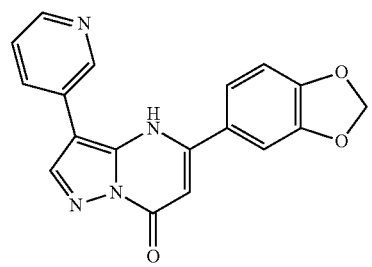 [SMILES: O=c1cc(-c2ccc3c(c2)OCO3)[nH]c2c(-c3cccnc3)cnn12]

Example 47

5-(Benzo[d][1,3]dioxol-5-yl)-3-(pyridin-2-yl)pyrazolo[1,5-a]pyrimidin-7(4H)-one

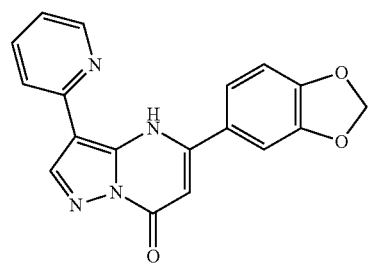 [SMILES: O=c1cc(-c2ccc3c(c2)OCO3)[nH]c2c(-c3ccccn3)cnn12]

A solution of 4-(pyridin-2-yl)-1H-pyrazol-5-amine (80 mg, 0.50 mmol, 1.00 equiv) and ethyl 3-(benzo[d][1,3]dioxol-5-yl)-3-oxopropanoate (122 mg, 0.55 mmol, 1.10 equiv) and acetic acid (2 mL) was placed in an 8-mL sealed tube and stirred overnight at 110° C. The resulting solution was concentrated to dryness, diluted with 5 mL methanol and filtered. The resulting solid was washed with methanol and dried in vacuo to afford 70 mg (42%) of 5-(benzo[d][1,3]dioxol-5-yl)-3-(pyridin-2-yl)pyrazolo[1,5-a]pyrimidin-7(4H)-one as a yellow solid.

LC-MS (ES, m/z): 256 [M+H]+

$^1$H-NMR (300 MHz, DMSO, ppm) 8.69-7.15 (m, 8H), 6.27 (s, 1H), 6.18 (s, 1H)

Example 48

5-(Benzo[d][1,3]dioxol-5-yl)-2-methyl-3-(pyridin-2-yl)pyrazolo[1,5-a]pyrimidin-7(4H)-one

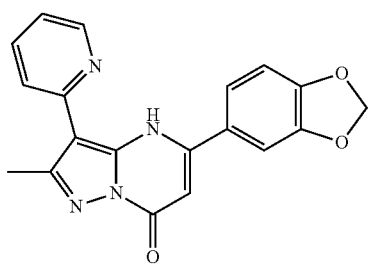 [SMILES: Cc1nn2c(=O)cc(-c3ccc4c(c3)OCO4)[nH]c2c1-c1ccccn1]

Example 49

5-(Benzo[d][1,3]dioxol-5-yl)-2-methyl-3-(pyridin-3-yl)pyrazolo[1,5-a]pyrimidin-7(4H)-one

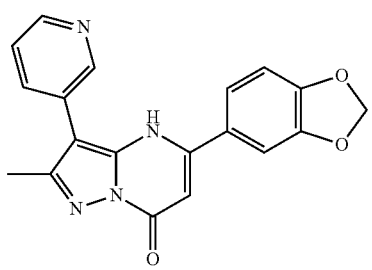 [SMILES: Cc1nn2c(=O)cc(-c3ccc4c(c3)OCO4)[nH]c2c1-c1cccnc1]

Example 50

5-(2,3-Dihydrobenzo[b][1,4]dioxin-6-yl)-2-methyl-3-(pyridin-2-yl)pyrazolo[1,5-a]pyrimidin-7(4H)-one

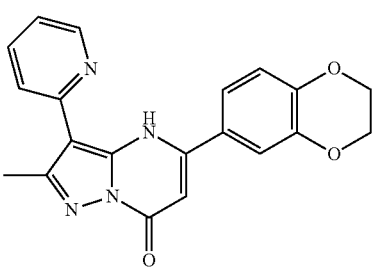 [SMILES: Cc1nn2c(=O)cc(-c3ccc4c(c3)OCCO4)[nH]c2c1-c1ccccn1]

Example 51

5-(2,3-Dihydrobenzo[b][1,4]dioxin-6-yl)-2-methyl-3-(pyridin-3-yl)pyrazolo[1,5-a]pyrimidin-7(4H)-one

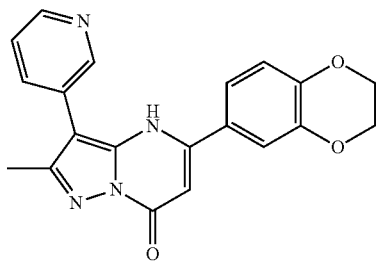 [SMILES: Cc1nn2c(=O)cc(-c3ccc4c(c3)OCCO4)[nH]c2c1-c1cccnc1]

Example 52

5-Phenyl-3-(pyridin-2-yl)pyrazolo[1,5-a]pyrimidin-7(4H)-one

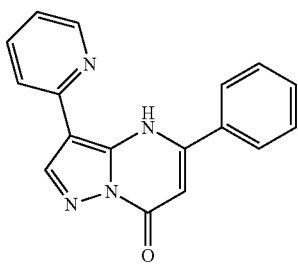 [SMILES: O=c1cc(-c2ccccc2)[nH]c2c(-c3ccccn3)cnn12]

A mixture of 4-(pyridin-2-yl)-1H-pyrazol-5-amine (80 mg, 0.50 mmol, 1.00 equiv) and methyl 3-oxo-3-phenylpropanoate (98 mg, 0.55 mmol, 1.10 equiv) and acetic acid (2 mL) was placed in a 8-mL sealed tube and stirred overnight at 110° C. The resulting solution was concentrated to dryness, diluted with 5 mL methanol and filtered, the solids obtained were washed with methanol and dried in vacuo to afford 90 mg (62%) of 5-phenyl-3-(pyridin-2-yl)pyrazolo[1,5-a]pyrimidin-7(4H)-one as a yellow solid.

LC-MS (ES, m/z): 289 [M+H]$^+$ $^1$H-NMR (300 MHz, DMSO, ppm) 8.70-7.26 (m, 8H), 6.38 (s, 1H)

Example 53

3-(4-Fluorophenyl)-5-(4-methoxyphenyl)pyrazolo[1,5-a]pyrimidin-7(4H)-one

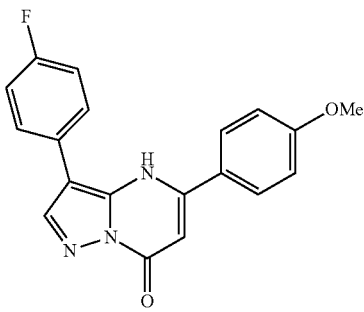 [SMILES: COc1ccc(-c2cc(=O)n3ncc(-c4ccc(F)cc4)c3[nH]2)cc1]

Example 54

5-(2,3-Dihydrobenzo[b][1,4]dioxin-6-yl)-2-methyl-3-phenylpyrazolo[1,5-a]pyrimidin-7(4H)-one

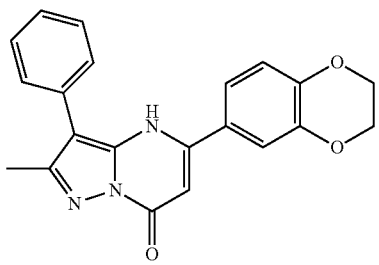 [SMILES: Cc1nn2c(=O)cc(-c3ccc4c(c3)OCCO4)[nH]c2c1-c1ccccc1]

Example 55

5-(2,3-Dihydrobenzofuran-5-yl)-2-methyl-3-phenylpyrazolo[1,5-a]pyrimidin-7(4H)-one

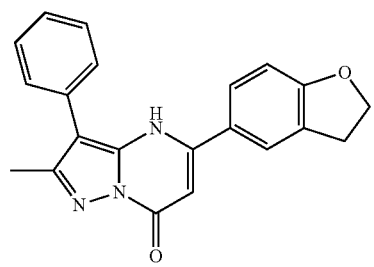 [SMILES: Cc1nn2c(=O)cc(-c3ccc4c(c3)CCO4)[nH]c2c1-c1ccccc1]

Example 56

5-(4-Methoxyphenyl)-3-(pyridin-2-yl)pyrazolo[1,5-a]pyrimidin-7(4H)-one

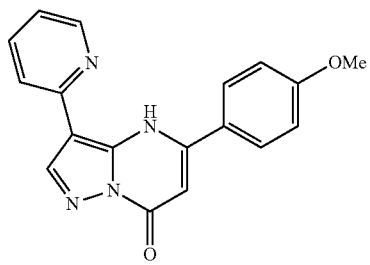 [SMILES: COc1ccc(-c2cc(=O)n3ncc(-c4ccccn4)c3[nH]2)cc1]

Example 57

3-(4-Chlorophenyl)-5-(4-methoxyphenyl)-2-methylpyrazolo[1,5-a]pyrimidin-7(4H)-one

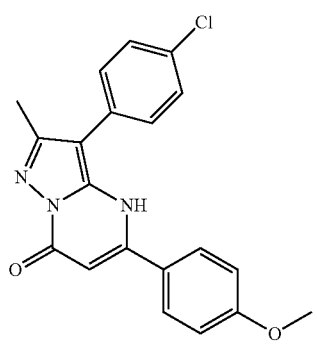 [SMILES: COc1ccc(-c2cc(=O)n3nc(C)c(-c4ccc(Cl)cc4)c3[nH]2)cc1]

Step 1. Methyl 3-(4-methoxyphenyl)-3-oxopropanoate

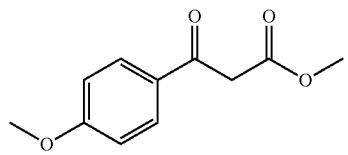

Into a 500-mL 3-necked round-bottom flask, was placed a solution of 1-(4-methoxyphenyl)ethanone (30 g, 200 mmol, 1.00 equiv) in dimethyl carbonate (50 mL). To the above was added NaH (13.6 g, 340 mmol, 1.70 equiv, 60%) in several batches. The resulting solution was allowed to react, with stirring, for 10 min while the temperature was maintained at reflux. It was poured into 400 mL of ice-water to get a solution, then washed with ether (50 mL×2), acidified with AcOH, extracted with ethyl acetate (200 mL×3), and the ethyl acetate layers were washed with saturated NaHCO$_3$ and dried over Na$_2$SO$_4$. The solution was concentrated to provide 37 g (87%) of methyl 3-(4-methoxyphenyl)-3-oxopropanoate as yellow oil.

Step 2. 3-(4-Chlorophenyl)-5-(4-methoxyphenyl)-2-methylpyrazolo[1,5-a]pyrimidin-7(4H)-one Into a 20-mL sealed tube, was placed a solution of 4-(4-chlorophenyl)-3-methyl-1H-pyrazol-5-amine (311 mg, 1.50 mmol, 1.00 equiv) in AcOH (3 mL). To the mixture was added methyl 3-(4-methoxyphenyl)-3-oxopropanoate (343.5 mg, 1.65 mmol, 1.10 equiv). The resulting solution was allowed to react, with stirring, overnight at 110° C. It was concentrated and purified by preparative TLC. The solid was washed with MeOH and dried to get 200 mg (36%) of 3-(4-chlorophenyl)-5-(4-methoxyphenyl)-2-methylpyrazolo[1,5-a]pyrimidin-7(4H)-one as a white solid.

LC-MS (ES, m/z): [M+H]$^+$ calcd. for C$_{20}$H$_{16}$ClN$_3$O$_2$: 366. Found: 366.

$^1$H-NMR (300 MHz, DMSO): δ 3.18 (3H, d, J=4.8 Hz), 3.82 (3H, s), 4.11 (1H, d, J=5.7 Hz), 7.04 (2H, d, J=7.5 Hz), 7.50 (2H, d, J=7.8 Hz), 7.94 (2H, s), 8.06 (2H, s).

Example 58

3,5-Bis(4-chlorophenyl)-2-methylpyrazolo[1,5-a]pyrimidin-7(4H)-one

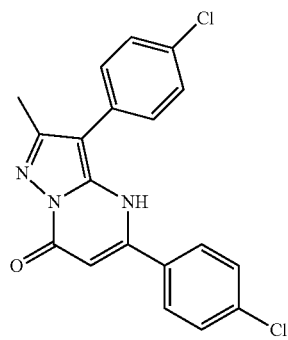 [SMILES: Cc1nn2c(=O)cc(-c3ccc(Cl)cc3)[nH]c2c1-c1ccc(Cl)cc1]

Into a 20-mL sealed tube, was placed a solution of 4-(4-chlorophenyl)-3-methyl-1H-pyrazol-5-amine (311 mg, 1.50 mmol, 1.00 equiv) in acetic acid (3 mL). To the mixture was added methyl 3-(4-chlorophenyl)-3-oxopropanoate (350 mg, 1.64 mmol, 1.10 equiv). The resulting solution was allowed to react, with stirring, overnight while the temperature was maintained at reflux. The resulting mixture was concentrated under vacuum. The resulting material was diluted with 5 mL of MeOH. The solids were collected by filtration and washed with 2×2 mL of MeOH. This resulted in 250 mg (43%) of 3,5-bis(4-chlorophenyl)-2-methylpyrazolo[1,5-a]pyrimidin-7(4H)-one as a white solid.

LC-MS (ES, m/z): [M+H]+ calcd. for $C_{19}H_{13}Cl_2N_3O$: 370. Found: 370

$^1$H-NMR (300 MHz, DMSO): δ 2.32 (3H, s), 6.00 (1H, s), 7.54 (4H, s), 7.63 (2H, d, J=8.4 Hz), 7.81 (2H, d, J=7.5 Hz), 12.14 (1H, s)

Example 59

5-(4-Chlorophenyl)-3-(4-methoxyphenyl)-2-methylpyrazolo[1,5-a]pyrimidin-7(4H)-one

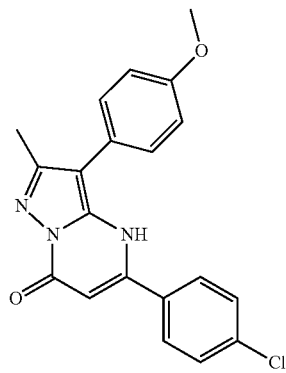 [SMILES: COc1ccc(-c2c(C)nn3c(=O)cc(-c4ccc(Cl)cc4)[nH]c23)cc1]

Step 1. 2-(4-Methoxyphenyl)-3-oxobutanenitrile

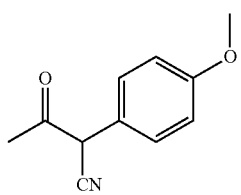

Into a 500-mL 3-necked round-bottom flask, was placed a solution of 2-(4-methoxyphenyl)acetonitrile (20 g, 136 mmol, 1.00 equiv) in ethyl acetate (400 mL). To the above was added sodium (3.8 g, 165 mmol, 1.21 equiv) in several batches. The resulting solution was allowed to react, with stirring, overnight while the temperature was maintained at reflux. The resulting mixture was filtered, and the solids were dissolved in 400 mL of $H_2O$. The resulting solution was extracted with 2×100 mL of ether and the aqueous layers combined, acidified with AcOH, and extracted with ethyl acetate (200 mL×3). The ethyl acetate layers were washed with Sat. $NaHCO_3$, dried over $Na_2SO_4$., and concentrated to get 24.7 g (95%) of 2-(4-methoxyphenyl)-3-oxobutanenitrile as a white solid.

Step 2.
4-(4-Methoxyphenyl)-3-methyl-1H-pyrazol-5-amine

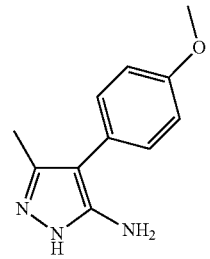

Into a 500-mL round-bottom flask, was placed a solution of 2-(4-methoxyphenyl)-3-oxobutanenitrile (9.46 g, 50 mmol, 1.00 equiv) in toluene (250 mL). To this was added $NH_2NH_2.H_2O$ (5 g, 100 mmol, 2.00 equiv). To the mixture was added acetic acid (10.2 g, 170 mmol, 3.40 equiv). The resulting solution was allowed to react, with stirring, overnight while the temperature was maintained at reflux. The resulting mixture was concentrated under vacuum and 6N HCl was added to the residue. The precipitate formed was filtered, washed with 10 mL of ethyl acetate, resulting in 8.6 g (84%) of 4-(4-methoxyphenyl)-3-methyl-1H-pyrazol-5-amine as a white solid.

Step 3. Methyl 3-(4-chlorophenyl)-3-oxopropanoate

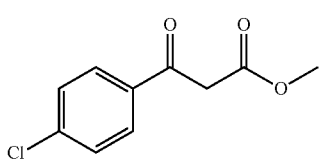

Into a 1000-mL 3-necked round-bottom flask, was placed a solution of 1-(4-chlorophenyl)ethanone (30 g, 194 mmol, 1.00 equiv) in THF (150 mL). To the mixture was added dimethyl carbonate (30 g, 333 mmol, 1.70 equiv). To the above was added NaH (13 g, 325 mmol, 1.70 equiv, 60%) in several batches. The resulting solution was allowed to react, with stirring, for 2 hr while the temperature was maintained at reflux. The reaction was then quenched by pouring into 100 mL of water/ice. The THF layer was separated and acidified with AcOH, then washed with sat. $NaHCO_3$, dried over $Na_2SO_4$, and concentrated to get 30 g (69%) of methyl 3-(4-chlorophenyl)-3-oxopropanoate as yellow oil.

Step 4. 5-(4-chlorophenyl)-3-(4-methoxyphenyl)-2-methylpyrazolo[1,5-a]pyrimidin-7(4H)-one

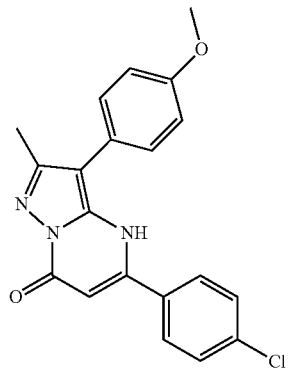 [SMILES: COc1ccc(-c2c(C)nn3c(=O)cc(-c4ccc(Cl)cc4)[nH]c23)cc1]

Into a 20-mL sealed tube, was placed a solution of 4-(4-methoxyphenyl)-3-methyl-1H-pyrazol-5-amine (304 mg, 1.50 mmol, 1.00 equiv) in AcOH (3 mL). To the mixture was added methyl 3-(4-chlorophenyl)-3-oxopropanoate (350 mg, 1.65 mmol, 1.10 equiv). The resulting solution was allowed to react, with stirring, overnight at 110° C. The resulting mixture was concentrated to dryness and 3 mL MeOH was added. The mixture was filtered and the collected solid was washed with 1×5 mL of MeOH. This resulted in 200 mg (33%) of 5-(4-chlorophenyl)-3-(4-methoxyphenyl)-2-methylpyrazolo[1,5-a]pyrimidin-7(4H)-one as a white solid.

LC-MS (ES, m/z): [M+H]+ calcd. for $C_{20}H_{16}ClN_3O_2$: 366. Found: 366

$^1$H-NMR (300 MHz, DMSO): δ 2.38 (3H, s), 3.80 (3H, s), 6.46 (1H, s), 7.04 (2H, d, J=8.1 Hz), 7.55 (2H, d, J=7.8 Hz), 7.73 (2H, s), 8.11 (2H, s)

Example 60

2-Methyl-3,5-diphenylpyrazolo[1,5-a]pyrimidin-7(4H)-one

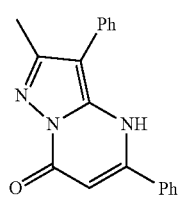 [SMILES: Cc1nn2c(=O)cc(-c3ccccc3)[nH]c2c1-c1ccccc1]

Step 1. 3-Oxo-2-phenylbutanenitrile

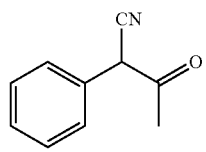

Into a 1-L round-bottom flask, was placed a solution of 2-phenylacetonitrile (20.65 g, 176 mmol, 1.00 equiv) in EtOAc (400 mL). To the mixture was added Na (5.70 g, 248 mmol, 1.40 equiv). The resulting solution was allowed to react, with stirring, overnight while the temperature was maintained at 80° C. in an oil bath. The solids were collected by filtration. The resulting solution was diluted with water. The pH value of the solution was adjusted to 5 with acetic acid. The resulting solution was extracted with ethyl acetate and the organic layers were combined, washed with aqueous NaHCO$_3$ (sat.), dried over anhydrous Na$_2$SO$_4$, and concentrated under vacuum. This resulted in 21.70 g (77%) of 3-oxo-2-phenylbutanenitrile as a brown solid.

Step 2. 3-Methyl-4-phenyl-1H-pyrazol-5-amine

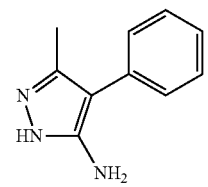

Into a 500-mL round-bottom flask, was placed a solution of 3-oxo-2-phenylbutanenitrile (10.05 g, 63.2 mmol, 1.00 equiv) in toluene (250 mL). To this was added NH$_2$NH$_2$.H$_2$O (6.41 g, 128 mmol, 2.03 equiv). To the mixture was added acetic acid (13.05 g, 217 mmol, 3.44 equiv). The resulting solution was allowed to react, with stirring, overnight at 115° C. The resulting mixture was concentrated under vacuum. The pH value of the solution was adjusted to 1 with HCl (1:1). The resulting solution was extracted with ether and the aqueous layers were combined. NH$_3$.H$_2$O was employed to adjust the pH to 10. The solids were collected by filtration. This resulted in 9.95 g (91%) of 3-methyl-4-phenyl-1H-pyrazol-5-amine as a yellow solid.

Step 3. Methyl 3-oxo-3-phenylpropanoate

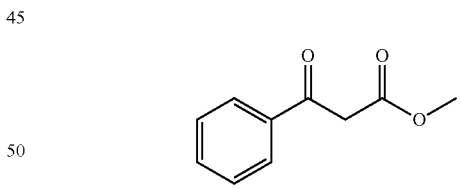

Into a 1000-mL round-bottom flask, was placed acetophenone (19.97 g, 166 mmol, 1.00 equiv). To this was added dimethyl carbonate (50 mL). To the mixture was added NaH (11.45 g, 477 mmol, 2.87 equiv). The resulting solution was allowed to react, with stirring, for 5 min at 70° C. The reaction was then quenched by the addition of water/ice. The resulting mixture was washed with ether. AcOH was employed to adjust the pH to 5. The resulting solution was extracted with 3×50 mL of ethyl acetate and the organic layers were combined, washed with aqueous NaHCO$_3$ (sat.), dried over anhydrous Na$_2$SO$_4$, and concentrated under vacuum. This resulted in 19.31 g (crude) of methyl 3-oxo-3-phenylpropanoate as a brown oil.

Step 4. 2-Methyl-3,5-diphenylpyrazolo[1,5-a]pyrimidin-7(4H)-one

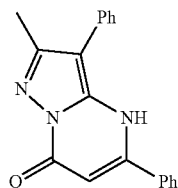 [SMILES: Cc1nn2c(=O)cc(-c3ccccc3)[nH]c2c1-c1ccccc1]

Into a 10-mL sealed tube, was placed a solution of 3-methyl-4-phenyl-1H-pyrazol-5-amine (220 mg, 1.27 mmol, 1.00 equiv) in AcOH (2 mL). To the mixture was added methyl 3-oxo-3-phenylpropanoate (270 mg, 1.52 mmol, 1.19 equiv). The resulting solution was allowed to react, with stirring, overnight at 115° C. After cooling, the reaction mixture was concentrated in vacuo. The resultant residue was diluted with MeOH. The solids formed were filtered, washed with MeOH, dried to result in 0.09 g (24%) of 2-methyl-3,5-diphenylpyrazolo[1,5-a]pyrimidin-7(4H)-one as a straw yellow solid.

LC-MS (ES, m/z): [M+H]+ calcd. for $C_{19}H_{16}N_3O$: 302. Found: 302

$^1$H-NMR: (DMSO, ppm): δ 8.08-7.14 (10H, m), 6.07 (1H, s), 2.51 (3H, s)

Example 61

3-(4-Chlorobenzyl)-5-(4-chlorophenyl)-2-methylpyrazolo[1,5-a]pyrimidin-7(4H)-one

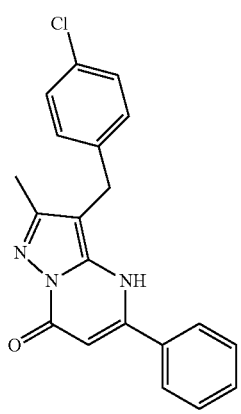 [SMILES: Cc1nn2c(=O)cc(-c3ccccc3)[nH]c2c1Cc1ccc(Cl)cc1]

Into a 10-mL sealed tube, was placed a solution of 4-(4-chlorobenzyl)-3-methyl-1H-pyrazol-5-amine (240 mg, 1.08 mmol, 1.00 equiv) in acetic acid (2 mL), and methyl 3-oxo-3-phenylpropanoate (212 mg, 1.19 mmol, 1.10 equiv). The resulting solution was stirred overnight at 110° C. It was concentrated in vacuo and chromatographed (MeOH:CH$_2$Cl$_2$=1:20) to get 110 mg (26%) of 3-(4-chlorobenzyl)-5-(4-chlorophenyl)-2-methylpyrazolo[1,5-a]pyrimidin-7(4H)-one as a white solid.

LC-MS (ES, m/z): 350 [M+H]+

$^1$H-NMR (300 MHz, DMSO, ppm): δ 2.13 (3H, s), 4.07 (2H, s), 5.91 (1H, s), 7.21-7.81 (9H, m), 12.20 (1H, s)

Example 62

3-Benzyl-2-methyl-5-phenylpyrazolo[1,5-a]pyrimidin-7(4H)-one

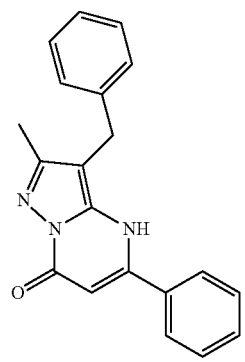

Step 1. 2-Benzylidene-3-oxobutanenitrile

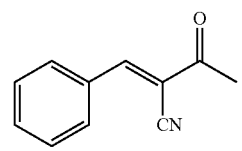

Into a 100-mL round-bottom flask, was placed a solution of 3-oxobutanenitrile (4.15 g, 50.00 mmol, 1.00 equiv) in toluene (50 mL), benzaldehyde (5.3 g, 50.00 mmol, 1.00 equiv), piperidine (430 mg, 5.06 mmol, 0.10 equiv), and acetic acid (600 mg, 10.00 mmol, 0.20 equiv). The resulting solution was heated to reflux for 8 hr. The resulting mixture was concentrated under vacuum. The residue was applied onto a silica gel column with ethyl acetate/petroleum ether (1:10). This resulted in 2.3 g (24%) of 2-benzylidene-3-oxobutanenitrile as a yellow solid.

Step 2. 2-Benzyl-3-oxobutanenitrile

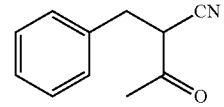

Into a 50-mL round-bottom flask, was placed a solution of 2-benzylidene-3-oxobutanenitrile (1.3 g, 6.84 mmol, 1.00 equiv, 90%) in methanol (20 mL), and anhydrous palladium on carbon (0.5 g, 10%). The resulting solution was stirred overnight at 30° C. The solids were filtered off and the resulting mixture was concentrated under vacuum. This resulted in 1.2 g (91%) of 2-benzyl-3-oxobutanenitrile as a brown oil.

Step 3. 4-Benzyl-3-methyl-1H-pyrazol-5-amine

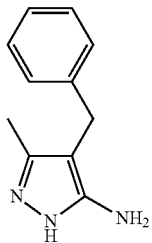

Into a 100-mL round-bottom flask, was placed a solution of 2-benzyl-3-oxobutanenitrile (1.2 g, 6.24 mmol, 1.00 equiv, 90%) in ethanol (40 mL), and NH$_2$NH$_2$.H$_2$O (690 mg, 13.80 mmol, 2.00 equiv). The resulting solution was heated to reflux overnight. The resulting mixture was concentrated under vacuum. The resulting solution was diluted with 50/50 mL of EA/water. The aqueous layer was extracted with 3×30 mL of ethyl acetate and the organic layers combined and dried over anhydrous sodium sulfate. Filtration and concentration in vacuo provided 1 g (80%) of 4-benzyl-3-methyl-1H-pyrazol-5-amine as brown oil.

Step 4. 3-Benzyl-2-methyl-5-phenylpyrazolo[1,5-a]pyrimidin-7(4H)-one

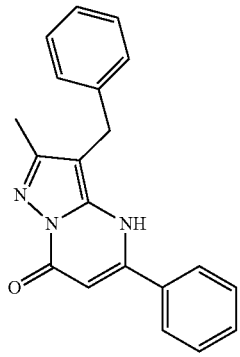 [SMILES: Cc1nn2c(=O)cc(-c3ccccc3)[nH]c2c1Cc1ccccc1]

Into a 10-mL sealed tube, was placed a solution of 4-benzyl-3-methyl-1H-pyrazol-5-amine (187 mg, 1.00 mmol, 1.00 equiv) in acetic acid (2 mL), and methyl 3-oxo-3-phenylpropanoate (178 mg, 1.00 mmol, 1.00 equiv). The resulting solution was stirred overnight at 110° C. The reaction was monitored by TLC (EA:PE=1:5). The resulting mixture was concentrated under vacuum. This resulted in 50 mg (16%) of 3-benzyl-2-methyl-5-phenylpyrazolo[1,5-a]pyrimidin-7(4H)-one as a yellow solid.

LC-MS: 315 [M+H]+

$^1$H-NMR (300 MHz, DMSO, ppm): δ 2.16 (3H, s), 4.06 (2H, s), 5.92 (1H, s), 7.17-7.84 (10H, m), 12.20 (1H, s)

Example 63

3-(4-Chlorobenzyl)-5-(4-isopropoxyphenyl)-2-methylpyrazolo[1,5-a]pyrimidin-7(4H)-one

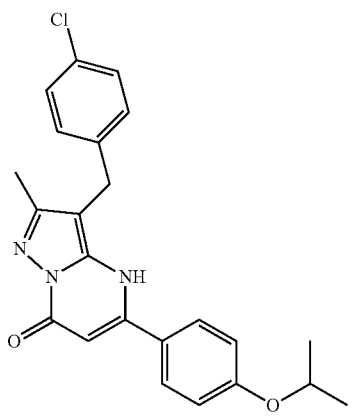 [SMILES: Cc1nn2c(=O)cc(-c3ccc(OC(C)C)cc3)[nH]c2c1Cc1ccc(Cl)cc1]

Step 1. 1-(4-Isopropoxyphenyl)ethanone

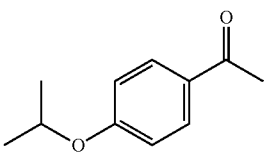

Into a 500-mL 3-necked round-bottom flask, was placed a solution of 1-(4-hydroxyphenyl)ethanone (20.3 g, 149.26 mmol, 1.00 equiv) in CH$_3$CN (200 mL), i-PrBr (60.53 g, 496.15 mmol, 3.32 equiv), potassium carbonate (62.15 g, 450.36 mmol, 3.02 equiv),. The resulting solution was stirred overnight at 70° C. The solids were filtered out. The resulting mixture was concentrated under vacuum. This resulted in 26.38 g (99%) of 1-(4-isopropoxyphenyl)ethanone as a straw yellow solid.

Step 2. Methyl 3-(4-isopropoxyphenyl)-3-oxopropanoate

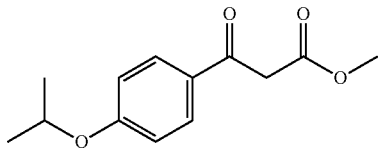 [SMILES: COC(=O)CC(=O)c1ccc(OC(C)C)cc1]

Into a 500-mL 3-necked round-bottom flask, was placed 1-(4-isopropoxyphenyl)ethanone (16.50 g, 92.70 mmol, 1.00 equiv), dimethyl carbonate (50 mL), and sodium hydride (5.47 g, 159.54 mmol, 1.72 equiv, 70%). The resulting solution was stirred for 5 mins at 80° C. The solids were collected by filtration. The resulting solution was extracted with 3×100 mL of ethyl acetate and the layers combined and concentrated under vacuum. This resulted in 21.33 g (98%) of methyl 3-(4-isopropoxyphenyl)-3-oxopropanoate as straw yellow oil.

Step 3. 3-(4-Chlorobenzyl)-5-(4-isopropoxyphenyl)-2-methylpyrazolo[1,5-a]pyrimidin-7(4H)-one

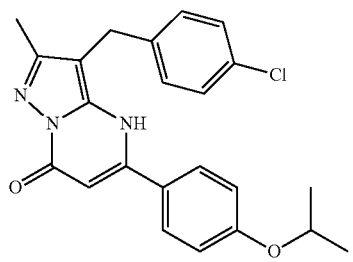 [SMILES: Cc1nn2c(=O)cc(-c3ccc(OC(C)C)cc3)[nH]c2c1Cc1ccc(Cl)cc1]

Into a 8-mL sealed tube, was placed 4-(4-chlorobenzyl)-3-methyl-1H-pyrazol-5-amine (410 mg, 1.86 mmol, 1.00 equiv), methyl 3-(4-isopropoxyphenyl)-3-oxopropanoate (980 mg, 4.15 mmol, 2.24 equiv), and AcOH (2 mL). The resulting solution was stirred overnight at 110° C. The resulting mixture was concentrated under vacuum. The resulting mixture was washed with 3×5 mL of methanol. This resulted in 0.1986 g (26%) of 3-(4-chlorobenzyl)-5-(4-isopropoxyphenyl)-2-methylpyrazolo[1,5-a]pyrimidin-7(4H)-one as a white solid.

LC-MS (ES, m/z): 408 [M+H]+
$^1$H-NMR (300 MHz, DMSO, ppm): δ 11.95 (H, s), 7.74-7.09 (8H, m), 5.86 (H, s), 4.79-4.71 (H, m), 4.06 (2H, s), 2.12 (3H, s), 1.32 (3H, s), 1.30 (3H, s)

Example 64

3-(4-Chlorobenzyl)-5-(3-methoxyphenyl)-2-methylpyrazolo[1,5-a]pyrimidin-7(4H)-one

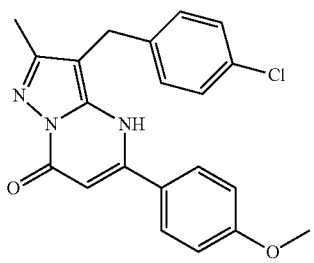 [SMILES: COc1ccc(-c2cc(=O)n3nc(C)c(Cc4ccc(Cl)cc4)c3[nH]2)cc1]

Step 1. Methyl 3-(3-methoxyphenyl)-3-oxopropanoate

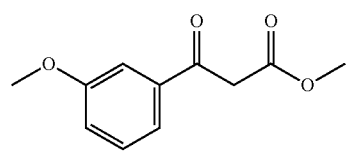

Into a 500-mL 3-necked round-bottom flask, was placed 1-(3-methoxyphenyl)ethanone (12.10 g, 80.67 mmol, 1.00 equiv), dimethyl carbonate (50 mL), and sodium hydride (5.60 g, 140.00 mmol, 1.74 equiv, 60%). The resulting solution was stirred for 7 mins at 80° C. After cooling to 0° C., the reaction mixture was poured into the ice-water (200 ml). The reaction mixture was extracted with ether. The aqueous layer was acidified to pH about 4, and extracted with ethyl acetate. The organic layer were combined and washed with brine, dried over anhydrous Na$_2$SO$_4$, concentrated in vacuo to result in 13.8 g (82%) of methyl 3-(3-methoxyphenyl)-3-oxopropanoate as a straw yellow oil.

Step 2. 3-(4-Chlorobenzyl)-5-(3-methoxyphenyl)-2-methylpyrazolo[1,5-a]pyrimidin-7(4H)-one

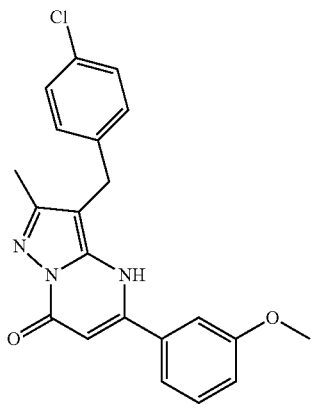 [SMILES: COc1cccc(-c2cc(=O)n3nc(C)c(Cc4ccc(Cl)cc4)c3[nH]2)c1]

Into a 10-mL sealed tube, was placed a solution of 4-(4-chlorobenzyl)-3-methyl-1H-pyrazol-5-amine (333 mg, 1.50 mmol, 1.00 equiv) in AcOH (3 mL), and methyl 3-(3-methoxyphenyl)-3-oxopropanoate (343 mg, 1.65 mmol, 1.10 equiv). The resulting solution was stirred overnight at 110° C. Then it was concentrated to dryness, diluted with 5 mL MeOH, and filtered. The collected solid was washed with MeOH and dried to get 330 mg (57%) of 3-(4-chlorobenzyl)-5-(3-methoxyphenyl)-2-methylpyrazolo[1,5-a]pyrimidin-7(4H)-one as a white solid.

LC-MS (ES, m/z): 380 [M+H]+
$^1$H-NMR (300 MHz, DMSO, ppm): δ 12.11 (s, 1H), 7.15-7.52 (m, 8H), 5.94 (s, 1H) 4.10 (s, 2H), 3.86 (s, 3H), 2.13 (s, 3H)

Example 65

Methyl 4-(3-(4-chlorobenzyl)-2-methyl-7-oxo-4,7-dihydropyrazolo[1,5-a]pyrimidin-5-yl)benzoate

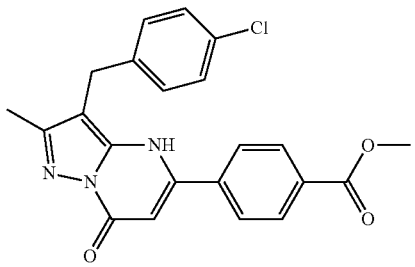

Step 1. Methyl 4-(3-methoxy-3-oxopropanoyl)benzoate

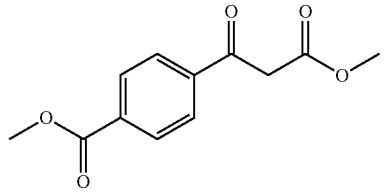

Into a 100-mL round-bottom flask purged with nitrogen, was added methyl 3-(4-bromophenyl)-3-oxopropanoate (1.54 g, 5.99 mmol, 1.00 equiv), methanol (6 mL), N,N-dimethylformamide (12 mL), DIEA (2.1 mL), and PdCl$_2$(dppf).CHCl$_3$ (152 mg, 0.18 mmol, 0.03 equiv). The resulting solution was stirred for 4 h at 70° C. under a CO atmosphere. The reaction was then quenched by the addition of 25 mL of 0.5 N hydrochloric acid. The solids were filtered out. The resulting solution was extracted with 3×50 mL of ethyl acetate and the organic layers combined and dried over anhydrous sodium sulfate and concentrated under vacuum. The residue was applied onto a silica gel column with ethyl acetate/petroleum ether (1:50). This resulted in 0.71 g (48%) of methyl 4-(3-methoxy-3-oxopropanoyl)benzoate as a pink solid.

Step 2. Methyl 4-(3-(4-chlorobenzyl)-2-methyl-7-oxo-4,7-dihydropyrazolo[1,5-a]pyrimidin-5-yl)benzoate

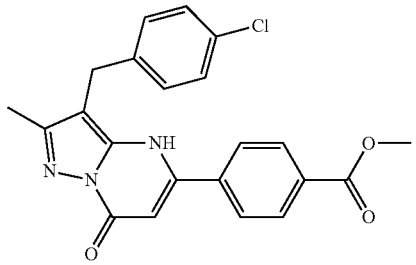

Into a 10-mL sealed tube, was placed a solution of 4-(4-chlorobenzyl)-3-methyl-1H-pyrazol-5-amine (222 mg, 1.00 mmol, 1.00 equiv) and methyl 4-(3-methoxy-3-oxopropanoyl)benzoate (260 mg, 1.10 mmol, 1.10 equiv) in acetic acid (2 mL). The resulting solution was stirred overnight at 110° C. Then it was concentrated to dryness and diluted with 5 mL MeOH, filtered, the solid was washed with MeOH and dried to afford 170 mg (40%) of methyl 4-(3-(4-chlorobenzyl)-2-methyl-7-oxo-4,7-dihydropyrazolo[1,5-a]pyrimidin-5-yl)benzoate as a yellow solid.

LC-MS-PH (ES, m/z): 408 [M+H]$^+$ $^1$H-NMR (300 MHz, DMSO, ppm) 12.26 (s, 1H), 8.11 (d, J=8.1 Hz, 2H), 7.93 (d, J=8.4 Hz, 2H), 7.33 (d, J=8.4 Hz, 2H), 7.21 (d, J=8.4 Hz, 2H), 6.00 (s, 1H), 4.07 (s, 2H), 3.91 (s, 3H), 2.13 (s, 3H)

Example 66

4-(3-(4-Chlorobenzyl)-2-methyl-7-oxo-4,7-dihydropyrazolo[1,5-a]pyrimidin-5-yl)benzamide

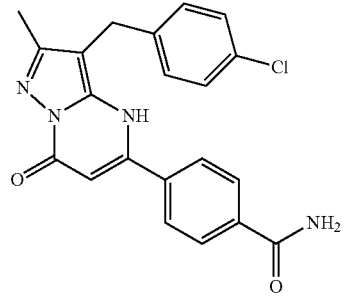 [SMILES: Cc1nn2c(=O)cc(-c3ccc(C(N)=O)cc3)[nH]c2c1Cc1ccc(Cl)cc1]

Into a 40-mL sealed tube purged and maintained with an inert atmosphere of nitrogen, was placed tetrahydrofuran (15 mL) and Al(CH$_3$)$_3$ (3 mL). To the above, NH$_3$(g) was introduced. The resulting solution was stirred for 1 hr. To the above methyl 4-(3-(4-chlorobenzyl)-2-methyl-7-oxo-4,7-dihydropyrazolo[1,5-a]pyrimidin-5-yl)benzoate (210 mg, 0.47 mmol, 1.00 equiv, 91%) was added. The resulting solution was stirred overnight at 60° C. The reaction was then quenched by the addition of 10 mL of hydrochloric acid. The resulting solution was extracted with 2×5 mL of dichloromethane and the organic layers combined and concentrated under vacuum. This resulted in 0.05 g (27%) of 4-(3-(4-chlorobenzyl)-2-methyl-7-oxo-4,7-dihydropyrazolo[1,5-a]pyrimidin-5-yl)benzamide as a light yellow solid.

LC-MS-PH (ES, m/z): 393 [M+H]$^+$ $^1$H-NMR (300 MHz, DMSO, ppm): 812.17 (s, 1H), 8.15-7.21 (m, 10H), 5.97 (s, 1H), 4.06 (s, 2H), 2.11 (s, 3H)

Example 67

3-(4-Chlorobenzyl)-2-methyl-5-(4-(trifluoromethyl)phenyl)pyrazolo[1,5-a]pyrimidin-7(4H)-one

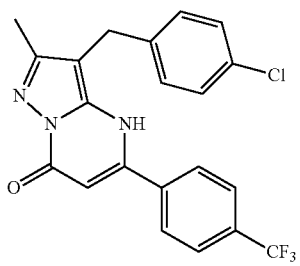 [SMILES: Cc1nn2c(=O)cc(-c3ccc(C(F)(F)F)cc3)[nH]c2c1Cc1ccc(Cl)cc1]

Step 1. Methyl 3-oxo-3-(4-(trifluoromethyl)phenyl)propanoate

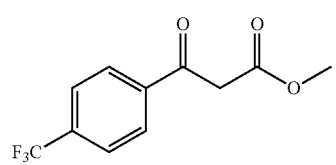 [SMILES: COC(=O)CC(=O)c1ccc(C(F)(F)F)cc1]

Into a 500-mL 3-necked round-bottom flask, was placed 1-(4-(trifluoromethyl)phenyl)ethanone (15.27 g, 81.22 mmol, 1.00 equiv), dimethyl carbonate (50 mL), sodium hydride (5.53 g, 138.25 mmol, 1.70 equiv, 60%). The resulting solution was stirred for 5 mins at 25° C. The mixture was concentrated by evaporation. The solids were collected by filtration and washed with 3×50 ml of H₂O. This resulted in 19.28 g (96%) of methyl 3-oxo-3-(4-(trifluoromethyl)phenyl)propanoate as a yellow solid.

Step 2. 3-(4-Chlorobenzyl)-2-methyl-5-(4-(trifluoromethyl)phenyl)pyrazolo[1,5-a]pyrimidin-7(4H)-one

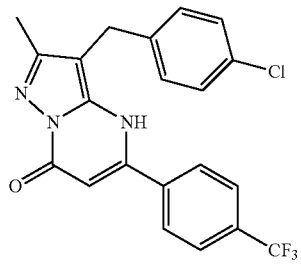 [SMILES: Cc1nn2c(=O)cc(-c3ccc(C(F)(F)F)cc3)[nH]c2c1Cc1ccc(Cl)cc1]

Into a 8-mL sealed tube, was placed 4-(4-chlorobenzyl)-3-methyl-1H-pyrazol-5-amine (460 mg, 2.08 mmol, 1.00 equiv), methyl 3-oxo-3-(4-(trifluoromethyl)phenyl)propanoate (620 mg, 2.52 mmol, 1.21 equiv), AcOH (2 mL). The resulting solution was stirred overnight at 110° C. The resulting mixture was concentrated under vacuum. The resulting mixture was washed with 3×5 mL of methanol. This resulted in 0.277 g (32%) of 3-(4-chlorobenzyl)-2-methyl-5-(4-(trifluoromethyl)phenyl)pyrazolo[1,5-a]pyrimidin-7(4H)-one as a straw yellow solid.

LC-MS (ES, m/z): 418 [M+H]+
¹H-NMR (300 MHz, DMSO, ppm): δ 12.29 (H, s), 8.04-7.22 (8H, m), 6.00 (H, s), 4.07 (2H, s), 2.13 (3H, s)

Example 68

3-Benzyl-5-(3,4-dimethoxyphenyl)-2-methylpyrazolo[1,5-a]pyrimidin-7(4H)-one

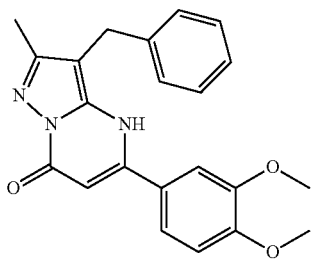 [SMILES: COc1ccc(-c2cc(=O)n3nc(C)c(Cc4ccccc4)c3[nH]2)cc1OC]

Into a 8-mL sealed tube, was placed 4-benzyl-3-methyl-1H-pyrazol-5-amine (460 mg, 2.46 mmol, 1.00 equiv), methyl 3-(3,4-dimethoxyphenyl)-3-oxopropanoate (740 mg, 3.11 mmol, 1.26 equiv), AcOH (2 mL). The resulting solution was stirred overnight at 110° C. The resulting mixture was concentrated under vacuum. The resulting residue was diluted with MeOH, filtered, washed with methanol, and dried to result in 0.35 g (38%) of 3-benzyl-5-(3,4-dimethoxyphenyl)-2-methylpyrazolo[1,5-a]pyrimidin-7(4H)-one as a white solid.

LC-MS (ES, m/z): 376 [M+H]+
¹H-NMR (300 MHz, DMSO, ppm): δ 11.97 (H, s), 7.38-7.14 (8H, m), 5.94 (H, s), 4.07 (2H, s), 3.88 (3H, s), 3.84 (3H, s), 2.12 (3H, s)

Example 69

3-(4-Chlorobenzyl)-5-(3,4-dimethoxyphenyl)-2-methylpyrazolo[1,5-a]pyrimidin-7(4H)-one

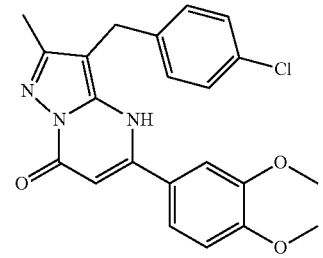 [SMILES: COc1ccc(-c2cc(=O)n3nc(C)c(Cc4ccc(Cl)cc4)c3[nH]2)cc1OC]

Step 1. Methyl 3-(3,4-dimethoxyphenyl)-3-oxopropanoate

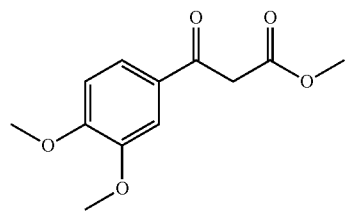

Into a 1000-mL 3-necked round-bottom flask, was placed 1-(3,4-dimethoxyphenyl)ethanone (15.33 g, 85.17 mmol, 1.00 equiv), dimethyl carbonate (50 mL), and sodium hydride (6.06 g, 151.50 mmol, 1.78 equiv, 60%). The resulting solution was stirred for 7 min at 75° C. After cooling, the reaction mixture was poured into ice-water (200 ml). The pH of aqueous layer was adjusted to 4 with 4N HCl. The resulting solution was extracted with 3×100 mL of ethyl acetate and the organic layers combined, dried over anhydrous Na₂SO₄, and concentrated under vacuum. This resulted in 19.66 g (97%) of methyl 3-(3,4-dimethoxyphenyl)-3-oxopropanoate as brown yellow oil.

Step 2. 3-(4-Chlorobenzyl)-5-(3,4-dimethoxyphenyl)-2-methylpyrazolo[1,5-a]pyrimidin-7(4H)-one

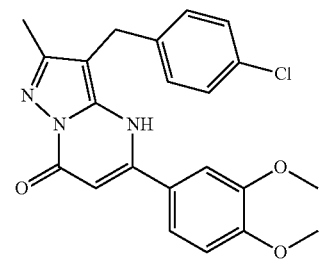 [SMILES: COc1ccc(-c2cc(=O)n3nc(C)c(Cc4ccc(Cl)cc4)c3[nH]2)cc1OC]

Into a 8-mL sealed tube, was placed 4-(4-chlorobenzyl)-3-methyl-1H-pyrazol-5-amine (470 mg, 2.13 mmol, 1.00 equiv), methyl 3-(3,4-dimethoxyphenyl)-3-oxopropanoate (670 mg, 2.82 mmol, 1.32 equiv), and AcOH (2 mL). The resulting solution was stirred overnight at 110° C. The resulting mixture was concentrated under vacuum and washed with 5 mL of methanol. This resulted in 0.095 g (11%) of 3-(4-chlorobenzyl)-5-(3,4-dimethoxyphenyl)-2-methylpyrazolo[1,5-a]pyrimidin-7(4H)-one as a straw yellow solid.

LC-MS (ES, m/z): 410 [M+H]+

$^1$H-NMR (300 MHz, DMSO, ppm): δ 11.95 (H, s), 7.37-7.14 (7H, m), 5.94 (H, s), 4.02 (2H, s), 3.88 (3H, s), 3.83 (3H, s), 2.12 (3H, s)

Example 70

3-(2-Chlorobenzyl)-5-(4-methoxyphenyl)-2-methylpyrazolo[1,5-a]pyrimidin-7-(4H)-one

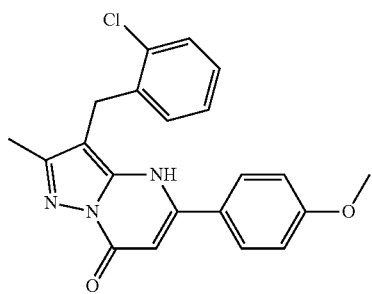

Step 1. 2-(2-Chlorobenzyl)-3-oxobutanenitrile

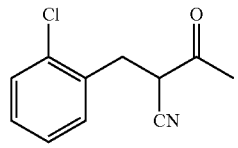

Into a 250-mL 3-necked round-bottom flask, was placed ethanol (100 mL). This was followed by the addition of Na (1.72 g, 74.78 mmol, 1.50 equiv) in several batches. The reaction was refluxed until the Na dissolved. To this was added a solution of 3-oxobutanenitrile (4.15 g, 50.00 mmol, 1.00 equiv) in ethanol (20 mL) dropwise with stirring, while the temperature was maintained at reflux. The reaction was refluxed for 1 h. Then, a solution of 1-(bromomethyl)-2-chlorobenzene (10.25 g, 50.00 mmol, 1.00 equiv) in ethanol (20 mL) was added dropwise with stirring, while the temperature was maintained at reflux. Refluxing continued for 2 hrs. Then the reaction was cooled to room temperature, concentrated to dryness and then suspended between water and ether. The aqueous layer was separated and extracted with ether. The aqueous layer was acidified with 3N HCl to pH<6 and extracted with EA. The organic layer was dried over Na$_2$SO$_4$, filtered and concentrated to dryness. The residue was chromatographed (PE:EA=1:50) to get 2.9 g (27%) of 2-(2-chlorobenzyl)-3-oxobutanenitrile as a colorless oil.

Step 2.
4-(2-Chlorobenzyl)-3-methyl-1H-pyrazol-5-amine

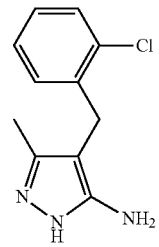

Into a 100-mL round-bottom flask, was placed a solution of 2-(2-chlorobenzyl)-3-oxobutanenitrile (2.9 g, 13.94 mmol, 1.00 equiv) in ethanol (30 mL), and NH$_2$NH$_2$.H$_2$O (1.39 g, 27.80 mmol, 2.00 equiv). The resulting solution was heated to reflux overnight. It was concentrated to dryness and 20 mL of 6N HCl was added. The precipitate formed was filtered, washed with water, and MeOH to afford a slurry. The slurry was trituated with ether, and dried to get 3.0 g (94%) of 4-(2-chlorobenzyl)-3-methyl-1H-pyrazol-5-amine as a white solid.

Step 3. 3-(2-Chlorobenzyl)-5-(4-methoxyphenyl)-2-methylpyrazolo[1,5-a]pyrimidin-7(4H)-one

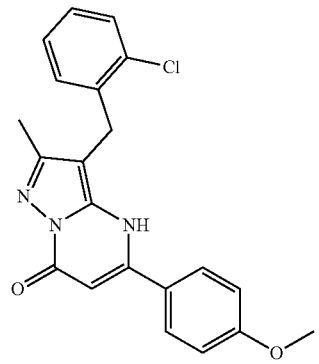 [SMILES: COc1ccc(-c2cc(=O)n3nc(C)c(Cc4ccccc4Cl)c3[nH]2)cc1]

Into a 10-mL sealed tube, was placed a solution of 4-(2-chlorobenzyl)-3-methyl-1H-pyrazol-5-amine (333 mg, 1.50 mmol, 1.00 equiv) in acetic acid (2 mL), methyl 3-(4-methoxyphenyl)-3-oxopropanoate (343 mg, 1.65 mmol, 1.10 equiv). The resulting solution was stirred overnight at 110° C. It was concentrated to dryness. Then 2 mL MeOH and 5 mL Ether were added. The reaction was filtered and the remaining solid was dried to afford 120 mg (20%) of 3-(2-chlorobenzyl)-5-(4-methoxyphenyl)-2-methylpyrazolo[1,5-a]pyrimidin-7(4H)-one as a white solid.

LC-MS (ES, m/z): 380 [M+H]+

$^1$H-NMR (300 MHz, DMSO, ppm): δ 11.95 (s, 1H), 6.95-7.75 (m, 8H), 5.88 (s, 1H), 4.13 (s, 2H), 3.84 (s, 3H), 2.08 (s, 3H)

Example 71

5-(4-Methoxyphenyl)-2-methyl-3-propylpyrazolo[1,5-a]pyrimidin-7(4H)-one

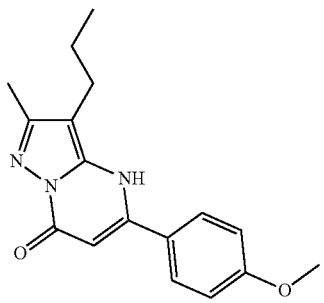

Step 1. 2-Acetylpentanenitrile

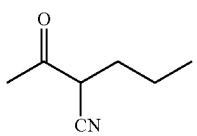

Into a 500-mL 3-necked round-bottom flask purged and maintained with an inert atmosphere of nitrogen, was placed a solution of diisopropylamine (11.1 g, 109.90 mmol, 1.10 equiv) in tetrahydrofuran (150 mL). This was followed by the addition of n-butyllithium (44 mL, 1.10 equiv, 2.5M in hexane) dropwise with stirring at −78° C. The resulting solution was stirred at −78° C. for 30 min. To this was added a solution of pentanenitrile (9.1 g, 109.64 mmol, 1.10 equiv) in tetrahydrofuran (50 mL) dropwise with stirring at −78° C. Then the mixture was stirred at −78° C. for 2 h. To the mixture was added a solution of ethyl acetate (8.8 g, 100.00 mmol, 1.00 equiv) in tetrahydrofuran (50 mL) dropwise with stirring at −78° C. The resulting solution was stirred for 1 h at −78° C. and slowly warmed to 0° C. The reaction was then quenched by the addition of 50 mL of saturated ammonium chloride at 0° C. The resulting solution was extracted with 3×50 mL of ethyl acetate and the organic layers were combined and dried over anhydrous sodium sulfate and concentrated under vacuum. This resulted in 11.2 g (81%) of 2-acetylpentanenitrile as yellow oil.

Step 2. 3-Methyl-4-propyl-1H-pyrazol-5-amine

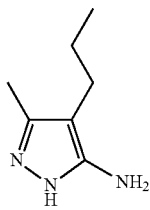

2-Acetylpentanenitrile (9.4 g, 75.20 mmol, 1.00 equiv) was placed into a 250-mL round-bottom flask with 150 mL of ethanol. Hydrazine hydrate (7.52 g, 150.40 mmol, 2.00 equiv) was added and the resulting solution was heated to reflux for 3 hr, and concentrated to dryness. The residue was dissolved in 30 mL 6N hydrochloric acid, and extracted with ethyl acetate (30 mL×2). The aqueous layer was basified to pH>7 with ammonia solution (25%), and then extracted with ethyl acetate (50 mL×3). The organic layer was dried over anhydrous sodium sulfate, and concentrated to dryness to afford 6.03 g (55%) of 3-methyl-4-propyl-1H-pyrazol-5-amine as yellow oil.

LC-MS: (ES, m/z): 140 [M+H]$^+$

Step 3. 5-(4-Methoxyphenyl)-2-methyl-3-propylpyrazolo[1,5-a]pyrimidin-7(4H)-one

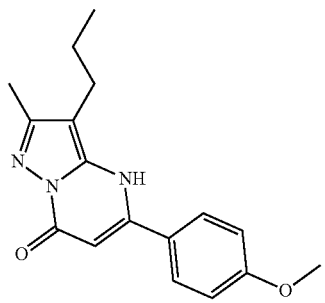

A solution of 3-methyl-4-propyl-1H-pyrazol-5-amine (278 mg, 2.00 mmol, 1.00 equiv) and methyl 3-(4-methoxyphenyl)-3-oxopropanoate (458 mg, 2.20 mmol, 1.10 equiv) in acetic acid (3 mL) was placed into an 8-mL sealed tube. The resulting solution was stirred overnight at 110° C. Then it was concentrated to dryness, diluted with 5 mL methanol, and the solids were collected via filtration. The solids were washed with methanol and dried to provide 245 mg (41%) of 5-(4-methoxyphenyl)-2-methyl-3-propylpyrazolo[1,5-a]pyrimidin-7(4H)-one as a white solid.

LC-MS: (ES, m/z): 298 [M+H]$^+$ $^1$H NMR (300 MHz, DMSO, ppm): δ 11.76 (s, 1H), 7.71 (d, J=8.1 Hz, 2H), 7.14 (d, J=8.7 Hz, 2H), 3.85 (s, 3H), 5.77 (d, J=1.5 Hz, 1H), 2.59 (t, J=7.5 Hz, 2H), 2.26 (s, 3H), 1.52 (q, J=7.5 Hz, 2H), 0.92 (t, J=7.5 Hz, 3H)

Example 72

5-(4-Methoxyphenyl)-3-(pyridin-3-yl)pyrazolo[1,5-a]pyrimidin-7(4H)-one

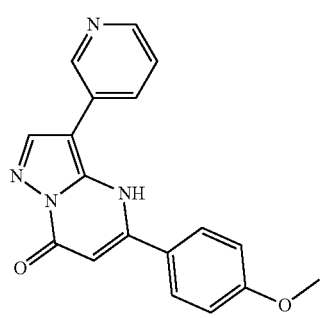 [SMILES: COc1ccc(-c2cc(=O)n3ncc(-c4cccnc4)c3[nH]2)cc1]

A solution of 4-(pyridin-3-yl)-1H-pyrazol-5-amine (200 mg, 1.25 mmol, 1.00 equiv) in acetic acid (3 mL) was placed into an 8-mL sealed tube. Then methyl 3-(4-methoxyphenyl)-3-oxopropanoate (286 mg, 1.38 mmol, 1.10 equiv) was added. The resulting solution was stirred overnight at 110° C. The resulting mixture was concentrated in vacuo. The resulting residue was purified by chromatography utilizing a neutral Al$_2$O$_3$ column with DCM:MeOH:Ammonia water (50:50:1). This resulted in 13.8 mg (3%) of 5-(4-methoxyphenyl)-3-(pyridin-3-yl)pyrazolo[1,5-a]pyrimidin-7(4H)-one as a yellow-green solid.

LC-MS: (ES, m/z): 319 [M+H]$^+$ $^1$H NMR (300 MHz, DMSO, ppm): δ 12.294-12.143 (s, 1H), 8.97 (s, 1H), 8.53 (s, 1H), 8.29 (s, 1H), 8.18 (s, 1H), 7.87 (d, J=8.1 Hz, 2H), 7.54 (s, 1H), 7.14 (d, J=8.1 Hz, 2H), 6.06 (s, 1H), 3.86 (s, 3H)

Example 73

3-Benzyl-2-methyl-5-(quinolin-6-yl)pyrazolo[1,5-a]pyrimidin-7(4H)-one

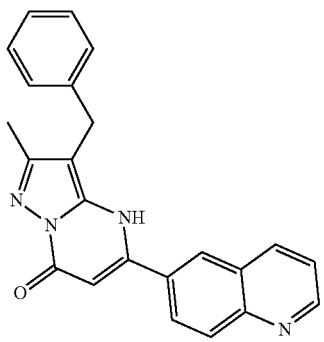 [SMILES: Cc1nn2c(=O)cc(-c3ccc4ncccc4c3)[nH]c2c1Cc1ccccc1]

Step 1. Quinoline-6-carboxylic acid

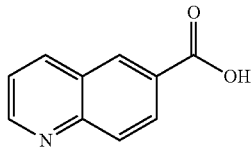 [SMILES: O=C(O)c1ccc2ncccc2c1]

Into a 500-mL 3-necked round-bottom flask, was placed 4-aminobenzoic acid (13.7 g, 100.00 mmol, 1.00 equiv), 4-nitrobenzoic acid (10.7 g, 64.07 mmol, 0.64 equiv), boric acid (5.9 g), FeSO$_4$.7H$_2$O (6.4 g), glycerol (38 mL), and concentrated sulfuric acid (18 mL). The resulting solution was stirred overnight at 140° C. The reaction mixture was cooled. The pH value of the solution was adjusted to 10 with sodium hydroxide (10%). The resulting solution was extracted with 2×100 mL of ethyl acetate and the aqueous layers were combined. The pH value of the aqueous layers was adjusted to pH 6 with conc. hydrochloric acid. The solids were collected by filtration. The resulting solution was diluted with 200 mL of methanol and the resulting solids were collected by filtration. The solid was dried to afford 17.3 g (95%) of quinoline-6-carboxylic acid as a dark-grey solid.

LC-MS: (ES, m/z):174 [M+H]$^+$

Step 2. 2,2-Dimethyl-5-(quinoline-6-carbonyl)-1,3-dioxane-4,6-dione

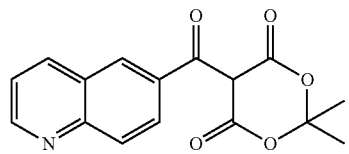 [SMILES: CC1(C)OC(=O)C(C(=O)c2ccc3ncccc3c2)C(=O)O1]

Into a 250-mL round-bottom flask, was placed a solution of quinoline-6-carboxylic acid (3.46 g, 20.00 mmol, 1.00 equiv), 2,2-dimethyl-1,3-dioxane-4,6-dione (3.17 g, 22.01 mmol, 1.10 equiv), 4-dimethylaminopyridine (3.66 g, 30.00 mmol, 1.50 equiv), and EDC (5 g, 26.04 mmol, 1.30 equiv) in dichloromethane (80 mL). The resulting solution was stirred overnight at room temperature. The reaction was quenched by the addition of 50 mL of 1N hydrochloric acid. The solids were filtered off. The resulting solution was extracted with 2×100 mL of dichloromethane, the organic layers were combined, dried over anhydrous sodium sulfate, and concentrated in vacuo. This resulted in 2.5 g (crude) of 2,2-dimethyl-5-(quinoline-6-carbonyl)-1,3-dioxane-4,6-dione as a brown solid.

Step 3. Ethyl 3-oxo-3-(quinolin-6-yl)propanoate

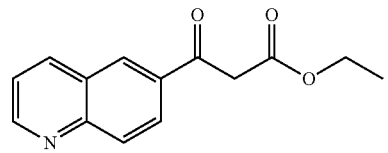 [SMILES: CCOC(=O)CC(=O)c1ccc2ncccc2c1]

A solution of 2,2-dimethyl-5-(quinoline-6-carbonyl)-1,3-dioxane-4,6-dione (2.5 g, 8.36 mmol, 1.00 equiv) in ethanol (150 mL) was placed into a 250-mL round-bottom flask. The resulting solution was heated to reflux overnight. Then it was cooled and concentrated to dryness. The mixture was applied onto a silica gel column with ethyl acetate/petroleum ether (1:10). This resulted in 200 mg (crude) of ethyl 3-oxo-3-(quinolin-6-yl)propanoate as red-brown oil.

Step 4. 3-Benzyl-2-methyl-5-(quinolin-6-yl)pyrazolo[1,5-a]pyrimidin-7(4H)-one

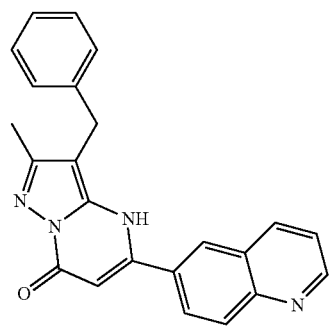 [SMILES: Cc1nn2c(=O)cc(-c3ccc4ncccc4c3)[nH]c2c1Cc1ccccc1]

Into a 8-mL sealed tube, was placed a solution of ethyl 3-oxo-3-(quinolin-6-yl)propanoate (200 mg, crude) and 4-benzyl-3-methyl-1H-pyrazol-5-amine (100 mg, 0.53 mmol, 1.00 equiv) in acetic acid (2 mL). The resulting solution was stirred overnight at 110° C. The resulting solution was concentrated to dryness and diluted with methanol. The solids were collected by filtration and washed with methanol. This resulted in 40 mg (20%) of 3-benzyl-2-methyl-5-(quinolin-6-yl)pyrazolo[1,5-a]pyrimidin-7(4H)-one as a yellow solid.

LC-MS: (ES, m/z): 367 [M+H]+

1H-NMR (300 MHz, DMSO, ppm) 12.31 (s, 1H), 9.03-7.16 (m, 11H), 6.08 (d, J=1.2 Hz, 1H), 4.11 (s, 2H), 2.14 (s, 3H)

Example 74

3-Benzyl-5-(1H-indol-6-yl)-2-methylpyrazolo[1,5-a]pyrimidin-7(4H)-one

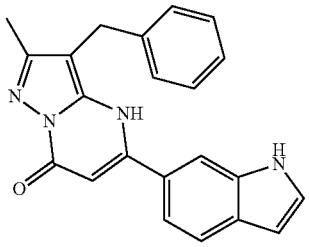 [SMILES: Cc1nn2c(=O)cc(-c3ccc4cc[nH]c4c3)[nH]c2c1Cc1ccccc1]

Step 1. Methyl 4-methyl-3-nitrobenzoate

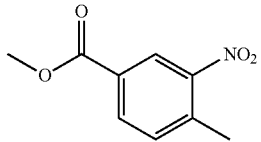

A solution of 4-methyl-3-nitrobenzoic acid (20.6 g, 113.81 mmol, 1.00 equiv) in methanol (200 mL) was placed into a 500-mL round-bottom flask. Then 2 mL of concentrated hydrochloric acid was added. The resulting solution was heated to reflux for 3 h. The resulting mixture was concentrated in vacuo, and diluted with 200 mL of ethyl acetate. The pH value of the solution was adjusted to pH 8 with sat. NaHCO₃. The resulting mixture was concentrated under vacuum. This resulted in 15.3 g (69%) of methyl 4-methyl-3-nitrobenzoate as a brown yellow solid.

Step 2. (E)-Methyl 4-(2-(dimethylamino)vinyl)-3-nitrobenzoate

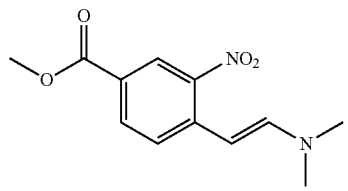

A solution of methyl 4-methyl-3-nitrobenzoate (10.5 g, 53.85 mmol, 1.00 equiv) in N,N-dimethylformamide (100 mL) was placed into a 500-mL round-bottom flask. Then DMF-DMA (18.7 g, 157.14 mmol, 2.92 equiv) was added and the resulting solution was stirred for 3 h at 100° C. Then the reaction was quenched by the addition of 300 mL of ice/water. The solids were collected by filtration. This resulted in 12.5 g (93%) of (E)-methyl 4-(2-(dimethylamino)vinyl)-3-nitrobenzoate as a red solid.

Step 3. Methyl 1H-indole-6-carboxylate

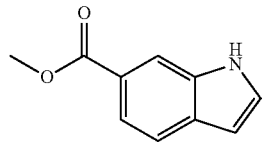

A solution of (E)-methyl 4-(2-(dimethylamino)vinyl)-3-nitrobenzoate (2.2 g, 8.80 mmol, 1.00 equiv) in tetrahydrofuran (50 mL) was placed into a 100-mL round-bottom flask. Then 2.4 g of palladium on carbon was added. An atmosphere of hydrogen gas was placed over the contents of the flask, and the reaction was stirred overnight at room temperature. Then the solids were filtered off, and the resulting mixture was concentrated in vacuo. This resulted in 1.3 g (84%) of methyl 1H-indole-6-carboxylate as brown oil.

Step 4. 1H-Indole-6-carboxylic acid

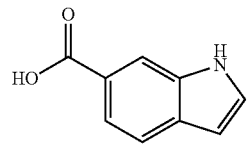 [SMILES: O=C(O)c1ccc2cc[nH]c2c1]

A solution of methyl 1H-indole-6-carboxylate (1.3 g, 7.43 mmol, 1.00 equiv) in tetrahydrofuran (20 mL) was placed into a 250-mL round-bottom flask. Then CH₃OH (20 mL), H₂O (10 mL), LiOH.H₂O (1.9 g, 45.24 mmol, 6.09 equiv) were added. The resulting solution was stirred overnight at 60° C. The resulting mixture was concentrated in vacuo, and diluted with water. The resulting solution was extracted with 2×100 mL of ether and the aqueous layers were combined. The pH value of the solution was adjusted to pH 3 with hydrochloric acid, and the solids were collected by filtration. This resulted in 0.68 g (57%) of 1H-indole-6-carboxylic acid as a light yellow solid.

Step 5. 5-(1H-Indole-6-carbonyl)-2,2-dimethyl-1,3-dioxane-4,6-dione

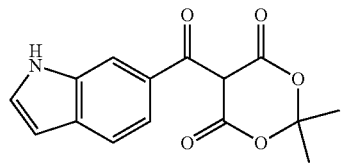 [SMILES: CC1(C)OC(=O)C(C(=O)c2ccc3cc[nH]c3c2)C(=O)O1]

2,2-Dimethyl-1,3-dioxane-4,6-dione (3.7 g, 25.69 mmol, 1.29 equiv), 4-dimethylaminopyridine (4.5 g, 36.89 mmol, 1.86 equiv), dichloromethane (30 mL), 1H-indole-6-carboxylic acid (3.2 g, 19.88 mmol, 1.00 equiv), EDC.HCl (4.9 g, 25.52 mmol, 1.28 equiv) were placed into a 100-mL round-bottom flask. The resulting solution was stirred overnight at room temperature. The pH value of the solution was adjusted to pH 3 with hydrochloric acid. The resulting solution was extracted with dichloromethane and the organic layers combined. The resulting mixture was concentrated in vacuo. This resulted in 5.3 g (93%) of 5-(1H-indole-6-carbonyl)-2,2-dimethyl-1,3-dioxane-4,6-dione as a yellow solid.

Step 6. Ethyl 3-(1H-indol-6-yl)-3-oxopropanoate

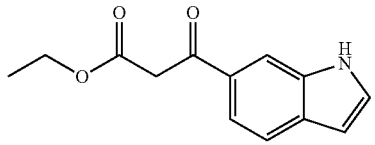 [SMILES: CCOC(=O)CC(=O)c1ccc2cc[nH]c2c1]

5-(1H-Indole-6-carbonyl)-2,2-dimethyl-1,3-dioxane-4,6-dione (5.3 g, 18.47 mmol, 1.00 equiv) and ethanol (200 mL) were placed into a 500-mL round-bottom flask. The resulting solution was stirred overnight at 95° C. Then the resulting mixture was concentrated in vacuo. This resulted in 4.2 g (crude) of ethyl 3-(1H-indol-6-yl)-3-oxopropanoate as brown red oil.

Step 7. 3-Benzyl-5-(1H-indol-6-yl)-2-methylpyrazolo[1,5-a]pyrimidin-7(4H)-one

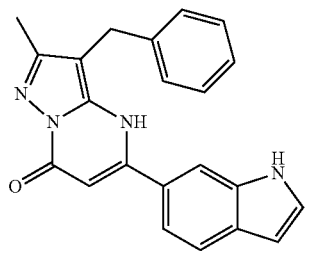 [SMILES: Cc1nn2c(=O)cc(-c3ccc4cc[nH]c4c3)[nH]c2c1Cc1ccccc1]

Into a 8-mL sealed tube, was placed 4-benzyl-3-methyl-1H-pyrazol-5-amine (190 mg, 1.02 mmol, 1.00 equiv), ethyl 3-(1H-indol-6-yl)-3-oxopropanoate (790 mg, 3.42 mmol, 3.37 equiv), AcOH (2 mL). The resulting solution was stirred overnight at 110° C. in an oil bath. The resulting mixture was concentrated under vacuum. The resulting mixture was washed with 3×5 mL of methanol. This resulted in 0.015 g (4%) of 3-benzyl-5-(1H-indol-6-yl)-2-methylpyrazolo[1,5-a]pyrimidin-7(4H)-one as a yellow solid.

LC-MS: (ES, m/z): 355 [M+H]+

1H-NMR (300 MHz, DMSO, ppm): δ 12.08 (s, 1H), 11.50 (s, 1H), 7.82-7.16 (m 1H), 6.55 (s, 1H), 5.89 (s, 1H), 4.05 (s, 2H), 2.14 (s, 3H)

Example 75

3-(3-Chlorobenzyl)-5-(benzo[d][1,3]dioxol-5-yl)-2-methylpyrazolo[1,5-a]pyrimidin-7(4H)-one

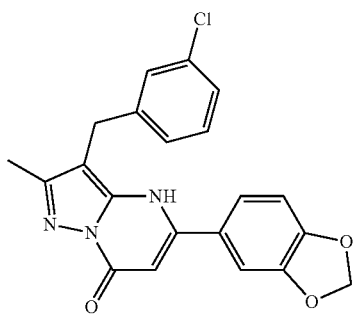 [SMILES: Cc1nn2c(=O)cc(-c3ccc4c(c3)OCO4)[nH]c2c1Cc1cccc(Cl)c1]

4-(3-Chlorobenzyl)-3-methyl-1H-pyrazol-5-amine (240 mg, 1.09 mmol, 1.00 equiv), ethyl 3-(benzo[d][1,3]dioxol-5-yl)-3-oxopropanoate (330 mg, 1.40 mmol, 1.29 equiv) and AcOH (2 mL) were placed into an 8-mL sealed tube. The resulting solution was stirred overnight at 110° C. Then the reaction was concentrated in vacuo, and the residue was washed with 3×5 mL of methanol. This resulted in 0.052 g (12%) of 3-(3-chlorobenzyl)-5-(benzo[d][1,3]dioxol-5-yl)-2-methylpyrazolo[1,5-a]pyrimidin-7(4H)-one as a white solid.

LC-MS: (ES, m/z): 394 [M+H]+

1H NMR (300 MHz, DMSO, ppm): δ 11.97 (s, 1H), 7.39-7.10 (m, 7H), 6.13 (s, 2H), 5.88 (s, 1H), 4.07 (s, 2H), 2.128 (s, 3H)

Example 76

3-(4-Chlorobenzyl)-5-(benzo[d][1,3]dioxol-5-yl)-2-methylpyrazolo[1,5-a]pyrimidin-7(4H)-one

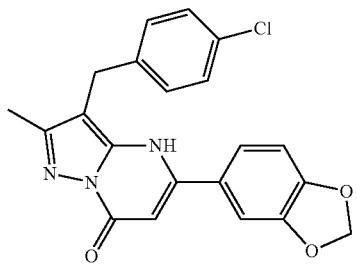 [SMILES: Cc1nn2c(=O)cc(-c3ccc4c(c3)OCO4)[nH]c2c1Cc1ccc(Cl)cc1]

4-(4-Chlorobenzyl)-3-methyl-1H-pyrazol-5-amine (220 mg, 1.00 mmol, 1.00 equiv), ethyl 3-(benzo[d][1,3]dioxol-5-yl)-3-oxopropanoate (370 mg, 1.57 mmol, 1.57 equiv), and AcOH (2 mL) were placed into an 8-mL sealed tube. The resulting reaction was stirred overnight at 110° C. Then the reaction was concentrated in vacuo and was washed with 3×5 mL of methanol. This resulted in 0.11 g (28%) of 3-(4-chlorobenzyl)-5-(benzo[d][1,3]dioxol-5-yl)-2-methylpyrazolo[1,5-a]pyrimidin-7(4H)-one as a white solid.

LC-MS: (ES, m/z): 394 [M+H]+

1H-NMR (300 MHz, DMSO, ppm): δ 11.94 (s, 1H), 7.38-7.10 (m, 7H), 6.14 (s, 2H), 5.86 (s, 1H), 4.04 (s, 2H), 2.10 (s, 3H)

Example 77

3-(4-Fluorophenyl)-2-methyl-5-(pyridin-3-yl)pyrazolo[1,5-a]pyrimidin-7(4H)-one

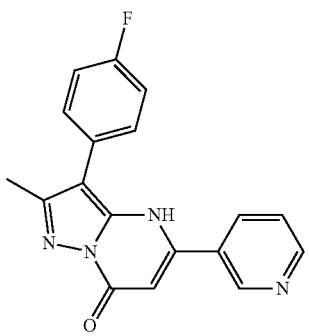 [SMILES: Cc1nn2c(=O)cc(-c3cccnc3)[nH]c2c1-c1ccc(F)cc1]

Step 1. 2-(4-Fluorophenyl)-3-oxobutanenitrile

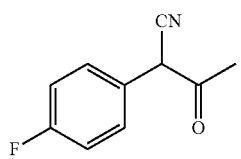

A solution of 2-(4-fluorophenyl)acetonitrile (20 g, 148.15 mmol, 1.00 equiv) in ethyl acetate (250 mL) was placed into a 500-mL 3-necked round-bottom flask. This was followed by the addition of Na metal (4.1 g, 1.20 equiv) in several batches. The reaction was heated to reflux overnight. After cooling to room temperature, the solids were filtered off and washed with ethyl acetate. The solid was dissolved in water and acidified with 10% HCl. The aqueous solution was extracted with ethyl acetate (3×). The organic layers were dried over anhydrous $Na_2SO_4$, and concentrated to dryness to afford 13 g (48%) of 2-(4-fluorophenyl)-3-oxobutanenitrile as a white solid.

LC-MS: (ES, m/z): 178 [M+H]$^+$

Step 2. 4-(4-Fluorophenyl)-3-methyl-1H-pyrazol-5-amine

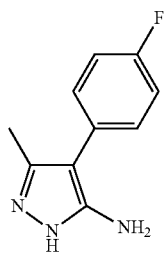

A solution of 2-(4-fluorophenyl)-3-oxobutanenitrile (10.6 g, 59.89 mmol, 1.00 equiv), hydrazine hydrate (7.5 g, 120.00 mmol, 2.00 equiv, 80%) and acetic acid (12.6 g, 210.00 mmol, 1.50 equiv) in toluene (150 mL) was placed into a 250-mL round-bottom flask. The resulting solution was heated to reflux for 3 hr, and then concentrated to dryness. The resulting residue was diluted with 30 mL of 6N hydrochloric acid. The solids were filtered off and washed with ethyl acetate. The solids were dissolved in water and the pH was adjusted to pH>9 with ammonia water. The aqueous solution was extracted with ethyl acetate. The organic layers was dried over anhydrous $Na_2SO_4$ and concentrated in vacuo to afford 8.2 g (65%) of 4-(4-fluorophenyl)-3-methyl-1H-pyrazol-5-amine as a white solid.

LC-MS (ES, m/z): 192 [M+H]$^+$

Step 3. 3-(4-Fluorophenyl)-2-methyl-5-(pyridin-3-yl)pyrazolo[1,5-a]pyrimidin-7(4H)-one

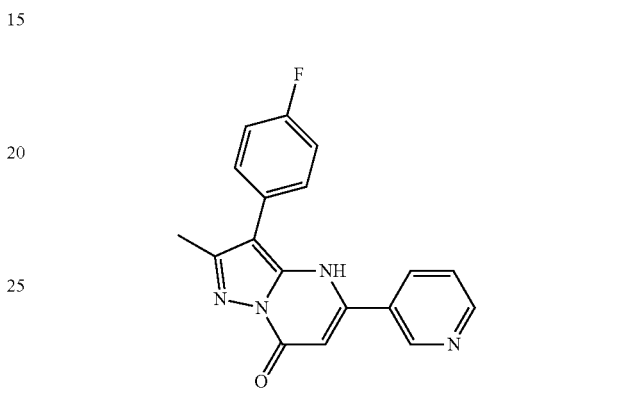

A mixture of 4-(4-fluorophenyl)-3-methyl-1H-pyrazol-5-amine (127 mg, 0.60 mmol, 1.00 equiv, 90%) and ethyl 3-oxo-3-(pyridin-3-yl)propanoate (116 mg, 0.60 mmol, 1.00 equiv) in acetic acid (2 mL) was placed into an 8-mL sealed tube. The resulting mixture was stirred overnight at 110° C. Then the reaction was concentrated to dryness, and the residue was suspended in 5 mL of methanol. The resulting solids were collected by filtration and washed with methanol. Drying afforded 130 g (67%) of 3-(4-fluorophenyl)-2-methyl-5-(pyridin-3-yl)pyrazolo[1,5-a]pyrimidin-7(4H)-one as a yellow solid.

LC-MS: (ES, m/z): 321 [M+H]$^+$ $^1$H-NMR (300 MHz, DMSO, ppm): δ 12.23 (s, 1H), 8.96 (s, 1H), 8.74 (d, J=4.8 Hz, 1H), 8.19 (d, J=6.9 Hz, 1H), 7.58 (d, J=4.8 Hz, 3H), 7.31 (t, J=8.7 Hz, 1H), 6.07 (s, 1H), 2.32 (s, 3H)

Example 78

3-(4-Fluorophenyl)-5-(pyridin-3-yl)pyrazolo[1,5-a]pyrimidin-7(4H)-one

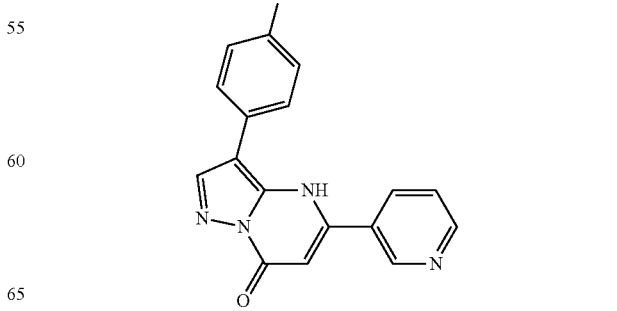

A solution of 4-(4-fluorophenyl)-1H-pyrazol-5-amine (124 mg, 0.70 mmol, 1.00 equiv) and ethyl 3-oxo-3-(pyridin-3-yl)propanoate (135 mg, 0.70 mmol, 1.00 equiv) in acetic acid (2 mL) was placed into an 8-mL sealed tube. The resulting solution was stirred overnight at 110° C. Then the reaction was concentrated to dryness, and the residue was diluted with 5 mL of methanol. The resulting solids were collected by filtration and washed with methanol. Drying afforded 158 mg (73%) of 3-(4-fluorophenyl)-5-(pyridin-3-yl)pyrazolo[1,5-a]pyrimidin-7(4H)-one as a yellow solid.

LC-MS: (ES, m/z): 307 [M+H]+

$^1$H-NMR (300 MHz, DMSO, ppm): δ 12.37 (s, 1H), 9.05 (s, 1H), 8.77 (dd, J=1.5, 4.8 Hz, 1H), 8.26 (s, 2H), 7.76 (s, 1H), 7.61 (dd, J=4.8, 7.9 Hz, 1H), 7.31 (t, J=8.7 Hz, 2H), 6.17 (s, 1H)

Example 79

3-(4-Fluorophenyl)-5-(pyridin-2-yl)pyrazolo[1,5-a]pyrimidin-7(4H)-one

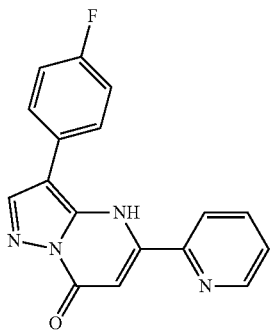 [SMILES: O=c1cc(-c2ccccn2)[nH]c2c(-c3ccc(F)cc3)cnn12]

A solution of 4-(4-fluorophenyl)-1H-pyrazol-5-amine (124 mg, 0.70 mmol, 1.00 equiv), ethyl 3-oxo-3-(pyridin-2-yl)propanoate (135 mg, 0.70 mmol, 1.00 equiv) in acetic acid (2 mL) was placed into an 8-mL sealed tube. The resulting solution was stirred overnight at 110° C., and then concentrated in vacuo. The resulting residue was diluted with 5 mL of methanol. The solids were collected by filtration and washed with methanol. Drying afforded 173 mg (80%) of 3-(4-fluorophenyl)-5-(pyridin-2-yl)pyrazolo[1,5-a]pyrimidin-7(4H)-one as a dark-grey solid.

LC-MS: (ES, m/z): 307 [M+H]+

$^1$H-NMR (300 MHz, DMSO-$d_6$, ppm): δ 11.62 (s, 1H), 8.82 (d, J=4.2 Hz, 1H), 8.33 (d, J=8.1 Hz, 2H), 8.08 (m, 1H), 7.73 (s, 2H), 7.64 (dd, J=5.4, 5.8 Hz, 1H), 7.35 (m, 2H), 6.68 (s, 1H)

Example 80

5-(2,3-Dihydrobenzo[b][1,4]dioxin-6-yl)-3-(4-fluorophenyl)-2-methylpyrazolo[1,5-a]pyrimidin-7(4H)-one

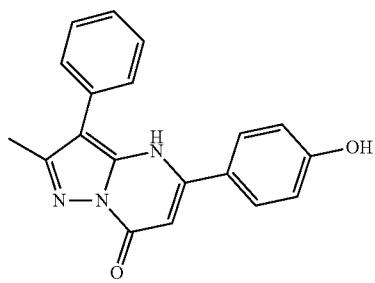 [SMILES: Cc1nn2c(=O)cc(-c3ccc(O)cc3)[nH]c2c1-c1ccccc1]

Step 1. Methyl 3-(4-hydroxyphenyl)-3-oxopropanoate

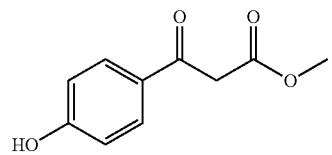

Into a 250-mL 3-necked round-bottom flask purged and maintained with an inert atmosphere of nitrogen, was placed a solution of 1-(4-hydroxyphenyl)ethanone (5 g, 36.76 mmol, 1.00 equiv) in N,N-dimethylformamide (50 mL). This was followed by the addition of sodium hydride (3.5 g, 145.83 mmol, 4.00 equiv) in several batches at 5° C. The resulting solution was stirred for 30 min at room temperature. To this was added dimethyl carbonate (16.58 g, 184.02 mmol, 5.01 equiv) dropwise with stirring. The resulting solution was stirred for overnight at room temperature. The pH value of the solution was adjusted to 5-6 with 1N hydrogen chloride. The resulting solution was concentrated under vacuum. The residue was applied onto a silica gel column with ethyl acetate/petroleum ether (50:1). This resulted in 4.5 g (crude) of methyl 3-(4-hydroxyphenyl)-3-oxopropanoate as a yellow solid.

LC-MS: (ES, m/z): 195 [M+H]+

Step 2. 5-(4-Hydroxyphenyl)-2-methyl-3-phenylpyrazolo[1,5-a]pyrimidin-7(4H)-one

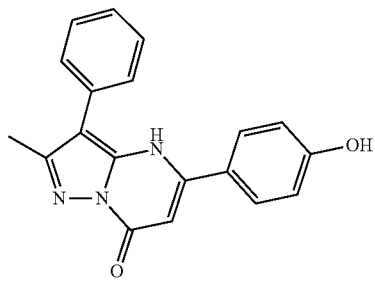 [SMILES: Cc1nn2c(=O)cc(-c3ccc(O)cc3)[nH]c2c1-c1ccccc1]

3-Methyl-4-phenyl-1H-pyrazol-5-amine (200 mg, 1.03 mmol, 1.00 equiv), methyl 3-(4-hydroxyphenyl)-3-oxopropanoate (196 mg, 1.13 mmol, 1.00 equiv), and acetic acid (4 mL) were placed into an 8-mL sealed tube. The resulting solution was stirred overnight at 110° C. in an oil bath. The resulting mixture was concentrated in vacuo. The crude product (260 mg) was purified by Prep-HPLC under the following conditions (1#-Waters 2767-1): Column, SunFire Prep C18, 5 um, 19*100 mm; mobile phase, water with 0.1% FA and methanol (50% methanol up to 70% in 6 min); Detector, UV 254 nm. This resulted in 113.2 mg (34%) of 5-(4-hydroxyphenyl)-2-methyl-3-phenylpyrazolo[1,5-a]pyrimidin-7(4H)-one as a off-white solid.

LC-MS: (ES, m/z): 318 [M+H]+

$^1$H-NMR (300 MHz, DMSO, ppm): δ 11.91 (s, 1H), 10.07 (s, 1H), 8.28 (s, 1H), 7.64-7.61 (d, J=9 Hz, 2H), 7.50-7.45 (t, J=7.5 Hz, 4H), 7.37-7.35 (d, J=6 Hz, 1H), 6.91-6.88 (d, J=9 Hz, 2H), 5.88 (s, 1H), 2.31 (s, 1H)

Example 81

5-(2,3-Dihydrobenzo[b][1,4]dioxin-6-yl)-3-(4-fluorophenyl)-2-methylpyrazolo[1,5-a]pyrimidin-7(4H)-one

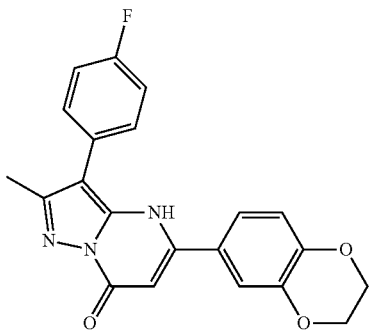 [SMILES: Cc1nn2c(=O)cc(-c3ccc4c(c3)OCCO4)[nH]c2c1-c1ccc(F)cc1]

A solution of 4-(4-fluorophenyl)-3-methyl-1H-pyrazol-5-amine (191 mg, 1.00 mmol, 1.00 equiv) in acetic acid (2 mL), ethyl 3-(2,3-dihydrobenzo[b][1,4]dioxin-6-yl)-3-oxopropanoate (611 mg, 1.10 mmol, 1.10 equiv, 45%) was placed into an 8-mL sealed tube. The resulting solution was stirred overnight at 110° C. Then the reaction was concentrated to dryness, the solids were washed with methanol, and collected by filtration. The solids were dried to afford 220 mg (58%) of 5-(2,3-dihydrobenzo[b][1,4]dioxin-6-yl)-3-(4-fluorophenyl)-2-methylpyrazolo[1,5-a]pyrimidin-7(4H)-one as a white solid.

LC-MS: (ES, m/z): 378 [M+H]+

$^1$H-NMR (300 MHz, DMSO, ppm): δ 11.91 (s, 1H), 7.53 (d, J=5.8 Hz, 2H), 7.30 (m, 4H), 7.01 (d, J=8.4 Hz, 1H), 5.90 (s, 1H), 4.31 (s, 4H), 2.28 (s, 3H)

Example 82

5-(2,3-Dihydrobenzo[b][1,4]dioxin-6-yl)-3-(4-methoxyphenyl)pyrazolo[1,5-a]pyrimidin-7(4H)-one

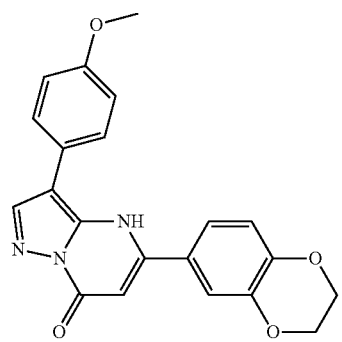 [SMILES: COc1ccc(-c2cnn3c(=O)cc(-c4ccc5c(c4)OCCO5)[nH]c23)cc1]

Step 1. 2-(4-Methoxyphenyl)-3-oxopropanenitrile

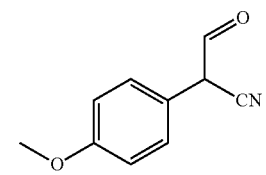

A solution of 2-(4-methoxyphenyl)acetonitrile (14.7 g, 100.00 mmol, 1.00 equiv) in ethyl formate (200 mL) was placed into a 500-mL round-bottom flask. Then Na metal (2.76 g, 120.00 mmol, 1.20 equiv) was added in several batches. The resulting solution was stirred for 1 h at room temperature and then at 50° C. overnight. The reaction was cooled to room temperature, diluted with 500 mL of H$_2$O, and the solids were filtered off. The pH value of the aqueous solution was adjusted to pH 5 with aqueous hydrogen chloride (6 mol/L). The resulting aqueous solution was extracted with 4×100 mL of ethyl acetate. The organic layers were combined, dried over anhydrous sodium sulfate, and concentrated in vacuo. This resulted in 18.6 g (96%) of 2-(4-methoxyphenyl)-3-oxopropanenitrile as a brown solid.

GC-MS: (m/z): 175 [M]+

$^1$H-NMR (300 MHz, CDCl$_3$, ppm): δ 7.63 (d, J=9 Hz, 1H), 7.46-7.28 (m, 2H), 7.03-6.92 (m, 3H), 3.85 (d, J=4.2 Hz, 3H)

Step 2. 4-(4-Methoxyphenyl)-1H-pyrazol-5-amine

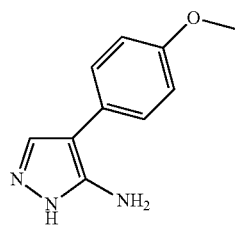

A solution of 2-(4-methoxyphenyl)-3-oxopropanenitrile (1.75 g, 10.00 mmol, 1.00 equiv) in toluene (30 mL) was placed into a 100-mL round-bottom flask. Then N₂H₄H₂O (1 g, 20.00 mmol, 2.00 equiv) and acetic acid (2.1 g, 35.00 mmol, 3.50 equiv) were added. The resulting reaction was heated to reflux for 3 hrs. The reaction was concentrated in vacuo and diluted with 5 ml of MeOH. The resulting solid was filtered and washed with methanol. The solid was dried in an oven in vacuo. This resulted in 1.0 g (52%) of 4-(4-methoxyphenyl)-1H-pyrazol-5-amine as a yellow solid.

LC-MS: (ES, m/z): 190 [M+H]⁺

¹H-NMR (300 MHz, DMSO, ppm): δ 11.60 (s, 1H), 7.58 (s, 1H), 7.43 (d, J=8.7 Hz, 2H), 6.92 (d, J=8.7 Hz, 2H), 4.61 (s, 2H), 3.75 (s, 3H)

Step 3. 5-(2,3-Dihydrobenzo[b][1,4]dioxin-6-yl)-3-(4-methoxyphenyl)pyrazolo[1,5-a]pyrimidin-7(4H)-one

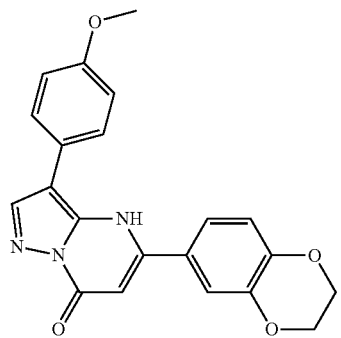 [SMILES: COc1ccc(-c2cnn3c(=O)cc(-c4ccc5c(c4)OCCO5)[nH]c23)cc1]

A solution of 4-(4-methoxyphenyl)-1H-pyrazol-5-amine (189 mg, 1.00 mmol, 1.00 equiv) in acetic acid (2 mL) was placed into an 8-mL tube. Then ethyl 3-(2,3-dihydrobenzo[b][1,4]dioxin-6-yl)-3-oxopropanoate (289 mg, 1.156 mmol, 1.1 equiv, 90%) was added and the tube was sealed. The reaction was stirred overnight at 110° C. Then the reaction was concentrated in vacuo to dryness. The residue was diluted with 5 mL of methanol and the resulting solids were collected by filtration, and washed with methanol. Drying afforded 240 mg (63%) of 5-(2,3-dihydrobenzo[b][1,4]dioxin-6-yl)-3-(4-methoxyphenyl)pyrazolo[1,5-a]pyrimidin-7(4H)-one as a white solid.

LC-MS: (ES, m/z): 376 [M+H]⁺

¹H-NMR (300 MHz, DMSO, ppm): δ 11.97 (s, 1H), 8.08 (s, 1H), 7.55 (d, J=8.1 Hz, 2H), 7.37 (s, 1H), 7.32 (d, J=8.1 Hz, 1H), 7.03 (q, J=4.2 Hz, 3H), 5.95 (s, 1H), 4.32 (s, 4H), 3.80 (s, 3H)

Example 83

3-(4-Fluorophenyl)-2-methyl-5-(quinolin-6-yl)pyrazolo[1,5-a]pyrimidin-7(4H)-one

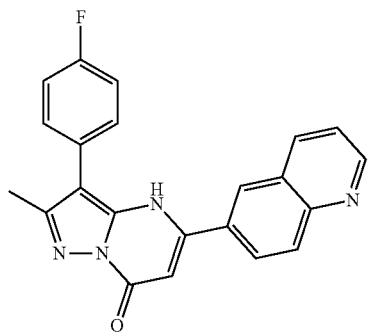 [SMILES: Cc1nn2c(=O)cc(-c3ccc4ncccc4c3)[nH]c2c1-c1ccc(F)cc1]

Step 1. 3-(4-Fluorophenyl)-2-methylpyrazolo[1,5-a]pyrimidine-5,7(4H,6H)-dione

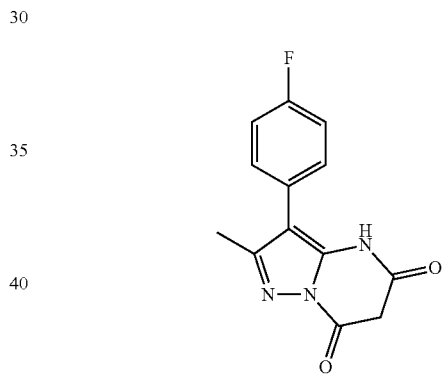

Methanol (10 mL) was placed into a 25-mL sealed tube. Then Na metal (730 mg, 31.74 mmol, 6.00 equiv) was added in several batches over 15 min. The resulting solution was stirred 15 min. This was followed by the addition of 4-(4-fluorophenyl)-3-methyl-1H-pyrazol-5-amine (1 g, 5.26 mmol, 1.00 equiv) and dimethyl malonate (1.39 g, 10.53 mmol, 2.00 equiv). The resulting solution was stirred overnight at 70° C. in an oil bath. Then the reaction was cooled to room temperature and concentrated in vacuo. The reaction was quenched by the addition of 20 mL of water and the pH value of the solution was adjusted to pH 6 with aq. hydrochloric acid (1 mol/L). The resulting solids were collected by filtration resulting in 1.35 g (96%) of 3-(4-fluorophenyl)-2-methylpyrazolo[1,5-a]pyrimidine-5,7(4H,6H)-dione as a white solid.

LC-MS: (ES, m/z): 260 [M+H]⁺

Step 2. 5,7-Dichloro-3-(4-fluorophenyl)-2-methylpyrazolo[1,5-a]pyrimidine

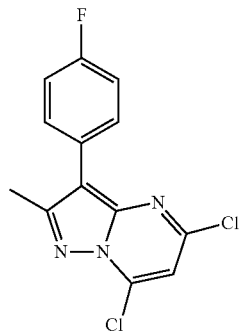 [SMILES: Cc1nn2c(Cl)cc(Cl)nc2c1-c1ccc(F)cc1]

3-(4-Fluorophenyl)-2-methylpyrazolo[1,5-a]pyrimidine-5,7(4H,6H)-dione (1.35 g, 5.21 mmol, 1.00 equiv), POCl₃ (7.92 g, 52.11 mmol, 10.00 equiv) and N,N-diethylbenzenamine (11.73 g, 78.72 mmol, 15.00 equiv) was placed into a 50-mL round-bottom flask. The resulting solution was stirred for 44 hr at 110° C. in an oil bath. The reaction was cooled to room temperature then quenched by the addition of 150 mL of water/ice. The solids were collected by filtration resulting in 1.52 g (96%) of 5,7-dichloro-3-(4-fluorophenyl)-2-methylpyrazolo[1,5-a]pyrimidine as a pale yellow solid.

LC-MS: (ES, m/z): 296 [M+H]⁺

Step 3. 5-Chloro-3-(4-fluorophenyl)-2-methylpyrazolo[1,5-a]pyrimidin-7(4H)-one

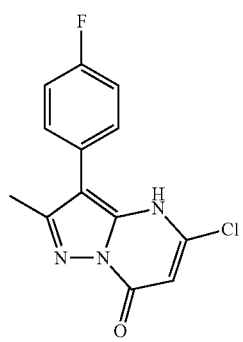 [SMILES: Cc1nn2c(=O)cc(Cl)[nH]c2c1-c1ccc(F)cc1]

5,7-Dichloro-3-(4-fluorophenyl)-2-methylpyrazolo[1,5-a]pyrimidine (1.5 g, 5.07 mmol, 1.00 equiv) and 5% sodium hydroxide solution in water (25 mL) were placed into a 25-mL sealed tube. The resulting solution was stirred for 3 hr at 100° C. in an oil bath. The reaction mixture was cooled to room temperature, and the pH value of the solution was adjusted to pH 6 with aq. hydrochloric acid (1 mol/L). The resulting solids were collected by filtration, dried, resulting in 1.28 g (83%) of 5-chloro-3-(4-fluorophenyl)-2-methylpyrazolo[1,5-a]pyrimidin-7(4H)-one as a grey solid.

LC-MS: (ES, m/z): 278 [M+H]⁺

Step 4. 3-(4-Fluorophenyl)-2-methyl-5-(quinolin-6-yl)pyrazolo[1,5-a]pyrimidin-7(4H)-one

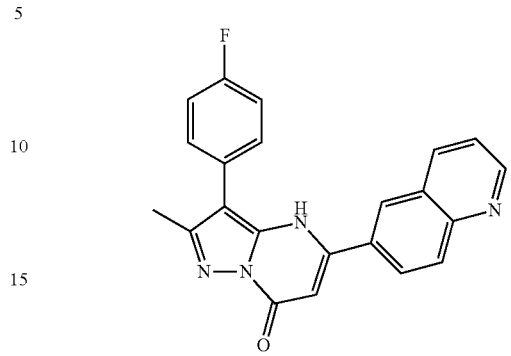

5-Chloro-3-(4-fluorophenyl)-2-methylpyrazolo[1,5-a]pyrimidin-7(6H)-one (300 mg, 1.09 mmol, 1.00 equiv), 6-(4,4,5,5-tetramethyl-1,3,2-dioxaborolan-2-yl)quinoline (1.66 g, 6.51 mmol, 6.00 equiv), X-Phos (204 mg, 0.43 mmol, 0.40 equiv), Pd₂(dba)₃ (200 mg, 0.22 mmol, 0.20 equiv), K₃PO₄ (1.38 mg, 0.01 mmol, 6.00 equiv), 1,4-dioxane (12 mL), and water (4 mL) were placed into a 20-mL sealed tube. The reaction was stirred overnight at 100° C. in an oil bath. The reaction was cooled to room temperature and the resulting solids were filtered off. The resulting filtrate was concentrated under vacuum and purified by silica gel column chromatography with DCM:MeOH (50:1). This resulted in 170 mg (42%) of 3-(4-fluorophenyl)-2-methyl-5-(quinolin-6-yl)pyrazolo[1,5-a]pyrimidin-7(4H)-one as a yellow solid.

LC-MS: (ES, m/z): 371 [M+H]⁺

¹H-NMR (300 MHz, DMSO, ppm): 8.950 (s, 1H), 8.643 (s, 1H), 8.527-8.505 (d, J=6.6 Hz, 2H), 8.123 (s, 1H), 7.940 (s, 2H), 7.598 (s, 1H), 7.306 (s, 2H), 6.355 (s, 1H)

Example 84

3-(4-Methoxyphenyl)-2-methyl-5-(quinolin-6-yl)pyrazolo[1,5-a]pyrimidin-7(4H)-one

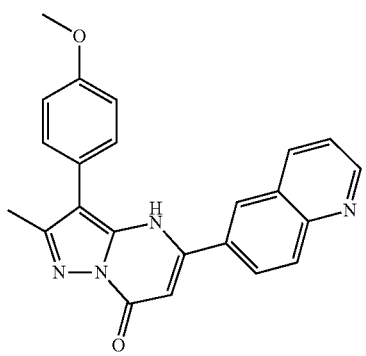 [SMILES: COc1ccc(-c2c(C)nn3c(=O)cc(-c4ccc5ncccc5c4)[nH]c23)cc1]

Step 1. 6-Bromoquinoline

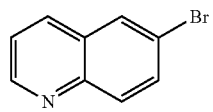

4-Bromobenzenamine (25 g, 145.32 mmol, 1.00 equiv), sodium 3-nitrobenzenesulfonate (55.5 g, 246.64 mmol, 1.70 equiv), propane-1,2,3-triol (50.8 g, 551.63 mmol, 3.80 equiv), and sulfuric acid (170 mL, 70%) were placed into a 500-mL round-bottom flask. The resulting solution was stirred overnight at 140° C. The pH value of the solution was adjusted to with 10% aqueous sodium hydroxide. The resulting solution was extracted with 5×150 mL of ethyl acetate. The organic layers were combined and dried over anhydrous sodium sulfate, and concentrated in vacuo. The residue was purified by silica gel column chromatography eluting with ethyl acetate/petroleum ether (1:50). This resulted in 17.2 g (42%) of 6-bromoquinoline as yellow oil.

Step 2. 6-(4,4,5,5-Tetramethyl-1,3,2-dioxaborolan-2-yl)quinoline

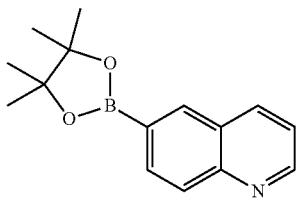 [SMILES: CC1(C)OB(c2ccc3ncccc3c2)OC1(C)C]

A 100-mL round-bottom flask was purged and maintained with an inert atmosphere of nitrogen. Then a solution of 6-bromoquinoline (5 g, 23.92 mmol, 1.00 equiv) in tetrahydrofuran (20 mL) was added. This was followed by the addition of KOAc (3.55 g, 1.50 equiv), 4,4,5,5-tetramethyl-2-(4,4,5,5-tetramethyl-1,3,2-dioxaborolan-2-yl)-1,3,2-dioxaborolane (18.23 g, 71.77 mmol, 3.00 equiv), and Pd(dppf)$_2$Cl$_2$ (1.95 g, 2.39 mmol, 0.10 equiv). The reaction was stirred overnight at 80° C. in an oil bath. The resulting solids were filtered off. The filtrate was concentrated in vacuo and purified by silica gel column chromatography eluting with ethyl acetate/petroleum ether (1:50). This resulted in 6.62 g (109%) of 6-(4,4,5,5-tetramethyl-1,3,2-dioxaborolan-2-yl)quinoline as red oil.

Step 3. 3-(4-Methoxyphenyl)-2-methyl-5-(quinolin-6-yl)pyrazolo[1,5-a]pyrimidin-7(4H)-one

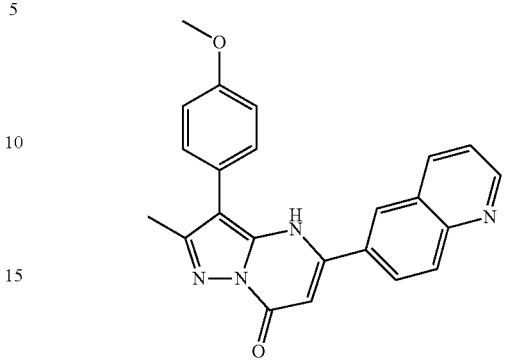

5-Chloro-3-(4-methoxyphenyl)-2-methylpyrazolo[1,5-a]pyrimidin-7(4H)-one (200 mg, 0.69 mmol, 1.00 equiv), 6-(4,4,5,5-tetramethyl-1,3,2-dioxaborolan-2-yl)quinoline (1.06 g, 4.16 mmol, 6.00 equiv), X-Phos (130 mg, 0.28 mmol, 0.40 equiv), Pd$_2$(dba)$_3$ (127 mg, 0.14 mmol, 0.20 equiv), K$_3$PO$_4$ (883 mg, 4.17 mmol, 6.00 equiv), 1,4-dioxane (12 mL), water (4 mL) were placed into a 20-mL sealed tube. The reaction was stirred overnight at 100° C. in an oil bath. The reaction was cooled to room temperature and the resulting solids were filtered off. The filtrate was concentrated in vacuo and purified by silica gel column chromatography eluting with ethyl acetate/petroleum ether (1:10). The resulting product (150 mg) was purified further by Prep-HPLC under the following conditions (1#-Waters 2767-2): Column, SunFire Prep C18, 5 um, 19*150 mm; mobile phase, water with 0.05% TFA and CH$_3$CN (30% CH$_3$CN up to 50% in 6 min, up to 100% in 1.5 min); Detector, uv 220&254 nm. This resulted in 56 mg (21%) of 3-(4-methoxyphenyl)-2-methyl-5-(quinolin-6-yl)pyrazolo[1,5-a]pyrimidin-7(4H)-one as a orange solid.

LC-MS: (ES, m/z): 383 [M+H]$^+$ $^1$H-NMR (300 MHz, DMSO, ppm): 9.030-9.011 (m, 1H), 8.563-8.535 (d, J=8.1 Hz, 1H), 8.472 (s, 1H), 8.136 (s, 2H), 7.688-7.646 (m, 1H), 7.473-7.447 (d, J=7.8 Hz, 2H), 7.072-7.043 (d, J=8.7 Hz, 2H), 6.106 (s, 1H), 3.811 (s, 3H), 2.310 (s, 3H).

Example 85

5-(2,3-Dihydrobenzo[b][1,4]dioxin-6-yl)-3-(4-methoxyphenyl)-2-methylpyrazolo[1,5-a]pyrimidin-7(4H)-one

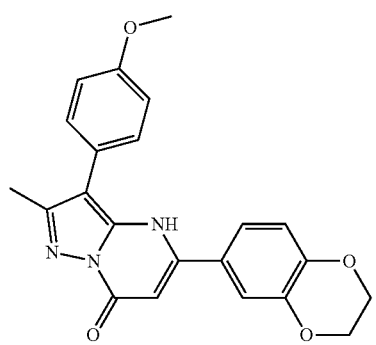 [SMILES: COc1ccc(-c2c(C)nn3c(=O)cc(-c4ccc5c(c4)OCCO5)[nH]c23)cc1]

A solution of 4-(4-methoxyphenyl)-3-methyl-1H-pyrazol-5-amine (203 mg, 1.00 mmol, 1.00 equiv) in acetic acid (3 mL) was placed into an 8-mL tube. Then ethyl 3-(2,3-dihydrobenzo[b][1,4]dioxin-6-yl)-3-oxopropanoate (611 mg, 1.10 mmol, 1.10 equiv, 45%) was added and the tube was sealed. The reaction was stirred overnight at 110° C. Then it was cooled to room temperature and concentrated to dryness. It was diluted with 3 mL MeOH, and the solids were filtered off and washed with DCM/MeOH to afford 60 mg (15%) of 5-(2,3-dihydrobenzo[b][1,4]dioxin-6-yl)-3-(4-methoxyphenyl)-2-methylpyrazolo[1,5-a]pyrimidin-7(4H)-one as a brown solid.

LC-MS: (ES, m/z): 390 [M+H]+

1H-NMR (300 MHz, DMSO, ppm): 11.86 (s, 1H), 7.47 (d, J=8.4 Hz, 2H), 7.26 (t, J=8.4 Hz, 2H), 7.03 (q, J=8.4 Hz, 3H), 5.87 (s, 1H), 4.31 (s, 4H), 3.82 (s, 3H), 2.27 (s, 3H)

Example 86

5-(2,3-Dihydrobenzo[b][1,4]dioxin-6-yl)-3-(4-fluorophenyl)pyrazolo[1,5-a]pyrimidin-7(4H)-one

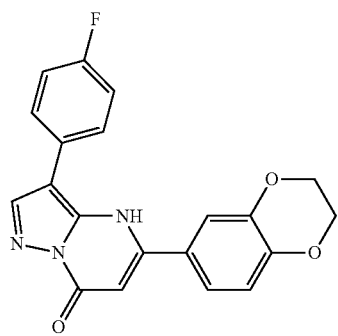 [SMILES: O=c1cc(-c2ccc3c(c2)OCCO3)[nH]c2c(-c3ccc(F)cc3)cnn12]

4-(4-Fluorophenyl)-1H-pyrazol-5-amine (200 mg, 1.13 mmol, 1.00 equiv), ethyl 3-(2,3-dihydrobenzo[b][1,4]dioxin-6-yl)-3-oxopropanoate (310.7 mg, 1.24 mmol, 1.10 equiv) and acetic acid (3 mL) were placed into an 8-mL sealed tube. The reaction was stirred overnight at 110° C. in an oil bath, then it was cooled to room temperature and concentrated under vacuum. The resulting solid was washed with methanol and filtered. This resulted in 213.7 mg (52%) of 5-(2,3-dihydrobenzo[b][1,4]dioxin-6-yl)-3-(4-fluorophenyl)pyrazolo[1,5-a]pyrimidin-7(4H)-one as a white solid.

LC-MS: (ES, m/z):364 [M+H]+

1H-NMR (300 MHz, DMSO, ppm): 12.026 (s, 1H), 8.141 (s, 1H), 8.316 (s, 1H), 7.687 (s, 1H), 7.387-7.268 (m, 4H), 7.036-7.015 (d, J=6.3 Hz, 1H), 5.978 (s, 1H), 4.323 (s, 4H)

Example 87

5-(1H-Indol-5-yl)-2-methyl-3-phenylpyrazolo[1,5-a]pyrimidin-7(4H)-one

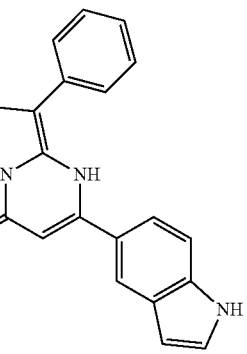

Step 1. 2-Methyl-3-phenylpyrazolo[1,5-a]pyrimidine-5,7(4H,6H)-dione

A solution of Na metal (791 mg, 34.39 mmol, 3.00 equiv) in methanol (15 mL) was placed into a 30-mL tube. The resulting solution was stirred for 30 min at 0° C. Then 3-methyl-4-phenyl-1H-pyrazol-5-amine (1.5 g, 8.66 mmol, 1.00 equiv) and dimethyl malonate (1.25 g, 9.46 mmol, 1.00 equiv) were added and the tube was sealed. The reaction was stirred for overnight at 80° C. Then it was cooled to room temperature, and concentrated under vacuum, diluted with 30 mL of H2O. The pH value of the aqueous solution was adjusted to pH 4 with aq. hydrochloric acid (1 mol/L). The resulting solids were collected by filtration and dried in a vacuum oven. This resulted in 1.6 g (77%) of 2-methyl-3-phenylpyrazolo[1,5-a]pyrimidine-5,7(4H,6H)-dione as a yellow solid.

Step 2. 5,7-Dichloro-2-methyl-3-phenyl-6,7-dihydropyrazolo[1,5-a]pyrimidine

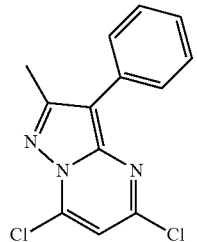 [SMILES: Cc1nn2c(Cl)cc(Cl)nc2c1-c1ccccc1]

2-Methyl-3-phenylpyrazolo[1,5-a]pyrimidine-5,7(4H,6H)-dione (1.6 g, 6.64 mmol, 1.00 equiv), N,N-diethylbenzenamine (8 g, 53.69 mmol), POCl$_3$ (100 mL) were placed in a round bottom flask. The resulting solution was stirred for 2 days at 110° C. in an oil bath. Then the reaction was cooled to room temperature and quenched by the addition of 100 mL of ice water. The pH value of the solution was adjusted to pH 8 with sat. aqueous NaHCO$_3$. The resulting solution was extracted with 3×200 ml of dichloromethane and the organic layers were combined and concentrated under vacuum. The residue was purified via silica gel column chromatography with PE:EA (20:1). This resulted in 0.7 g (38%) of 5,7-dichloro-2-methyl-3-phenyl-6,7-dihydropyrazolo[1,5-a]pyrimidine as a yellow solid.

Step 3. 5-Chloro-2-methyl-3-phenylpyrazolo[1,5-a]pyrimidin-7(4H)-one

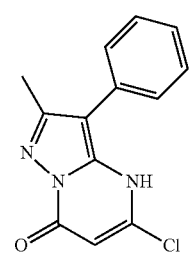 [SMILES: Cc1nn2c(=O)cc(Cl)[nH]c2c1-c1ccccc1]

Into a 10-mL sealed tube, was placed 5,7-dichloro-2-methyl-3-phenylpyrazolo[1,5-a]pyrimidine (1 g, 3.60 mmol, 1.00 equiv), 5% aq sodium hydroxide (20 mL). The resulting solution was heated to reflux for 1.5 h at in an oil bath. The reaction mixture was cooled to room temperature with a water bath. The pH value of the solution was adjusted to 5 with 3N aq HCl. The resulting solids were collected by filtration. The solid was dried in an oven under reduced pressure. This resulted in 550 mg (59%) of 5-chloro-2-methyl-3-phenylpyrazolo[1,5-a]pyrimidin-7(4H)-one as a yellow solid.

Step 4. 5-(1H-Indol-5-yl)-2-methyl-3-phenylpyrazolo[1,5-a]pyrimidin-7(4H)-one

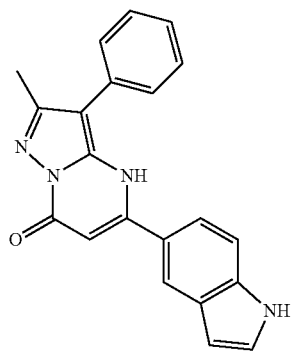 [SMILES: Cc1nn2c(=O)cc(-c3ccc4[nH]ccc4c3)[nH]c2c1-c1ccccc1]

Into a 25-mL sealed tube purged and maintained with an inert atmosphere of nitrogen, was placed 5-chloro-2-methyl-3-phenylpyrazolo[1,5-a]pyrimidin-7(4H)-one (200 mg, 0.77 mmol, 1.00 equiv), 5-(4,4,5,5-tetramethyl-1,3,2-dioxaborolan-2-yl)-1H-indole (373 mg, 1.53 mmol, 2.00 equiv), X-phos (144 mg, 0.31 mmol, 0.40 equiv), Pd$_2$(dba)$_3$ (144 mg, 0.16 mmol, 0.20 equiv), K$_3$PO$_4$ (652 mg, 3.08 mmol, 4.00 equiv), 1,4-dioxane (15 mL). The resulting solution was stirred overnight at 100° C. in an oil bath. The resulting mixture was concentrated under vacuum. The residue was applied onto a silica gel column with DCM:MeOH (50:1). This resulted in 25 mg (10%) of 5-(1H-indol-5-yl)-2-methyl-3-phenylpyrazolo[1,5-a]pyrimidin-7(4H)-one as a yellow solid.

LC-MS: (ES, m/z): 341 [M+H]$^+$ $^1$H-NMR (300 MHz, DMSO, ppm): 12.017 (s, 1H), 11.399 (s, 1H), 7.998 (s, 1H), 7.519-7.494 (m, 6H), 7.363 (m, 1H), 6.577 (s, 1H), 5.937 (s, 1H), 2.318 (s, 3H)

Example 88

5-Phenyl-3-(6-(piperidin-1-yl)pyridin-3-yl)pyrazolo[1,5-a]pyrimidin-7(4H)-one

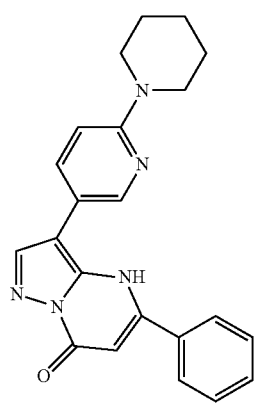 [SMILES: O=c1cc(-c2ccccc2)[nH]c2c(-c3ccc(N4CCCCC4)nc3)cnn12]

181

Step 1. 1-(4-Methoxybenzyl)-4-(6-(piperidin-1-yl)pyridin-3-yl)-1H-pyrazol-5-amine

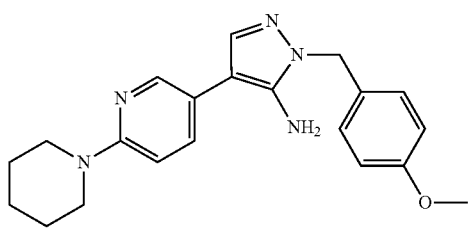 [SMILES: COc1ccc(Cn2ncc(-c3ccc(N4CCCCC4)nc3)c2N)cc1]

Into a 10-mL sealed tube, was placed 1-(4-methoxybenzyl)-4-(6-fluoropyridin-3-yl)-1H-pyrazol-5-amine (298 mg, 1.00 mmol, 1.00 equiv), piperidine (850 mg, 9.98 mmol, 10.00 equiv), DMSO (3 mL). The resulting solution was stirred overnight at 100° C. in an oil bath. The reaction was then quenched by the addition of 20 ml of EA. The resulting mixture was washed with 5×20 mL of sat sodium chloride. The mixture was dried over sodium sulfate and concentrated under vacuum. This resulted in 300 mg (83%) of 1-(4-methoxybenzyl)-4-(6-(piperidin-1-yl)pyridin-3-yl)-1H-pyrazol-5-amine as brown oil.

LC-MS: (ES, m/z): 364 [M+H]+

Step 2. 4-(6-(Piperidin-1-yl)pyridin-3-yl)-1H-pyrazol-5-amine

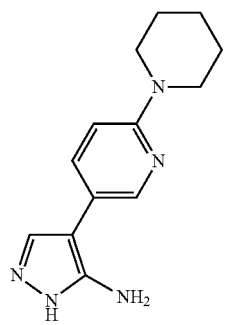 [SMILES: Nc1[nH]ncc1-c1ccc(N2CCCCC2)nc1]

Into a 10-mL sealed tube, was placed 1-(4-methoxybenzyl)-4-(6-(piperidin-1-yl)pyridin-3-yl)-1H-pyrazol-5-amine (300 mg, 0.83 mmol, 1.00 equiv), CF$_3$COOH (4 mL), (CF$_3$SO$_2$)$_2$O (1 mL). The resulting solution was stirred for 2 hrs at 30° C. in an oil bath. The resulting mixture was concentrated under vacuum. The crude product (300 mg) was purified by Flash-Prep-HPLC with the following conditions (IntelFlash-1): Column, C18; mobile phase, CH$_3$CN/H$_2$O=5% increasing to CH$_3$CN/H$_2$O=40% within 30 min; Detector, UV 254 nm 200 mg product was obtained. This resulted in 200 mg of 4-(6-(piperidin-1-yl)pyridin-3-yl)-1H-pyrazol-5-amine as a yellow solid.

182

Step 3. 5-Phenyl-3-(6-(piperidin-1-yl)pyridin-3-yl)pyrazolo[1,5-a]pyrimidin-7(4H)-one

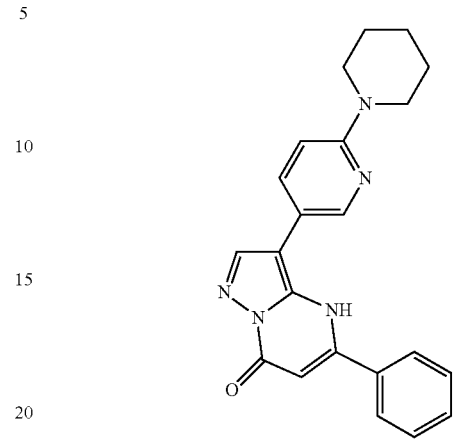

Into a 10-mL sealed tube, was placed 4-(6-(piperidin-1-yl)pyridin-3-yl)-1H-pyrazol-5-amine (200 mg, 0.82 mmol, 1.00 equiv), methyl 3-oxo-3-phenylpropanoate (146 mg, 0.82 mmol, 1.00 equiv), acetic acid (5 mL). The resulting solution was stirred overnight at 100° C. in an oil bath. The resulting mixture was concentrated under vacuum and purified by prep-HPLC. This resulted in 25 mg (8%) of 5-phenyl-3-(6-(piperidin-1-yl)pyridin-3-yl)pyrazolo[1,5-a]pyrimidin-7(4H)-one as a white solid.

LC-MS (ES, m/z): 372 [M+H]+

$^1$H-NMR (400 MHz, DMSO, ppm): 1.614-1.754 (m, 6H), 3.662 (m, 4H), 6.059 (m, 1H), 7.313 (s, 1H, 7.551-7.625 (m, 3H), 7.833 (m, 2H), 8.068-8.302 (m, 3H), 12.292-12.334 (s, 1H)

Example 89

5-(2,3-Dihydrobenzo[b][1,4]dioxin-6-yl)-3-(6-(piperidin-1-yl)pyridin-3-yl)pyrazolo[1,5-a]pyrimidin-7(4H)-one

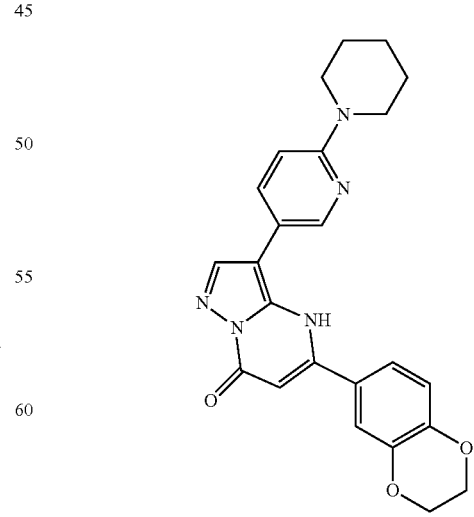

Into a 8-mL sealed tube, was placed 4-(6-(piperidin-1-yl)pyridin-3-yl)-1H-pyrazol-5-amine (200 mg, 0.82 mmol, 1.00 equiv), methyl 3-(2,3-dihydrobenzo[b][1,4]dioxin-6-yl)-3-oxopropanoate (194 mg, 0.82 mmol, 1.00 equiv), acetic acid (3 mL). The resulting solution was stirred overnight at 100° C. in an oil bath. The resulting mixture was concentrated under vacuum. The crude product (150 mg) was purified by Prep-HPLC with the following conditions (1#-Waters 2767-1): Column, SunFire Prep C18, 5 um, 19*150 mm; mobile phase, water with 0.05% TFA and CH$_3$CN (17% CH$_3$CN up to 32% in 8 min, up to 100% in 1.5 min); Detector, UV 220 254 nm. This resulted in 20 mg (5%) of 5-(2,3-dihydrobenzo[b][1,4]dioxin-6-yl)-3-(6-(piperidin-1-yl)pyridin-3-yl)pyrazolo[1,5-a]pyrimidin-7(4H)-one as a yellow solid.

LC-MS: (ES, m/z): 430 [M+H]$^+$ $^1$H-NMR (300 MHz, DMSO, ppm): 12.121 (s, 1H), 8.312 (s, 1H), 8.163 (s, 1H), 8.028 (s, 1H), 7.398-7.278 (m, 3H), 7.106-6.936 (m, 1H), 6.003 (s, 1H), 4.320 (s, 4H), 3.655 (m, 4H), 1.643 (m, 6H)

Example 90

3-(3-Chlorophenyl)-5-(2,3-dihydrobenzo[b][1,4]dioxin-6-yl)pyrazolo[1,5-a]pyrimidin-7(4H)-one

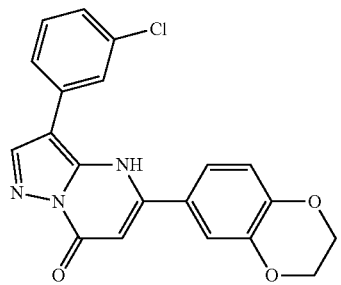 [SMILES: O=c1cc(-c2ccc3c(c2)OCCO3)[nH]c2c(-c3cccc(Cl)c3)cnn12]

Step 1. 2-(3-Chlorophenyl)-3-oxopropanenitrile

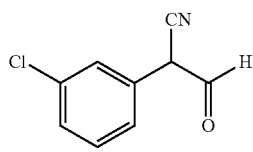 [SMILES: N#CC(C=O)c1cccc(Cl)c1]

Into a 250-mL 3-necked round-bottom flask, was placed ethanol (80 mL). Na (4.6 g, 2.00 equiv) was added in batches, and the reaction mixture was refluxed until the Na was solubilized. To the resulting solution, was added dropwise a solution of 2-(3-chlorophenyl)acetonitrile (15.2 g, 100.00 mmol, 1.00 equiv) and ethyl formate (11.1 g, 150.00 mmol, 1.50 equiv) in ethanol (20 mL). The resulting solution was heated to reflux for 16 hours, concentrated to dryness and dissolved in 150 mL of H$_2$O. Then the pH was adjusted to pH 6 with 3N hydrochloric acid. The resulting aqueous solution was extracted with EtOAc (100 mL*3). The organic layer was combined and dried over Na$_2$SO$_4$, and concentrated to dryness. The resulting solid was collected by filtration and washed with EtOAc to afford 7.5 g (crude) of 2-(3-chlorophenyl)-3-oxopropanenitrile as a white solid.

Step 2. 4-(3-Chlorophenyl)-1H-pyrazol-5-amine

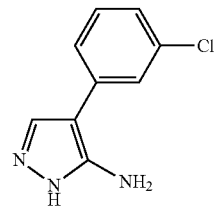 [SMILES: Nc1[nH]ncc1-c1cccc(Cl)c1]

Into a 100-mL round-bottom flask, was placed a solution of 2-(3-chlorophenyl)-3-oxopropanenitrile (4.5 g, 25.14 mmol, 1.00 equiv), NH$_2$NH$_2$.H$_2$O (2.5 g, 40.00 mmol, 2.00 equiv, 80%) in ethanol (40 mL). The resulting solution was heated to reflux for 3 hr, then concentrated to dryness. The residue was dissolved in 30 mL concentrated hydrochloric acid and washed with EtOAc (50 mL*2). The pH of the aqueous layer was adjusted to 10 with ammonia water and extracted with EtOAc (50 mL*3). The organic layers were dried over Na$_2$SO$_4$ and concentrated to dryness to afford 0.3 g (6%) of 4-(3-chlorophenyl)-1H-pyrazol-5-amine as a yellow solid.

LC-MS: (ES, m/z): 194 [M+H]$^+$

Step 3. 3-(3-Chlorophenyl)-5-(2,3-dihydrobenzo[b][1,4]dioxin-6-yl)pyrazolo[1,5-a]pyrimidin-7(4H)-one

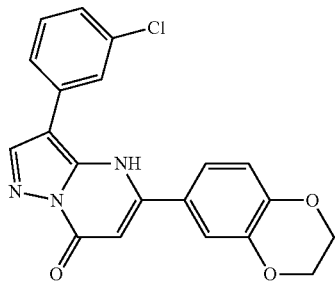 [SMILES: O=c1cc(-c2ccc3c(c2)OCCO3)[nH]c2c(-c3cccc(Cl)c3)cnn12]

Into a 8-mL sealed tube, was placed a solution of 4-(3-chlorophenyl)-1H-pyrazol-5-amine (150 mg, 0.77 mmol, 1.00 equiv) and ethyl 3-(2,3-dihydrobenzo[b][1,4]dioxin-6-yl)-3-oxopropanoate (213 mg, 0.85 mmol, 1.10 equiv) in acetic acid (2 mL). The resulting solution was stirred overnight at 110° C. Then it was cooled to room temperature and concentrated to dryness. The resulting solid was collected by filtration and washed with MeOH, then dried to afford 130 mg (44%) of 3-(3-chlorophenyl)-5-(2,3-dihydrobenzo[b][1,4]dioxin-6-yl)pyrazolo[1,5-a]pyrimidin-7(4H)-one as a white solid.

LC-MS: (ES, m/z): 380 [M+H]$^+$ $^1$H-NMR (300 MHz, DMSO, ppm): 12.10 (s, 1H), 8.22 (s, 1H), 7.73 (s, 1H), 7.64-7.61 (d, J=6.9 Hz, 1H), 7.50-7.45 (t, J=7.8 Hz, 1H), 7.40-7.31 (m, 2H), 7.05-7.02 (d, J=8.7 Hz, 1H), 6.00 (s, 1H), 4.32 (s, 4H)

Example 91

5-(2,3-Dihydrobenzo[b][1,4]dioxin-6-yl)-3-(3-fluorophenyl)pyrazolo[1,5-a]pyrimidin-7(4H)-one

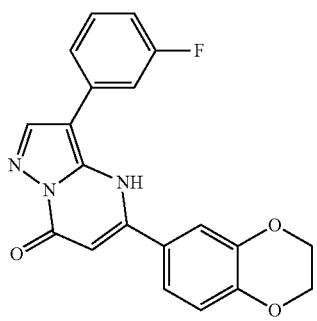 [SMILES: O=c1cc(-c2ccc3c(c2)OCCO3)[nH]c2c(-c3cccc(F)c3)cnn12]

Step 1.
3-(Dimethylamino)-2-(3-fluorophenyl)acrylonitrile

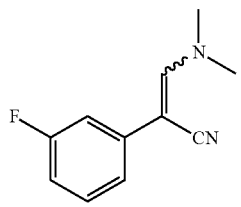

Into a 100-mL round-bottom flask, was placed a solution of 2-(3-fluorophenyl)acetonitrile (5 g, 37.04 mmol, 1.00 equiv) in DMF-DMA (25 mL). The resulting solution was stirred for 24 h at 50° C. The reaction mixture was cooled. The resulting solids were collected by filtration and washed with Hexane/EtOAc (10/1). This resulted in 2.9 g (39%) of 3-(dimethylamino)-2-(3-fluorophenyl)acrylonitrile as a red-brown solid.

LC-MS: (ES, m/z): 191 [M+H]+

$^1$H-NMR (300 MHz, CDCl$_3$, ppm): 7.30-7.21 (m, 1H), 7.12-7.08 (m, 1H), 7.04-6.98 (m, 1H), 6.95 (s, 1H), 6.86-6.79 (m, 1H), 3.21 (s, 6H)

Step 2. 4-(3-Fluorophenyl)-1H-pyrazol-5-amine

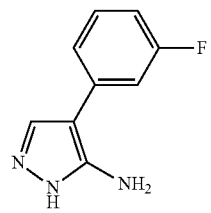 [SMILES: Nc1[nH]ncc1-c1cccc(F)c1]

Into a 100-mL round-bottom flask, was placed a mixture of 3-(dimethylamino)-2-(3-fluorophenyl)acrylonitrile (1.9 g, 10.00 mmol, 1.00 equiv), N$_2$H$_4$·HBr (11.3 g, 100.00 mmol, 10.00 equiv) in ethanol/water (50/5 mL). The resulting solution was stirred for 3 h at 80° C. The resulting mixture was concentrated under vacuum. The resulting solid was washed with dichloromethane until the solid changed to white. The dichloromethane filtrate was combined and washed with brine. The dichloromethane layer was dried over Na$_2$SO$_4$, and concentrated to afford 1.65 g (93%) of 4-(3-fluorophenyl)-1H-pyrazol-5-amine as a red solid.

LC-MS: (ES, m/z): 178 [M+H]+

$^1$H-NMR (300 MHz, CDCl$_3$, ppm): 7.55 (s, 1H), 7.41-7.33 (m, 1H), 7.28-7.17 (m, 2H), 6.99-6.92 (m, 1H), 5.20 (s, 3H)

Step 3. 5-(2,3-Dihydrobenzo[b][1,4]dioxin-6-yl)-3-(3-fluorophenyl)pyrazolo[1,5-a]pyrimidin-7(4H)-one

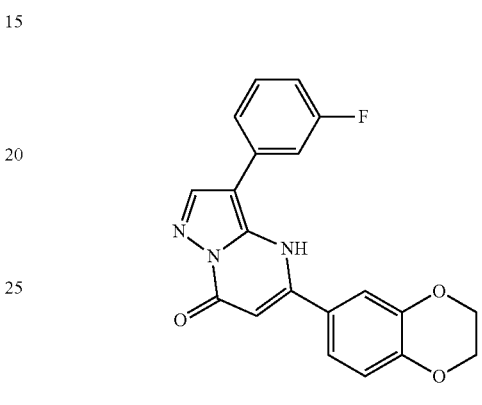

Into a 8-mL sealed tube, was placed a mixture of 4-(3-fluorophenyl)-1H-pyrazol-5-amine (177 mg, 1.00 mmol, 1.00 equiv), ethyl 3-(2,3-dihydrobenzo[b][1,4]dioxin-6-yl)-3-oxopropanoate (275 mg, 1.10 mmol, 1.10 equiv), AcOH (3 mL). The resulting solution was stirred for overnight at 110° C. Then it was cooled to room temperature and concentrated to dryness. The resulting solid was washed with methanol and dried. This resulted 185 mg (50%) of 5-(2,3-dihydrobenzo[b][1,4]dioxin-6-yl)-3-(3-fluorophenyl)pyrazolo[1,5-a]pyrimidin-7(4H)-one as a yellow solid.

LC-MS: (ES, m/z): 364 [M+H]+

$^1$H-NMR (300 MHz, DMSO, ppm): 12.06 (s, 1H), 8.22 (s, 1H), 7.55-7.32 (m, 5H), 7.16-7.09 (m, 1H), 7.05-7.02 (d, J=8.4 Hz, 1H), 6.00 (s, 1H), 4.32 (s, 4H)

Example 92

5-(2,3-Dihydrobenzo[b][1,4]dioxin-6-yl)-3-(3-methoxyphenyl)pyrazolo[1,5-a]pyrimidin-7(4H)-one

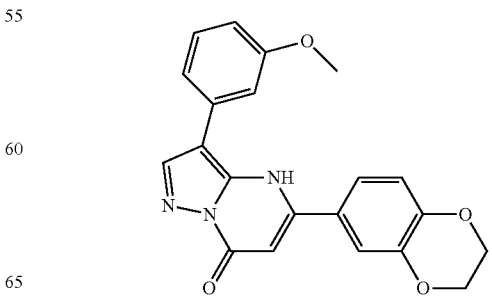

Step 1. 2-(3-Methoxyphenyl)-3-oxopropanenitrile

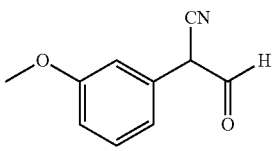

Into a 500-mL 3-necked round-bottom flask, was placed a solution of 2-(3-methoxyphenyl)acetonitrile (10.3 g, 70.07 mmol, 1.00 equiv) in ethyl formate (200 mL). This was followed by the addition of Na (2.42 g, 105.22 mmol, 1.50 equiv) in several batches. The resulting solution was stirred overnight at 50° C. The resulting solids were collected by filtration and washed with ethyl formate and then dissolved in 200 mL of H₂O. The pH value of the solution was adjusted to 7 with aqueous HCl (1M). The resulting solution was extracted with 4×100 mL of ethyl acetate and the organic layers combined and dried over Na₂SO₄ and concentrated under vacuum. The resulting solid was collected by filtration and washed with 2×20 mL of ethyl acetate. This resulted in 8 g (crude) of 2-(3-methoxyphenyl)-3-oxopropanenitrile as a yellow solid.

Step 2. 4-(3-Methoxyphenyl)-1H-pyrazol-5-amine

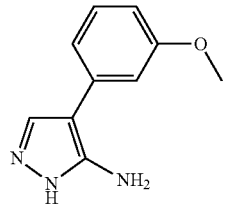

Into a 100-mL round-bottom flask, was placed 2-(3-methoxyphenyl)-3-oxopropanenitrile (8 g, crude), NH₂NH₂.H₂O (5.7 g, 91.20 mmol, 2.00 equiv, 80%) and ethanol (60 mL). The resulting solution was heated to reflux for 3 hr. The resulting mixture was concentrated in vacuo. The residue was purified silica gel column chromatography eluting with ethyl acetate/petroleum ether (1:5). This resulted in 230 mg (2%) of 4-(3-methoxyphenyl)-1H-pyrazol-5-amine as brown oil.

LC-MS: (ES, m/z): 190 [M+H]⁺

Step 3. 5-(2,3-Dihydrobenzo[b][1,4]dioxin-6-yl)-3-(3-methoxyphenyl)pyrazolo[1,5-a]pyrimidin-7(4H)-one

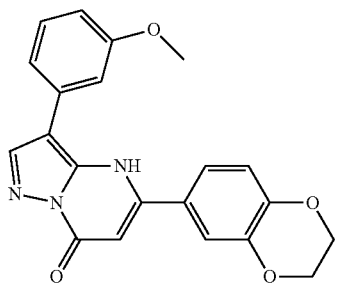 [SMILES: COc1cccc(-c2cnn3c(=O)cc(-c4ccc5c(c4)OCCO5)[nH]c23)c1]

Into a 8-mL sealed tube, was placed a mixture of 4-(3-methoxyphenyl)-1H-pyrazol-5-amine (230 mg, 0.97 mmol, 1.00 equiv, 80%), ethyl 3-(2,3-dihydrobenzo[b][1,4]dioxin-6-yl)-3-oxopropanoate (268 mg, 1.07 mmol, 1.10 equiv), acetic acid (3 mL). The resulting solution was stirred for overnight at 110° C. Then it was cooled to room temperature and concentrated to dryness. The resulting solids were collected by filtration and washed with methanol. The solids were dried in a vacuum oven to afford 45 mg (12%) of 5-(2,3-dihydrobenzo[b][1,4]dioxin-6-yl)-3-(3-methoxyphenyl)pyrazolo[1,5-a]pyrimidin-7(4H)-one as a grey solid.

LC-MS: (ES, m/z): 376 [M+H]⁺

¹H-NMR (300 MHz, DMSO, ppm): 12.04 (s, 1H), 8.18 (s, 1H), 7.44-7.30 (m, 3H), 7.22 (s, 2H), 7.04-7.01 (d, J=8.1 Hz, 1H), 6.90-6.87 (d, J=7.2 Hz, 1H), 5.98 (s, 1H), 4.32 (s, 4H), 3.85 (s, 3H)

Example 93

5-(Benzofuran-2-yl)-3-(pyridin-2-yl)pyrazolo[1,5-a]pyrimidin-7(4H)-one

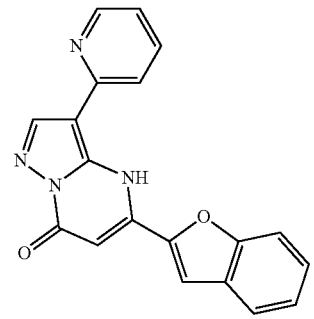 [SMILES: O=c1cc(-c2cc3ccccc3o2)[nH]c2c(-c3ccccn3)cnn12]

Step 1. 5-(Benzofuran-2-carbonyl)-2,2-dimethyl-1,3-dioxane-4,6-dione

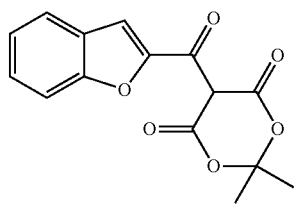 [SMILES: CC1(C)OC(=O)C(C(=O)c2cc3ccccc3o2)C(=O)O1]

Into a 100-mL round-bottom flask, was placed a solution of benzofuran-2-carboxylic acid (3 g, 18.52 mmol, 1.00 equiv) in dichloromethane (40 mL), 2,2-dimethyl-1,3-dioxane-4,6-dione (3.2 g, 22.22 mmol, 1.20 equiv), EDC.HCl (4.62 g, 24.06 mmol, 1.30 equiv), 4-dimethylaminopyridine (6.06 g, 27.80 mmol, 1.50 equiv). The resulting solution was stirred for overnight at room temperature. The resulting solution was diluted with 50 mL of DCM, washed with 3×20 mL of 1N HCl and 3×50 mL of brine. The DCM layers was dried over anhydrous sodium sulfate and concentrated under vacuum. This resulted in 3 g (56%) of 5-(benzofuran-2-carbonyl)-2,2-dimethyl-1,3-dioxane-4,6-dione as a yellow solid.

Step 2. Ethyl 3-(benzofuran-2-yl)-3-oxopropanoate

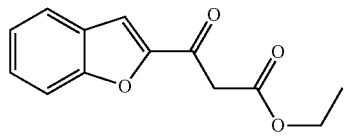 [SMILES: CCOC(=O)CC(=O)c1cc2ccccc2o1]

Into a 100-mL round-bottom flask, was placed a solution of 5-(benzofuran-2-carbonyl)-2,2-dimethyl-1,3-dioxane-4,6-dione (3 g, 10.42 mmol, 1.00 equiv) in ethanol (40 mL). The resulting solution was heated to reflux for 4 hr in an oil bath. The resulting mixture was concentrated under vacuum. The residue was applied onto a silica gel column with ethyl acetate/petroleum ether (1:40). This resulted in 700 mg (29%) of ethyl 3-(benzofuran-2-yl)-3-oxopropanoate as yellow oil.

Step 3. 5-(Benzofuran-2-yl)-3-(pyridin-2-yl)pyrazolo[1,5-a]pyrimidin-7(4H)-one

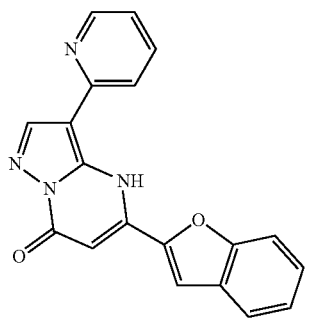 [SMILES: O=c1cc(-c2cc3ccccc3o2)[nH]c2c(-c3ccccn3)cnn12]

Into a 10-mL sealed tube, was placed a solution of ethyl 3-(benzofuran-2-yl)-3-oxopropanoate (200 mg, 0.86 mmol, 1.00 equiv), acetic acid (3 mL), 4-(pyridin-2-yl)-1H-pyrazol-5-amine (319 mg, 1.38 mmol, 1.59 equiv). The resulting solution was stirred for overnight at 100° C. in an oil bath. The resulting mixture was concentrated under vacuum. The resulting solid was collected by filtration and washed with 2×30 mL of methanol. This resulted in 200 mg (69%) of 5-(benzofuran-2-yl)-3-(pyridin-2-yl)pyrazolo[1,5-a]pyrimidin-7(4H)-one as a yellow solid.

LC-MS: (ES, m/z): 329 [M+H]$^+$ $^1$H-NMR (300 MHz, DMSO, ppm): δ 8.770-8.752 (d, J=3.6 Hz, 1H), 8.670 (s, 1H), 8.227-8.082 (m, 3H), 8.025 (s, 1H), 7.808-7.757 (m, 2H), 7.500-7.340 (m, 3H), 6.499 (s, 1H)

Example 94

5-(3,5-Dimethoxyphenyl)-3-(pyridin-2-yl)pyrazolo[1,5-a]pyrimidin-7(4H)-one

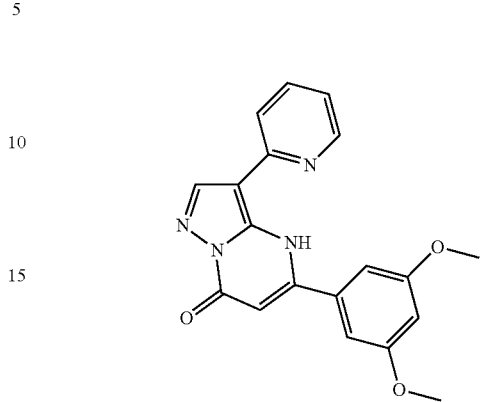

A solution of 4-(pyridin-2-yl)-1H-pyrazol-5-amine (100 mg, 0.62 mmol, 1.00 equiv) and ethyl 3-(3,5-dimethoxyphenyl)-3-oxopropanoate (173 mg, 0.69 mmol, 1.10 equiv) in acetic acid (2 mL) was stirred overnight at 110° C., and then concentrated in vacuo. The residue was diluted with 5 mL MeOH. The resulting solid was collected by filtration, washed with MeOH, and dried to afford 135 mg (60%) of 5-(3,5-dimethoxyphenyl)-3-(pyridin-2-yl)pyrazolo[1,5-a]pyrimidin-7(4H)-one as a yellow solid.

LC-MS: (ES, m/z): 249 [M+H]$^+$ $^1$H-NMR (300 MHz, DMSO, ppm): δ8.66-8.64 (m, 2H), 7.91-7.80 (m, 2H), 7.30-7.24 (m, 1H), 7.06-7.04 (d, J=2.1 Hz, 2H), 6.76-6.73 (t, J=2.4 Hz, 1H), 6.38 (s, 1H), 3.87 (s, 6H)

Example 95

5-(1H-Indol-6-yl)-3-phenylpyrazolo[1,5-a]pyrimidin-7(4H)-one

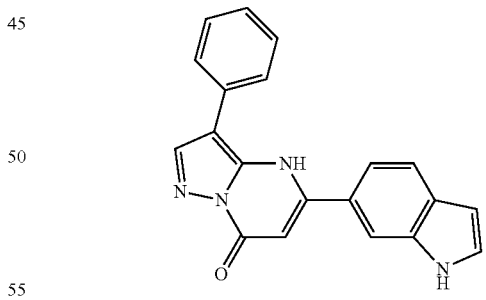

A solution of 4-phenyl-1H-pyrazol-5-amine (150 mg, 0.94 mmol, 1.00 equiv) and ethyl 3-(1H-indol-6-yl)-3-oxopropanoate (526.3 mg, 1.14 mmol, 1.20 equiv, 50%) in acetic acid (10 mL) was stirred overnight at 110° C. in an oil bath. The resulting mixture was concentrated under vacuum. The crude product (270 mg) was purified by Prep-HPLC with the following conditions (1#-UV1-SHIMADZU-SPD-20A): Column, SunFire Prep C18, 5 um, 19*100 mm; mobile phase, water with 0.05% TFA and CH$_3$CN (hold 45% CH$_3$CN in 8 min); Detector, UV 220 nm, resulting in 15 mg (5%) of 5-(1H-indol-6-yl)-3-phenylpyrazolo[1,5-a]pyrimidin-7(4H)-one as a light brown yellow solid.

LC-MS: (ES, m/z): 327 [M+H]+

¹H-NMR (300 MHz, DMSO, ppm): 12.15 (s, 1H), 11.48 (s, 1H), 8.22 (s, 2H), 7.90-7.28 (m, 8H), 6.52 (s, 1H), 6.08 (s, 1H)

Example 96

5-(2,3-Dihydrobenzofuran-5-yl)-3-(pyridin-2-yl)pyrazolo[1,5-a]pyrimidin-7(4H)-one

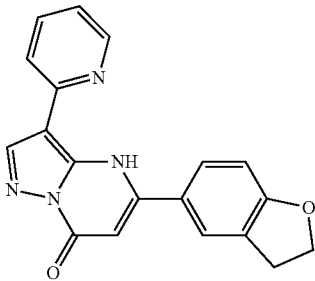 [SMILES: O=c1cc(-c2ccc3c(c2)CCO3)[nH]c2c(-c3ccccn3)cnn12]

A solution of 4-(pyridin-2-yl)-1H-pyrazol-5-amine (80 mg, 0.50 mmol, 1.00 equiv) and methyl 3-(2,3-dihydrobenzofuran-5-yl)-3-oxopropanoate (242 mg, 1.10 mmol, 2.20 equiv) in acetic acid (3 mL) was stirred overnight at 110° C., and then concentrated in vacuo. The resulting solid was collected by filtration and washed with 6 mL of DCM/MeOH (1/5) and dried to afford 40 mg (24%) of 5-(2,3-dihydrobenzofuran-5-yl)-3-(pyridin-2-yl)pyrazolo[1,5-a]pyrimidin-7(4H)-one as a yellow solid.

LC-MS: (ES, m/z): 331 [M+H]+

¹H-NMR (300 MHz, DMSO, ppm) 8.69-8.67 (m, 1H), 8.62 (m, 1H), 7.93-7.88 (m, 2H), 7.82 (s, 1H), 7.71-7.67 (dd, J=2.1, 8.4 Hz, 1H), 7.29-7.24 (m, 1H), 7.01-6.97 (d, J=8.4 Hz, 1H), 6.22 (s, 1H), 4.70-4.64 (t, J=8.7 Hz, 2H), 3.28-3.25 (t, J=8.7 Hz, 2H)

Example 97

5-(Benzofuran-5-yl)-3-phenylpyrazolo[1,5-a]pyrimidin-7(4H)-one

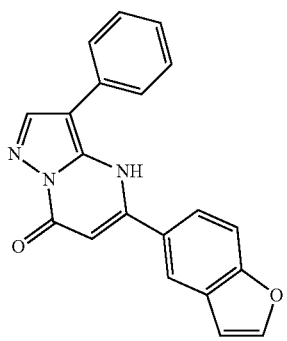 [SMILES: O=c1cc(-c2ccc3occc3c2)[nH]c2c(-c3ccccc3)cnn12]

A solution of methyl 3-(benzofuran-5-yl)-3-oxopropanoate (218 mg, 1.00 mmol, 1.00 equiv) and 4-phenyl-1H-pyrazol-5-amine (159 mg, 1.00 mmol, 1.00 equiv) in acetic acid (5 mL) was stirred overnight at 110° C. in an oil bath. The resulting mixture was concentrated in vacuo and then diluted with 10 mL of ether. The solids were collected by filtration, and then washed with methanol. The crude product (200 mg) was purified by Prep-HPLC with the following conditions (1#-Waters 2767-1): Column, SunFire Prep C18, 19*150 mm 5 um; mobile phase, water with 0.05% TFA and CH₃CN (37% CH₃CN up to 57% in 8 min, up to 100% in 1.5 min); Detector, UV 220 254 nm. This resulted in 50 mg (15%) of 5-(benzofuran-5-yl)-3-phenylpyrazolo[1,5-a]pyrimidin-7(4H)-one as a white solid.

LC-MS: (ES, m/z): 328 [M+H]+

¹H-NMR (300 MHz, DMSO, ppm): 12.261 (s, 1H), 8.193-8.136 (m, 3H), 7.778 (m, 2H), 7.697-7.673 (m, 2H), 7.493-7.442 (m, 2H), 7.342-7.293 (m, 1H), 7.117-7.111 (s, 1H), 6.055 (s, 1H).

Example 98

5-(2,3-Dihydrobenzofuran-5-yl)-3-phenylpyrazolo[1,5-a]pyrimidin-7(4H)-one

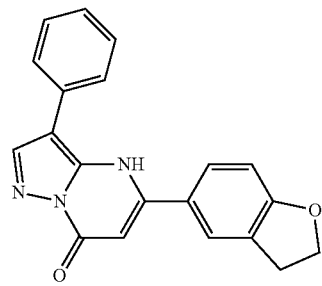 [SMILES: O=c1cc(-c2ccc3c(c2)CCO3)[nH]c2c(-c3ccccc3)cnn12]

A solution of 4-phenyl-1H-pyrazol-5-amine (158 mg, 1.00 mmol, 1.00 equiv) and methyl 3-(2,3-dihydrobenzofuran-5-yl)-3-oxopropanoate (242 mg, 1.10 mmol, 1.10 equiv) in acetic acid (3 mL) was stirred overnight at 110° C., and then concentrated in vacuo. The resulting solids were collected by filtration, washed with MeOH, and dried to afford 110 mg (33%) of 5-(2,3-dihydrobenzofuran-5-yl)-3-phenylpyrazolo[1,5-a]pyrimidin-7(4H)-one as a white solid.

LC-MS: (ES, m/z): 330 [M+H]+

¹H-NMR (300 MHz, DMSO, ppm): 12.05 (s, 1H), 8.16 (s, 1H), 7.74-7.59 (m, 4H), 7.49-7.43 (t, J=7.5 Hz, 2H), 7.34-7.28 (t, J=7.5 Hz, 1H), 6.95-6.91 (d, J=8.1 Hz, 1H), 5.96 (s, 1H), 4.67-4.60 (t, J=9.0 Hz, 2H), 3.31-3.24 (t, J=9.0 Hz, 2H)

Example 99

5-(2,3-Dihydrobenzofuran-5-yl)-3-(pyridin-3-yl)pyrazolo[1,5-a]pyrimidin-7(4H)-one

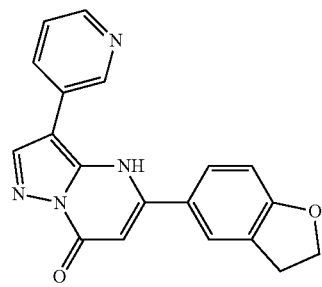 [SMILES: O=c1cc(-c2ccc3c(c2)CCO3)[nH]c2c(-c3cccnc3)cnn12]

A solution of 4-(pyridin-3-yl)-1H-pyrazol-5-amine hydrochloride (196 mg, 1.00 mmol, 1.00 equiv) and methyl 3-(2,3-dihydrobenzofuran-5-yl)-3-oxopropanoate (242 mg, 1.10 mmol, 1.08 equiv) in acetic acid (3 mL) was stirred overnight at 110° C. The resulting mixture was concentrated in vacuo. The residue was purified by silica gel column chromatography with dichloromethane/methanol (5:1). The resulting solids were washed with 2×5 mL of methanol. This afforded 45 mg (13%) of 5-(2,3-dihydrobenzofuran-5-yl)-3-(pyridin-3-yl)pyrazolo[1,5-a]pyrimidin-7(4H)-one as a grey-green solid.

LC-MS: (ES, m/z): 331 [M+H]+

1H-NMR (300 MHz, DMSO, ppm) 9.14 (s, 1H), 8.68-8.66 (d, J=5.1 Hz, 1H), 8.52-8.49 (d, J=5.1 Hz, 1H), 8.35 (s, 1H), 7.87-7.80 (m, 2H), 7.69-7.65 (d, J=8.1 Hz, 1H), 6.97-6.94 (d, J=8.4 Hz, 1H), 6.06 (s, 1H), 4.68-4.62 (t, J=8.7 Hz, 2H), 3.31-3.25 (t, J=8.7 Hz, 2H)

Example 100

5-(Benzo[d][1,3]dioxol-5-yl)-2-hydroxy-3-(pyridin-3-yl)pyrazolo[1,5-a]pyrimidin-7(4H)-one

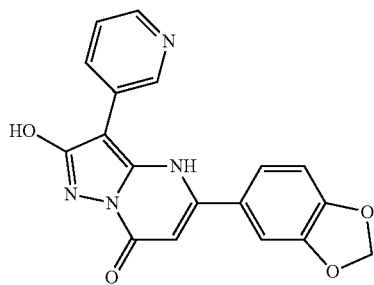 [SMILES: O=c1cc(-c2ccc3c(c2)OCO3)[nH]c2c(-c3cccnc3)c(O)nn12]

A mixture of 5-amino-4-(pyridin-3-yl)-1H-pyrazol-3-ol (156 mg, 0.89 mmol, 1.00 equiv) and ethyl 3-(benzo[d][1,3]dioxol-5-yl)-3-oxopropanoate (230 mg, 0.97 mmol, 1.10 equiv) in acetic acid (3 mL) was stirred overnight at 110° C., and then concentrated in vacuo. The resulting solid was collected by filtration, washed with MeOH, and dried to afford 110 mg (33%) of 5-(benzo[d][1,3]dioxol-5-yl)-2-hydroxy-3-(pyridin-3-yl)pyrazolo[1,5-a]pyrimidin-7(4H)-one as a yellow solid.

LC-MS: (ES, m/z): 349 [M+H]+

Example 101

5-(2,3-Dihydrobenzo[b][1,4]dioxin-6-yl)-2-hydroxy-3-(pyridin-3-yl)pyrazolo[1,5-a]pyrimidin-7(4H)-one

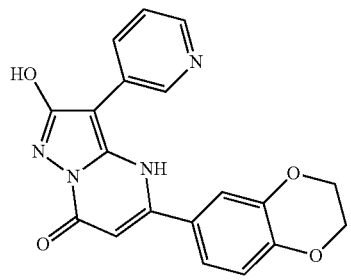 [SMILES: O=c1cc(-c2ccc3c(c2)OCCO3)[nH]c2c(-c3cccnc3)c(O)nn12]

A mixture of 5-amino-4-(pyridin-3-yl)-1H-pyrazol-3-ol (140 mg, 0.80 mmol, 1.00 equiv) and ethyl 3-(2,3-dihydrobenzo[b][1,4]dioxin-6-yl)-3-oxopropanoate (219 mg, 0.88 mmol, 1.10 equiv) in acetic acid (3 mL) was stirred overnight at 110° C., and then concentrated in vacuo. The solid was diluted with 5 mL of methanol and filtered. The solid was washed with methanol. This crude product (80 mg) was purified by Prep-HPLC with the following conditions (1#-Waters 2767-2): Column, SunFire Prep C18, 19*150 mm 5 um; mobile phase, water with 0.05% TFA and CH3CN (15% CH3CN up to 30% in 8 min, up to 100% in 1 min); Detector, uv 220&254 nm. This resulted in 26 mg (9%) of 5-(2,3-dihydrobenzo[b][1,4]dioxin-6-yl)-2-hydroxy-3-(pyridin-3-yl)pyrazolo[1,5-a]pyrimidin-7(4H)-one as a yellow-green solid.

LC-MS: (ES, m/z): 363 [M+H]+

1H-NMR (300 MHz, DMSO, ppm): δ 9.26 (s, 1H), 8.73 (s, 1H), 8.58-8.55 (d, J=4.5 Hz, 1H), 7.94-7.86 (t, J=6.9 Hz, 1H), 7.46 (s, 1H), 7.41-7.37 (d, J=8.1 Hz, 1H), 7.02-6.98 (d, J=8.4 Hz, 1H), 6.03 (s, 1H), 4.31 (s, 4H)

Example 102

5-(2,3-Dihydrobenzo[b][1,4]dioxin-6-yl)-2-hydroxy-3-(pyridin-2-yl)pyrazolo[1,5-a]pyrimidin-7(4H)-one

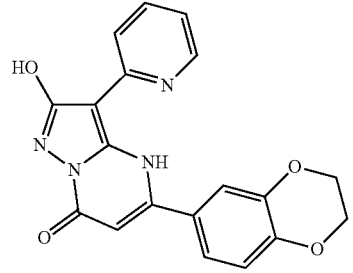 [SMILES: O=c1cc(-c2ccc3c(c2)OCCO3)[nH]c2c(-c3ccccn3)c(O)nn12]

A mixture of 5-amino-4-(pyridin-2-yl)-1H-pyrazol-3-ol (176 mg, 1.00 mmol, 1.00 equiv) and ethyl 3-(2,3-dihydrobenzo[b][1,4]dioxin-6-yl)-3-oxopropanoate (275 mg, 1.10 mmol, 1.10 equiv) in acetic acid (3 mL) was stirred overnight at 110° C., and then concentrated in vacuo. Then it was diluted with 5 mL of methanol. The solids were filtered and washed with methanol and then dried to provide 80 mg (22%) of 5-(2,3-dihydrobenzo[b][1,4]dioxin-6-yl)-2-hydroxy-3-(pyridin-2-yl)pyrazolo[1,5-a]pyrimidin-7(4H)-one as a yellow solid.

LC-MS: (ES, m/z): 363 [M+H]+

1H-NMR (300 MHz, DMSO, ppm): δ 8.49-8.47 (d, J=5.1 Hz, 2H), 8.16-8.10 (t, J=7.5 Hz, 1H), 7.59-7.56 (m, 2H), 7.24-7.18 (t, J=6.3 Hz, 1H), 6.98-6.95 (d, J=9 Hz, 1H), 6.27 (s, 1H), 4.31 (s, 4H)

Example 103

5-(2,3-Dihydrobenzo[b][1,4]dioxin-6-yl)-2-hydroxy-3-phenylpyrazolo[1,5-a]pyrimidin-7(4H)-one

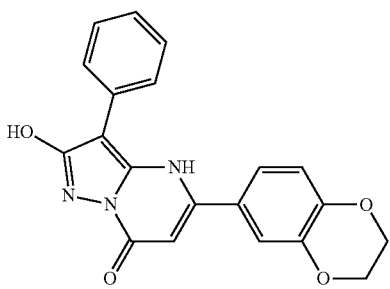 [SMILES: O=c1cc(-c2ccc3c(c2)OCCO3)[nH]c2c(-c3ccccc3)c(O)nn12]

A solution of 5-amino-4-phenyl-1H-pyrazol-3-ol (175 mg, 1.00 mmol, 1.00 equiv) and ethyl 3-(2,3-dihydrobenzo[b][1,4]dioxin-6-yl)-3-oxopropanoate (250 mg, 1.00 mmol, 1.00 equiv) in acetic acid (3 mL) was stirred overnight at 110° C., and then concentrated in vacuo. The resulting solids were collected by filtration, washed with MeOH, and dried to afford 85 mg (23%) of 5-(2,3-dihydrobenzo[b][1,4]dioxin-6-yl)-2-hydroxy-3-phenylpyrazolo[1,5-a]pyrimidin-7(4H)-one as a white solid.

LC-MS: (ES, m/z): 362 [M+H]+

$^1$H-NMR (300 MHz, DMSO, ppm): 11.77 (s, 1H), 7.62-7.60 (d, J=7.2 Hz, 2H), 7.45-7.39 (t, J=7.5 Hz, 2H), 7.33-7.31 (d, J=2.1 Hz, 1H), 7.28-7.23 (m, 2H), 7.01-6.98 (d, J=8.4 Hz, 1H), 5.87 (d, J=1.5 Hz, 1H), 4.31 (s, 4H)

Example 104

3-(4-Bromophenyl)-5-(2,3-dihydrobenzo[b][1,4]dioxin-6-yl)pyrazolo[1,5-a]pyrimidin-7(4H)-one

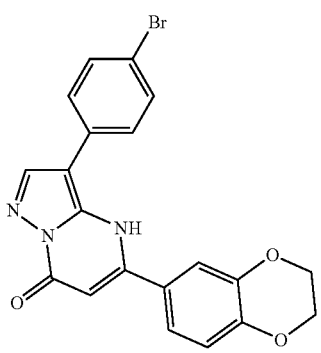 [SMILES: O=c1cc(-c2ccc3c(c2)OCCO3)[nH]c2c(-c3ccc(Br)cc3)cnn12]

A solution of 4-(4-bromophenyl)-1H-pyrazol-5-amine (595 mg, 2.50 mmol, 1.00 equiv) and ethyl 3-(2,3-dihydrobenzo[b][1,4]dioxin-6-yl)-3-oxopropanoate (688 mg, 2.75 mmol, 1.10 equiv) in acetic acid (4 mL) was stirred overnight at 110° C. The resulting mixture was concentrated in vacuo. The residue was purified by silica gel column chromatography with dichloromethane/methanol (10:1). The crude product (100 mg) was purified by Prep-HPLC under the following conditions (1#-Waters 2767-2): Column, SunFire Prep C18, 5 um, 19*150 mm; mobile phase, water with 0.05% TFA and CH$_3$CN (45% CH$_3$CN up to 75% in 8 min, up to 100% in 1.5 min); Detector, uv 220&254 nm. This resulted in 14.7 mg (1%) of 3-(4-bromophenyl)-5-(2,3-dihydrobenzo[b][1,4]dioxin-6-yl)pyrazolo[1,5-a]pyrimidin-7(4H)-one as a grey-green solid.

LC-MS: (ES, m/z): 426 [M+H]+

$^1$H-NMR (300 MHz, DMSO, ppm) δ 12.05 (s, 1H), 8.20 (s, 1H), 7.68-7.43 (m, 6H), 7.02-6.98 (d, J=8.4 Hz, 1H), 6.02 (s, 1H), 4.31 (s, 4H)

Example 105

3-(6-Hydroxypyridin-3-yl)-5-phenylpyrazolo[1,5-a]pyrimidin-7(4H)-one

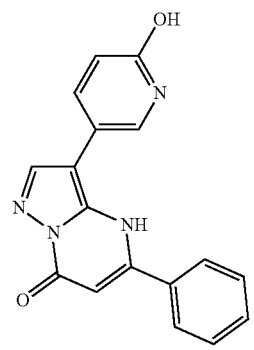 [SMILES: O=c1cc(-c2ccccc2)[nH]c2c(-c3ccc(O)nc3)cnn12]

A solution of 4-(6-fluoropyridin-3-yl)-1H-pyrazol-5-amine (180 mg, 1.01 mmol, 1.00 equiv) and methyl 3-oxo-3-phenylpropanoate (180 mg, 1.01 mmol, 1.00 equiv) in acetic acid (5 mL) was stirred overnight at 120° C. in an oil bath. The resulting mixture was concentrated in vacuo to afford a solid which was washed with MeOH and collected by filtration. This resulted in 40 mg (13%) of 3-(6-hydroxypyridin-3-yl)-5-phenylpyrazolo[1,5-a]pyrimidin-7(4H)-one as a yellow solid.

LC-MS: (ES, m/z): 305 [M+H]+

$^1$H-NMR (400 MHz, DMSO, ppm): 12.215 (s, 1H), 11.785 (s, 1H), 8.064 (s, 1H), 7.812-7.798 (m, 2H), 7.672-7.563 (m, 5H), 6.426-6.403 (d, J=6.9 Hz, 1H), 5.983 (s, 1H)

Example 106

5-(2,3-Dihydrobenzo[b][1,4]dioxin-6-yl)-3-(morpholine-4-carbonyl)pyrazolo[1,5-a]pyrimidin-7(4H)-one To a solution of morpholine (70 mg, 0.29 mmol, 2.50 equiv, 0.8 mmol) in chloroform (3 mL) was added trimethyl aluminum (0.1 mL, 3.50 equiv). The reaction was stirred for 1 h at room temperature. To this mixture was added ethyl 5-(2,3-dihydrobenzo[b][1,4]dioxin-6-yl)-7-oxo-4,7-dihydropyrazolo[1,5-a]pyrimidine-3-carboxylate (110 mg, 0.32 mmol, 1.00 equiv). The resulting mixture was stirred overnight at 50° C. The reaction was then quenched by the addition of 1 ml of H$_2$O. The resulting mixture was concentrated in vacuo. The crude product (100 mg) was purified by Prep-HPLC with the following conditions (com-flash): Column, C-18 column; mobile phase, CH$_3$CN/H$_2$O; Detector, UV254. This resulted in 44 mg (37%) of 5-(2,3-dihydrobenzo[b][1,4]dioxin-6-yl)-3-(morpholine-4-carbonyl)pyrazolo[1,5-a]pyrimidin-7(4H)-one as a white solid.

LC-MS: (ES, m/z): 383 [M+H]$^+$ $^1$H-NMR (300 MHz, DMSO, ppm): 11.876 (s, 1H), 8.166 (s, 1H), 7.356-7.257 (m, 2H), 7.078-7.050 (m, 1H), 6.158 (s, 1H), 4.331 (s, 4H), 3.651 (s, 8H)

Example 107

5-(2,3-Dihydrobenzo[b][1,4]dioxin-6-yl)-3-(4-methylpiperazine-1-carbonyl)pyrazolo[1,5-a]pyrimidin-7(4H)-one

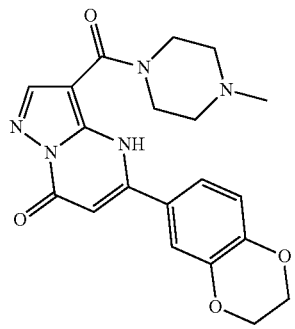 [SMILES: CN1CCN(C(=O)c2cnn3c(=O)cc(-c4ccc5c(c4)OCCO5)[nH]c23)CC1]

AlMe$_3$ (0.36 mL) was added to a solution of 1-methylpiperazine (102.64 mg, 1.03 mmol, 3.36 equiv) in chloroform (3 mL), and the resulting solution was stirred for 1 h at room temperature. To the reaction mixture, 5-(2,3-dihydrobenzo[b][1,4]dioxin-6-yl)-3-(ethoxymethyl)pyrazolo[1,5-a]pyrimidin-7(4H)-one (100 mg, 0.31 mmol, 1.00 equiv) was added. The resulting solution was stirred overnight at 50° C. The crude product (150 mg) was purified by Prep-HPLC with the following conditions (1#-Waters 2767-1): Column, SunFire Prep C18, 19*150 mm 5 um; mobile phase, water with 0.05% TFA and CH$_3$CN (10% CH$_3$CN up to 25% in 8 min, up to 100% in 1.5 min); Detector, UV 220 254 nm. This resulted in 25 mg (16%) of 5-(2,3-dihydrobenzo[b][1,4]dioxin-6-yl)-3-(4-methylpiperazine-1-carbonyl)pyrazolo[1,5-a]pyrimidin-7(4H)-one as a yellow solid.

LC-MS: (ES, m/z): 396 [M+H]$^+$ $^1$H-NMR (300 MHz, DMSO, ppm): 8.016 (s, 1H), 7.326-7.283 (m, 2H), 7.063-7.035 (d, J=8.4 Hz, 1H), 6.148 (s, 1H), 4.310 (m, 6H), 3.430-3.091 (m, 6H), 2.833 (s, 3H)

Example 108

N-Benzyl-5-(2,3-dihydrobenzo[b][1,4]dioxin-6-yl)-7-oxo-4,7-dihydropyrazolo[1,5-a]pyrimidine-3-carboxamide

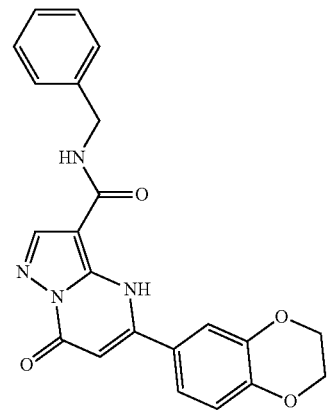 [SMILES: O=C(NCc1ccccc1)c1cnn2c(=O)cc(-c3ccc4c(c3)OCCO4)[nH]c12]

Step 1. Ethyl 5-(2,3-dihydrobenzo[b][1,4]dioxin-6-yl)-7-oxo-4,7-dihydropyrazolo[1,5-a]pyrimidine-3-carboxylate

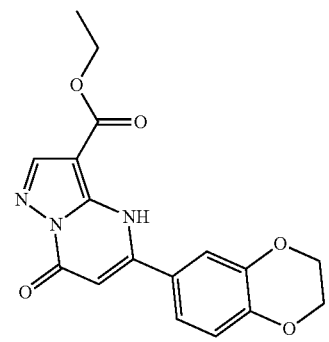 [SMILES: CCOC(=O)c1cnn2c(=O)cc(-c3ccc4c(c3)OCCO4)[nH]c12]

A solution of ethyl 5-amino-1H-pyrazole-4-carboxylate (1.24 g, 8.00 mmol, 1.00 equiv) and ethyl 3-(2,3-dihydrobenzo[b][1,4]dioxin-6-yl)-3-oxopropanoate (2 g, 8.00 mmol, 1.00 equiv) in acetic acid (15 mL) was stirred overnight at 110° C., and then concentrated in vacuo. The residue was purified by column chromatography, eluting with dichloromethane:methanol:ammonia (50:50:1). The resulting product was washed with methanol and dried to afford 310 mg (11%) of ethyl 5-(2,3-dihydrobenzo[b][1,4]dioxin-6-yl)-7-oxo-4,7-dihydropyrazolo[1,5-a]pyrimidine-3-carboxylate as a yellow solid.

LC-MS: (ES, m/z): 342 [M+H]$^+$ $^1$H-NMR (300 MHz, DMSO, ppm): 8.02 (s, 1H), 7.59-7.57 (d, J=2.1 Hz, 1H), 7.53-7.49 (dd, J=2.1, 8.7 Hz, 1H), 6.92-6.89 (d, J=8.7 Hz, 1H), 6.07 (s, 1H), 4.29 (s, 4H), 4.24-4.16 (q, J=6.9 Hz, 2H), 1.33-1.28 (t, J=6.9 Hz, 3H)

Step 2. N-Benzyl-5-(2,3-dihydrobenzo[b][1,4]dioxin-6-yl)-7-oxo-4,7-dihydropyrazolo[1,5-a]pyrimidine-3-carboxamide

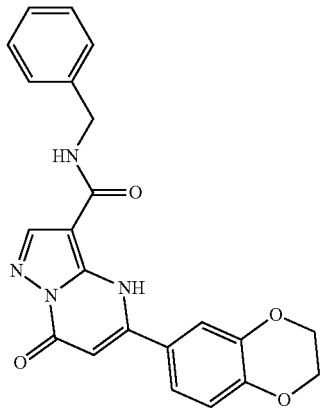 [SMILES: O=C(NCc1ccccc1)c1cnn2c(=O)cc(-c3ccc4c(c3)OCCO4)[nH]c12]

Trimethyl aluminum (3.4 mL, 2N in hexane) was added to a solution of phenylmethanamine (938 mg, 8.77 mmol, 13.00 equiv) in chloroform (10 mL) and the reaction was stirred at room temperature for 1 h. To this was added ethyl 5-(2,3-dihydrobenzo[b][1,4]dioxin-6-yl)-7-oxo-4,7-dihydropyrazolo[1,5-a]pyrimidine-3-carboxylate (230 mg, 0.67 mmol, 1.00 equiv). The resulting solution was stirred overnight at 50° C. The reaction was then quenched by the addition of water/ice. The pH of the aqueous solution was adjusted to 4 with HCl (1M), then extracted with of chloroform. The organic layers were combined, dried over anhydrous sodium sulfate, and concentrated in vacuo. The crude product (200 mg) was purified by Prep-HPLC under the following conditions (1#-Waters 2767-1): Column, SunFire Prep C18, 19*150 mm 5 um; mobile phase, water with 0.05% TFA and CH$_3$CN (45% CH$_3$CN up to 65% in 8 min, up to 100% in 1.5 min); Detector, UV 220 254 nm. This resulted in 32.3 mg (12%) of N-benzyl-5-(2,3-dihydrobenzo[b][1,4]dioxin-6-yl)-7-oxo-4,7-dihydropyrazolo[1,5-a]pyrimidine-3-carboxamide as a white solid.

LC-MS: (ES, m/z): 403 [M+H]$^+$ $^1$H-NMR (300 MHz, DMSO, ppm): 11.12 (s, 1H), 9.02 (s, 1H), 8.43 (s, 1H), 7.36-7.04 (m, 8H), 6.23 (s, 1H), 4.52-4.50 (d, J=5.4 Hz, 2H), 4.23 (s, 4H)

Example 109

5-(4-Chlorophenyl)-3-(pyridin-2-yl)pyrazolo[1,5-a]pyrimidin-7(4H)-one

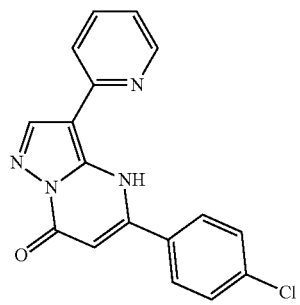 [SMILES: O=c1cc(-c2ccc(Cl)cc2)[nH]c2c(-c3ccccn3)cnn12]

A solution of 4-(pyridin-2-yl)-1H-pyrazol-5-amine (100 mg, 0.62 mmol, 1.00 equiv) and methyl 3-(4-chlorophenyl)-3-oxopropanoate (146 mg, 0.69 mmol, 1.10 equiv) in AcOH (2 mL) was stirred overnight at 110° C., and then concentrated in vacuo. The solid was collected by filtration, washed with MeOH, and dried to afford 105 mg (49%) of 5-(4-chlorophenyl)-3-(pyridin-2-yl)pyrazolo[1,5-a]pyrimidin-7(4H)-one as a yellow solid.

LC-MS: (ES, m/z): 323 [M+H]$^+$ $^1$H-NMR (300 MHz, DMSO, ppm): 8.69-8.67 (d, J=3.3 Hz, 2H), 8.11-7.99 (m, 4H), 7.70-7.66 (d, J=8.7 Hz, 2H), 7.35-7.30 (m, 2H), 6.36 (s, 1H)

Example 110

5-(2,4-Dimethoxyphenyl)-3-(pyridin-2-yl)pyrazolo[1,5-a]pyrimidin-7(4H)-one

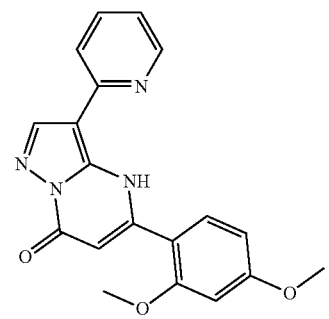 [SMILES: COc1ccc(-c2cc(=O)n3ncc(-c4ccccn4)c3[nH]2)c(OC)c1]

A solution of 4-(pyridin-2-yl)-1H-pyrazol-5-amine (100 mg, 0.62 mmol, 1.00 equiv) and methyl 3-(2,4-dimethoxyphenyl)-3-oxopropanoate (164 mg, 0.69 mmol, 1.10 equiv) in acetic acid (2 mL) was stirred overnight at 110° C., and then concentrated in vacuo. The solids were collected by filtration, washed with MeOH, and dried to afford 90 mg (41%) of 5-(2,4-dimethoxyphenyl)-3-(pyridin-2-yl)pyrazolo[1,5-a]pyrimidin-7(4H)-one as a yellow solid.

LC-MS: (ES, m/z): 349 [M+H]$^+$ $^1$H-NMR (300 MHz, DMSO, ppm): 12.66 (s, 1H), 8.69-8.66 (d, J=5.1 Hz, 1H), 8.62 (s, 1H), 7.93-7.84 (m, 3H), 7.28-7.23 (m, 1H), 6.85 (d, J=2.4 Hz, 1H), 6.76-6.71 (dd, J=2.4, 8.8 Hz, 1H), 6.28 (s, 1H), 4.11 (s, 3H), 3.89 (s, 3H)

Example 111

5-(3,4-Dimethoxyphenyl)-3-(pyridin-2-yl)pyrazolo[1,5-a]pyrimidin-7(4H)-one

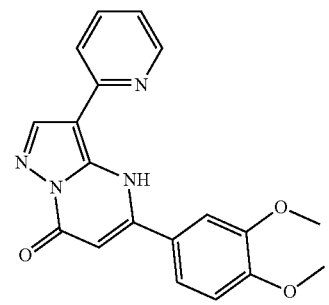 [SMILES: COc1ccc(-c2cc(=O)n3ncc(-c4ccccn4)c3[nH]2)cc1OC]

A solution of 4-(pyridin-2-yl)-1H-pyrazol-5-amine (100 mg, 0.62 mmol, 1.00 equiv) and methyl 3-(3,4-dimethoxyphenyl)-3-oxopropanoate (164 mg, 0.69 mmol, 1.10 equiv) in AcOH (2 mL) was stirred overnight at 110° C., and then concentrated in vacuo. The resulting solids were collected by filtration, washed with MeOH, and dried to afford 70 mg (31%) of 5-(3,4-dimethoxyphenyl)-3-(pyridin-2-yl)pyrazolo[1,5-a]pyrimidin-7(4H)-one as a yellow solid.

LC-MS: (ES, m/z): 349 [M+H]+

1H-NMR (300 MHz, DMSO, ppm): δ8.68-8.63 (m, 2H), 7.94-7.89 (m, 2H), 7.53-7.47 (m, 2H), 7.30-7.25 (m, 1H), 7.22-7.18 (d, J=8.4 Hz, 1H), 6.38 (s, 1H), 3.92 (s, 3H), 3.87 (s, 3H)

Example 112

3-(6-Methoxypyridin-3-yl)-5-phenylpyrazolo[1,5-a]pyrimidin-7(4H)-one

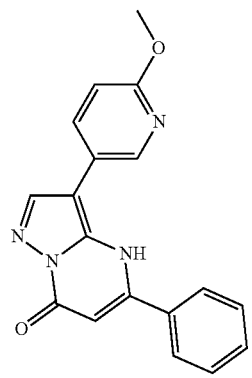 [SMILES: COc1ccc(-c2cnn3c(=O)cc(-c4ccccc4)[nH]c23)cn1]

A solution of 4-(6-methoxypyridin-3-yl)-1H-pyrazol-5-amine (155 mg, 0.81 mmol, 1.00 equiv) and methyl 3-oxo-3-phenylpropanoate (144 mg, 0.81 mmol, 1.00 equiv) in acetic acid (2 mL) was stirred overnight at 100° C. in an oil bath, then concentrated in vacuo. The crude product (150 mg) was purified by Prep-HPLC with the following conditions (1#-Waters 2767-2): Column, SunFire Prep C18, 5 um, 19*150 mm; mobile phase, water with 0.05% TFA and CH3CN (25% CH3CN up to 55% in 8 min, up to 100% in 1.5 min); Detector, uv 220&254 nm. This resulted in 40 mg (15%) of 3-(6-methoxypyridin-3-yl)-5-phenylpyrazolo[1,5-a]pyrimidin-7(4H)-one as a white solid.

LC-MS: (ES, m/z): 319 [M+H]+

1H-NMR (300 MHz, DMSO, ppm): 12.314 (s, 1H), 8.730-8.665 (s, 1H), 8.460 (s, 1H), 8.175 (s, 1H), 7.954-7.828 (m, 2H), 7.583 (m, 3H), 6.933-6.905 (m, 1H), 6.037 (s, 1H), 3.898 (s, 3H)

Example 113

5-(2,3-Dihydrobenzo[b][1,4]dioxin-6-yl)-7-oxo-4,7-dihydropyrazolo[1,5-a]pyrimidine-3-carbonitrile

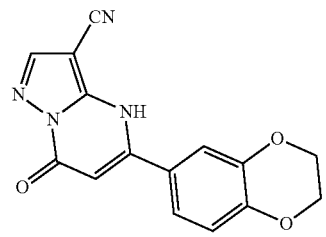 [SMILES: N#Cc1cnn2c(=O)cc(-c3ccc4c(c3)OCCO4)[nH]c12]

LC-MS: (ES, m/z): 295 [M+H]+

1H-NMR (300 MHz, DMSO, ppm): δ8.41 (s, 1H), 7.42-7.41 (d, J=1.8 Hz, 1H), 7.37-7.33 (dd, J=1.8, 8.4 Hz, 1H), 7.06-7.03 (d, J=8.4 Hz, 1H), 6.20 (s, 1H), 4.33 (s, 3H)

Example 114

5-(2,3-Dihydrobenzo[b][1,4]dioxin-6-yl)-7-oxo-4,7-dihydropyrazolo[1,5-a]pyrimidine-3-carboxamide

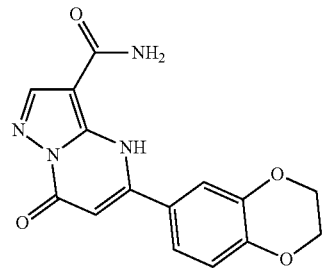 [SMILES: NC(=O)c1cnn2c(=O)cc(-c3ccc4c(c3)OCCO4)[nH]c12]

A mixture of 5-amino-1H-pyrazole-4-carbonitrile (400 mg, 3.70 mmol, 1.00 equiv) and ethyl 3-(2,3-dihydrobenzo[b][1,4]dioxin-6-yl)-3-oxopropanoate (925 mg, 3.70 mmol, 1.00 equiv) in acetic acid (5 mL) was stirred overnight at 110° C., and then concentrated to dryness. The resulting solid was washed with MeOH and purified by Prep-HPLC under the following conditions (1#-Waters 2767-1): Column, SunFire Prep C18, 19*150 mm 5 um; mobile phase, water with 0.05% TFA and CH3CN (25% CH3CN up to 45% in 8 min, up to 100% in 1.5 min); Detector, UV 220 254 nm. This resulted in 76 mg (P=98.2%, white solid) of 5-(2,3-dihydrobenzo[b][1,4]dioxin-6-yl)-7-oxo-4,7-dihydropyrazolo[1,5-a]pyrimidine-3-carbonitrile and 19.2 mg (P=97.2%, white solid) of 5-(2,3-dihydrobenzo[b][1,4]dioxin-6-yl)-7-oxo-4,7-dihydropyrazolo[1,5-a]pyrimidine-3-carboxamide.

LC/MS: (ES, m/z): 313 [M+H]+

1H-NMR (300 MHz, DMSO, ppm) δ 11.06 (s, 1H), 8.35 (s, 1H), 7.95 (s, 1H), 7.45 (s, 1H), 7.36-7.34 (d, J=2.1 Hz, 1H), 7.32-7.28 (dd, J=2.1, 8.4 Hz, 1H), 7.09-7.05 (d, J=8.4 Hz, 1H), 6.22 (s, 1H), 4.33 (s, 3H)

Example 115

5-(2,3-Dihydrobenzo[b][1,4]dioxin-6-yl)-7-oxo-4,7-dihydropyrazolo[1,5-a]pyrimidine-3-carboxylic acid

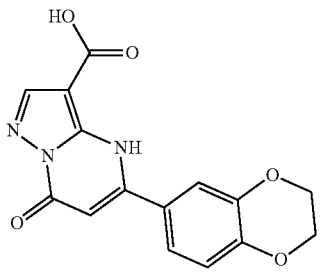 [SMILES: O=C(O)c1cnn2c(=O)cc(-c3ccc4c(c3)OCCO4)[nH]c12]

A solution of ethyl 5-(2,3-dihydrobenzo[b][1,4]dioxin-6-yl)-7-oxo-4,7-dihydropyrazolo[1,5-a]pyrimidine-3-carboxylate (80 mg, 0.23 mmol, 1.00 equiv) and sodium hydroxide (37 mg, 0.93 mmol, 3.94 equiv) in water (10 mL) and methanol (20 mL) was stirred for 4 days at 50° C. The resulting mixture was concentrated under vacuum, and diluted with 20 mL of H$_2$O. The resulting solids were filtered out. The pH of the filtrate was adjusted to 6 with HCl (1M). The resulting solids were collected by filtration and then washed with water. The solid was dried in an oven under reduced pressure. This resulted in 50 mg (65%) of 5-(2,3-dihydrobenzo[b][1,4]dioxin-6-yl)-7-oxo-4,7-dihydropyrazolo[1,5-a]pyrimidine-3-carboxylic acid as a white solid.

LC-MS: (ES, m/z): 314 [M+H]$^+$ $^1$H-NMR (300 MHz, DMSO, ppm): 11.30 (s, 1H), 8.20 (s, 1H), 7.34-7.27 (m, 2H), 7.07-7.03 (d, J=8.4 Hz, 1H), 6.21 (s, 1H), 3.35 (s, 4H)

Example 116

11-(Pyridin-2-yl)-5,6-dihydrobenzo[h]pyrazolo[5,1-b]quinazolin-7(12H)-one

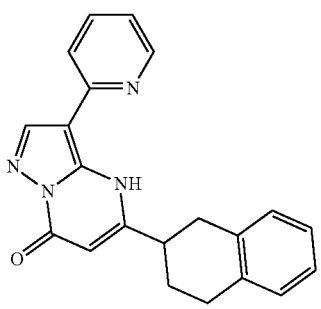 [SMILES: O=c1cc(C2CCc3ccccc3C2)[nH]c2c(-c3ccccn3)cnn12]

A solution of 4-(pyridin-2-yl)-1H-pyrazol-5-amine (100 mg, 0.62 mmol, 1.00 equiv) and methyl 1-oxo-1,2,3,4-tetrahydronaphthalene-2-carboxylate (140 mg, 0.69 mmol, 1.10 equiv) in acetic acid (2 mL) was stirred overnight at 110° C., then concentrated in vacuo. The crude product (200 mg) was purified by Prep-HPLC with the following conditions (1#-Waters 2767-1): Column, SunFire Prep C18, 19*150 mm 5 um; mobile phase, water with 0.05% TFA and CH$_3$CN (60% CH$_3$CN up to 80% in 8 min, up to 100% in 1.5 min); Detector, UV 220 254 nm. This resulted in 12.6 mg (6%) of 11-(pyridin-2-yl)-5,6-dihydrobenzo[h]pyrazolo[5,1-b]quinazolin-7(12H)-one as a yellow solid.

LC-MS: (ES, m/z): 315 [M+H]$^+$ $^1$H-NMR (300 MHz, DMSO, ppm): 8.86-8.73 (d, J=4.8 Hz, 1H), 8.63 (s, 1H), 7.96-7.87 (m, 3H), 7.54-7.43 (m, 3H), 7.30-7.25 (m, 1H), 2.98-2.92 (m, 2H), 2.82-2.76 (m, 2H)

Example 117

5-(2,3-Dihydrobenzo[b][1,4]dioxin-6-yl)-3-phenyl-2-(trifluoromethyl)pyrazolo[1,5-a]pyrimidin-7(4H)-one

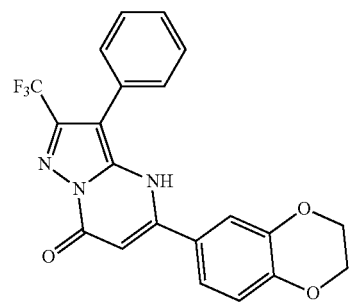 [SMILES: O=c1cc(-c2ccc3c(c2)OCCO3)[nH]c2c(-c3ccccc3)c(C(F)(F)F)nn12]

A solution of 4-phenyl-3-(trifluoromethyl)-1H-pyrazol-5-amine (228 mg, 1.00 mmol, 1.00 equiv) and ethyl 3-(2,3-dihydrobenzo[b][1,4]dioxin-6-yl)-3-oxopropanoate (275 mg, 1.10 mmol, 1.10 equiv) in acetic acid (3 mL) was stirred overnight at 110° C., and then concentrated in vacuo. The resulting solid was washed with MeOH, and dried to afford in 95 mg (23%) of 5-(2,3-dihydrobenzo[b][1,4]dioxin-6-yl)-3-phenyl-2-(trifluoromethyl)pyrazolo[1,5-a]pyrimidin-7(4H)-one as a white solid.

LC-MS: (ES, m/z): 414 [M+H]$^+$ $^1$H-NMR (300 MHz, DMSO, ppm): 12.45 (s, 1H), 7.50-7.43 (m, 5H), 7.29-7.22 (m, 2H), 7.02-6.98 (d, J=8.4 Hz, 1H), 6.10 (s, 1H), 4.30 (s, 4H)

Example 118

5-(2,3-Dihydrobenzo[b][1,4]dioxin-6-yl)-3-(6-morpholinopyridin-3-yl)pyrazolo[1,5-a]pyrimidin-7(4H)-one

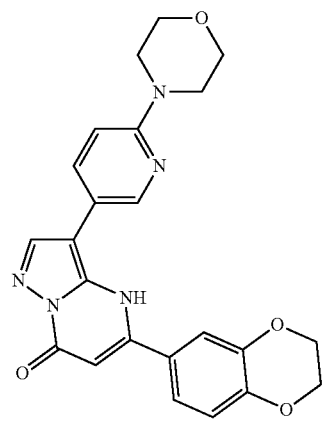 [SMILES: O=c1cc(-c2ccc3c(c2)OCCO3)[nH]c2c(-c3ccc(N4CCOCC4)nc3)cnn12]

Step 1.
4-(6-Fluoropyridin-3-yl)-1H-pyrazol-5-amine

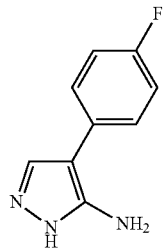 [SMILES: Nc1[nH]ncc1-c1ccc(F)cc1]

(Trifluoromethane)sulfonyl trifluoromethanesulfonate (7.5 mL) was added dropwise with stirring at 0° C. to a solution of 1-(4-methoxybenzyl)-4-(6-fluoropyridin-3-yl)-1H-pyrazol-5-amine (1 g, 3.35 mmol, 1.00 equiv) and $CF_3COOH$ (30 mL), and then the reaction was stirred for 5 hrs at 30° C. in an oil bath. The resulting mixture was concentrated in vacuo. The crude product (1 g) was purified by Flash-Prep-HPLC with the following conditions (IntelFlash-1): Column, C18; mobile phase, $CH_3CN/H_2O$=5% increasing to $CH_3CN/H_2O$=40% within 30 min; Detector, UV 254 nm. This resulted in 220 mg (37%) of 4-(6-fluoropyridin-3-yl)-1H-pyrazol-5-amine as yellow oil.

LC-MS: (ES, m/z): 179 [M+H]+

Step 2.
4-(6-Morpholinopyridin-3-yl)-1H-pyrazol-5-amine

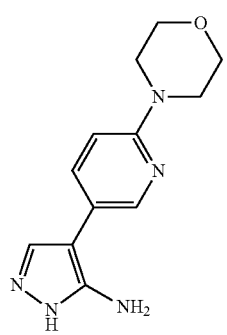 [SMILES: Nc1[nH]ncc1-c1ccc(N2CCOCC2)nc1]

A mixture of 4-(6-fluoropyridin-3-yl)-1H-pyrazol-5-amine (100 mg, 0.56 mmol, 1.00 equiv), morpholine (244 mg, 2.80 mmol, 4.99 equiv) and DMSO (2 mL) was stirred for 2 days at 115° C. in an oil bath. The crude product (150 mg) was purified by Flash-Prep-HPLC under the following conditions (IntelFlash-1): Column, C18 silica gel; mobile phase, $CH_3CN/H_2O$; Detector, UV 254 nm. This resulted in 60 mg (44%) of 4-(6-morpholinopyridin-3-yl)-1H-pyrazol-5-amine as a white solid.

Step 3. 5-(2,3-Dihydrobenzo[b][1,4]dioxin-6-yl)-3-(6-morpholinopyridin-3-yl)pyrazolo[1,5-a]pyrimidin-7(4H)-one

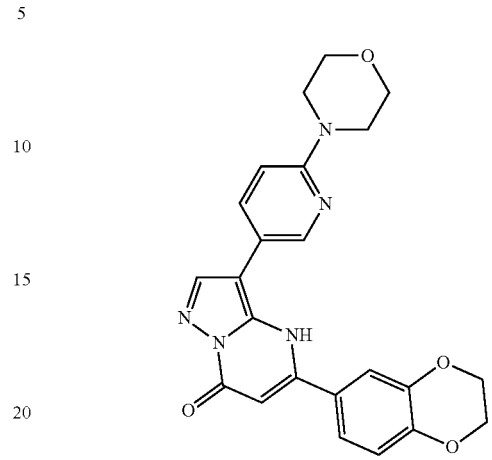

A solution of 4-(6-morpholinopyridin-3-yl)-1H-pyrazol-5-amine (60 mg, 0.24 mmol, 1.00 equiv) and ethyl 3-(2,3-dihydrobenzo[b][1,4]dioxin-6-yl)-3-oxopropanoate (68 mg, 0.27 mmol, 1.11 equiv) in acetic acid (2 mL) was stirred overnight at 100° C. in an oil bath, and then concentrated in vacuo. The crude product (60 mg) was purified by Flash-Prep-HPLC under the following conditions (CombiFlash-1): Column, C18 silica gel; mobile phase, water increasing to $H_2O$=MeOH/$H_2O$; Detector, UV 254 nm. This resulted in 25 mg (23%) of 5-(2,3-dihydrobenzo[b][1,4]dioxin-6-yl)-3-(6-morpholinopyridin-3-yl)pyrazolo[1,5-a]pyrimidin-7(4H)-one as a light yellow solid.

LC-MS: (ES, m/z): 432 [M+H]+
$^1$H-NMR (300 MHz, DMSO, ppm): δ 12.056 (s, 1H), 8.388 (s, 1H), 8.119 (s, 1H), 7.923 (s, 1H), 7.378-7.303 (m, 2H), 7.081-7.010 (m, 2H), 5.961 (s, 1H), 4.315 (s, 4H), 3.750-3.580 (m, 4H), 3.547-3.536 (d, J=3.3 Hz, 4H)

Example 119

5-(2,3-Dihydrobenzo[b][1,4]dioxin-6-yl)-3-(6-(pyrrolidin-1-yl)pyridin-3-yl)pyrazolo[1,5-a]pyrimidin-7(4H)-one

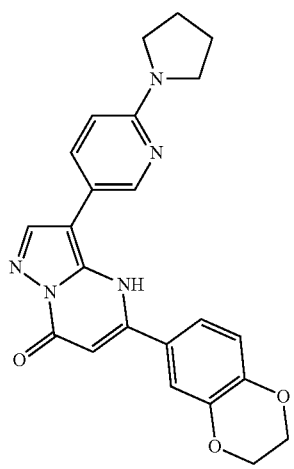 [SMILES: O=c1cc(-c2ccc3c(c2)OCCO3)[nH]c2c(-c3ccc(N4CCCC4)nc3)cnn12]

207

Step 1. 1-(4-Methoxybenzyl)-4-(6-(pyrrolidin-1-yl)pyridin-3-yl)-1H-pyrazol-5-amine

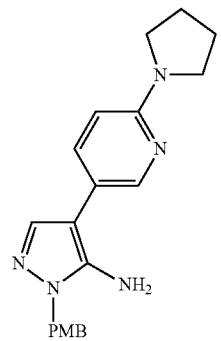

A mixture of 1-(4-methoxybenzyl)-4-(6-fluoropyridin-3-yl)-1H-pyrazol-5-amine (665.7 mg, 2.23 mmol, 1.00 equiv), pyrrolidine (1.59 g, 22.39 mmol, 10.00 equiv), and n-BuOH (6 mL) was stirred overnight at 100° C. in an oil bath. The resulting mixture was concentrated in vacuo, and the residue was taken up in ether. The resulting solids were collected by filtration and washed with ether. This resulted in 561.4 mg (71%) of 1-(4-methoxybenzyl)-4-(6-(pyrrolidin-1-yl)pyridin-3-yl)-1H-pyrazol-5-amine as a white solid.

LC-MS: (ES, m/z): 350 [M+H]$^+$

Step 2. 4-(6-(Pyrrolidin-1-yl)pyridin-3-yl)-1H-pyrazol-5-amine

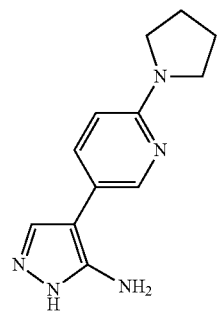 [SMILES: Nc1[nH]ncc1-c1ccc(N2CCCC2)nc1]

A mixture of 1-(4-methoxybenzyl)-4-(6-(pyrrolidin-1-yl)pyridin-3-yl)-1H-pyrazol-5-amine (349 mg, 1.00 mmol, 1.00 equiv), trifluoroacetic acid (12 mL), and Tf$_2$O (3 mL) was stirred for 2 hrs at 30° C. in an oil bath. The resulting mixture was concentrated under vacuum. The residue was purified via reverse phase flash chromatography using C18 column with mobile phase (CH$_3$CN/H$_2$O: 5%-40%). This resulted in 100 mg (44%) of 4-(6-(pyrrolidin-1-yl)pyridin-3-yl)-1H-pyrazol-5-amine as a white solid.

LC-MS: (ES, m/z): 230 [M+H]$^+$ $^1$H-NMR (300 MHz, DMSO, ppm): 8.123-8.092 (d, J=9.3 Hz, 2H), 7.980-7.934 (m, 2H), 7.114-7.083 (m, 1H), 3.551-3.509 (m, 4H), 2.057-2.015 (m, 4H)

208

Step 3. 5-(2,3-Dihydrobenzo[b][1,4]dioxin-6-yl)-3-(6-(pyrrolidin-1-yl)pyridin-3-yl)pyrazolo[1,5-a]pyrimidin-7(4H)-one

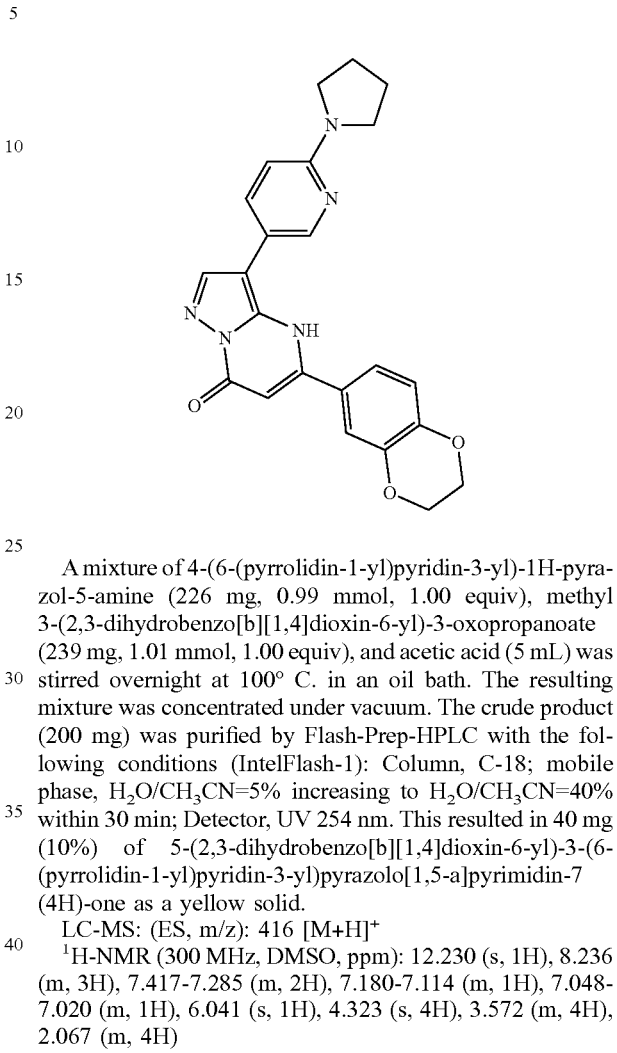

A mixture of 4-(6-(pyrrolidin-1-yl)pyridin-3-yl)-1H-pyrazol-5-amine (226 mg, 0.99 mmol, 1.00 equiv), methyl 3-(2,3-dihydrobenzo[b][1,4]dioxin-6-yl)-3-oxopropanoate (239 mg, 1.01 mmol, 1.00 equiv), and acetic acid (5 mL) was stirred overnight at 100° C. in an oil bath. The resulting mixture was concentrated under vacuum. The crude product (200 mg) was purified by Flash-Prep-HPLC with the following conditions (IntelFlash-1): Column, C-18; mobile phase, H$_2$O/CH$_3$CN=5% increasing to H$_2$O/CH$_3$CN=40% within 30 min; Detector, UV 254 nm. This resulted in 40 mg (10%) of 5-(2,3-dihydrobenzo[b][1,4]dioxin-6-yl)-3-(6-(pyrrolidin-1-yl)pyridin-3-yl)pyrazolo[1,5-a]pyrimidin-7(4H)-one as a yellow solid.

LC-MS: (ES, m/z): 416 [M+H]$^+$ $^1$H-NMR (300 MHz, DMSO, ppm): 12.230 (s, 1H), 8.236 (m, 3H), 7.417-7.285 (m, 2H), 7.180-7.114 (m, 1H), 7.048-7.020 (m, 1H), 6.041 (s, 1H), 4.323 (s, 4H), 3.572 (m, 4H), 2.067 (m, 4H)

Example 120

3-(Pyridin-2-yl)-5-p-tolylpyrazolo[1,5-a]pyrimidin-7(4H)-one

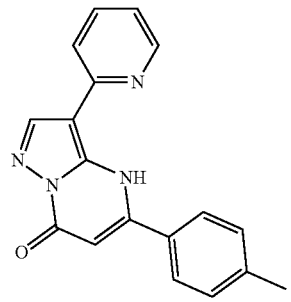

A mixture of 4-(pyridin-2-yl)-1H-pyrazol-5-amine (80 mg, 0.50 mmol, 1.00 equiv), methyl 3-oxo-3-p-tolylpropanoate (106 mg, 0.55 mmol, 1.10 equiv), and acetic acid (2 mL) was stirred overnight at 110° C., then concentrated in vacuo, and diluted with 5 mL of methanol. The resulting solids were collected by filtration and washed with methanol. This resulted in 51 mg (33%) of 3-(pyridin-2-yl)-5-p-tolylpyrazolo[1,5-a]pyrimidin-7(4H)-one as a yellow solid.

LC-MS: (ES, m/z): 302 [M+H]$^+$ $^1$H-NMR (400 MHz, DMSO, ppm): 8.69-8.64 (m, 2H), 7.97-7.89 (m, 2H), 7.85-7.82 (d, J=8.1 Hz, 2H), 7.46-7.42 (d, J=7.8 Hz, 2H), 7.30-7.24 (m, 1H), 6.30 (s, 1H), 2.42 (s, 3H)

Example 121

3-Methoxy-11-(pyridin-2-yl)-5,6-dihydrobenzo[h]pyrazolo[5,1-b]quinazolin-7(12H)-one

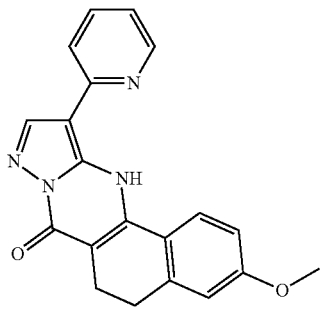 [SMILES: COc1ccc2c(c1)CCc1c-2[nH]c2c(-c3ccccn3)cnn2c1=O]

A solution of 4-(pyridin-2-yl)-1H-pyrazol-5-amine (250 mg, 1.56 mmol, 1.00 equiv), methyl 6-methoxy-1-oxo-1,2,3,4-tetrahydronaphthalene-2-carboxylate (366 mg, 1.56 mmol, 1.00 equiv), p-toluenesulfonic acid (134 mg, 0.78 mmol, 0.50 equiv), and toluene (8 mL) was stirred overnight at 110° C., and then concentrated in vacuo. The resulting solids were collected by filtration and washed with 6×10 mL of dichloromethane/methanol (1:2). This resulted in 18.7 mg (3%) of 3-methoxy-11-(pyridin-2-yl)-5,6-dihydrobenzo[h]pyrazolo[5,1-b]quinazolin-7(12H)-one as a light yellow solid.

LC-MS: (ES, m/z): 345 [M+H]$^+$ $^1$H-NMR (300 MHz, DMSO, ppm): δ 8.736-8.720 (d, J=4.8 Hz, 1H), 8.605 (s, 1H), 7.927-7.915 (d, J=3.6 Hz, 2H), 7.815-7.788 (d, J=8.1 Hz, 1H), 7.287-7.245 (m, 1H), 7.079-7.051 (d, J=8.4 Hz, 2H), 3.864 (s, 3H), 2.947-2.900 (t, J=7.1 Hz 2H), 2.791-2.742 (t, J=7.4 Hz, 2H)

Example 122

5-(2,4-Dimethoxyphenyl)-2-hydroxy-3(pyridin-2-yl)pyrazolo[1,5-a]pyrimidin-7(4H)-one

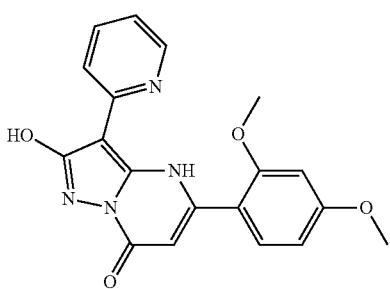 [SMILES: COc1ccc(-c2cc(=O)n3nc(O)c(-c4ccccn4)c3[nH]2)c(OC)c1]

A mixture of 5-amino-4-(pyridin-2-yl)-1H-pyrazol-3-ol (210.7 mg, 1.20 mmol, 1.00 equiv), methyl 3-(2,4-dimethoxyphenyl)-3-oxopropanoate (313.4 mg, 1.32 mmol, 1.10 equiv), and acetic acid (3 mL) was stirred overnight at 110° C. in an oil bath, and then concentrated in vacuo. The resulting solids were collected by filtration and washed with methanol/DMSO (20:1). This resulted in 95 mg (21%) of 5-(2,4-dimethoxyphenyl)-2-hydroxy-3-(pyridin-2-yl)pyrazolo[1,5-a]pyrimidin-7(4H)-one as a off-white solid.

LC-MS: (ES, m/z): 365 [M+H]$^+$ $^1$H-NMR (300 MHz, DMSO, ppm): 8.37-8.34 (t, J=4.5 Hz, 2H), 7.92-7.89 (d, J=6 Hz, 1H), 7.80-7.74 (m, 1H), 7.00-6.95 (t, J=6 Hz, 1H), 6.68-6.64 (t, J=6 Hz, 2H), 6.11 (s, 1H), 3.84-3.82 (d, J=6 Hz, 6H)

Example 123

5-(4-Chlorophenyl)-2-hydroxy-3-(pyridin-2-yl)pyrazolo[1,5-a]pyrimidin-7(4H)-one

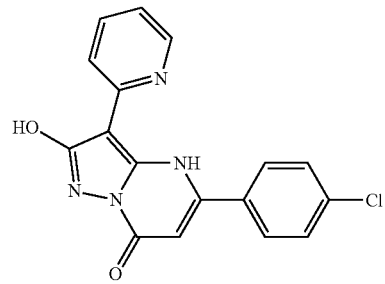 [SMILES: O=c1cc(-c2ccc(Cl)cc2)[nH]c2c(-c3ccccn3)c(O)nn12]

A mixture of 5-amino-4-(pyridin-2-yl)-1H-pyrazol-3-ol (200 mg, 1.14 mmol, 1.00 equiv), methyl 3-(4-chlorophenyl)-3-oxopropanoate (265 mg, 1.25 mmol, 1.10 equiv), and acetic acid (3 mL) was stirred overnight at 110° C. Then the reaction was concentrated in vacuo. The solids were collected by filtration and washed with methanol and methanol/DMSO (20:1). This resulted in 96 mg (24%) of 5-(4-chlorophenyl)-2-hydroxy-3-(pyridin-2-yl)pyrazolo[1,5-a]pyrimidin-7(4H)-one as a yellow solid.

LC-MS: (ES, m/z): 339 [M+H]$^+$ $^1$H-NMR (300 MHz, DMSO, ppm) 8.44-8.38 (t, J=9 Hz, 2H), 8.12-8.10 (d, J=6 Hz, 2H), 7.84 (s, 1H), 7.52-7.50 (t, J=6 Hz, 2H), 7.04-7.00 (t, J=6 Hz, 1H), 6.11 (s, 1H)

Example 124

5-(2,4-Dichlorophenyl)-3-(pyridin-2-yl)pyrazolo[1,5-a]pyrimidin-7(4H)-one

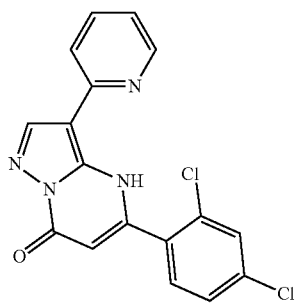 [SMILES: O=c1cc(-c2ccc(Cl)cc2Cl)[nH]c2c(-c3ccccn3)cnn12]

A solution of 4-(pyridin-2-yl)-1H-pyrazol-5-amine (306 mg, 1.91 mmol, 1.00 equiv) in acetic acid (15 mL) and methyl 3-(2,4-dichlorophenyl)-3-oxopropanoate (470 mg, 1.90 mmol, 1.00 equiv) was stirred overnight at 100° C., and then concentrated in vacuo. The solids were collected by filtration and washed with 6×10 mL of methanol/dichloromethane (4:1). This afforded 60 mg (9%) of 5-(2,4-dichlorophenyl)-3-(pyridin-2-yl)pyrazolo[1,5-a]pyrimidin-7(4H)-one as a yellow solid.

LC-MS: (ES, m/z): 357 [M+H]+

1H-NMR (300 MHz, DMSO, ppm) δ 8.606 (s, 1H), 8.547-8.531 (d, J=4.8 Hz, 1H), 7.889-7.878 (d, J=3.3 Hz, 2H), 7.242-7.197 (m, 1H), 7.152 (s, 1H), 7.082 (s, 2H), 4.465-4.344 (m, 4H), 2.392-2.341 (t, J=7.7 Hz, 2H), 1.511-1.436 (m, 2H), 0.817-0.768 (t, J=7.4 Hz, 3H)

Example 125

5-(4-Fluorophenyl)-3-(pyridin-2-yl)pyrazolo[1,5-a]pyrimidin-7(4H)-one

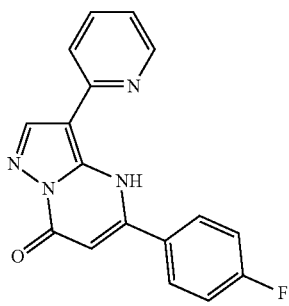 [SMILES: O=c1cc(-c2ccc(F)cc2)[nH]c2c(-c3ccccn3)cnn12]

A solution of methyl 3-(4-fluorophenyl)-3-oxopropanoate (400 mg, 2.04 mmol, 1.00 equiv) and 4-(pyridin-2-yl)-1H-pyrazol-5-amine (320 mg, 2.00 mmol, 1.00 equiv) in acetic acid (15 mL) was stirred overnight at 110° C. Then concentrated in vacuo and diluted with 10 mL of methanol. The resulting solids were collected by filtration and dried in an oven under reduced pressure. This resulted in 80 mg (13%) of 5-(4-fluorophenyl)-3-(pyridin-2-yl)pyrazolo[1,5-a]pyrimidin-7(4H)-one as a yellow solid.

LC-MS: (ES, m/z): 307 [M+H]+

1H-NMR (300 MHz, DMSO, ppm) 8.629 (m, 2H), 8.072-7.938 (m, 4H), 7.479-7.422 (m, 2H), 7.273 (m, 1H), 6.370 (s, 1H)

Example 126

5-(3,4-Dichlorophenyl)-3-(pyridin-2-yl)pyrazolo[1,5-a]pyrimidin-7(4H)-one

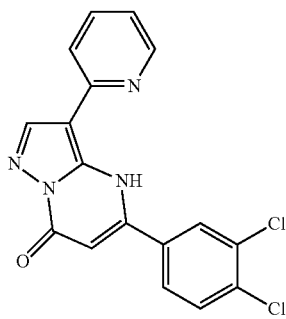 [SMILES: O=c1cc(-c2ccc(Cl)c(Cl)c2)[nH]c2c(-c3ccccn3)cnn12]

A solution of 4-(pyridin-2-yl)-1H-pyrazol-5-amine (320 mg, 2.00 mmol, 1.00 equiv) and methyl 3-(3,4-dichlorophenyl)-3-oxopropanoate (490 mg, 1.98 mmol, 1.00 equiv) in 15 mL of acetic acid was stirred overnight at 100° C., and then concentrated in vacuo. The resulting solids were collected by filtration and washed with 6×10 mL of methanol/dichloromethane (3:1). This resulted in 220 mg (30%) of 5-(3,4-dichlorophenyl)-3-(pyridin-2-yl)pyrazolo[1,5-a]pyrimidin-7(4H)-one as a yellow green solid.

LC-MS: (ES, m/z): 357 [M+H]+

1H-NMR (300 MHz, DMSO, ppm) δ 8.663-8.636 (d, J=8.1 Hz, 2H), 8.296 (s, 1H), 8.228-8.201 (d, J=8.1 Hz, 1H), 8.127-8.103 (d, J=7.2 Hz, 1H), 8.028-8.000 (d, J=8.4 Hz, 1H), 7.831-7.803 (d, J=8.4 Hz, 1H) 7.372-7.329 (t, J=6.5 Hz, 1H), 6.389 (s, 1H)

Example 127

5-(Benzofuran-5-yl)-2-hydroxy-3-phenylpyrazolo[1,5-a]pyrimidin-7(4H)-one

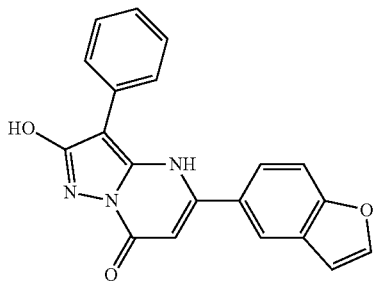 [SMILES: O=c1cc(-c2ccc3occc3c2)[nH]c2c(-c3ccccc3)c(O)nn12]

A mixture of 5-amino-4-phenyl-1H-pyrrol-3-ol (200 mg, 1.14 mmol, 1.00 equiv), methyl 3-(benzofuran-5-yl)-3-oxopropanoate (275.6 mg, 1.26 mmol, 1.10 equiv), and acetic acid (3 mL) was stirred overnight at 110° C., then concentrated in vacuo. The solids were collected by filtration and purified by Prep-HPLC under the following conditions (1#-UV1-SHIMADZU-SPD-20A): Column, Xbridge Prep C18, 5 um, 19*150 mm; mobile phase, water with 0.03% ammonia and CH3CN (hold 10% CH3CN in 1 min, up to 30% in 11 min); Detector, UV 254 nm. This resulted in 80 mg (20%)

of 5-(benzofuran-5-yl)-2-hydroxy-3-phenylpyrazolo[1,5-a]pyrimidin-7(4H)-one as a light brown solid.

LC-MS: (ES, m/z): 344 [M+H]+

¹H-NMR (300 MHz, DMSO, ppm): 8.61-8.59 (d, J=6 Hz, 2H), 8.35 (s, 1H), 8.11-8.09 (d, J=6 Hz, 1H), 8.01-8.00 (d, J=3 Hz, 1H), 7.68-7.65 (d, J=9 Hz, 1H), 7.33-7.28 (t, J=7.5 Hz, 2H), 7.07 (s, 1H), 6.98-6.94 (t, J=6 Hz, 1H), 6.12 (s, 1H)

Example 128

5-(4-Chlorophenyl)-2-hydroxy-3-(pyridin-3-yl)pyrazolo[1,5-a]pyrimidin-7(4H)-one

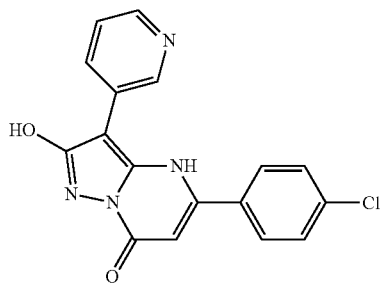 [SMILES: O=c1cc(-c2ccc(Cl)cc2)[nH]c2c(-c3cccnc3)c(O)nn12]

A mixture of 5-amino-4-(pyridin-3-yl)-1H-pyrazol-3-ol (219.7 mg, 1.25 mmol, 1.00 equiv), methyl 3-(4-chlorophenyl)-3-oxopropanoate (291 mg, 1.37 mmol, 1.10 equiv), and acetic acid (3 mL) was stirred overnight at 110° C., and then concentrated in vacuo. The solids were collected by filtration and washed with methanol. The crude product (140 mg) was purified by Prep-HPLC under the following conditions (1#-Waters 2767-1): Column, XbridgePrep Shield RP 18, 5 um, 19*150 mm; mobile phase, water with 0.05% TFA and CH₃CN (16% CH₃CN up to 36% in 8 min, up to 100% in 2 min); Detector, UV 220 254 nm. This afforded 32 mg (8%) of 5-(4-chlorophenyl)-2-hydroxy-3-(pyridin-3-yl)pyrazolo[1,5-a]pyrimidin-7(4H)-one as a off-white solid.

LC-MS: (ES, m/z): 339 [M+H]+

¹H-NMR (400 MHz, DMSO, ppm): 9.69-9.68 (d, J=4 Hz, 1H), 8.81-8.79 (d, J=8 Hz, 1H), 8.13-8.08 (m, 3H), 7.53-7.50 (d, J=12 Hz, 2H), 7.28-7.25 (m, 1H), 6.05 (s, 1H)

Example 129

5-(2,3-Dihydrobenzofuran-5-yl)-2-hydroxy-3-(pyridin-2-yl)pyrazolo[1,5-a]pyrimidin-7(4H)-one

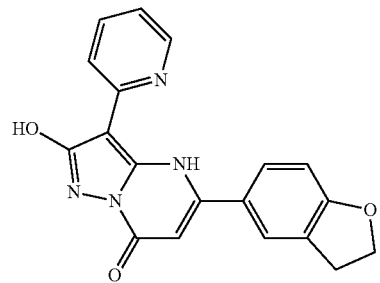 [SMILES: O=c1cc(-c2ccc3c(c2)CCO3)[nH]c2c(-c3ccccn3)c(O)nn12]

A mixture of 5-amino-4-(pyridin-2-yl)-1H-pyrazol-3-ol (200 mg, 1.14 mmol, 1.00 equiv), methyl 3-(2,3-dihydrobenzofuran-5-yl)-3-oxopropanoate (275 mg, 1.25 mmol, 1.10 equiv), and acetic acid (3 mL) was stirred overnight at 110° C., and then concentrated in vacuo. The resulting solids were collected by filtration and washed methanol/DMSO (20:1). This afforded 60 mg (15%) of 5-(2,3-dihydrobenzofuran-5-yl)-2-hydroxy-3-(pyridin-2-yl)pyrazolo[1,5-a]pyrimidin-7(4H)-one as a yellow solid.

LC-MS: (ES, m/z): 347 [M+H]+

¹H-NMR (300 MHz, DMSO, ppm) 8.46-8.37 (m, 2H), 7.96 (s, 1H), 7.90-7.81 (m, 2H), 7.02-6.97 (m, 1H), 6.84-6.82 (d, J=6 Hz, 1H), 6.00 (s, 1H), 4.61-4.56 (t, J=7.5 Hz, 2H), 3.29-3.24 (t, J=7.5 Hz, 3H)

Example 130

5-(2,3-Dihydrobenzofuran-5-yl)-2-hydroxy-3-(pyridin-3-yl)pyrazolo[1,5-a]pyrimidin-7(4H)-one

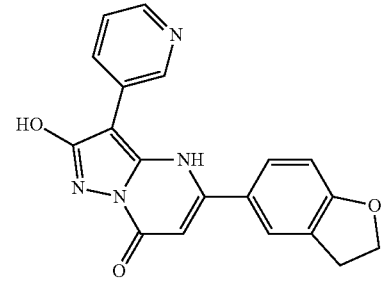 [SMILES: O=c1cc(-c2ccc3c(c2)CCO3)[nH]c2c(-c3cccnc3)c(O)nn12]

A mixture of 5-amino-4-(pyridin-3-yl)-1H-pyrazol-3-ol (264 mg, 1.50 mmol, 1.00 equiv), methyl 3-(2,3-dihydrobenzofuran-5-yl)-3-oxopropanoate (363 mg, 1.65 mmol, 1.10 equiv), and acetic acid (4 mL) was stirred overnight at 110° C., and then concentrated in vacuo. The crude product (400 mg) was purified by Prep-HPLC with the following conditions (Gilson Pre-HPLC (Max. pressure: 8 MPa)): Column, Xbridge Prep C18, 5 um, 19*150 mm; mobile phase, water with 0.05% TFA and CH₃CN (6% CH₃CN up to 35% in 10 min, up to 100% in 0.1 min, hold 100% in 1.9 min); Detector, UV 220 nm. This resulted in 94.7 mg (18%) of 5-(2,3-dihydrobenzofuran-5-yl)-2-hydroxy-3-(pyridin-3-yl)pyrazolo[1,5-a]pyrimidin-7(4H)-one as an off-white solid.

LC-MS: (ES, m/z): 347 [M+H]+

¹H-NMR (400 MHz, DMSO, ppm): 9.20 (m, 1H), 8.60 (s, 2H), 7.90-7.86 (t, J=8 Hz, 1H), 7.89 (s, 1H), 7.67-7.65 (d, J=8 Hz, 1H), 6.93-6.91 (d, J=8 Hz, 1H), 6.01 (s, 1H), 4.66-4.61 (t, J=7.5 Hz, 3H), 3.29-3.24 (t, J=7.5 Hz, 2H)

Example 131

5-(Benzofuran-5-yl)-2-hydroxy-3-(pyridin-2-yl)pyrazolo[1,5-a]pyrimidin-7(4H)-one

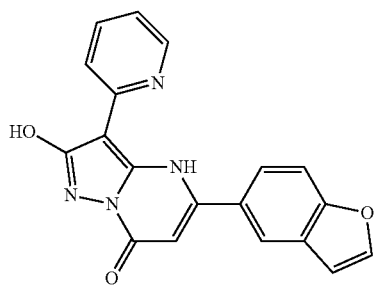 [SMILES: O=c1cc(-c2ccc3occc3c2)[nH]c2c(-c3ccccn3)c(O)nn12]

To a solution of 5-amino-4-(pyridin-2-yl)-1H-pyrazol-3-ol (600 mg, 3.40 mmol) in butan-1-ol (30 mL) was added butyl 3-(benzofuran-6-yl)-3-oxopropanoate (1.0 g, 4.59 mmol) and 4-methylbenzenesulfonic acid (29.27 mg, 0.17 mmol). The resulting solution was stirred for 48 h at 120° C. The solids were collected by filtration to afford 5-(benzofuran-5-yl)-2-hydroxy-3-(pyridin-2-yl)pyrazolo[1,5-a]pyrimidin-7(4H)-one as a yellow solid (290.0 mg, 25%).

LC/MS: (ES, m/z):[M+H]$^+$345.0

$^1$H-NMR (300 MHz, DMSO), δ8.59 (s, 1H), 8.52 (d, J=5.7 Hz, 1H), 8.40 (s, 1H), 8.18-8.20 (m, 1H), 8.05-8.09 (m, 2H), 7.72 (d, J=8.7 Hz, 1H), 7.25-7.29 (t, J=6.9 Hz, 1H), 7.07 (d, J=1.5 Hz, 1H), 6.44 (s, 1H)

Example 132

3-benzyl-5-(4-chlorophenyl)pyrazolo[1,5-a]pyrimidin-7(4H)-one

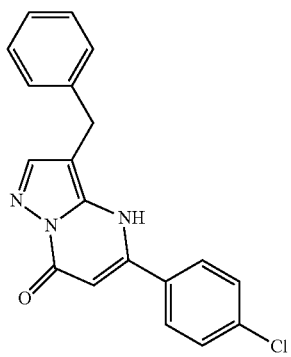 [SMILES: O=c1cc(-c2ccc(Cl)cc2)[nH]c2c(Cc3ccccc3)cnn12]

A solution of 4-benzyl-1H-pyrazol-5-amine (150 mg, 0.87 mmol, 1.00 equiv), methyl 3-(4-chlorophenyl)-3-oxopropanoate (201 mg, 0.95 mmol, 1.10 equiv), and acetic acid (2 mL) was stirred overnight at 100° C., and then concentrated in vacuo. The crude product (120 mg) was purified by Prep-HPLC under the following conditions (1#-Waters 2767-1): Column, SunFire Prep C18, 19*150 mm 5 um; mobile phase, water with 0.05% TFA and CH$_3$CN (15% CH$_3$CN up to 42% in 2 min, hold 42% in 14 min, up to 100% in 2 min); Detector, UV 220 254 nm. This afforded 100 mg (34%) of 3-benzyl-5-(4-chlorophenyl)pyrazolo[1,5-a]pyrimidin-7(4H)-one as a white solid.

LC-MS: (ES, m/z): 336 [M+H]$^+$ $^1$H-NMR (300 MHz, DMSO, ppm) δ 7.838-7.817 (d, J=6.3 Hz, 2H), 7.748 (s, 1H), 7.679-7.658 (d, J=6.3 Hz, 2H), 7.317-7.263 (m, 4H), 7.209-7.171 (m, 1H), 5.969 (s, 1H), 4.064 (s, 2H)

Example 133

5-(Benzo[d][1,3]dioxol-5-yl)-3-benzylpyrazolo[1,5-a]pyrimidin-7(4H)-one

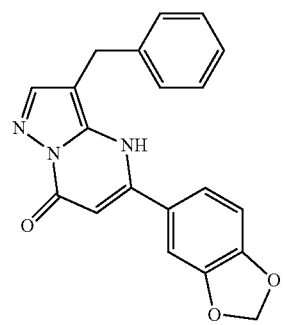 [SMILES: O=c1cc(-c2ccc3c(c2)OCO3)[nH]c2c(Cc3ccccc3)cnn12]

A solution of 4-benzyl-1H-pyrazol-5-amine (107 mg, 0.62 mmol, 1.00 equiv), ethyl 3-(benzo[d][1,3]dioxol-5-yl)-3-oxopropanoate (143 mg, 0.61 mmol, 1.00 equiv) in 4 mL of acetic acid was stirred overnight at 100° C., and then concentrated in vacuo. The crude product (100 mg) was purified by Prep-HPLC under the following conditions (AGILENT Pre-HPLC (UV-Directed)): Column, SunFire Prep C18, 19*150 mm 5 um; mobile phase, water with 0.05% TFA and CH$_3$CN (30% CH$_3$CN up to 40% in 8 min, hold 40% in 5 min, up to 100% in 0.1 min, hold 100% in 0.9 min); Detector, uv 220&254 nm. This resulted in 25 mg (12%) of 5-(benzo[d][1,3]dioxol-5-yl)-3-benzylpyrazolo[1,5-a]pyrimidin-7(4H)-one as a white solid.

LC-MS: (ES, m/z): 346 [M+H]$^+$ $^1$H-NMR (300 MHz, DMSO, ppm): 12.069 (s, 1H), 7.715 (m, 1H), 7.395-7.117 (m, 8H), 6.153 (s, 2H), 5.903 (s, 1H), 4.100-4.066 (s, 2H)

Example 134

5-(Benzo[d][1,3]dioxol-5-yl)-3-propylpyrazolo[1,5-a]pyrimidin-7(4H)-one

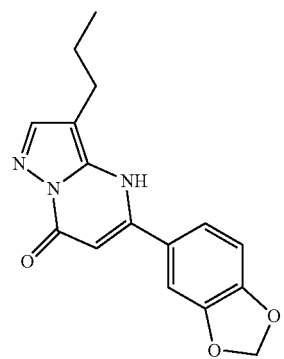 [SMILES: CCCc1cnn2c(=O)cc(-c3ccc4c(c3)OCO4)[nH]c12]

A solution of 4-propyl-1H-pyrazol-5-amine (200 mg, 1.60 mmol, 1.00 equiv) and ethyl 3-(benzo[d][1,3]dioxol-5-yl)-3-oxopropanoate (377 mg, 1.60 mmol, 1.00 equiv) in 5 mL of acetic acid was stirred overnight at 100° C., and then concentrated in vacuo. The residue was diluted with 1 mL of ether. The resulting solids were collected by filtration and dried in an oven under reduced pressure to afford 50 mg (10%) of 5-(benzo[d][1,3]dioxol-5-yl)-3-propylpyrazolo[1,5-a]pyrimidin-7(4H)-one as a navy blue solid.

LC-MS: (ES, m/z): 298 [M+H]$^+$ $^1$H-NMR (300 MHz, DMSO, ppm): 8.004 (s, 3H), 7.107 (s, 1H), 6.141 (s, 2H), 2.502-2.312 (s, 2H), 1.204-0.537 (s, 2H), 0.537-0.005 (s, 3H)

Example 135

5-(2-Methoxyphenyl)-3-(pyridin-2-yl)pyrazolo[1,5-a]pyrimidin-7(4H)-one

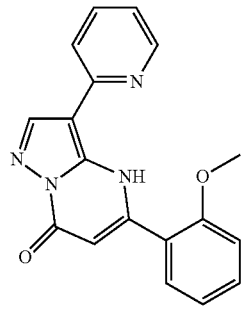 [SMILES: COc1ccccc1-c1cc(=O)n2ncc(-c3ccccn3)c2[nH]1]

A solution of 4-(pyridin-2-yl)-1H-pyrazol-5-amine (320 mg, 2.00 mmol, 1.00 equiv) and methyl 3-(2-methoxyphenyl)-3-oxopropanoate (416 mg, 2.00 mmol, 1.00 equiv) in 15 mL of acetic acid was stirred overnight at 100° C., and then concentrated in vacuo. The solids were collected by filtration and washed by methanol. This resulted in 253 mg (39%) of 5-(2-methoxyphenyl)-3-(pyridin-2-yl)pyrazolo[1,5-a]pyrimidin-7(4H)-one as a white solid.

LC-MS: (ES, m/z): 319 [M+H]$^+$ $^1$H-NMR (300 MHz, DMSO, ppm) δ12.624 (s, 1H), 8.681-8.656 (m, 2H), 7.957-7.888 (m, 3H), 7.647-7.604 (t, J=6.5 Hz, 1H), 7.378-7.358 (d, J=6.0 Hz, 1H), 7.277-7.243 (m, 1H), 7.196-7.156 (t, J=6.0 Hz, 1H), 6.353 (s, 1H), 4.100 (s, 3H)

Example 136

5-(4-Chloro-2-methoxyphenyl)-3-(pyridin-2-yl)pyrazolo[1,5-a]pyrimidin-7(4H)-one

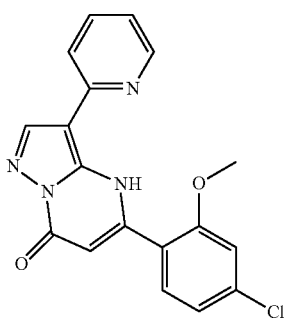 [SMILES: COc1cc(Cl)ccc1-c1cc(=O)n2ncc(-c3ccccn3)c2[nH]1]

A mixture of methyl 3-(4-chloro-2-methoxyphenyl)-3-oxopropanoate (225 mg, 0.93 mmol, 1.00 equiv) and 4-(pyridin-2-yl)-1H-pyrazol-5-amine (139 mg, 0.87 mmol, 1.00 equiv) in acetic acid (5 mL) was stirred overnight at 100° C., and then concentrated in vacuo. The solids were collected by filtration and washed with 2×20 mL of methanol. This resulted in 60 mg (18%) of 5-(4-chloro-2-methoxyphenyl)-3-(pyridin-2-yl)pyrazolo[1,5-a]pyrimidin-7(4H)-one as a grey solid.

LC-MS: (ES, m/z): 353 [M+H]$^+$ $^1$H-NMR (300 MHz, DMSO, ppm) δ 8.672-8.656 (d, J=4.8 Hz, 2H), 7.960-7.895 (m, 3H), 7.467 (s, 1H), 7.282-7.220 (m, 2H), 6.336 (s, 1H), 4.117 (s, 3H)

Example 137

5-(4-Fluorophenyl)-2-hydroxy-3-(pyridin-2-yl)pyrazolo[1,5-a]pyrimidin-7(4H)-one

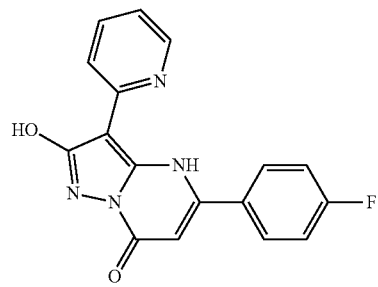 [SMILES: O=c1cc(-c2ccc(F)cc2)[nH]c2c(-c3ccccn3)c(O)nn12]

A solution of 5-amino-4-(pyridin-2-yl)-1H-pyrazol-3-ol (205 mg, 1.16 mmol, 1.00 equiv) and methyl 3-(4-fluorophenyl)-3-oxopropanoate (251 mg, 1.28 mmol, 1.10 equiv) in 3 mL of acetic acid was stirred overnight at 110° C., and then concentrated in vacuo. The resulting solids were collected by filtration and washed with methanol/DMSO (20:1) to afford 100 mg (26%) of 5-(4-fluorophenyl)-2-hydroxy-3-(pyridin-2-yl)pyrazolo[1,5-a]pyrimidin-7(4H)-one as a yellow solid.

LC-MS: (ES, m/z): 323 [M+H]$^+$ $^1$H-NMR (300 MHz, DMSO, ppm) 8.46-8.38 (m, 2H), 8.17-8.12 (m, 2H), 7.87-7.82 (m, 1H), 7.44-7.25 (m, 2H), 7.04-7.00 (t, J=6 Hz, 1H), 5.74 (m, 1H)

Example 138

5-(4-Chlorophenyl)-2-methoxy-7-oxo-4,7-dihydropyrazolo[1,5-a]pyrimidine-3-carbonitrile

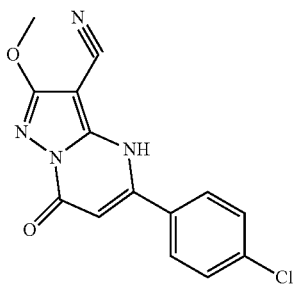 [SMILES: COc1nn2c(=O)cc(-c3ccc(Cl)cc3)[nH]c2c1C#N]

A solution of 5-amino-3-methoxy-1H-pyrazole-4-carbonitrile (100 mg, 0.72 mmol, 1.00 equiv), methyl 3-(4-chlorophenyl)-3-oxopropanoate (153 mg, 0.72 mmol, 1.00 equiv), and 4-methylbenzenesulfonic acid (125 mg, 0.73 mmol, 1.00 equiv) in 5 mL of 1,2-dichlorobenzene was stirred overnight at 110° C. The resulting solids were collected by filtration and washed with CH$_3$OH to afford 49 mg (22%) of 5-(4-chlorophenyl)-2-methoxy-7-oxo-4,7-dihydropyrazolo[1,5-a]pyrimidine-3-carbonitrile as a white solid.

LC-MS: (ES, m/z): 301 [M+H]$^+$ $^1$H-NMR (300 MHz, DMSO, ppm): δ 13.356 (s, 1H), 7.858-7.837 (d, J=6.3 Hz, 2H), 7.652-7.631 (d, J=6.3 Hz, 2H), 6.249 (s, 1H), 4.023 (s, 3H)

Example 139

5-(4-Chlorophenyl)-2-hydroxy-7-oxo-4,7-dihydropyrazolo[1,5-a]pyrimidine-3-carbonitrile

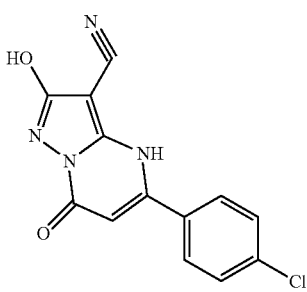 [SMILES: N#Cc1c(O)nn2c(=O)cc(-c3ccc(Cl)cc3)[nH]c12]

A mixture of 5-(4-chlorophenyl)-2-methoxy-7-oxo-4,7-dihydropyrazolo[1,5-a]pyrimidine-3-carbonitrile (120 mg, 0.40 mmol, 1.00 equiv) and 3 mL of HBr-HOAc was stirred for 24 hr at room temperature, and then quenched by the addition of 10 mL of water/ice. The resulting solids were collected by filtration. The crude product (100 mg) was purified by Prep-HPLC under the following conditions (1#-Waters 2767-2): Column, SunFire Prep C18, 19*150 mm 5 um; mobile phase, water with 0.05% TFA and CH$_3$CN (30% CH$_3$CN up to 35% in 10 min, hold 35% in 1 min, up to 100% in 0.1 min, hold 100% in 0.9 min); Detector, UV 220&254 nm. This afforded 32 mg (27%) of 5-(4-chlorophenyl)-2-hydroxy-7-oxo-4,7-dihydropyrazolo[1,5-a]pyrimidine-3-carbonitrile as a white solid.

LC-MS: (ES, m/z): 287 [M+H]$^+$ $^1$H-NMR (300 MHz, DMSO, ppm) δ 13.432 (s, 1H), 7.847-7.827 (d, J=6.0 Hz, 2H), 7.643-7.622 (d, J=6.3 Hz, 2H), 6.201 (s, 1H)

Example 140

5-(4-(Methylsulfonyl)phenyl)-3-(pyridin-2-yl)pyrazolo[1,5-a]pyrimidin-7(4H)-one

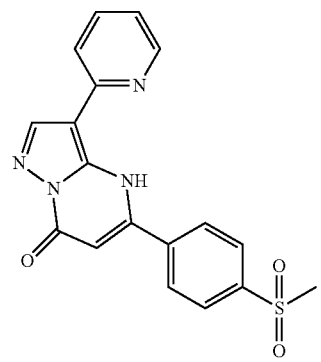 [SMILES: CS(=O)(=O)c1ccc(-c2cc(=O)n3ncc(-c4ccccn4)c3[nH]2)cc1]

A solution of ethyl 3-(4-(methylsulfonyl)phenyl)-3-oxopropanoate (270 mg, 1.00 mmol, 1.00 equiv) and 4-(pyridin-2-yl)-1H-pyrazol-5-amine (160 mg, 1.00 mmol, 1.00 equiv) in 5 mL of acetic acid was stirred overnight at 100° C., and then concentrated in vacuo and diluted with 5 mL of methanol. The resulting solids were collected by filtration and dried in a vacuum oven. This provided 200 mg (55%) of 5-(4-(methylsulfonyl)phenyl)-3-(pyridin-2-yl)pyrazolo[1,5-a]pyrimidin-7(4H)-one as a yellow solid.

LC-MS (ES, m/z): 367 [M+H]$^+$ $^1$H-NMR (300 MHz, DMSO, ppm): 8.679-8.654 (s, 3H), 8.295-8.192 (m, 3H), 8.112-8.059 (m, 3H), 7.377-7.331 (m, 1H), 6.418 (s, 1H), 3.3 (s, 3H)

Example 141

2-Amino-5-(4-chlorophenyl)-3-phenylpyrazolo[1,5-a]pyrimidin-7(4H)-one

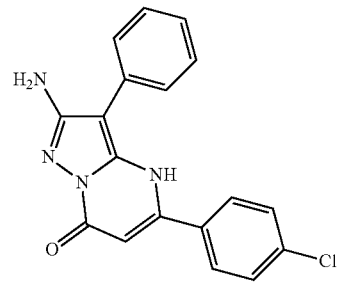 [SMILES: Nc1nn2c(=O)cc(-c3ccc(Cl)cc3)[nH]c2c1-c1ccccc1]

A solution of 4-phenyl-1H-pyrazole-3,5-diamine (100 mg, 0.57 mmol, 1.00 equiv), methyl 3-(4-chlorophenyl)-3-oxopropanoate (121 mg, 0.57 mmol, 1.00 equiv), and 4-methylbenzenesulfonic acid (49 mg, 0.28 mmol, 0.50 equiv) in 4 mL of toluene was stirred overnight at 110° C., and then concentrated in vacuo. The crude product (130 mg) was purified by Prep-HPLC under the following conditions (1#-Waters 2767-1): Column, SunFire Prep C18, 19*150 mm 5 um; mobile phase, water with 0.05% TFA and CH$_3$CN (30% CH$_3$CN up to 50% in 8 min, up to 100% in 2 min); Detector, UV 220 254 nm. This afforded 43 mg (22%) of 2-amino-5-(4-chlorophenyl)-3-phenylpyrazolo[1,5-a]pyrimidin-7(4H)-one as a white solid.

LC-MS (ES, m/z): 337 [M+H]+

1H-NMR (300 MHz, DMSO, ppm) δ 11.857 (s, 1H), 7.810-7.784 (d, J=7.8 Hz, 2H), 7.588-7.559 (d, J=8.7 Hz, 4H), 7.484-7.433 (t, J=7.6 Hz, 2H), 7.327-7.279 (t, J=7.2 Hz, 1H), 5.930 (s, 1H)

Example 142

2-Amino-5-(2,3-dihydrobenzo[b][1,4]dioxin-6-yl)-3-phenylpyrazolo[1,5-a]pyrimidin-7(4H)-one

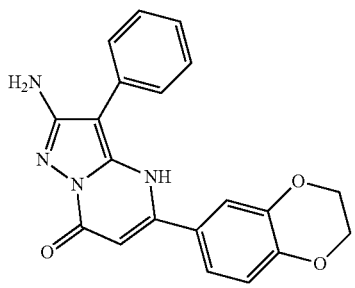 [SMILES: Nc1nn2c(=O)cc(-c3ccc4c(c3)OCCO4)[nH]c2c1-c1ccccc1]

A solution of 4-phenyl-1H-pyrazole-3,5-diamine (100 mg, 0.57 mmol, 1.00 equiv), ethyl 3-(2,3-dihydrobenzo[b][1,4]dioxin-6-yl)-3-oxopropanoate (144 mg, 0.58 mmol, 1.00 equiv), and 4-methylbenzenesulfonic acid (98 mg, 0.57 mmol, 1.00 equiv) in 6 mL of toluene was stirred overnight at 110° C. Then the reaction mixture was concentrated in vacuo. The resulting crude product (100 mg) was purified by Prep-HPLC under the following conditions (1#-Waters 2767-1): Column, SunFire Prep C18, 19*150 mm 5 um; mobile phase, water with 0.05% TFA and CH3CN (28% CH3CN up to 48% in 8 min, up to 100% in 2 min); Detector, UV 220 254 nm. This afforded 62 mg (30%) of 2-amino-5-(2,3-dihydrobenzo[b][1,4]dioxin-6-yl)-3-phenylpyrazolo[1,5-a]pyrimidin-7(4H)-one as a white solid.

LC-MS: (ES, m/z): 361 [M+H]+

1H-NMR (300 MHz, DMSO, ppm) δ 11.565 (s, 1H), 7.526-7.424 (m, 4H), 7.317-7.201 (m, 3H), 6.983-6.955 (d, J=8.4 Hz, 1H), 5.766 (s, 1H), 5.243 (s, 1H), 4.290 (s, 4H)

Example 143

N-Benzyl-5-(2,3-dihydrobenzo[b][1,4]dioxin-6-yl)-N-methyl-7-oxo-4,7-dihydropyrazolo[1,5-a]pyrimidine-3-carboxamide

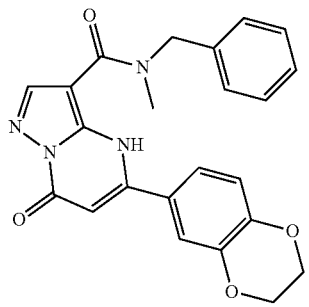 [SMILES: CN(Cc1ccccc1)C(=O)c1cnn2c(=O)cc(-c3ccc4c(c3)OCCO4)[nH]c12]

To a solution of N-methyl-1-phenylmethanamine (185 mg, 1.53 mmol, 3.50 equiv) in chloroform (5 mL) under an inert atmosphere of nitrogen was added AlMe3 (0.5 mL, 2.50 equiv, 2M in hexane). The reaction was stirred for 1 h at room temperature, and then ethyl 5-(2,3-dihydrobenzo[b][1,4]dioxin-6-yl)-7-oxo-4,7-dihydropyrazolo[1,5-a]pyrimidine-3-carboxylate (150 mg, 0.44 mmol, 1.00 equiv) was added. The resulting solution was stirred overnight at 50° C. The reaction was quenched with 1 mL of water and concentrated in vacuo. The crude product (150 mg) was purified by Prep-HPLC under the following conditions (1#-Waters 2767-2): Column, SunFire Prep C18, 19*150 mm 5 um; mobile phase, water with 0.05% TFA and CH3CN (35% CH3CN up to 47% in 8 min, hold 47% in 3.2 min, up to 100% in 0.1 min, hold 100% in 1.2 min); Detector, uV 220&254 nm. This resulted in 25 mg (14%) of N-benzyl-5-(2,3-dihydrobenzo[b][1,4]dioxin-6-yl)-N-methyl-7-oxo-4,7-dihydropyrazolo[1,5-a]pyrimidine-3-carboxamide as a white solid.

LC-MS (ES, m/z): 417 [M+H]+

1H-NMR (300 MHz, DMSO, ppm) 8.321 (s, 1H), 7.402-7.268 (m, 7H), 7.101-7.073 (d, J=8.4 Hz, 1H), 6.254 (s, 1H), 4.767 (s, 2H), 4.339 (s, 4H), 3.202 (s, 3H)

Example 144

N-Benzyl-5-(4-chlorophenyl)-7-oxo-4,7-dihydropyrazolo[1,5-a]pyrimidine-3-carboxamide

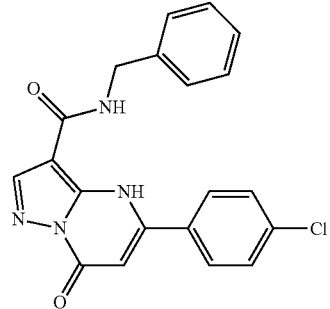 [SMILES: O=C(NCc1ccccc1)c1cnn2c(=O)cc(-c3ccc(Cl)cc3)[nH]c12]

Phenylmethanamine (94.5 mg, 0.80 mmol, 3.50 equiv) and AlMe3 (0.3 mL, 2.50 equiv) were dissolved in chloroform (5 mL) under nitrogen. The resulting solution was stirred for 1 hr at room temperature and then ethyl 5-(4-chlorophenyl)-7-oxo-4,7-dihydropyrazolo[1,5-a]pyrimidine-3-carboxylate (80 mg, 0.25 mmol, 1.00 equiv) was added. The resulting solution was stirred overnight at 50° C. Then the reaction was quenched by the addition of 1 ml of water. The resulting mixture was concentrated in vacuo. The residue was purified by prep-HPLC to provide 47 mg (49%) of N-benzyl-5-(4-chlorophenyl)-7-oxo-4,7-dihydropyrazolo[1,5-a]pyrimidine-3-carboxamide as a white solid.

LC-MS (ES, m/z): 379 [M+H]+

1H-NMR (400 MHz, DMSO, ppm): 11.44 (s, 1H), 9.03-9.00 (t, J=6 Hz, 1H), 8.45 (s, 1H), 7.85-7.82 (d, J=12H, 2H), 7.65-7.64 (d, J=4 Hz, 2H), 7.54-7.26 (m, 6H), 6.28 (m, 1H), 4.52-4.50 (d, J=8 Hz, 2H)

Example 145

5-(2,3-Dihydrobenzo[b][1,4]dioxin-6-yl)-7-oxo-N-propyl-4,7-dihydropyrazolo[1,5-a]pyrimidine-3-carboxamide

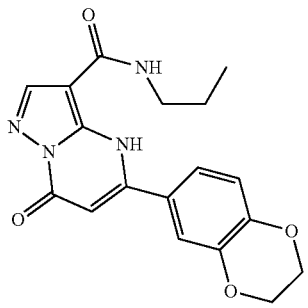 [SMILES: CCCNC(=O)c1cnn2c(=O)cc(-c3ccc4c(c3)OCCO4)[nH]c12]

AlMe$_3$ (0.7 mL, 2.50 equiv, 1M in hexane) was added to a solution of propan-1-amine (60 mg, 1.02 mmol, 3.50 equiv) in chloroform (4 mL) under an inert atmosphere of nitrogen. The resulting solution was stirred for 1 h at room temperature. Then ethyl 5-(2,3-dihydrobenzo[b][1,4]dioxin-6-yl)-7-oxo-4,7-dihydropyrazolo[1,5-a]pyrimidine-3-carboxylate (100 mg, 0.29 mmol, 1.00 equiv) was added. The resulting solution was stirred overnight at 50° C. The reaction was then quenched by the addition of 1 mL of water. The resulting mixture was concentrated in vacuo. The crude product (100 mg) was purified by Prep-HPLC with the following conditions (1#-Waters 2767-1): Column, SunFire Prep C18, 19*150 mm 5 um; mobile phase, water with 0.05% TFA and CH$_3$CN (55% CH$_3$CN up to 75% in 8 min, up to 100% in 2 min); Detector, UV 220 254 nm. This resulted in 30 mg (28%) of 5-(2,3-dihydrobenzo[b][1,4]dioxin-6-yl)-7-oxo-N-propyl-4,7-dihydropyrazolo[1,5-a]pyrimidine-3-carboxamide as a white solid.

LC-MS: (ES, m/z): 355 [M+H]$^+$ $^1$H-NMR (300 MHz, DMSO, ppm) 11.084 (s, 1H), 8.461-8.383 (m, 2H), 7.448-7.298 (m, 2H), 7.079-7.052 (d, J=8.1 Hz, 1H), 6.220 (s, 1H), 4.332

Example 146

5-(2,3-Dihydrobenzo[b][1,4]dioxin-6-yl)-3-(pyrrolidine-1-carbonyl)pyrazolo[1,5-a]pyrimidin-7(4H)-one

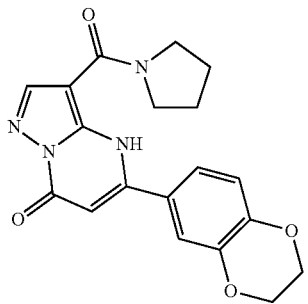 [SMILES: O=C(c1cnn2c(=O)cc(-c3ccc4c(c3)OCCO4)[nH]c12)N1CCCC1]

To a solution of pyrrolidine (74 mg, 1.04 mmol, 3.50 equiv) in chloroform (5 mL) under an inert atmosphere of nitrogen was added AlMe$_3$ (0.35 mL, 2.50 equiv, 2M in hexane). The resulting solution was stirred for 1 h at room temperature. Then ethyl 5-(2,3-dihydrobenzo[b][1,4]dioxin-6-yl)-7-oxo-4,7-dihydropyrazolo[1,5-a]pyrimidine-3-carboxylate (120 mg, 0.35 mmol, 1.00 equiv) was added. The reaction was stirred overnight at 50° C., and then quenched by the addition of 1 ml of H$_2$O. The resulting mixture was concentrated in vacuo. The crude product (130 mg) was purified by Prep-HPLC with the following conditions (1#-Waters 2767-2): Column, SunFire Prep C18, 19*150 mm 5 um; mobile phase, water with 0.05% TFA and methanol (50% methanol up to 55% in 8 min, hold 55% in 2.3 min, up to 100% in 0.1 min, hold 100% in 0.6 min); Detector, UV 220&254 nm. This resulted in 22 mg (17%) of 5-(2,3-dihydrobenzo[b][1,4]dioxin-6-yl)-3-(pyrrolidine-1-carbonyl)pyrazolo[1,5-a]pyrimidin-7(4H)-one as a white solid.

LC-MS (ES, m/z): 367 [M+H]$^+$ $^1$H-NMR (300 MHz, DMSO, ppm): 11.490 (s, 1H), 8.322 (s, 1H), 7.371-7.294 (m, 2H), 7.097-7.069 (s, J=8.7 Hz, 1H), 6.295 (s, 1H), 4.334 (s, 4H), 3.775 (m, 2H), 3.529 (m, 2H), 2.000-1.986 (m, 2H), 1.879-1.858 (m, 2H)

Example 147

5-(Benzofuran-5-yl)-2-hydroxy-3-(pyridin-3-yl)pyrazolo[1,5-a]pyrimidin-7(4H)-one

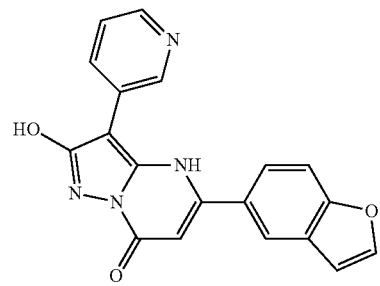 [SMILES: O=c1cc(-c2ccc3occc3c2)[nH]c2c(-c3cccnc3)c(O)nn12]

A solution of 5-amino-4-(pyridin-3-yl)-1H-pyrazol-3-ol (200 mg, 1.14 mmol, 1.00 equiv), methyl 3-(benzofuran-5-yl)-3-oxopropanoate (272.5 mg, 1.25 mmol, 1.10 equiv), and acetic acid (3 mL) was stirred overnight at 110° C., and then concentrated in vacuo. The crude product (200 mg) was purified by Prep-HPLC under the following conditions (1#-Waters 2767-1): Column, SunFire Prep C18, 19*150 mm 5 um; mobile phase, water with 0.05% TFA and CH$_3$CN (16% CH$_3$CN up to 20% in 8 min, hold 20% in 3 min, up to 100% in 0.1 min, hold 100% in 0.9 min); Detector, UV 220&254 nm. This afforded 44 mg (11%) of 5-(benzofuran-5-yl)-2-hydroxy-3-(pyridin-3-yl)pyrazolo[1,5-a]pyrimidin-7(4H)-one as a light yellow solid.

LC-MS: (ES, m/z): 345 [M+H]$^+$ $^1$H-NMR (300 MHz, DMSO, ppm) 9.27 (s, 1H), 8.56-8.55 (d, J=3 Hz, 2H), 8.23 (s, 1H), 8.13-8.12 (d, J=3 Hz, 1H), 7.87-7.75 (m, 3H), 7.09-7.08 (d, J=3 Hz, 1H), 6.12 (s, 1H)

Example 148

2-Amino-5-(2,3-dihydrobenzo[b][1,4]dioxin-6-yl)-3-(pyridin-2-yl)pyrazolo[1,5-a]pyrimidin-7(4H)-one

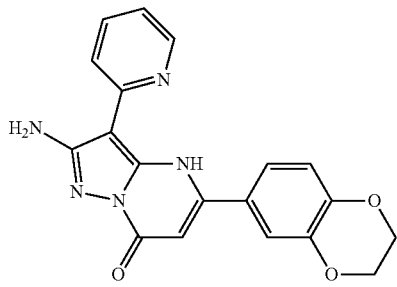 [SMILES: Nc1nn2c(=O)cc(-c3ccc4c(c3)OCCO4)[nH]c2c1-c1ccccn1]

To a solution of 4-(pyridin-2-yl)-1H-pyrazole-3,5-diamine (150.0 mg, 0.86 mmol) in n-BuOH (20 mL) was added ethyl 3-(2,3-dihydrobenzo[b][1,4]dioxin-6-yl)-3-oxopropanoate (242.7 mg, 0.97 mmol), and 4-methylbenzenesulfonic acid (7.4 mg, 0.04 mmol). The reaction was stirred overnight at 120° C. and the product was collected by filtration to afford 2-amino-5-(2,3-dihydrobenzo[1)][1,4]dioxin-6-yl)-3-(pyridin-2-yl)pyrazolo[1,5-a]pyrimidin-7(4H)-one as a yellow solid (160.0 mg, 51%).

LC-MS (ES, m/z): [M+H]$^+$362.0

$^1$H-NMR (300 MHz, DMSO) δ 8.72 (s, 1H), 7.31-7.92 (m, 4H), 7.18 (d, J=19.2 Hz, 1H), 7.04 (s, 1H), 6.14-6.28 (m, 1H), 4.33 (s, 4H)

Example 149

5-(Benzofuran-2-yl)-3-(pyridin-2-yl)pyrazolo[1,5-a]pyrimidin-7(4H)-one

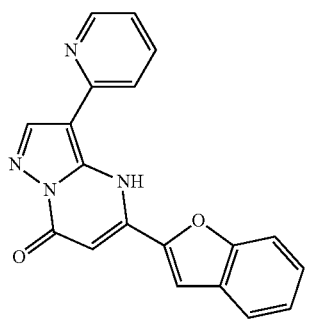 [SMILES: O=c1cc(-c2cc3ccccc3o2)[nH]c2c(-c3ccccn3)cnn12]

A solution of ethyl 3-(benzofuran-2-yl)-3-oxopropanoate (200 mg, 0.86 mmol, 1.00 equiv), and 4-(pyridin-2-yl)-1H-pyrazol-5-amine (319 mg, 1.38 mmol, 1.59 equiv) in 3 mL of acetic acid was stirred overnight at 100° C. The resulting mixture was concentrated in vacuo, and the resulting solids were collected by filtration and washed with 2×30 mL of methanol. This afforded 200 mg (69%) of 5-(benzofuran-2-yl)-3-(pyridin-2-yl)pyrazolo[1,5-a]pyrimidin-7(4H)-one as a yellow solid.

LC-MS: (ES, m/z): 329 [M+H]$^+$ $^1$H-NMR (300 MHz, DMSO, ppm): δ 8.770-8.752 (d, J=3.6 Hz, 1H), 8.670 (s, 1H), 8.227-8.082 (m, 3H), 8.025 (s, 1H), 7.808-7.757 (m, 2H), 7.500-7.340 (m, 3H), 6.499 (s, 1H)

Example 150

2-Amino-5-(benzo[d][1,3]dioxol-5-yl)-3-(pyridin-2-yl)pyrazolo[1,5-a]pyrimidin-7(4H)-one

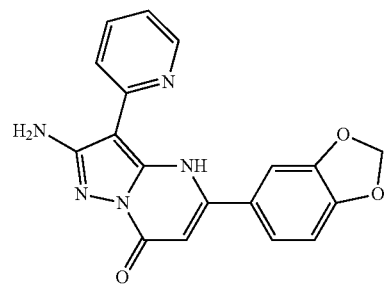 [SMILES: Nc1nn2c(=O)cc(-c3ccc4c(c3)OCO4)[nH]c2c1-c1ccccn1]

To a solution of 4-(pyridin-2-yl)-1H-pyrazole-3,5-diamine (100 mg, 0.57 mmol) in n-BuOH (20 mL) was added methyl 3-(2H-1,3-benzodioxol-5-yl)-3-oxopropanoate (194 mg, 0.87 mmol) and 4-methylbenzene-1-sulfonic acid (5 mg, 0.03 mmol). After stirring for 36 h at 130° C., the solids were collected by filtration to afford 2-amino-5-(benzo[d][1,3]dioxol-5-yl)-3-(pyridin-2-yl)pyrazolo[1,5-a]pyrimidin-7(4H)-one as a yellow green solid (47.4 mg, 24%).

(ES, m/z): [M+H]$^+$ 348.1

$^1$H-NMR (300 MHz, DMSO) δ 8.47-8.77 (m, 1H), 7.80-8.13 (m, 2H), 7.77 (s, 2H), 7.04-7.57 (m, 2H), 6.21-6.40 (m, 3H)

Example 151

2-Amino-5-(benzofuran-2-yl)-3-(pyridin-2-yl)pyrazolo[1,5-a]pyrimidin-7(4H)-one

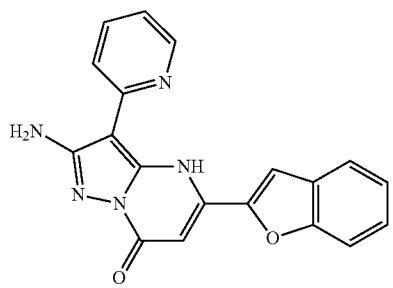 [SMILES: Nc1nn2c(=O)cc(-c3cc4ccccc4o3)[nH]c2c1-c1ccccn1]

To a solution of 4-(pyridin-2-yl)-1H-pyrazole-3,5-diamine (100 mg, 0.57 mmol) in n-BuOH (20 mL) was added ethyl 3-(benzofuran-2-yl)-3-oxopropanoate (200 mg, 0.86 mmol) and 4-methylbenzene-1-sulfonic acid (5 mg, 0.03 mmol). After stirring for 36 h at 130° C., the solid was collected by filtration to afford 2-amino-5-(benzofuran-2-yl)-3-(pyridin-2-yl)pyrazolo[1,5-a]pyrimidin-7(4H)-one as a light yellow solid (60 mg, 31%).

LC/MS (ES, m/z):[M+H]$^+$ 344.1

$^1$H-NMR (300 MHz, DMSO) δ 8.57-8.80 (m, 2H), 7.87-7.92 (t, J=7.5 Hz, 1H), 7.63-7.79 (m, 3H), 7.30-7.45 (m, 2H), 7.13 (s, 1H), 6.44 (s, 1H)

Example 152

2-Amino-5-(4-chlorophenyl)-3-(pyridin-2-yl)pyrazolo[1,5-a]pyrimidin-7(4H)-one

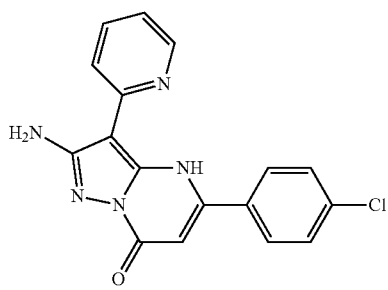 [SMILES: Nc1nn2c(=O)cc(-c3ccc(Cl)cc3)[nH]c2c1-c1ccccn1]

To a solution of 4-(pyridin-2-yl)-1H-pyrazole-3,5-diamine (100 mg, 0.57 mmol) in n-BuOH (20 mL) was added methyl 3-(4-chlorophenyl)-3-oxopropanoate (121 mg, 0.57 mmol) and 4-methylbenzene-1-sulfonic acid (5 mg, 0.03 mmol). After stirring for 36 h at 130° C., the solid was collected by filtration to afford 2-amino-5-(4-chlorophenyl)-3-(pyridin-2-yl)pyrazolo[1,5-a]pyrimidin-7(4H)-one as a yellow green solid (54.6 mg, 29%).

LC/MS (ES, m/z): [M+H]$^+$338.0

$^1$H-NMR (300 MHz, DMSO) δ 8.59 (d, J=2.7 Hz, 2H), 8.05-8.10 (m, 2H), 7.82-7.93 (m, 1H), 7.59-7.68 (m, 2H), 7.17-7.21 (t, J=6.0 Hz, 1H), 6.34 (s, 1H)

Example 153

2-Amino-5-(3,4-dichlorophenyl)-3-(pyridin-2-yl)pyrazolo[1,5-a]pyrimidin-7(4H)-one

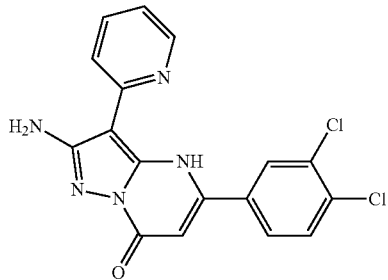 [SMILES: Nc1nn2c(=O)cc(-c3ccc(Cl)c(Cl)c3)[nH]c2c1-c1ccccn1]

Methyl 3-(3,4-dichlorophenyl)-3-oxopropanoate (211 mg, 0.86 mmol) and 4-methylbenzene-1-sulfonic acid (5 mg, 0.03 mmol) were added to a solution of 4-(pyridin-2-yl)-1H-pyrazole-3,5-diamine (100 mg, 0.57 mmol) in n-BuOH (20 mL). After stirring for 24 hours at 130° C., the solids were collected by filtration to afford 2-amino-5-(3,4-dichlorophenyl)-3-(pyridin-2-yl)pyrazolo[1,5-a]pyrimidin-7(4H)-one as a light yellow solid (75 mg, 35%).

LC/MS (ES, m/z):[M+H]$^+$373.9

$^1$H-NMR (300 MHz, DMSO) δ 8.58 (s, 2H), 8.31 (s, 1H), 8.08-8.19 (m, 1H), 7.93-8.03 (m, 1H), 7.77-7.87 (m, 1H), 7.19 (s, 1H), 6.41-6.52 (m, 1H)

Example 154

2-Hydroxy-5-phenyl-3-(pyridin-3-yl)pyrazolo[1,5-a]pyrimidin-7(4H)-one

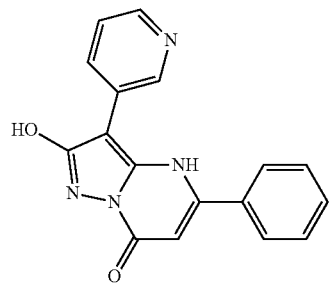 [SMILES: O=c1cc(-c2ccccc2)[nH]c2c(-c3cccnc3)c(O)nn12]

Methyl 3-oxo-3-phenylpropanoate (150 mg, 0.84 mmol) and 4-methylbenzene-1-sulfonic acid (5 mg, 0.03 mmol) were added to a solution of 5-amino-4-(pyridin-3-yl)-1H-pyrazol-3-ol (100 mg, 0.57 mmol) in n-BuOH (20 mL). After stirring for 36 hours at 130° C., the solids were collected by filtration to afford 2-hydroxy-5-phenyl-3-(pyridin-3-yl)pyrazolo[1,5-a]pyrimidin-7(4H)-one as a yellow green solid (22.2 mg, 13%).

LC/MS (ES, m/z):[M+H]$^+$305.0

$^1$H-NMR (300 MHz, DMSO) δ 9.72 (d, J=1.8 Hz, 1H), 8.81-8.85 (m, 1H), 8.05-8.13 (m, 3H), 7.38-7.49 (m, 3H), 7.24-7.28 (m, 1H), 6.05 (s, 1H)

Example 155

N-(5-(Benzo[d][1,3]dioxol-5-yl)-7-oxo-3-(pyridin-2-yl)-4,7-dihydropyrazolo[1,5-a]pyrimidin-2-yl)acetamide

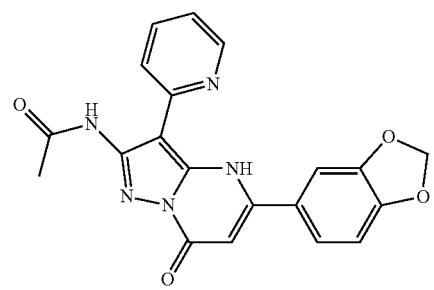 [SMILES: CC(=O)Nc1nn2c(=O)cc(-c3ccc4c(c3)OCO4)[nH]c2c1-c1ccccn1]

Ac$_2$O (110 mg, 1.08 mmol) was added to a solution of 2-amino-5-(benzo[d][1,3]dioxol-5-yl)-3-(pyridin-2-yl)pyrazolo[1,5-a]pyrimidin-7(4H)-one (250 mg, 0.72 mmol) in pyridine (10 ml). After stirring for 3 hours at room temperature, the reaction was quenched by water (30 mL) and, the solids were collected by filtration to afford N-(5-(benzo[d][1,3]dioxol-5-yl)-7-oxo-3-(pyridin-2-yl)-4,7-dihydropyrazolo[1,5-a]pyrimidin-2-yl)acetamide as a yellow solid (207.4 mg, 74%).

LC/MS (ES, m/z): [M+H]$^+$390.1

$^1$H-NMR (300 MHz, CD$_3$OD) δ 8.65 (d, J=5.1 Hz, 1H), 7.89-7.94 (t, J=6.9 Hz, 1H), 7.49-7.88 (m, 1H), 7.43-7.49 (t, J=8.4 Hz, 2H), 7.25-7.30 (t, J=7.2 Hz, 1H), 7.05 (d, J=8.1 Hz, 1H), 6.27 (s, 1H), 6.11 (s, 2H), 2.29 (s, 3H)

Example 156

5-(Benzo[d][1,3]dioxol-5-yl)-2-(ethylamino)-3-(pyridin-2-yl)pyrazolo[1,5-a]pyrimidin-7(4H)-one

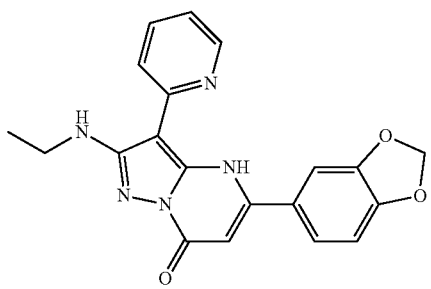 [SMILES: CCNc1nn2c(=O)cc(-c3ccc4c(c3)OCO4)[nH]c2c1-c1ccccn1]

Ethyl 3-(benzo[d][1,3]dioxol-5-yl)-3-oxopropanoate (174 mg, 0.74 mmol) and 4-methylbenzene-1-sulfonic acid (5 mg, 0.03 mmol) were added to a solution of N³-ethyl-4-(pyridin-2-yl)-1H-pyrazole-3,5-diamine (100 mg, 0.49 mmol) in n-BuOH (20 mL). After stirring for 24 hours at 130° C., the solids were collected by filtration to afford 5-(benzo[d][1,3]dioxol-5-yl)-2-(ethylamino)-3-(pyridin-2-yl)pyrazolo[1,5-a]pyrimidin-7(4H)-one as a yellow solid (53 mg, 29%).

LC/MS (ES, m/z): [M+H]⁺376.1

¹H-NMR (300 MHz, CD₃OD) δ 8.53 (d, J=7.8 Hz, 1H), 7.83-7.89 (m, 1H), 7.72-7.75 (m, 1H), 7.32-7.36 (m, 1H), 7.29 (s, 1H), 7.14-7.18 (t, J=6.0 Hz, 1H), 6.96 (d, J=8.1 Hz, 1H), 6.08 (s, 2H), 6.07 (s, 1H), 3.46-3.53 (m, 2H), 1.32-1.36 (t, J=6.6 Hz, 3H)

Example 157

5-(Benzo[d][1,3]dioxol-5-yl)-2-methoxy-3-(pyridin-2-yl)pyrazolo[1,5-a]pyrimidin-7(4H)-one

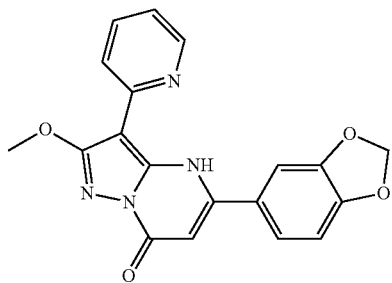 [SMILES: COc1nn2c(=O)cc(-c3ccc4c(c3)OCO4)[nH]c2c1-c1ccccn1]

To a solution of 3-methoxy-4-(pyridin-2-yl)-1H-pyrazol-5-amine (170 mg, 0.89 mmol) in n-BuOH (20 mL) was added ethyl 3-(benzo[d][1,3]dioxol-5-yl)-3-oxopropanoate (300 mg, 1.27 mmol) and 4-methylbenzene-1-sulfonic acid (5 mg, 0.03 mmol). After stirring for 24 hours at 130° C., the solids were collected by filtration to give 5-(benzo[d][1,3]dioxol-5-yl)-2-methoxy-3-(pyridin-2-yl)pyrazolo[1,5-a]pyrimidin-7(4H)-one as a yellow solid (62.9 mg, 19%).

LC/MS (ES, m/z): [M+H]⁺ 363.1

¹H-NMR (300 MHz, CD₃OD) δ 14.13 (s, 1H), 8.66 (d, J=5.7 Hz, 1H), 8.49 (d, J=5.4 Hz, 1H), 8.23-8.28 (t, J=4.8 Hz, 1H), 7.66-7.70 (m, 2H), 7.27-7.32 (t, J=6.3 Hz, 1H), 7.00 (d, J=5.1 Hz, 1H), 6.34 (s, 1H), 6.11 (s, 2H), 3.63 (s, 3H)

Example 158

5-(2,2-Difluorobenzo[d][1,3]dioxol-5-yl)-3-(pyridin-2-yl)pyrazolo[1,5-a]pyrimidin-7(4H)-one

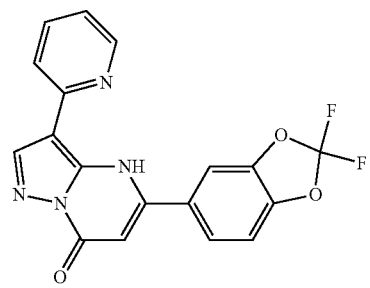 [SMILES: O=c1cc(-c2ccc3c(c2)OC(F)(F)O3)[nH]c2c(-c3ccccn3)cnn12]

To a solution of 4-(pyridin-2-yl)-1H-pyrazol-5-amine (250 mg, 1.56 mmol) in n-BuOH (30 ml) was added ethyl 3-(2,2-difluorobenzo[d][1,3]dioxol-5-yl)-3-oxopropanoate (600 mg, 2.20 mmol) and 4-methylbenzene-1-sulfonic acid (18 mg, 0.10 mmol). After stirring for 24 hours at 130° C., the solids were collected by filtration to afford 5-(2,2-difluorobenzo[d][1,3]dioxol-5-yl)-3-(pyridin-2-yl)pyrazolo[1,5-a]pyrimidin-7(4H)-one as a yellow solid (249 mg, 43%).

LC/MS (ES, m/z):[M+H]⁺ 369.0

¹H-NMR (300 MHz, DMSO) δ 8.66 (d, J=6.0 Hz, 2H), 8.04-8.17 (m, 3H), 7.87-7.90 (m, 1H), 7.61 (d, J=8.4 Hz, 1H), 7.31-7.36 (m, 1H), 6.34 (s, 1H)

Example 159

2-Amino-5-(1H-indazol-5-yl)-3-(pyridin-2-yl)pyrazolo[1,5-a]pyrimidin-7(4H)-one

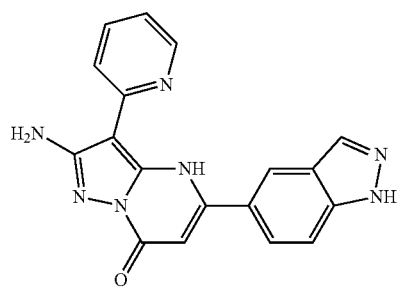

231

Step 1. 2-Amino-5-(1-(methoxymethyl)-1H-indazol-5-yl)-3-(pyridin-2-yl)pyrazolo[1,5-a]pyrimidin-7(4H)-one

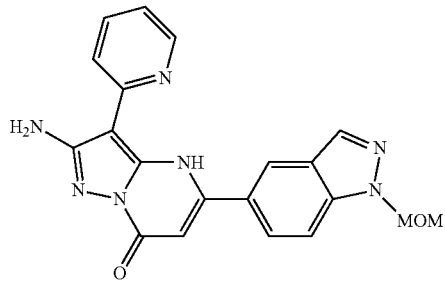

To a solution of 4-(pyridin-2-yl)-1H-pyrazole-3,5-diamine (180 mg, 1.03 mmol) in n-BuOH (20 mL) was added ethyl 3-[1-(methoxymethyl)-1H-indazol-5-yl]-3-oxopropanoate (400 mg, 1.45 mmol) and 4-methylbenzene-1-sulfonic acid (10 mg, 0.06 mmol, 0.05 equiv). After stirring for 36 hours at 130° C., the solids were collected by filtration to afford of 2-amino-5-(1-(methoxymethyl)-1H-indazol-5-yl)-3-(pyridin-2-yl)pyrazolo[1,5-a]pyrimidin-7(4H)-one as a yellow solid (120 mg, 30%).

LC/MS (ES, m/z): [M+H]$^+$388.0

Step 2. 2-Amino-5-(1H-indazol-5-yl)-3-(pyridin-2-yl)pyrazolo[1,5-a]pyrimidin-7(4H)-one

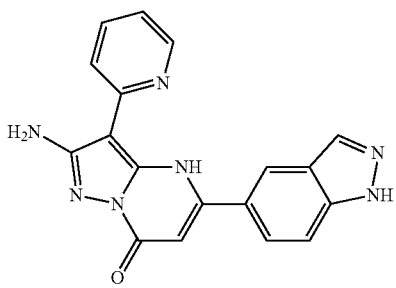

To a solution of 2-amino-5-(1-(methoxymethyl)-1H-indazol-5-yl)-3-(pyridin-2-yl)pyrazolo[1,5-a]pyrimidin-7(4H)-one (120 mg, 0.31 mmol) in methanol (15 mL) was added HCl (15 mL). After stirring for 2 days at 40° C., the crude product was purified by Prep-HPLC to provide 2-amino-5-(1H-indazol-5-yl)-3-(pyridin-2-yl)pyrazolo[1,5-a]pyrimidin-7(4H)-one as a yellow solid (13.4 mg, 13%).

LC/MS (ES, m/z): [M+H]$^+$ 344.1

$^1$H-NMR (300 MHz, DMSO) δ 8.87 (d, J=8.7 Hz, 1H), 8.45 (s, 1H), 8.40 (d, J=4.2 Hz, 1H), 8.17 (d, J=5.1 Hz, 2H), 7.71-7.75 (t, J=7.2 Hz, 2H), 7.59 (t, J=8.7 Hz, 1H), 6.88-6.92 (t, J=6.3 Hz, 1H), 6.24 (s, 1H), 6.09 (s, 1H)

Example 160

5-(1H-Indazol-5-yl)-3-(pyridin-2-yl)pyrazolo[1,5-a]pyrimidin-7(4H)-one

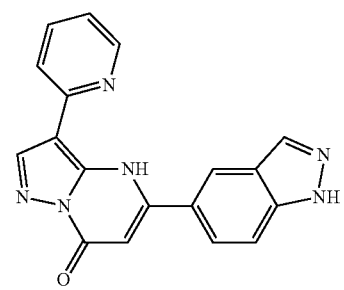

Step 1. 5-(1-(Methoxymethyl)-1H-indazol-5-yl)-3-(pyridin-2-yl)pyrazolo[1,5-a]pyrimidin-7(4H)-one

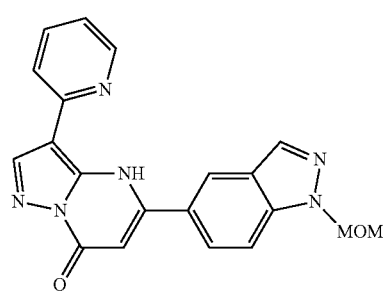

To a solution of 4-(pyridin-2-yl)-1H-pyrazol-5-amine (200 mg, 1.25 mmol) in n-BuOH (20 ml) was added ethyl 3-[1-(methoxymethyl)-1H-indazol-5-yl]-3-oxopropanoate (450 mg, 1.63 mmol), and 4-methylbenzene-1-sulfonic acid (10 mg, 0.06 mmol). The resulting mixture was stirred for 36 hours at 130° C., and the product was collected by filtration to afford 5-(1-(methoxymethyl)-1H-indazol-5-yl)-3-(pyridin-2-yl)pyrazolo[1,5-a]pyrimidin-7(4H)-one as a yellow solid (160 mg, 34%).

$^1$H-NMR (300 MHz, DMSO): δ 8.76 (d, J=8.1 Hz, 1H), 8.52 (d, J=8.1 Hz, 1H), 8.44-8.46 (m, 1H), 8.27-8.32 (m, 3H), 7.74-7.84 (m, 2H), 6.99-7.03 (m, 1H), 6.14 (s, 1H), 5.73 (s, 2H). 3.22-3.60 (m, 3H)

Step 2. 5-(1H-Indazol-5-yl)-3-(pyridin-2-yl)pyrazolo[1,5-a]pyrimidin-7(4H)-one

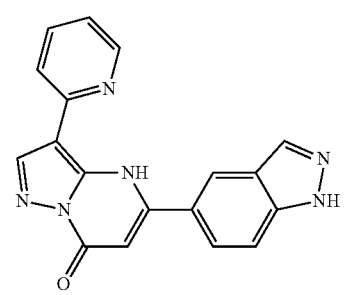

To a solution of 5-(1-(methoxymethyl)-1H-indazol-5-yl)-3-(pyridin-2-yl)pyrazolo[1,5-a]pyrimidin-7(4H)-one (160 mg, 0.43 mmol) in methanol (15 ml) was added HCl (conc.) (15 ml). The resulting mixture was stirred for 2 days at 40° C. in an oil bath. The solids were collected by filtration and dried in an oven under reduced pressure to afford 5-(1H-indazol-5-yl)-3-(pyridin-2-yl)pyrazolo[1,5-a]pyrimidin-7(4H)-one as a yellow solid (48.9 mg, 25%).

LC/MS [M+H]$^+$329.0

$^1$H-NMR (300 MHz, DMSO): δ 13.42 (s, 1H), 8.70 (d, J=6 Hz, 1H), 8.66 (s, 1H), 8.43 (s, 1H), 8.31 (s, 1H), 7.89-7.98 (m, 3H), 7.76 (d, J=8.7 Hz), 7.27-7.31 (m, 1H), 6.35 (s, 1H)

Example 161

5-(Benzo[d][1,3]dioxol-5-yl)-2-ethyl-3-(pyridin-2-yl)pyrazolo[1,5-a]pyrimidin-7(4H)-one

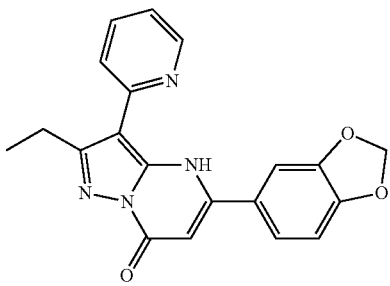 [SMILES: CCc1nn2c(=O)cc(-c3ccc4c(c3)OCO4)[nH]c2c1-c1ccccn1]

To a solution of 3-ethyl-4-(pyridin-2-yl)-1H-pyrazol-5-amine (100 mg, 0.53 mmol) in n-BuOH (20 mL) was added ethyl 3-(benzo[d][1,3]dioxol-5-yl)-3-oxopropanoate (188 mg, 0.79 mmol) and 4-methylbenzene-1-sulfonic acid (5 mg, 0.03 mmol). After stirring for 24 hours at 130° C., the solids were collected by filtration to afford 5-(benzo[d][1,3]dioxol-5-yl)-2-ethyl-3-(pyridin-2-yl)pyrazolo[1,5-a]pyrimidin-7(4H)-one as a yellow solid (50 mg, 26%).

LC/MS (ES, m/z):[M+H]$^+$361.1

$^1$H-NMR (300 MHz, DMSO) δ 12.34 (s, 1H), 8.70 (d, J=4.2 Hz, 1H), 7.92-7.98 (m, 1H), 7.69 (d, J=7.8 Hz, 1H), 7.51 (d, J=1.5 Hz, 1H), 7.41-7.45 (m, 1H), 7.26-7.31 (m, 1H), 7.14 (d, J=8.1 Hz, 1H), 6.21 (s, 1H), 6.17 (s, 2H), 3.00-3.08 (s, 2H), 1.30-1.35 (t, J=7.5 Hz, 3H)

Example 162

5-(4-Chloro-2-fluorophenyl)-3-(pyridin-2-yl)pyrazolo[1,5-a]pyrimidin-7(4H)-one

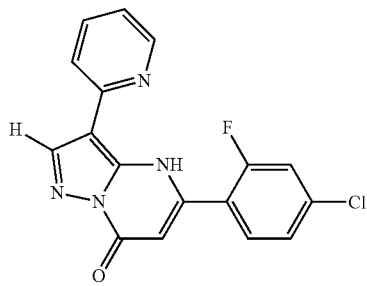 [SMILES: O=c1cc(-c2ccc(Cl)cc2F)[nH]c2c(-c3ccccn3)cnn12]

To a solution of ethyl 3-(4-chloro-2-fluorophenyl)-3-oxopropanoate (229 mg, 0.94 mmol) in n-BuOH (20 mL) was added 4-(pyridin-2-yl)-1H-pyrazol-5-amine (100 mg, 0.63 mmol) and 4-methylbenzene-1-sulfonic acid (5 mg, 0.03 mmol). After stirring for 24 hours at 130° C., the solids were collected by filtration to afford 5-(4-chloro-2-fluorophenyl)-3-(pyridin-2-yl)pyrazolo[1,5-a]pyrimidin-7(4H)-one as a yellow solid (100 mg, 47%).

LC/MS (ES, m/z):[M+H]$^+$ 341.0

$^1$H-NMR (300 MHz, DMSO) δ 8.68 (s, 1H), 8.58-8.60 (m, 1H), 7.94-8.03 (m, 3H), 7.71-7.75 (m, 1H), 7.50-7.54 (m, 1H), 7.26-7.31 (m, 1H), 6.23 (s, 1H)

Example 163

2-Amino-5-(4-chloro-2-fluorophenyl)-3-(pyridin-2-yl)pyrazolo[1,5-a]pyrimidin-7(4H)-one

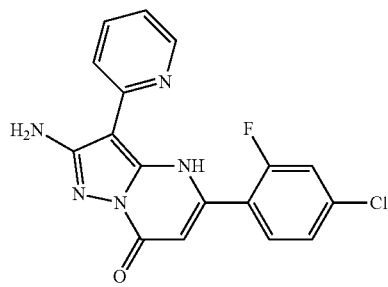 [SMILES: Nc1nn2c(=O)cc(-c3ccc(Cl)cc3F)[nH]c2c1-c1ccccn1]

To a solution of 4-(pyridin-2-yl)-1H-pyrazole-3,5-diamine (100 mg, 0.57 mmol) in n-BuOH (20 mL) was added ethyl 3-(4-chloro-2-fluorophenyl)-3-oxopropanoate (209 mg, 0.85 mmol) and 4-methylbenzene-1-sulfonic acid (6 mg, 0.03 mmol). After stirring for 24 hours at 130° C., the solids were collected by filtration to afford 2-amino-5-(4-chloro-2-fluorophenyl)-3-(pyridin-2-yl)pyrazolo[1,5-a]pyrimidin-7(4H)-one as a yellow solid (55 mg, 27%).

LC/MS (ES, m/z):[M+H]$^+$ 356.0; $^1$H NMR (300 MHz, DMSO) δ 8.56 (d, J=8.1 Hz, 1H), 7.80-8.00 (m, 3H), 7.66 (d, J=10.8 Hz, 1H), 7.47-7.50 (m, 1H), 7.18-7.22 (m, 1H), 6.16 (s, 1H)

Example 164

5-(Benzo[d][1,3]dioxol-5-yl)-3-(3-fluoropyridin-2-yl)pyrazolo[1,5-a]pyrimidin-7(4H)-one

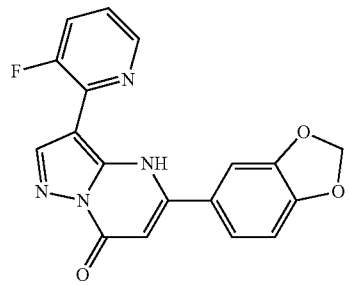 [SMILES: O=c1cc(-c2ccc3c(c2)OCO3)[nH]c2c(-c3ncccc3F)cnn12]

To a solution of 4-(3-fluoropyridin-2-yl)-1H-pyrazol-5-amine (140 mg, 0.79 mmol) in n-BuOH (25 mL) was added ethyl 3-(benzo[d][1,3]dioxol-5-yl)-3-oxopropanoate (223 mg, 0.94 mmol) and TsOH (7 mg, 0.04 mmol). The resulting solution was stirred for 24 hours at 130° C., and the reaction mixture was filtered and the solids were collected and washed with CH₃OH and Et₂O to afford 5-(benzo[d][1,3]dioxol-5-yl)-3-(3-fluoropyridin-2-yl)pyrazolo[1,5-a]pyrimidin-7(4H)-one as a light yellow oil (173.6 mg, 63%).

LC/MS (ES, m/z):[M+H]⁺ 351.0

¹H-NMR (300 MHz, DMSO): δ 11.72 (s, 1H), 8.56-8.59 (m, 1H), 8.37 (d, J=3.6 Hz, 1H), 7.86-7.93 (m, 1H), 7.52 (d, J=3.9 Hz, 2H), 7.36-7.46 (m, 2H), 7.16 (d, J=8.1 Hz, 1H), 6.32 (s, 1H), 6.19 (s, 2H)

Example 165

2-Amino-5-(benzofuran-5-yl)-3-(pyridin-2-yl)pyrazolo[1,5-a]pyrimidin-7(4H)-one

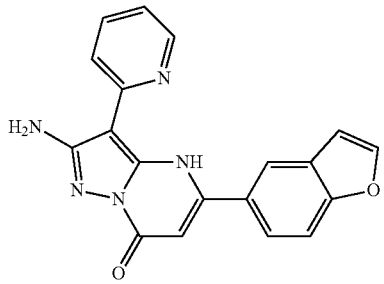 [SMILES: Nc1nn2c(=O)cc(-c3ccc4occc4c3)[nH]c2c1-c1ccccn1]

To a solution of 4-(pyridin-2-yl)-1H-pyrazole-3,5-diamine (300 mg, 1.71 mmol) in n-BuOH (20 ml) was added ethyl 3-(benzofuran-5-yl)-3-oxopropanoate (670 mg, 2.89 mmol) and TsOH (15 mg, 0.09 mmol), and the resulting mixture was stirred for 24 hours at 130° C. The reaction progress was monitored by LCMS. The solids were collected by filtration to afford 2-amino-5-(benzofuran-5-yl)-3-(pyridin-2-yl)pyrazolo[1,5-a]pyrimidin-7(4H)-one as a brown solid (266 mg, 45%).

LC/MS (ES, m/z): [M+H]⁺ 344.1

¹H-NMR (300 MHz, DMSO): δ 8.63 (d, J=5.1 Hz, 1H), 8.19 (d, J=1.5 Hz, 1H), 7.82-7.96 (m, 4H), 7.71 (d, J=8.7 Hz, 1H), 7.20-7.25 (m, 1H), 7.04 (d, J=1.8 Hz, 1H), 6.27 (s, 1H)

Example 166

2-Amino-5-(3-methylbenzofuran-5-yl)-3-(pyridin-2-yl)pyrazolo[1,5-a]pyrimidin-7(4H)-one

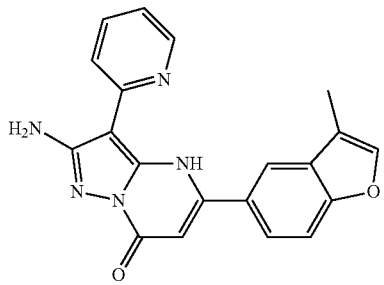

Ethyl 3-(3-methylbenzofuran-5-yl)-3-oxopropanoate (421.7 mg, 1.71 mmol), and TsOH (9.8 mg, 0.06 mmol) were added to a solution of 4-(pyridin-2-yl)-1H-pyrazole-3,5-diamine (200 mg, 1.14 mmol) in n-BuOH (20 ml). The mixture was stirred for 24 hours at 130° C. and the solids were collected by filtration to afford 2-amino-5-(3-methylbenzofuran-5-yl)-3-(pyridin-2-yl)pyrazolo[1,5-a]pyrimidin-7(4H)-one as a yellow solid (110 mg, 27%).

LC/MS (ES, m/z): [M+H]⁺ 358.1

¹H-NMR (300 MHz, DMSO) δ 8.50-8.80 (m, 1H), 8.10-8.40 (m, 1H), 7.51-7.93 (m, 5H), 7.21 (s, 1H), 6.30 (s, 1H), 2.29 (s, 3H)

Example 167

5-(3-Methylbenzofuran-5-yl)-3-(pyridin-2-yl)pyrazolo[1,5-a]pyrimidin-7(4H)-one

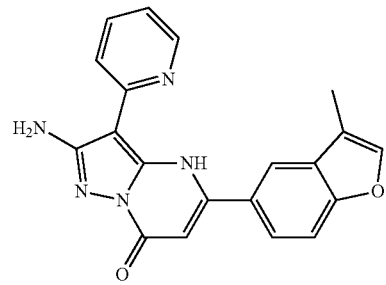 [SMILES: Cc1coc2ccc(-c3cc(=O)n4nc(N)c(-c5ccccn5)c4[nH]3)cc12]

Ethyl 3-(3-methylbenzofuran-5-yl)-3-oxopropanoate (300 mg, 1.22 mmol) and TsOH (5.4 mg, 0.03 mmol) were added to a solution of 4-(pyridin-2-yl)-1H-pyrazol-3,5-diamine (100 mg, 0.62 mmol) in n-BuOH (20 ml), and the reaction was stirred for 24 hours at 130° C. The solids were collected by filtration and washed with MeOH (10 ml) and ether (10 ml) to afford 2-amino-5-(3-methylbenzofuran-5-yl)-3-(pyridin-2-yl)pyrazolo[1,5-a]pyrimidin-7(4H)-one as a yellow solid (27.6 mg, 13%).

LC/MS (ES, m/z): [M+H]⁺ 343.1

¹H-NMR (300 MHz, DMSO) δ 8.67-8.70 (t, J=9.0 Hz, 2H), 8.25 (d, J=1.8 Hz, 1H), 7.87-7.98 (m, 4H), 7.78 (d, J=8.7 Hz, 1H), 7.27-7.31 (m, 1H), 6.14 (s, 1H), 2.33 (s, 3H)

Example 168

2-Hydroxy-5-(3-methylbenzofuran-5-yl)-3-(pyridin-2-yl)pyrazolo[1,5-a]pyrimidin-7(4H)-one

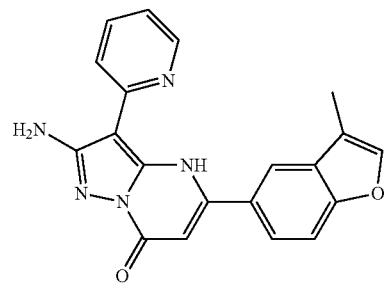 [SMILES: Cc1coc2ccc(-c3cc(=O)n4nc(N)c(-c5ccccn5)c4[nH]3)cc12]

Ethyl 3-(3-methylbenzofuran-5-yl)-3-oxopropanoate (280 mg, 1.10 mmol) and TsOH (7.4 mg, 0.04 mmol) were added to a solution of 5-amino-4-(pyridin-2-yl)-1H-pyrazol-3-ol (150 mg, 0.85 mmol) in n-BuOH (20 ml), and the reaction was stirred for 24 hours at 130° C. Then the mixture was cooled and the solids were collected by filtration to afford 2-hydroxy-5-(3-methylbenzofuran-5-yl)-3-(pyridin-2-yl)pyrazolo[1,5-a]pyrimidin-7(4H)-one as a yellow solid (55.9 mg, 18%).

LC/MS (ES, m/z): [M+H]⁺ 359.1

¹H-NMR (300 MHz, DMSO) δ 8.51-8.80 (m, 2H), 8.31 (s, 1H), 8.15-8.27 (m, 1H), 8.08-8.14 (m, 1H), 7.85 (s, 1H), 7.64 (d, J=9.0 Hz, 1H), 7.24-7.29 (t, J=6.3 Hz, 1H), 6.50 (s, 1H), 2.31 (s, 3H)

Example 169

5-(2-Methylbenzofuran-5-yl)-3-(pyridin-2-yl)pyrazolo[1,5-a]pyrimidin-7(4H)-one

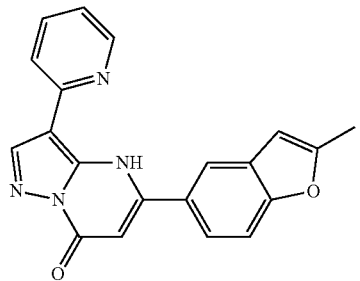 [SMILES: Cc1cc2cc(-c3cc(=O)n4ncc(-c5ccccn5)c4[nH]3)ccc2o1]

Ethyl 3-(2-methylbenzofuran-5-yl)-3-oxopropanoate (220 mg, 0.86 mmol) and TsOH (4.9 mg, 0.03 mmol) were added to a solution of 4-(pyridin-2-yl)-1H-pyrazol-5-amine (100 mg, 0.62 mmol) in n-BuOH (10 ml). The mixture was stirred for 24 hours at 130° C. The solids were collected by filtration and washed with MeOH (3 ml) and ether (5 ml) to afford 5-(2-methylbenzofuran-5-yl)-3-(pyridin-2-yl)pyrazolo[1,5-a]pyrimidin-7(4H)-one as a yellow solid (46.2 mg, 22%).

LC/MS (ES, m/z): [M+H]⁺ 343.1

¹H-NMR (300 MHz, DMSO) δ 8.67 (d, J=4.8 Hz, 1H), 8.66 (s, 1H), 8.14 (d, J=1.5 Hz, 1H), 7.94-7.97 (m, 2H), 7.72-7.81 (m, 2H), 7.26-7.31 (m, 1H), 6.77 (s, 1H), 6.32 (s, 1H), 2.51 (s, 3H)

Example 170

2-Amino-5-(2-methylbenzofuran-5-yl)-3-(pyridin-2-yl)pyrazolo[1,5-a]pyrimidin-7(4H)-one

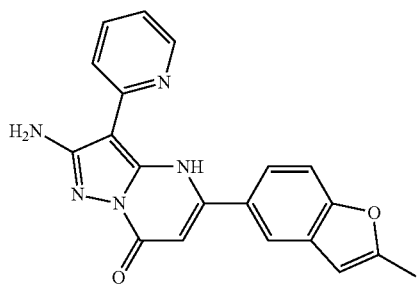 [SMILES: Cc1cc2cc(-c3cc(=O)n4nc(N)c(-c5ccccn5)c4[nH]3)ccc2o1]

Ethyl 3-(2-methylbenzofuran-5-yl)-3-oxopropanoate (421.7 mg, 1.71 mmol) and TsOH (9.8 mg, 0.06 mmol) were added to a solution of 4-(pyridin-2-yl)-1H-pyrazole-3,5-diamine (200 mg, 1.14 mmol) in n-BuOH (20 ml). The resulting solution was stirred for 36 hours at 130° C. Then the mixture was cooled, and the solids were collected by filtration and dried to afford 2-amino-5-(2-methylbenzofuran-5-yl)-3-(pyridin-2-yl)pyrazolo[1,5-a]pyrimidin-7(4H)-one as a yellow solid (103.7 mg, 25%).

LC/MS (ES, m/z): [M+H]⁺ 358.1

¹H-NMR (300 MHz, DMSO) δ 8.64 (d, J=4.5 Hz, 1H), 8.02 (s, 1H), 7.89-7.94 (m, 1H), 7.82-7.88 (m, 1H), 7.62-7.74 (m, 1H), 7.59-7.62 (m, 1H), 7.20-7.24 (t, J=6.9 Hz, 1H), 6.63 (s, 1H), 6.24 (s, 1H), 2.52 (s, 3H)

Example 171

2-Amino-5-(4-fluorophenyl)-3-(pyridin-2-yl)pyrazolo[1,5-a]pyrimidin-7(4H)-one

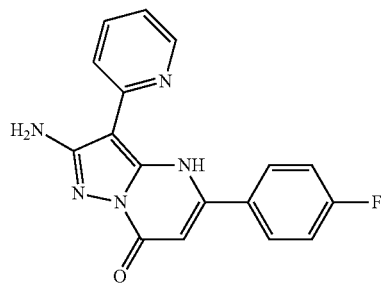

Ethyl 3-(4-fluorophenyl)-3-oxopropanoate (360 mg, 1.71 mmol) and TsOH (10 mg, 0.06 mmol) were added to a solution of 4-(pyridin-2-yl)-1H-pyrazole-3,5-diamine (200 mg, 1.14 mmol) in n-BuOH (10 mL). The mixture was stirred for 24 hours at 130° C. and then cooled. The solids were collected by filtration to afford 2-amino-5-(4-fluorophenyl)-3-(pyridin-2-yl)pyrazolo[1,5-a]pyrimidin-7(4H)-one as a light brown solid (25.7 mg, 6%).

LC/MS (ES, m/z): [M+H]⁺ 322.1

¹H-NMR (300 MHz, CD3OD): δ 8.60 (d, J=4.8 Hz, 1H), 7.89-7.99 (m, 4H), 7.30-7.35 (t, J=8.7 Hz, 2H), 7.20-7.25 (t, J=7.5 Hz, 2H), 6.25 (s, 1H)

Example 172

2-amino-3-(pyridin-2-yl)-5-(4-(trifluoromethyl)phenyl)pyrazolo[1,5-a]pyrimidin-7(4H)-one

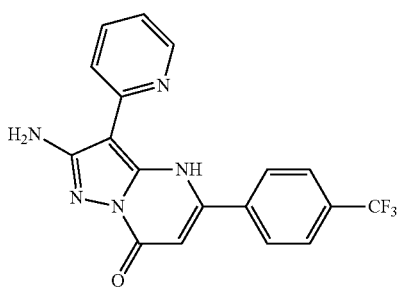 [SMILES: Nc1nn2c(=O)cc(-c3ccc(C(F)(F)F)cc3)[nH]c2c1-c1ccccn1]

To a solution of 4-(pyridin-2-yl)-1H-pyrazole-3,5-diamine (150 mg, 0.86 mmol) in n-BuOH (25 mL) was added ethyl 3-oxo-3-(4-(trifluoromethyl)phenyl)propanoate (334 mg, 1.29 mmol) and TsOH (7 mg, 0.04 mmol). The resulting solution was stirred overnight at 130° C., and then the reaction mixture was filtered, and the solids were collected and washed with CH₃OH and Et₂O to afford 2-amino-3-(pyridin-2-yl)-5-(4-(trifluoromethyl)phenyl)pyrazolo[1,5-a]pyrimidin-7(4H)-one as a light yellow solid (138 mg, 43%).

LC/MS (ES, m/z):[M+H]⁺ 372.1

¹H-NMR (300 MHz, CD₃OD): δ 8.60-8.62 (d, 1H), 8.17 (d, J=8.1 Hz, 2H), 8.01-8.10 (m, 2H), 7.86-7.89 (d, J=8.1 Hz, 2H), 7.23-7.29 (m, 1H), 6.41 (s, 1H)

Example 173

3-(Pyridin-2-yl)-5-(4-(trifluoromethyl)phenyl)pyrazolo[1,5-a]pyrimidin-7(4H)-one

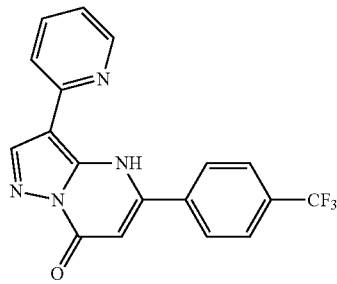 [SMILES: O=c1cc(-c2ccc(C(F)(F)F)cc2)[nH]c2c(-c3ccccn3)cnn12]

To a solution of 4-(pyridin-2-yl)-1H-pyrazol-5-amine (150 mg, 0.94 mmol) in n-BuOH (25 mL) were added ethyl 3-oxo-3-(4-(trifluoromethyl)phenyl)propanoate (366 mg, 1.4 mmol) and TsOH (8 mg, 0.05 mmol). The resulting solution was stirred overnight at 130° C., and then the reaction mixture was filtered, and the solids were collected and washed by CH₃OH and Et₂O to afford 3-(pyridin-2-yl)-5-(4-(trifluoromethyl)phenyl)pyrazolo[1,5-a]pyrimidin-7(4H)-one as a yellow solid (70.3 mg, 21%).

LC/MS (ES, m/z):[M+H]⁺357.0

¹H-NMR (300 MHz, DMSO): δ 8.66-8.68 (t, J=2.7 Hz, 2H), 8.16-8.24 (m, 3H), 8.04-8.10 (m, 1H), 7.92 (d, J=8.4 Hz, 2H), 7.32-7.37 (m, 1H), 6.41 (s, 1H)

Example 174

2-Amino-5-(3-fluorophenyl)-3-(pyridin-2-yl)pyrazolo[1,5-a]pyrimidin-7(4H)-one

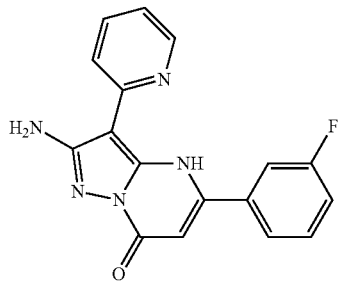 [SMILES: Nc1nn2c(=O)cc(-c3cccc(F)c3)[nH]c2c1-c1ccccn1]

Ethyl 3-(3-fluorophenyl)-3-oxopropanoate (270 mg, 1.29 mmol) and TsOH (7 mg, 0.04 mmol) were added to a solution of 4-(pyridin-2-yl)-1H-pyrazole-3,5-diamine (150 mg, 0.86 mmol) in n-BuOH (25 mL). The resulting solution was stirred overnight at 130° C., and then the reaction mixture was filtered, and the solids were collected and washed with CH₃OH and Et₂O to afford 2-amino-5-(3-fluorophenyl)-3-(pyridin-2-yl)pyrazolo[1,5-a]pyrimidin-7(4H)-one as a light yellow solid (68.5 mg, 25%).

LC/MS (ES, m/z): [M+H]⁺ 322.1

¹H-NMR (300 MHz, CD₃OD): δ 8.59 (d, J=4.2 Hz, 1H), 7.94-8.04 (m, 2H), 7.73-7.80 (m, 2H), 7.55-7.63 (m, 1H), 7.23-7.32 (m, 2H), 6.32 (s, 1H)

Example 175

5-(3-Fluorophenyl)-3-(pyridin-2-yl)pyrazolo[1,5-a]pyrimidin-7(4H)-one

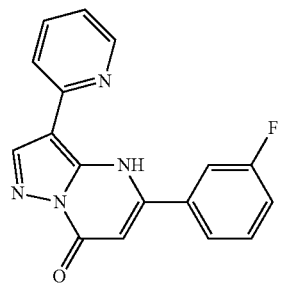 [SMILES: O=c1cc(-c2cccc(F)c2)[nH]c2c(-c3ccccn3)cnn12]

Ethyl 3-(3-fluorophenyl)-3-oxopropanoate (295 mg, 1.40 mmol) and TsOH (8 mg, 0.05 mmol) were added to a solution of 4-(pyridin-2-yl)-1H-pyrazol-5-amine (150 mg, 0.94 mmol) in n-BuOH (25 mL). The resulting solution was stirred overnight at 130° C., and then the reaction mixture was filtered; the solids were collected and washed with CH₃OH and Et₂O to afford 5-(3-fluorophenyl)-3-(pyridin-2-yl)pyrazolo[1,5-a]pyrimidin-7(4H)-one as a light yellow solid (45.7 mg, 16%).

LC/MS (ES, m/z): [M+H]⁺ 307.0

¹H-NMR (300 MHz, DMSO): δ 8.67 (s, 2H), 8.00-8.12 (m, 2H), 7.84-7.90 (m, 2H), 7.62-7.69 (m, 1H), 7.44-7.48 (m, 1H), 7.30-7.34 (m, 1H), 6.38 (s, 1H)

Example 176

2-Amino-5-(2,4-difluorophenyl)-3-(pyridin-2-yl)pyrazolo[1,5-a]pyrimidin-7(4H)-one

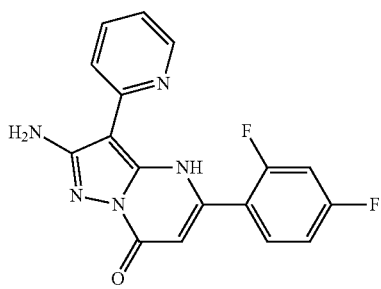 [SMILES: Nc1nn2c(=O)cc(-c3ccc(F)cc3F)[nH]c2c1-c1ccccn1]

Ethyl 3-(2,4-difluorophenyl)-3-oxopropanoate (293 mg, 1.28 mmol) and TsOH (7 mg, 0.04 mmol) were added to a solution of 4-(pyridin-2-yl)-1H-pyrazole-3,5-diamine (150 mg, 0.86 mmol) in n-BuOH (25 ml). The mixture was stirred for 36 h at 130° C., and the solids were collected by filtration and washed with ether (10 ml) to afford 2-amino-5-(2,4- difluorophenyl)-3-(pyridin-2-yl)pyrazolo[1,5-a]pyrimidin-7(4H)-one as a yellow solid (30 mg, 10%).

LC/MS (ES, m/z): [M+H]⁺340.1

¹H-NMR (300 MHz, DMSO) δ 8.50-8.60 (m, 1H), 7.77-8.17 (m, 3H), 7.66-7.71 (m, 1H), 7.32-7.49 (m, 1H), 7.10-7.29 (m, 1H), 6.14 (s, 1H)

Example 177

5-(2,4-Difluorophenyl)-3-(pyridin-2-yl)pyrazolo[1,5-a]pyrimidin-7(4H)-one

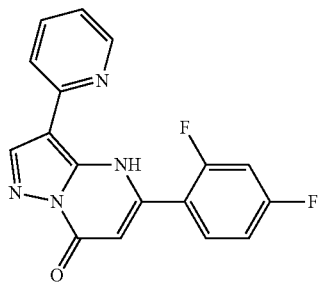 [SMILES: O=c1cc(-c2ccc(F)cc2F)[nH]c2c(-c3ccccn3)cnn12]

To a solution of 4-(pyridin-2-yl)-1H-pyrazol-5-amine (150 mg, 0.94 mmol) in n-BuOH (25 ml) was added ethyl 3-(2,4-difluorophenyl)-3-oxopropanoate (321 mg, 1.41 mmol) and TsOH (8 mg, 0.05 mmol). The resulting solution was stirred overnight at 130° C., and the resulting solids were collected via filtration and washed with ether (10 ml) to afford 5-(2,4-difluorophenyl)-3-(pyridin-2-yl)pyrazolo[1,5-a]pyrimidin-7(4H)-one as a yellow solid (71.7 mg, 24%).

LC/MS (ES, m/z): (ES, m/z): [M+H]+ 325.1

¹H-NMR (300 MHz, DMSO) δ 8.67 (s, 1H), 8.59 (d, J=4.8 Hz, 1H), 7.97-8.02 (m, 3H), 7.50-7.60 (m, 1H), 7.20-7.40 (m, 2H), 6.21 (s, 1H)

Example 178

2-Amino-5-(benzo[d][1,3]dioxol-5-yl)-7-oxo-N-propyl-4,7-dihydropyrazolo[1,5-a]pyrimidine-3-carboxamide

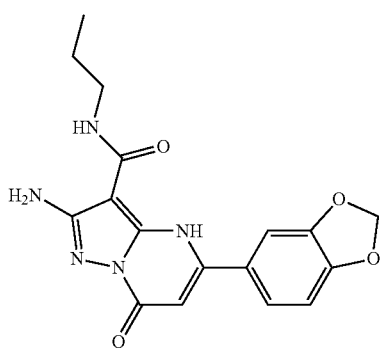 [SMILES: CCCNC(=O)c1c(N)nn2c(=O)cc(-c3ccc4c(c3)OCO4)[nH]c12]

Ethyl 3-(benzo[d][1,3]dioxol-5-yl)-3-oxopropanoate (385 mg, 1.64 mmol) and 4-methylbenzene-1-sulfonic acid (10 mg, 0.06 mmol) were added to a solution of 3,5-diamino-N-propyl-1H-pyrazole-4-carboxamide (200 mg, 1.09 mmol) in n-BuOH (20 ml). After stirring for 48 hours at 130° C., the solids were collected by filtration to afford 2-amino-5-(benzo[d][1,3]dioxol-5-yl)-7-oxo-N-propyl-4,7-dihydropyrazolo[1,5-a]pyrimidine-3-carboxamide as a light yellow solid (102.7 mg, 27%).

LC/MS (ES, m/z):[M+H]⁺ 356.1

¹H-NMR (300 MHz, DMSO) δ 8.13 (s, 1H), 7.55 (s, 2H), 7.02 (d, J=8.4 Hz, 1H), 6.31 (s, 1H), 6.11 (s, 2H), 3.27-3.39 (m, 2H), 1.51-1.63 (m, 2H), 0.85-0.99 (m, 3H)

Example 179

2-Amino-5-(2,2-difluorobenzo[d][1,3]dioxol-5-yl)-3-(pyridin-2-yl)pyrazolo[1,5-a]pyridin-7(4H)-one

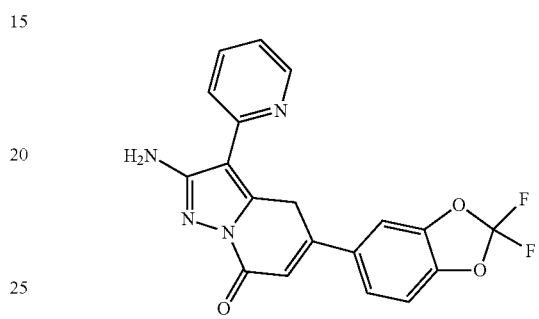

4-(Pyridin-2-yl)-1H-pyrazole-3,5-diamine (200 mg, 1.14 mmol) and 4-methylbenzene-1-sulfonic acid (10 mg, 0.06 mmol) were added to a solution of ethyl 3-(2,2-difluorobenzo[d][1,3]dioxol-5-yl)-3-oxopropanoate (465 mg, 1.71 mmol) in n-BuOH (25 ml). After stirring for 24 hours at 130° C., the solids were collected by filtration to afford 2-amino-5-(2,2-difluorobenzo[d][1,3]dioxol-5-yl)-3-(pyridin-2-yl)pyrazolo[1,5-a]pyridin-7(4H)-one as a yellow solid (43 mg, 10%).

LC/MS (ES, m/z):[M+H]⁺ 384.0

¹H-NMR (300 MHz, DMSO) δ 8.59 (d, J=5.1 Hz, 1H), 7.96-8.03 (m, 2H), 7.90 (d, J=1.5 Hz, 1H), 7.80-7.83 (m, 1H), 7.38 (d, J=8.4 Hz, 1H), 7.20-7.25 (m, 1H), 6.30 (s, 1H)

Example 180

N-(5-(Benzo[d][1,3]dioxol-5-yl)-7-oxo-3-(pyridin-2-yl)-4,7-dihydropyrazolo[1,5-a]pyrimidin-2-yl)propionamide

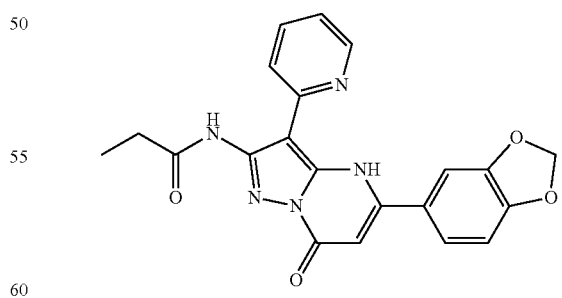

To a solution of 2-amino-5-(benzo[d][1,3]dioxol-5-yl)-3-(pyridin-2-yl)pyrazolo[1,5-a]pyrimidin-7(4H)-one (150 mg, 0.43 mmol) in THF (25 ml) was added triethylamine (130 mg, 1.28 mmol) and propionyl chloride (91 mg, 0.85 mmol), and the resulting mixture was stirred for 4 days at room temperature. The resulting mixture was concentrated under vacuum, diluted with water (30 ml), extracted with ethyl acetate (3×30 ml), dried over anhydrous magnesium sulfate and concentrated under vacuum. The product was precipitated by the addition of petroleum ether and collected by filtration to afford N-(5-(benzo[d][1,3]dioxol-5-yl)-7-oxo-3-(pyridin-2-yl)-4,7-dihydropyrazolo[1,5-a]pyrimidin-2-yl)propionamide as a solid (53.5 mg, 46%).

LC/MS (ES, m/z):[M+H]+ 404.1

$^1$H-NMR (300 MHz, CD3OD) δ 8.60-8.70 (m, 1H), 7.85-7.95 (m, 1H), 7.60-7.80 (m, 1H), 7.35-7.40 (m, 2H), 7.23-7.30 (m, 1H), 6.95-7.10 (m, 1H), 6.25 (s, 1H), 6.11 (s, 2H), 2.57-2.60 (m, 2H), 1.25-1.30 (t, J=7.2 Hz, 3H)

Example 181

N-(5-(Benzo[d][1,3]dioxol-5-yl)-7-oxo-3-(pyridin-2-yl)-4,7-dihydropyrazolo[1,5-a]pyrimidin-2-yl)isobutyramide

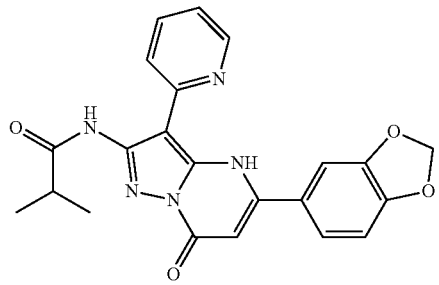 [SMILES: CC(C)C(=O)Nc1nn2c(=O)cc(-c3ccc4c(c3)OCO4)[nH]c2c1-c1ccccn1]

To a solution of 2-amino-5-(benzo[d][1,3]dioxol-5-yl)-3-(pyridin-2-yl)pyrazolo[1,5-a]pyrimidin-7(4H)-one (150 mg, 0.43 mmol) in THF (25 ml) was added triethylamine (130 mg, 1.28 mmol), and isobutyryl chloride (91 mg, 0.85 mmol), and the resulting mixture was stirred for 7 days at room temperature. The resulting mixture was concentrated under vacuum, extracted with ethyl acetate (3×30 ml), concentrated under vacuum, and the product precipitated by the addition of petroleum ether (5 ml) and collected by filtration to afford N-(5-(benzo[d][1,3]dioxol-5-yl)-7-oxo-3-(pyridin-2-yl)-4,7-dihydropyrazolo[1,5-a]pyrimidin-2-yl)isobutyramide as a solid (13.1 mg, 7%).

LC/MS (ES, m/z):[M+H]+ 418.1

$^1$H-NMR (300 MHz, DMSO) δ 12.26 (s, 1H), 8.75 (d, J=7.8 Hz, 1H), 8.53 (d, J=3.0 Hz, 1H), 7.90-7.95 (t, J=6.9 Hz, 1H), 7.71 (s, 2H), 7.11 (s, 1H), 7.01 (d, J=8.7 Hz, 1H), 6.28 (s, 1H), 6.10 (s, 2H), 2.65-2.70 (m, 1H), 1.16-1.24 (m, 6H)

Example 182

N-(5-(1H-Indazol-5-yl)-7-oxo-3-(pyridin-2-yl)-4,7-dihydropyrazolo[1,5-a]pyrimidin-2-yl)acetamide

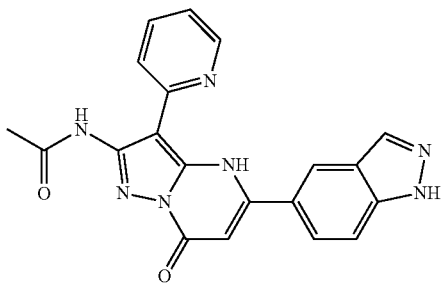 [SMILES: CC(=O)Nc1nn2c(=O)cc(-c3ccc4[nH]ncc4c3)[nH]c2c1-c1ccccn1]

Step 1. 2-Amino-5-(1-(methoxymethyl)-1H-indazol-5-yl)-3-(pyridin-2-yl)pyrazolo[1,5-a]pyrimidin-7(4H)-one

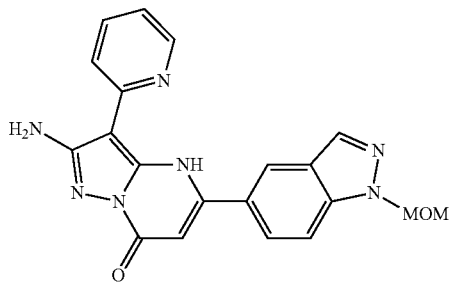

To a solution of 4-(pyridin-2-yl)-1H-pyrazole-3,5-diamine (300 mg, 1.71 mmol) in n-BuOH (30 ml) was added ethyl 3-[1-(methoxymethyl)-1H-indazol-5-yl]-3-oxopropanoate (615 mg, 2.23 mmol) and 4-methylbenzene-1-sulfonic acid (14.7 mg, 0.09 mmol). After stirring for 24 h at 130° C., the solids were collected by filtration to afford of 2-amino-5-(1-(methoxymethyl)-1H-indazol-5-yl)-3-(pyridin-2-yl)pyrazolo[1,5-a]pyrimidin-7(4H)-one as a yellow solid (400 mg, 60%).

LC/MS (ES, m/z): [M+H]+ 388.1

Step 2. 2-Amino-5-(1H-indazol-5-yl)-3-(pyridin-2-yl)pyrazolo[1,5-a]pyrimidin-7(4H)-one

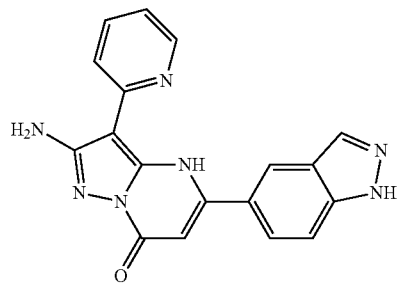 [SMILES: Nc1nn2c(=O)cc(-c3ccc4[nH]ncc4c3)[nH]c2c1-c1ccccn1]

To a solution of 2-amino-5-(1-(methoxymethyl)-1H-indazol-5-yl)-3-(pyridin-2-yl)pyrazolo[1,5-a]pyrimidin-7(4H)-one (400 mg, 1.03 mmol) in methanol (15 ml) was added HCl (15 ml). After stirring for 3 days at 50° C., the solids were collected by filtration to afford 2-amino-5-(1H-indazol-5-yl)-3-(pyridin-2-yl)pyrazolo[1,5-a]pyrimidin-7(4H)-one (300 mg, crude).

LC/MS (ES, m/z): [M+H]⁺ 344.0

Step 3. N-(5-(1-Acetyl-1H-indazol-5-yl)-7-oxo-3-(pyridin-2-yl)-4,7-dihydropyrazolo[1,5-a]pyrimidin-2-yl)acetamide

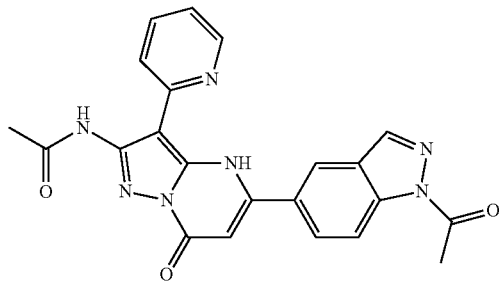 [SMILES: CC(=O)Nc1nn2c(=O)cc(-c3ccc4c(cnn4C(C)=O)c3)[nH]c2c1-c1ccccn1]

To a solution of 2-amino-5-(1H-indazol-5-yl)-3-(pyridin-2-yl)pyrazolo[1,5-a]pyrimidin-7(4H)-one (240 mg, 0.70 mmol) in pyridine (10 mL) was added acetic anhydride (71.4 mg, 0.70 mmol), and the resulting solution was stirred for 40 minutes at room temperature. The reaction mixture was diluted with water (200 ml), extracted with dichloromethane (3×100 ml), and the organic layers combined, dried over anhydrous sodium sulfate, and concentrated under vacuum to afford N-(5-(1-acetyl-1H-indazol-5-yl)-7-oxo-3-(pyridin-2-yl)-4,7-dihydropyrazolo[1,5-a]pyrimidin-2-yl)acetamide as a gray solid (260 mg, crude).

LC/MS (ES, m/z): [M+H]⁺ 428.0

Step 4. N-(5-(1H-Indazol-5-yl)-7-oxo-3-(pyridin-2-yl)-4,7-dihydropyrazolo[1,5-a]pyrimidin-2-yl)acetamide

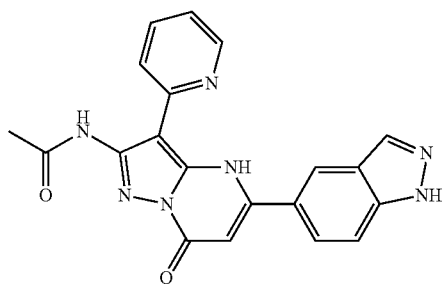 [SMILES: CC(=O)Nc1nn2c(=O)cc(-c3ccc4[nH]ncc4c3)[nH]c2c1-c1ccccn1]

To a solution of N-(5-(1-acetyl-1H-indazol-5-yl)-7-oxo-3-(pyridin-2-yl)-4,7-dihydropyrazolo[1,5-a]pyrimidin-2-yl)acetamide (260 mg, 0.61 mmol) in methanol (30 ml) was added potassium carbonate (84 mg, 0.61 mmol), and the resulting mixture was stirred for 2 hours at room temperature. The reaction mixture was concentrated under vacuum to give the crude product, which was purified by Prep-HPLC to provide N-(5-(1H-indazol-5-yl)-7-oxo-3-(pyridin-2-yl)-4,7-dihydropyrazolo[1,5-a]pyrimidin-2-yl)acetamide as a yellow solid (50 mg).

LC/MS (ES, m/z): [M+H]⁺ 386.1

¹H-NMR (300 MHz, DMSO) δ 13.41 (s, 1H), 10.49 (s, 1H), 8.74 (s, 1H), 8.44 (s, 1H), 8.30 (s, 1H), 7.90 (d, J=7.2 Hz, 2H), 7.78 (s, 1H), 7.58 (s, 1H), 7.31 (s, 1H), 6.37 (s, 1H), 2.18 (s, 3H)

Example 183

2-Ethyl-5-(1H-indazol-5-yl)-3-(pyridin-2-yl)pyrazolo[1,5-a]pyrimidin-7(4H)-one

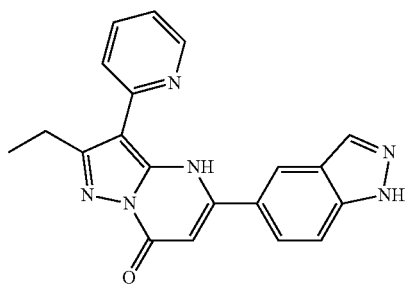

Step 1. 2-Ethyl-5-(1-(methoxymethyl)-1H-indazol-5-yl)-3-(pyridin-2-yl)pyrazolo[1,5-a]pyrimidin-7(4H)-one

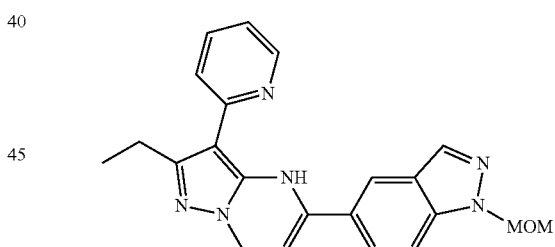

To a solution of 3-ethyl-4-(pyridin-2-yl)-1H-pyrazol-5-amine (200 mg, 1.06 mmol) in n-BuOH (20 ml) was added ethyl 3-[1-(methoxymethyl)-1H-indazol-5-yl]-3-oxopropanoate (411 mg, 1.49 mmol) and TsOH (9 mg, 0.05 mmol), and the resulting mixture was stirred for 24 hours at 130° C. The solids were collected by filtration to afford 2-ethyl-5-(1-(methoxymethyl)-1H-indazol-5-yl)-3-(pyridin-2-yl)pyrazolo[1,5-a]pyrimidin-7(4H)-one as a yellow solid (250 mg, 59%).

LC/MS (ES, m/z): [M+H]⁺ 401.0

¹H-NMR (300 MHz, DMSO) δ 8.76 (d, J=4.5 Hz, 1H), 8.38 (d, J=12.0 Hz, 2H), 7.95-8.00 (m, 3H), 7.72 (d, J=8.1 Hz, 1H), 7.29-7.34 (m, 1H), 6.34 (s, 1H), 5.82 (s, 2H), 3.24 (s, 3H), 3.03-3.11 (m, 2H), 1.32-1.37 (t, J=7.5 Hz, 3H)

Step 2. 2-Ethyl-5-(1H-indazol-5-yl)-3-(pyridin-2-yl)pyrazolo[1,5-a]pyrimidin-7(4H)-one

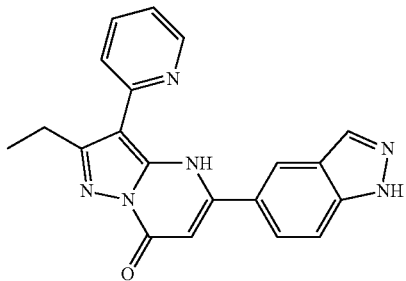

To a solution of 2-ethyl-5-(1-(methoxymethyl)-1H-indazol-5-yl)-3-(pyridin-2-yl)pyrazolo[1,5-a]pyrimidin-7(4H)-one (250 mg, 0.62 mmol) in methanol (15 ml) was added HCl (15 ml). After stirring for 3 days at 50° C., the solids were collected by filtration to afford 2-ethyl-5-(1H-indazol-5-yl)-3-(pyridin-2-yl)pyrazolo[1,5-a]pyrimidin-7(4H)-one as a white solid (65 mg, 29%).

LC/MS (ES, m/z): [M+H]$^+$ 357.1

$^1$H-NMR (300 MHz, DMSO) δ 12.61 (s, 1H), 8.88 (d, J=5.4 Hz, 1H), 8.37 (d, J=8.4 Hz, 2H), 8.28 (s, 1H), 8.01 (d, J=7.5 Hz, 1H), 7.85-7.88 (m, 1H), 7.73 (d, J=8.7 Hz, 1H), 6.27 (s, 1H), 2.91-2.98 (m, 2H), 1.24-1.29 (t, J=4.5 Hz, 3H)

Example 184

2-Amino-5-(1-methyl-1H-indazol-5-yl)-3-(pyridin-2-yl)pyrazolo[1,5-a]pyrimidin-7(4H)-one

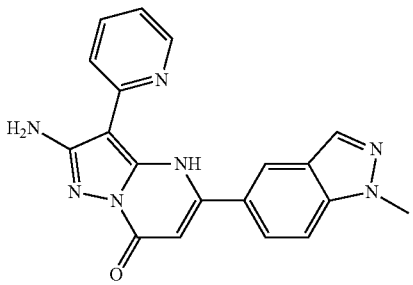 [SMILES: Cn1ncc2cc(-c3cc(=O)n4nc(N)c(-c5ccccn5)c4[nH]3)ccc21]

To a solution of 4-(pyridin-2-yl)-1H-pyrazole-3,5-diamine (200 mg, 1.14 mmol) in n-BuOH (20 ml) was added ethyl 3-(1-methyl-1H-indazol-5-yl)-3-oxopropanoate (421.7 mg, 1.71 mmol), and TsOH (9.8 mg, 0.06 mmol). The resulting mixture was stirred for 48 hours at 130° C. The solids were collected by filtration to afford 2-amino-5-(1-methyl-1H-indazol-5-yl)-3-(pyridin-2-yl)pyrazolo[1,5-a]pyrimidin-7(4H)-one as a yellow solid (45 mg, 18%).

LC/MS (ES, m/z): [M+H]$^+$ 358.1

$^1$H NMR (300 MHz, DMSO) δ 8.40-8.65 (m, 3H), 8.23 (s, 1H), 7.83-8.15 (m, 3H), 7.20 (s, 1H), 6.28 (s, 1H), 4.12 (s, 3H)

Example 185

5-(1H-Benzo[d][1,2,3]triazol-5-yl)-3-benzyl-2-methylpyrazolo[1,5-a]pyrimidin-7(4H)-one

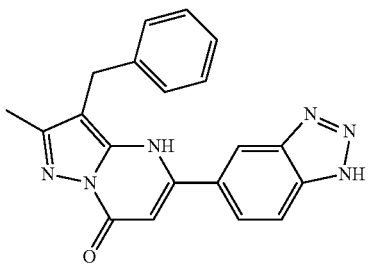 [SMILES: Cc1nn2c(=O)cc(-c3ccc4[nH]nnc4c3)[nH]c2c1Cc1ccccc1]

A solution of 4-benzyl-3-methyl-1H-pyrazol-5-amine (100 mg, 0.53 mmol), ethyl 3-(1H-benzo[d][1,2,3]triazol-5-yl)-3-oxopropanoate (159 mg, 0.68 mmol), and 4-methylbenzene-1-sulfonic acid (6 mg, 0.03 mmol) in n-BuOH (3 mL) was stirred for 36 hours at 135° C. The resulting solids were collected by filtration and washed with methanol (2 mL) to afford 5-(1H-benzo[d][1,2,3]triazol-5-yl)-3-benzyl-2-methylpyrazolo[1,5-a]pyrimidin-7(4H)-one as an off-white solid (95.7 mg, 50%).

LS/MS (ES, m/z):[M+H]$^+$357.1

$^1$H-NMR (300 MHz, CD$_3$OD): δ 8.33 (s, 1H), 8.02 (d, J=8.7 Hz, 1H), 7.83-7.86 (m, 1H), 7.18-7.34 (m, 5H), 6.10 (s, 1H), 4.13 (s, 2H), 2.24 (s, 3H)

Example 186

5-(1-Methyl-1H-indazol-5-yl)-3-(pyridin-2-yl)pyrazolo[1,5-a]pyrimidin-7(4H)-one

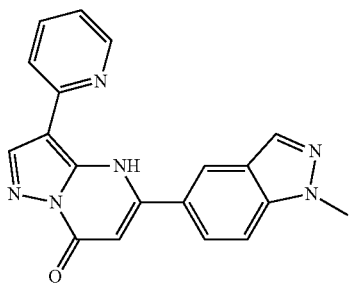 [SMILES: Cn1ncc2cc(-c3cc(=O)n4ncc(-c5ccccn5)c4[nH]3)ccc21]

A solution of 4-(pyridin-2-yl)-1H-pyrazol-5-amine (200 mg, 1.25 mmol), ethyl 3-(1-methyl-1H-indazol-5-yl)-3-oxopropanoate (461.25 mg, 1.87 mmol), and TsOH (10.75 mg, 0.06 mmol) in n-BuOH (20 ml) was stirred for 24 hours at 130° C., and the resulting solids were collected by filtration to afford 5-(1-methyl-1H-indazol-5-yl)-3-(pyridin-2-yl)pyrazolo[1,5-a]pyrimidin-7(4H)-one as a yellow solid (242.9 mg, 57%).

LC/MS (ES, m/z): [M+H]$^+$ 343.1

$^1$H-NMR (300 MHz, DMSO) δ 8.70 (d, J=5.1 Hz, 1H), 8.66 (s, 1H), 8.42 (s, 1H), 8.28 (s, 1H), 7.87-7.97 (m, 4H), 7.27-7.31 (m, 1H), 6.38 (s, 1H), 4.14 (s, 3H)

Example 187

2-Hydroxy-5-(1H-indazol-5-yl)-3-(pyridin-2-yl)pyrazolo[1,5-a]pyrimidin-7(4H)-one

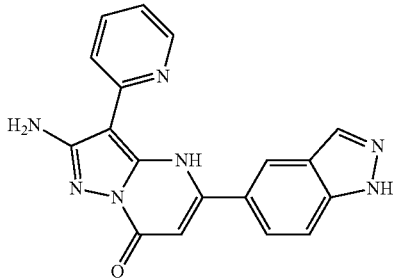 [SMILES: Nc1nn2c(=O)cc(-c3ccc4[nH]ncc4c3)[nH]c2c1-c1ccccn1]

Step 1. 2-Hydroxy-5-(1-(methoxymethyl)-1H-indazol-5-yl)-3-(pyridin-2-yl)pyrazolo[1,5-a]pyrimidin-7(4H)-one

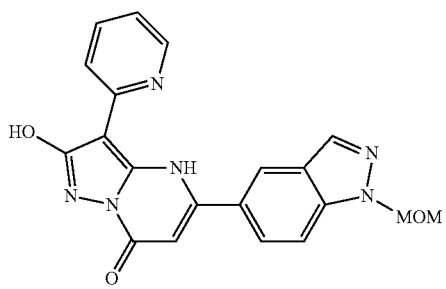

A solution of 5-amino-4-(pyridin-2-yl)-1H-pyrazol-3-ol (200 mg, 1.14 mmol), ethyl 3-[1-(methoxymethyl)-1H-indazol-5-yl]-3-oxopropanoate (439 mg, 1.59 mmol) and TsOH (9.8 mg, 0.06 mmol) in n-BuOH (20 ml) was stirred for 24 hours at 130° C. The resulting solids were collected by filtration to afford 2-hydroxy-5-(1-(methoxymethyl)-1H-indazol-5-yl)-3-(pyridin-2-yl)pyrazolo[1,5-a]pyrimidin-7(4H)-one as a yellow solid (240 mg, crude).

LC/MS (ES, m/z): [M+H]$^+$389.0

Step 2. 2-Hydroxy-5-(1H-indazol-5-yl)-3-(pyridin-2-yl)pyrazolo[1,5-a]pyrimidin-7(4H)-one

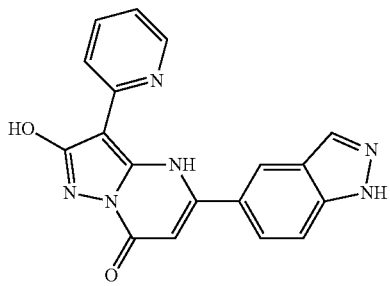 [SMILES: O=c1cc(-c2ccc3[nH]ncc3c2)[nH]c2c(-c3ccccn3)c(O)nn12]

A solution of 2-hydroxy-5-(1-(methoxymethyl)-1H-indazol-5-yl)-3-(pyridin-2-yl)pyrazolo[1,5-a]pyrimidin-7(4H)-one (240 mg, 0.62 mmol) and HCl (15 ml) in methanol (30 ml) was stirred for 3 days at 50° C. The resulting solids were collected by filtration to afford 2-hydroxy-5-(1H-indazol-5-yl)-3-(pyridin-2-yl)pyrazolo[1,5-a]pyrimidin-7(4H)-one as a yellow solid (70 mg, 33%).

LC/MS (ES, m/z): [M+H]$^+$ 345.1

$^1$H-NMR (300 MHz, DMSO) δ 8.54-8.58 (m, 3H), 8.20-8.29 (m, 2H), 8.05-8.08 (m, 1H), 7.65 (d, J=8.7 Hz, 1H), 7.30-7.34 (m, 1H), 6.43 (s, 1H)

Example 188

2-Amino-5-(3-methyl-1H-indazol-5-yl)-3-(pyridin-2-yl)pyrazolo[1,5-a]pyrimidin-7(4H)-one

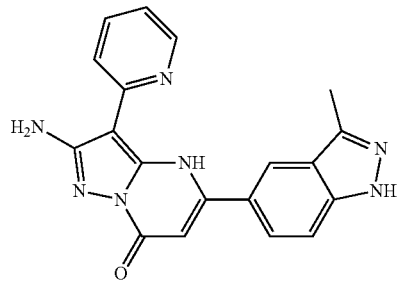 [SMILES: Cc1n[nH]c2ccc(-c3cc(=O)n4nc(N)c(-c5ccccn5)c4[nH]3)cc12]

Step 1. 5-(1-Acetyl-3-methyl-1H-indazol-5-yl)-2-amino-3-(pyridin-2-yl)pyrazolo[1,5-a]pyrimidin-7(4H)-one

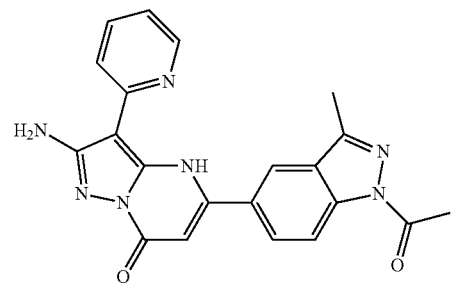 [SMILES: CC(=O)n1nc(C)c2cc(-c3cc(=O)n4nc(N)c(-c5ccccn5)c4[nH]3)ccc21]

A solution of 4-(pyridin-2-yl)-1H-pyrazole-3,5-diamine (150 mg, 0.86 mmol), ethyl 3-(1-acetyl-3-methyl-1H-indazol-5-yl)-3-oxopropanoate (296 mg, 1.03 mmol) and TsOH (7.37 mg, 0.04 mmol) in n-BuOH (20 mL) was stirred for 24 hours at 130° C., and the solids were collected by filtration to afford 5-(1-acetyl-3-methyl-1H-indazol-5-yl)-2-amino-3-(pyridin-2-yl)pyrazolo[1,5-a]pyrimidin-7(4H)-one as a yellow solid (200 mg, crude).

LC/MS (ES, m/z): [M+H]$^+$400.0

Step 2. 2-Amino-5-(3-methyl-1H-indazol-5-yl)-3-(pyridin-2-yl)pyrazolo[1,5-a]pyrimidin-7(4H)-one

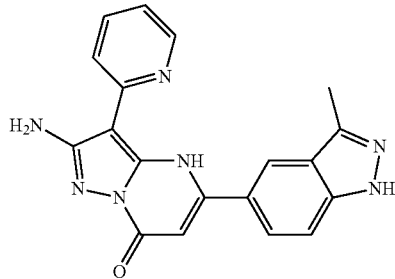 [SMILES: Cc1n[nH]c2ccc(-c3cc(=O)n4nc(N)c(-c5ccccn5)c4[nH]3)cc12]

A solution of 5-(1-acetyl-3-methyl-1H-indazol-5-yl)-2-amino-3-(pyridin-2-yl)pyrazolo[1,5-a]pyrimidin-7(4H)-one (200 mg, 0.50 mmol) and potassium carbonate (69 mg, 0.50 mmol) in methanol (25 mL) was stirred overnight at room temperature. The reaction mixture was concentrated under reduced pressure to provide the crude product, which was purified by Pre-HPLC to provide 2-amino-5-(3-methyl-1H-indazol-5-yl)-3-(pyridin-2-yl)pyrazolo[1,5-a]pyrimidin-7 (4H)-one as a yellow solid (82.3 mg).

LC/MS (ES, m/z): [M+H]$^+$ 358.1

$^1$H-NMR (300 MHz, DMSO) δ 8.86 (d, J=8.4 Hz, 1H), 8.40 (d, J=4.2 Hz, 1H), 8.35 (s, 1H), 8.17 (d, J=8.7 Hz, 1H), 7.70-7.74 (t, J=6.9 Hz, 1H), 7.50 (d, J=8.7 Hz, 1H), 6.87-6.91 (t, J=5.7 Hz, 1H), 6.19 (s, 1H), 6.09 (s, 1H), 2.58 (s, 3H)

Example 189

5-(3-Methyl-1H-indazol-5-yl)-3-(pyridin-2-yl)pyrazolo[1,5-a]pyrimidin-7(4H)-one

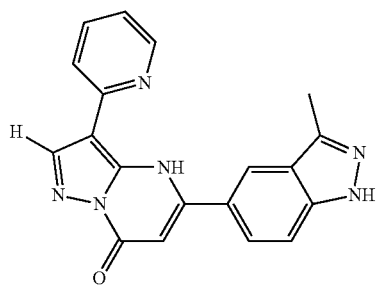 [SMILES: Cc1n[nH]c2ccc(-c3cc(=O)n4ncc(-c5ccccn5)c4[nH]3)cc12]

Step 1. 5-(1-Acetyl-3-methyl-1H-indazol-5-yl)-3-(pyridin-2-yl)pyrazolo[1,5-a]pyrimidin-7(4H)-one

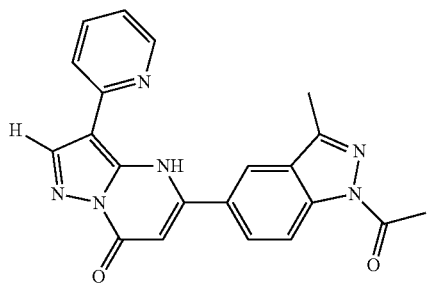 [SMILES: CC(=O)n1nc(C)c2cc(-c3cc(=O)n4ncc(-c5ccccn5)c4[nH]3)ccc21]

A solution of 4-(pyridin-2-yl)-1H-pyrazol-5-amine (100 mg, 0.62 mmol), ethyl 3-(1-acetyl-3-methyl-1H-indazol-5-yl)-3-oxopropanoate (216 mg, 0.75 mmol) and TsOH (5.3 mg, 0.03 mmol) in n-BuOH (20 ml) was stirred for 24 hours at 130° C., and the solids were collected by filtration to afford 5-(1-acetyl-3-methyl-1H-indazol-5-yl)-3-(pyridin-2-yl)pyrazolo[1,5-a]pyrimidin-7(4H)-one as a yellow solid (150 mg, crude).

LC/MS (ES, m/z): [M+H]$^+$ 385.1

Step 2. 5-(3-Methyl-1H-indazol-5-yl)-3-(pyridin-2-yl)pyrazolo[1,5-a]pyrimidin-7(4H)-one

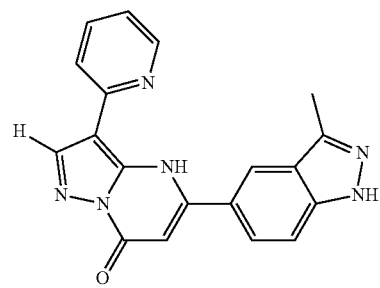 [SMILES: Cc1n[nH]c2ccc(-c3cc(=O)n4ncc(-c5ccccn5)c4[nH]3)cc12]

A solution of 5-(1-acetyl-3-methyl-1H-indazol-5-yl)-3-(pyridin-2-yl)pyrazolo[1,5-a]pyrimidin-7(4H)-one (150 mg, crude) and potassium carbonate (54 mg, 0.39 mmol) in methanol (25 ml) was stirred overnight at room temperature. The solids were collected by filtration and washed with water (3 ml) to afford of 5-(3-methyl-1H-indazol-5-yl)-3-(pyridin-2-yl)pyrazolo[1,5-a]pyrimidin-7(4H)-one as a yellow solid (100 mg).

LC/MS (ES, m/z): [M+H]$^+$ 343.1

$^1$H-NMR (300 MHz, DMSO) δ 12.67 (s, 1H), 8.76 (d, J=7.5 Hz, 1H), 8.45 (d, J=4.2 Hz, 1H), 8.39 (s, 1H), 8.31 (s, 1H), 8.22 (d, J=8.7 Hz, 1H), 7.74-7.79 (m, 1H), 7.52 (d, J=9.0 Hz, 1H), 6.99-7.03 (m, 1H), 6.17 (s, 1H), 2.58 (s, 3H)

Example 190

5-(4-Chlorophenyl)-2-ethyl-3-(pyridin-2-yl)pyrazolo[1,5-a]pyrimidin-7(4H)-one

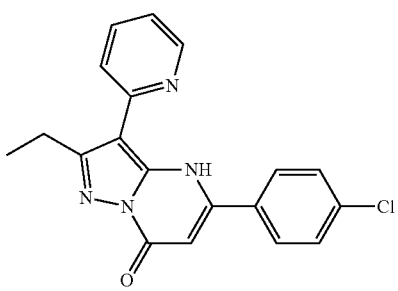 [SMILES: CCc1nn2c(=O)cc(-c3ccc(Cl)cc3)[nH]c2c1-c1ccccn1]

A solution of 3-ethyl-4-(pyridin-2-yl)-1H-pyrazol-5-amine (150 mg, 0.80 mmol), ethyl 3-(4-chlorophenyl)-3-oxopropanoate (220 mg, 1.03 mmol), and TsOH (7 mg, 0.04 mmol) in n-BuOH (20 ml) was stirred overnight at 130° C., and the mixture was cooled. The solids were collected by filtration to afford 5-(4-chlorophenyl)-2-ethyl-3-(pyridin-2-yl)pyrazolo[1,5-a]pyrimidin-7(4H)-one as a yellow solid (145.5 mg, 53%).

LC/MS (ES, m/z): [M+H]+ 351.0

$^1$H-NMR (300 MHz, DMSO) δ 8.74 (d, J=4.2 Hz, 1H), 7.99-8.02 (m, 3H), 7.73 (d, J=8.1 Hz, 1H), 7.66 (d, J=8.4 Hz, 1H), 7.31-7.35 (m, 1H), 6.31 (s, 1H), 3.02-3.09 (m, 2H), 1.30-1.35 (t, J=7.5 Hz, 3H)

Example 191

2-Amino-5-(1H-benzo[d][1,2,3]triazol-5-yl)-3-(pyridin-2-yl)pyrazolo[1,5-a]pyrimidin-7(4H)-one

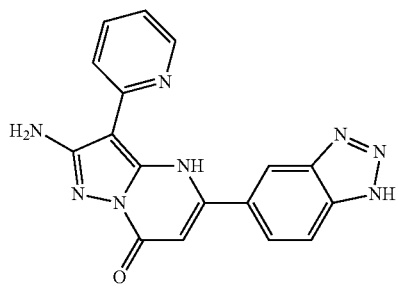 [SMILES: Nc1nn2c(=O)cc(-c3ccc4[nH]nnc4c3)[nH]c2c1-c1ccccn1]

A solution of ethyl 3-(1H-benzo[d][1,2,3]triazol-5-yl)-3-oxopropanoate (238 mg, 1.02 mmol), 4-(pyridin-2-yl)-1H-pyrazole-3,5-diamine (150 mg, 0.86 mmol), and 4-methylbenzene-1-sulfonic acid (6 mg, 0.03 mmol) in n-BuOH (20 ml) was stirred overnight at 130° C. The solids were collected by filtration, diluted with DMSO (4 ml) and H$_2$O (20 ml), and collected by filtration to afford 2-amino-5-(1H-benzo[d][1,2,3]triazol-5-yl)-3-(pyridin-2-yl)pyrazolo[1,5-a]pyrimidin-7(4H)-one as a yellow solid (130.7 mg 44%).

LC/MS (ES, m/z):[M+H]+ 345.1

$^1$H-NMR (300 MHz, CD$_3$OD) δ 8.81 (d, J=8.4 Hz, 1H), 8.60 (s, 1H), 8.47 (d, J=3.9 Hz, 1H), 8.13-8.16 (m, 1H), 7.91 (d, J=8.7 Hz, 1H), 7.76 (s, 1H), 6.95-7.05 (m, 1H), 6.39 (s, 1H)

Example 192

5-(1H-Benzo[d][1,2,3]triazol-5-yl)-3-(pyridin-2-yl)pyrazolo[1,5-a]pyrimidin-7(4H)-one

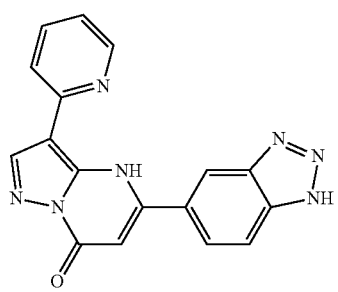

A solution of 4-(pyridin-2-yl)-1H-pyrazol-5-amine (120 mg, 0.75 mmol), ethyl 3-(1H-benzo[d][1,2,3]triazol-5-yl)-3-oxopropanoate (210 mg, 0.90 mmol), and 4-methylbenzene-1-sulfonic acid (6 mg, 0.03 mmol) in n-BuOH (20 ml) was stirred for 4 hours at 130° C. The solids were collected by filtration, diluted with DMSO (4 ml) and water (20 mL). The product was collected by filtration to get 5-(1H-benzo[d][1,2,3]triazol-5-yl)-3-(pyridin-2-yl)pyrazolo[1,5-a]pyrimidin-7(4H)-one as a solid (92.4 mg, 37%).

LC/MS (ES, m/z): [M+H]+ 330.1

$^1$H-NMR (300 MHz, DMSO) δ 15.94 (s, 1H), 8.40-8.59 (m, 4H), 8.00-8.30 (m, 2H), 7.88-7.93 (t, J=6.6 Hz, 1H), 7.18 (s, 1H), 6.43 (s, 1H)

Example 193

5-(1H-Benzo[d][1,2,3]triazol-5-yl)-2-hydroxy-3-(pyridin-2-yl)pyrazolo[1,5-a]pyrimidin-7(4H)-one

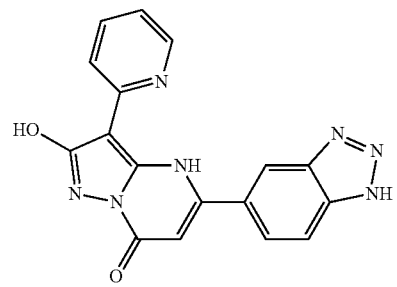 [SMILES: O=c1cc(-c2ccc3[nH]nnc3c2)[nH]c2c(-c3ccccn3)c(O)nn12]

A solution of 5-amino-4-(pyridin-2-yl)-1H-pyrazol-3-ol (100 mg, 0.57 mmol), ethyl 3-(1H-benzo[d][1,2,3]triazol-5-yl)-3-oxopropanoate (195 mg, 0.84 mmol), and 4-methylbenzene-1-sulfonic acid (8 mg, 0.05 mmol) in n-BuOH (5 ml) was stirred overnight at 130° C. The solids were collected by filtration to afford 5-(1H-benzo[d][1,2,3]triazol-5-yl)-2-hydroxy-3-(pyridin-2-yl)pyrazolo[1,5-a]pyrimidin-7(4H)-one as a yellow solid (169 mg, 86%).

LC/MS (ES, m/z): [M+H]+ 346.1

$^1$H-NMR (300 MHz, DMSO) δ 8.52-8.67 (m, 2H), 8.41 (d, J=4.5 Hz, 1H), 8.13-8.19 (m, 1H), 7.86-7.93 (m, 2H), 7.02-7.12 (m, 1H), 6.23 (s, 1H)

Example 194

2-Amino-5-(1-methyl-1H-benzo[d][1,2,3]triazol-5-yl)-3-(pyridin-2-yl)pyrazolo[1,5-a]pyrimidin-7(4H)-one

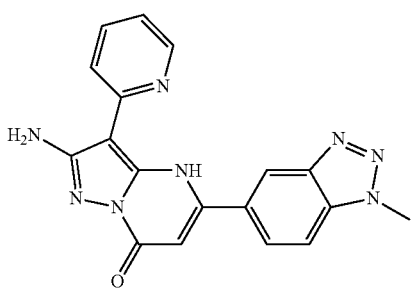

LC/MS (ES, m/z): [M+H]+ 359.1

$^1$H-NMR (300 MHz, DMSO) δ 8.81 (d, J=8.1 Hz, 1H), 8.72 (s, 1H), 8.46 (d, J=4.2 Hz, 1H), 8.37 (d, J=9.0 Hz, 1H), 7.83 (d, J=9.0 Hz, 1H), 7.76-7.83 (m, 1H), 6.97-6.98 (m, 1H), 6.39 (s, 1H), 4.39 (s, 3H)

Example 195

5-(1-Methyl-1H-benzo[d][1,2,3]triazol-5-yl)-3-(pyridin-2-yl)pyrazolo[1,5-a]pyrimidin-7(4H)-one

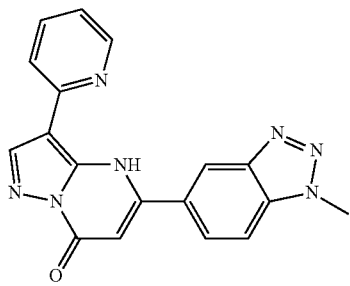

LC/MS (ES, m/z): [M+H]$^+$. 344.1

$^1$H-NMR (300 MHz, DMSO) δ 8.67-8.70 (m, 3H), 7.97-8.17 (m, 4H), 7.29-7.33 (m, 1H), 6.45 (s, 1H), 4.34 (s, 3H)

Example 196

2-Ethyl-5-(1-methyl-1H-indazol-5-yl)-3-(pyridin-2-yl)pyrazolo[1,5-a]pyrimidin-7(4H)-one

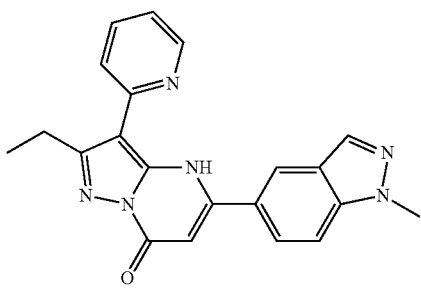 [SMILES: CCc1nn2c(=O)cc(-c3ccc4c(cnn4C)c3)[nH]c2c1-c1ccccn1]

LC/MS (ES, m/z): [M+H]$^+$ 371.1

$^1$H-NMR (300 MHz, DMSO) δ 12.47 (s, 1H), 8.77 (d, J=4.2 Hz, 1H), 8.38 (s, 1H), 8.27 (s, 1H), 7.86-8.00 (m, 3H), 7.72 (d, J=8.1 Hz, 1H), 7.29-7.34 (m, 1H), 6.33 (s, 1H), 4.13 (s, 3H), 3.06-3.32 (m, 2H), 1.32-1.37 (t, J=7.5 Hz, 3H)

Example 197

2-Amino-5-(1-methyl-1H-indazol-5-yl)-7-oxo-N-propyl-4,7-dihydropyrazolo[1,5-a]pyrimidine-3-carboxamide

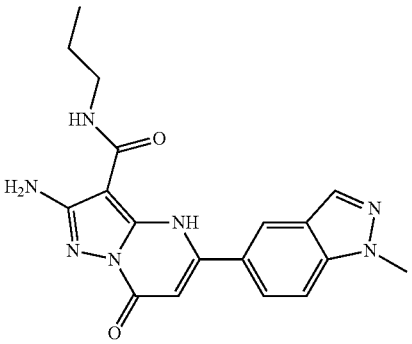 [SMILES: CCCNC(=O)c1c(N)nn2c(=O)cc(-c3ccc4c(cnn4C)c3)[nH]c12]

LC/MS (ES, m/z): [M+H]$^+$ 366.1 $^1$H-NMR (300 MHz, DMSO) δ 8.40-8.50 (m, 1H), 8.25-8.35 (m, 1H), 8.16-8.24 (m, 1H), 8.00-8.11 (m, 1H), 7.74 (d, J=8.4 Hz, 1H), 6.45 (s, 1H), 4.10 (s, 3H), 3.64-3.69 (m, 2H), 1.50-1.65 (m, 2H), 0.89-1.03 (m, 3H)

Example 198

2-Amino-5-(1H-indazol-5-yl)-7-oxo-N-propyl-4,7-dihydropyrazolo[1,5-a]pyrimidine-3-carboxamide

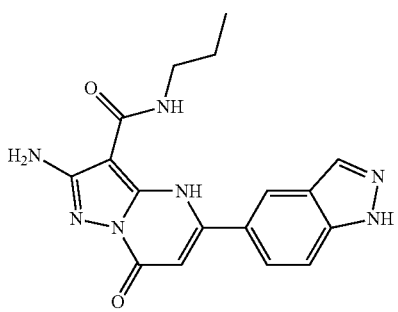 [SMILES: CCCNC(=O)c1c(N)nn2c(=O)cc(-c3ccc4[nH]ncc4c3)[nH]c12]

LC/MS [M+H]$^+$ 352.1

$^1$H-NMR (300 MHz, DMSO) δ 13.19 (s, 1H), 8.49 (s, 1H), 8.17 (s, 1H), 8.13 (s, 1H), 8.01 (s, 1H), 7.61 (d, J=8.7 Hz, 1H), 6.44 (s, 1H), 1.60-1.67 (m, 2H), 1.02-1.07 (t, J=7.4 Hz, 3H)

Example 199

2-Amino-5-(1H-benzo[d][1,2,3]triazol-5-yl)-3-phenylpyrazolo[1,5-a]pyrimidin-7(4H)-one

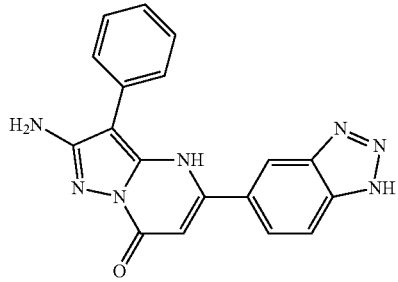 [SMILES: Nc1nn2c(=O)cc(-c3ccc4[nH]nnc4c3)[nH]c2c1-c1ccccc1]

LC/MS (ES, m/z): [M+H]⁺ 344.1
¹H-NMR (300 MHz, DMSO): δ 8.25-8.45 (m, 1H), 7.98-8.10 (m, 1H), 7.75-7.85 (m, 1H), 7.54-7.60 (s, 2H), 7.45-7.50 (m, 2H), 7.29-7.34 (m, 1H), 5.96 (s, 1H)

Example 200

5-(1H-Benzo[d][1,2,3]triazol-5-yl)-2-methyl-3-(pyridin-2-yl)pyrazolo[1,5-a]pyrimidin-7(4H)-one

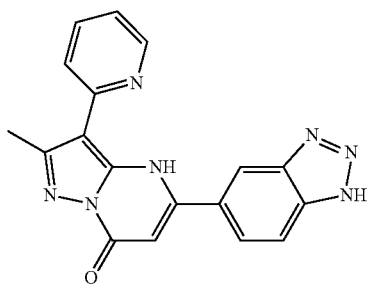 [SMILES: Cc1nn2c(=O)cc(-c3ccc4[nH]nnc4c3)[nH]c2c1-c1ccccn1]

LC/MS (ES, m/z):[M+H]⁺ 344.1
¹H-NMR (300 MHz, DMSO+D₂O) δ 8.86 (d, J=8.1 Hz, 1H), 8.49-8.51 (t, J=5.7 Hz, 2H), 8.16 (d, J=8.1 Hz, 1H), 7.91 (d, J=8.7 Hz, 1H), 7.73-7.79 (m, 1H), 6.98-7.02 (m, 1H), 6.14 (s, 1H), 2.73 (s, 3H)

Example 201

5-(1H-benzo[d][1,2,3]triazol-5-yl)-2-ethyl-3-(pyridin-2-yl)pyrazolo[1,5-a]pyrimidin-7(4H)-one

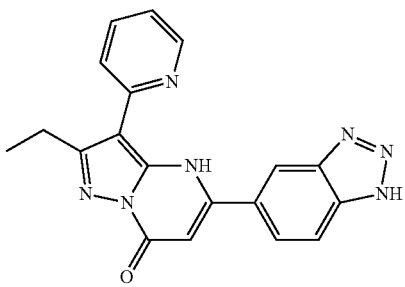 [SMILES: CCc1nn2c(=O)cc(-c3ccc4[nH]nnc4c3)[nH]c2c1-c1ccccn1]

LC/MS (ES, m/z):[M+H]⁺ 358.1
¹H-NMR (300 MHz, DMSO) δ 8.93 (d, J=8.1 Hz, 1H), 8.49 (s, 1H), 8.42 (s, 1H), 7.88 (d, J=1.5 Hz, 1H), 7.73 (m, d, J=8.4 Hz, 2H), 6.95-7.05 (m, 1H), 6.15 (s, 1H), 3.18-3.21 (m, 2H), 1.24-1.29 (t, J=7.5 Hz, 3H)

Example 202

N-(5-(1H-Benzo[d][1,2,3]triazol-5-yl)-7-oxo-3-(pyridin-2-yl)-4,7-dihydropyrazolo[1,5-a]pyrimidin-2-yl)acetamide

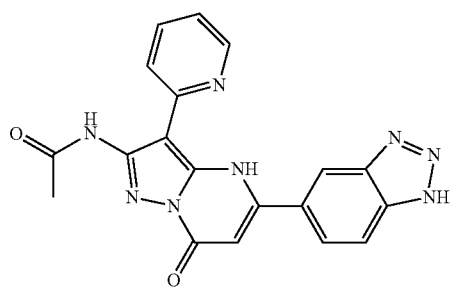 [SMILES: CC(=O)Nc1nn2c(=O)cc(-c3ccc4[nH]nnc4c3)[nH]c2c1-c1ccccn1]

Step 1. N-(5-(1-Acetyl-1H-benzo[d][1,2,3]triazol-5-yl)-7-oxo-3-(pyridin-2-yl)-4,7-dihydropyrazolo[1,5-a]pyrimidin-2-yl)acetamide

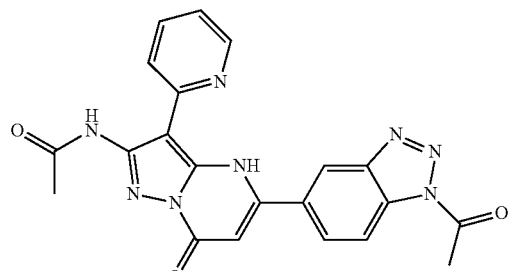

A solution of 2-amino-5-(1H-benzo[d][1,2,3]triazol-5-yl)-3-(pyridin-2-yl)pyrazolo[1,5-a]pyrimidin-7(4H)-one (150 mg, 0.44 mmol) and acetylperoxy acetate (1 mL) in pyridine (6 mL) was stirred for 4 hours at room temperature. Then the resulting mixture was concentrated in vacuo and diluted with water (40 mL). The product was precipitated and collected by filtration to afford N-(5-(1-acetyl-1H-benzo[d][1,2,3]triazol-5-yl)-7-oxo-3-(pyridin-2-yl)-4,7-dihydropyrazolo[1,5-a]pyrimidin-2-yl)acetamide as a yellow solid (120 mg, crude).

LC/MS (ES, m/z):[M+H]⁺ 429.1

Step 2. N-(5-(1H-Benzo[d][1,2,3]triazol-5-yl)-7-oxo-3-(pyridin-2-yl)-4,7-dihydropyrazolo[1,5-a]pyrimidin-2-yl)acetamide

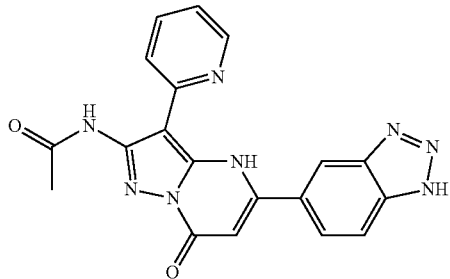 [SMILES: CC(=O)Nc1nn2c(=O)cc(-c3ccc4[nH]nnc4c3)[nH]c2c1-c1ccccn1]

A solution of N-(5-(1-acetyl-1H-benzo[d][1,2,3]triazol-5-yl)-7-oxo-3-(pyridin-2-yl)-4,7-dihydropyrazolo[1,5-a]pyrimidin-2-yl)acetamide (120 mg, crude) and K$_2$CO$_3$ (40 mg, 0.29 mmol) in methanol (20 mL) was for 0.5 hours. The solution was concentrated in vacuo and diluted with water (2 mL). The solid was precipitated and collected by filtration to afford a light yellow solid, which was purified by Flash-Prep-HPLC with the following conditions ((IntelFlash-1): Column, C18 silica gel; mobile phase, CH$_3$CN/H$_2$O increasing to CH$_3$CN/H$_2$O=46% within 17 min; Detector, UV 254 nm) to afford N-(5-(1H-benzo[d][1,2,3]triazol-5-yl)-7-oxo-3-(pyridin-2-yl)-4,7-dihydropyrazolo[1,5-a]pyrimidin-2-yl)acetamide as a yellow solid (23.7 mg, 12% 2 steps).

LC/MS (ES, m/z):[M+H]$^+$387.1

$^1$H-NMR (300 MHz, DMSO) δ 8.93 (d, J=8.1 Hz, 1H), 8.53 (s, 2H), 8.07 (d, J=8.1 Hz, 1H), 7.86-7.92 (t, J=9.0 Hz, 2H), 7.06-7.10 (t, J=5.7 Hz, 2H), 6.31 (s, 1H), 2.51 (s, 3H)

Example 203

N-(5-(1H-Benzo[d][1,2,3]triazol-6-yl)-7-oxo-3-(pyridin-2-yl)-4,7-dihydropyrazolo[1,5-a]pyrimidin-2-yl)propionamide

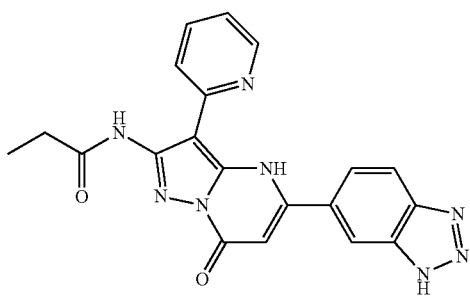 [SMILES: CCC(=O)Nc1nn2c(=O)cc(-c3ccc4nn[nH]c4c3)[nH]c2c1-c1ccccn1]

Step 1. N-(7-oxo-5-(1-propionyl-1H-benzo[d][1,2,3]triazol-5-yl)-3-(pyridin-2-yl)-4,7-dihydropyrazolo[1,5-a]pyrimidin-2-yl)propionamide

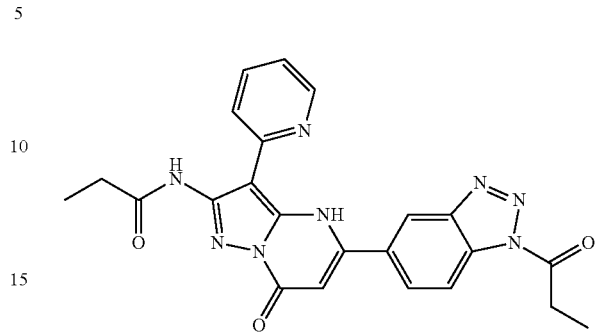

To a solution of 2-amino-5-(1H-benzo[d][1,2,3]triazol-6-yl)-3-(pyridin-2-yl)pyrazolo[1,5-a]pyrimidin-7(4H)-one (200 mg, 0.58 mmol) and triethylamine (352 mg, 3.48 mmol) in THF (50 mL) was added propionyl chloride (214 mg, 2.31 mmol) dropwise over 10 minutes at 0° C. Then the reaction mixture was warmed up to room temperature and stirred overnight. The reaction mixture was concentrated in vacuo to provide N-(7-oxo-5-(1-propionyl-1H-benzo[d][1,2,3]triazol-5-yl)-3-(pyridin-2-yl)-4,7-dihydropyrazolo[1,5-a]pyrimidin-2-yl)propionamide as a yellow solid 250 mg, crude).

LC/MS (ES, m/z): [M+H]$^+$ 457.0

Step 2. N-(5-(1H-Benzo[d][1,2,3]triazol-6-yl)-7-oxo-3-(pyridin-2-yl)-4,7-dihydropyrazolo[1,5-a]pyrimidin-2-yl)propionamide

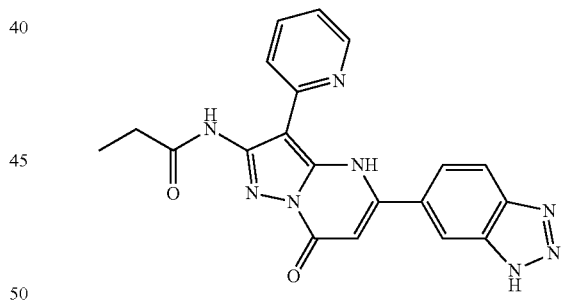

A solution of N-(7-oxo-5-(1-propionyl-1H-benzo[d][1,2,3]triazol-5-yl)-3-(pyridin-2-yl)-4,7-dihydropyrazolo[1,5-a]pyrimidin-2-yl)propionamide (250 mg, crude) and potassium carbonate (75.6 mg, 0.55 mmol) in methanol (60 mL) was stirred overnight at room temperature. The reaction mixture was concentrated in vacuo to provide the crude product, which was purified by Pre-HPLC to provide N-(5-(1H-benzo[d][1,2,3]triazol-6-yl)-7-oxo-3-(pyridin-2-yl)-4,7-dihydropyrazolo[1,5-a]pyrimidin-2-yl)propionamide as a yellow solid (95.3 mg).

LC/MS (ES, m/z): [M+H]$^+$ 401.1

$^1$H-NMR (300 MHz, DMSO) δ 8.94 (d, J=8.4 Hz, 1H), 8.51 (d, J=5.1 Hz, 2H), 8.03 (d, J=7.8 Hz, 1H), 7.83-7.93 (m, 2H), 7.06-7.09 (t, J=6.0 Hz, 1H), 6.30 (s, 1H), 2.65-2.74 (m, 2H), 1.17-1.24 (t, J=7.2 Hz, 3H)

Example 204

N-(5-(1-Ethyl-1H-indazol-5-yl)-7-oxo-3-(pyridin-2-yl)-4,7-dihydropyrazolo[1,5-a]pyrimidin-2-yl)acetamide

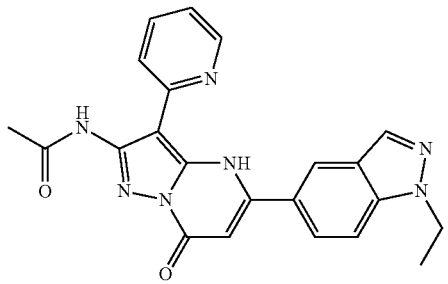 [SMILES: CCn1ncc2cc(-c3cc(=O)n4nc(NC(C)=O)c(-c5ccccn5)c4[nH]3)ccc21]

A solution of 2-amino-5-(1-ethyl-1H-indazol-5-yl)-3-(pyridin-2-yl)pyrazolo[1,5-a]pyrimidin-7(4H)-one (200 mg, 0.53 mmol) and acetic anhydride (109 mg, 1.07 mmol) in pyridine (5 mL) was stirred for 2 hours at room temperature and diluted with water (30 mL). The solids were collected by filtration to afford N-(5-(1-ethyl-1H-indazol-5-yl)-7-oxo-3-(pyridin-2-yl)-4,7-dihydropyrazolo[1,5-a]pyrimidin-2-yl)acetamide as a yellow solid (90.4 mg, 61%).

LC/MS (ES, m/z): [M+H]+ 414.1

1H-NMR (300 MHz, DMSO) δ12.13 (s, 1H), 8.85-8.97 (m, 1H), 8.52-8.59 (m, 2H), 8.17-8.36 (m, 2H), 7.91-7.95 (m, 1H), 7.75-7.85 (m, 1H), 7.16-7.25 (m, 1H), 6.39 (s, 1H), 4.45-4.51 (m, 2H), 2.33 (s, 3H), 1.40-1.45 (t, J=7.2 Hz, 3H)

Example 205

N-(5-(1-Methyl-1H-indazol-5-yl)-7-oxo-3-(pyridin-2-yl)-4,7-dihydropyrazolo[1,5-a]pyrimidin-2-yl)acetamide

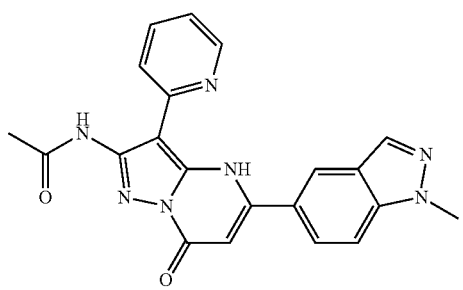 [SMILES: CC(=O)Nc1nn2c(=O)cc(-c3ccc4c(cnn4C)c3)[nH]c2c1-c1ccccn1]

A solution of 2-amino-5-(1-methyl-1H-indazol-5-yl)-3-(pyridin-2-yl)pyrazolo[1,5-a]pyrimidin-7(4H)-one (150 mg, 0.42 mmol) and acetic anhydride (64 mg, 0.63 mol) in pyridine (7 mL) was stirred for 2 hours at room temperature. The product was precipitated by the addition of water, collected by filtration, and dried in an oven under reduced pressure to afford N-(5-(1-methyl-1H-indazol-5-yl)-7-oxo-3-(pyridin-2-yl)-4,7-dihydropyrazolo[1,5-a]pyrimidin-2-yl)acetamide as a red solid (60.1 mg, 36%).

LC/MS (ES, m/z): [M+H]+ 400.1

1H-NMR (300 MHz, CD3COCD3) δ 9.04 (d, J=8.1 Hz, 1H), 8.58 (s, 1H), 8.52 (d, J=4.5 Hz, 1H), 8.31 (d, J=9.0 Hz, 1H), 8.10 (s, 1H), 7.81-7.87 (m, 1H), 7.66 (d, J=8.7 Hz, 1H), 7.05-7.09 (t, J=6.3 Hz, 1H), 6.43 (s, 1H), 4.11 (s, 3H), 2.28 (s, 3H)

Example 206

5-(1H-Benzo[d][1,2,3]triazol-5-yl)-2-ethyl-3-phenylpyrazolo[1,5-a]pyrimidin-7(4H)-one

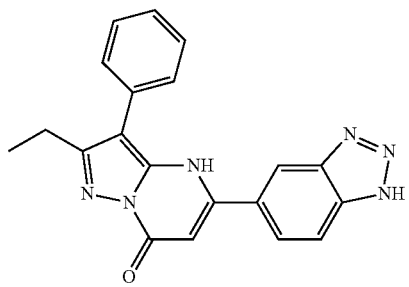

LC/MS (ES, m/z): [M+H]+ 357.1

1H-NMR (300 MHz, CD3OD) δ 8.31 (s, 1H), 7.99 (d, J=9.0 Hz, 1H), 7.81-7.85 (m, 1H), 7.49-7.56 (m, 4H), 7.40-7.44 (m, 1H), 6.15 (s, 1H), 2.79-2.86 (m, 2H), 1.21-1.28 (m, 3H)

Example 207

5-(1H-Benzo[d][1,2,3]triazol-5-yl)-3-benzylpyrazolo[1,5-a]pyrimidin-7(4H)-one

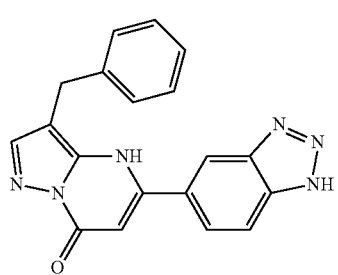 [SMILES: O=c1cc(-c2ccc3[nH]nnc3c2)[nH]c2c(Cc3ccccc3)cnn12]

LC/MS (ES, m/z):[M+H]+ 343.1

1H-NMR (300 MHz, CD3OD) δ 8.36 (s, 1H), 8.03 (d, J=8.7 Hz, 1H), 7.84-7.87 (m, 1H), 7.74 (s, 1H), 7.21-7.36 (m, 5H), 6.14 (s, 1H), 4.12 (d, J=9.6 Hz, 2H)

Example 208

2-Amino-5-(1H-benzo[d][1,2,3]triazol-5-yl)-3-benzylpyrazolo[1,5-a]pyrimidin-7(4H)-one

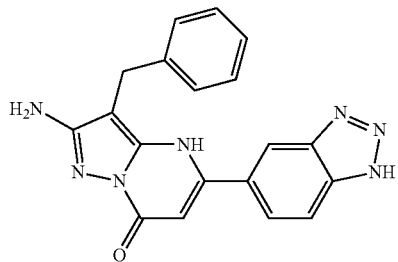 [SMILES: Nc1nn2c(=O)cc(-c3ccc4[nH]nnc4c3)[nH]c2c1Cc1ccccc1]

LC/MS (ES, m/z): [M+H]$^+$ 358.1
$^1$H-NMR (300 MHz, CD$_3$OD) δ 8.21 (s, 1H), 7.88 (d, J=8.7 Hz, 1H), 7.65-7.69 (m, 1H), 7.27-7.36 (m, 4H), 7.18 (d, J=6.9 Hz, 1H), 6.03 (s, 1H), 4.04 (s, 2H)

Example 209

5-(1H-Benzo[d][1,2,3]triazol-5-yl)-3-benzyl-2-hydroxypyrazolo[1,5-a]pyrimidin-7(4H)-one

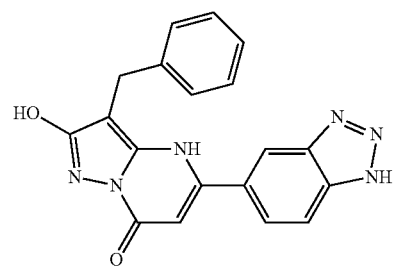 [SMILES: O=c1cc(-c2ccc3[nH]nnc3c2)[nH]c2c(Cc3ccccc3)c(O)nn12]

LC/MS (ES, m/z): [M+H]$^+$ 359.1
$^1$H-NMR (300 MHz, DMSO) δ 16.04 (s, 1H), 12.07 (s, 1H), 11.00 (s, 1H), 8.51 (s, 1H), 7.70-8.54 (m, 4H), 7.28 (d, J=4.2 Hz, 3H), 7.15-7.20 (m, 1H), 5.97 (d, J=1.5 Hz, 3H), 3.93 (s, 2H)

Example 210

5-(Benzo[d][1,3]dioxol-5-yl)-2-methyl-3-(pyridin-2-ylmethyl)pyrazolo[1,5-a]pyrimidin-7(4H)-one

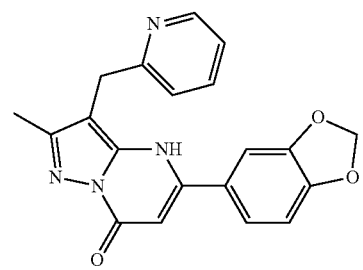 [SMILES: Cc1nn2c(=O)cc(-c3ccc4c(c3)OCO4)[nH]c2c1Cc1ccccn1]

LC/MS (ES, m/z): [M+H]$^+$ 361.0
$^1$H-NMR (300 MHz, DMSO) δ 12.03 (s, 1H), 8.48-8.50 (t, J=1.5 Hz, 1H), 7.68-7.71 (m, 1H), 7.40 (d, J=1.5 Hz, 1H), 7.33-7.36 (m, 1H), 7.33, 7.20-7.24 (m, 2H), 7.12 (d, J=8.1 Hz, 1H), 6.15 (s, 2H), 5.87 (s, 1H), 4.20 (s, 2H), 2.17 (s, 3H)

Example 211

5-(Benzo[d][1,3]dioxol-5-yl)-3-(pyridin-2-ylmethyl)-pyrazolo[1,5-a]pyrimidin-7(4H)-one

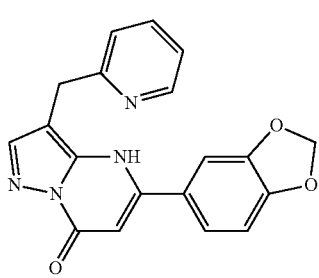 [SMILES: O=c1cc(-c2ccc3c(c2)OCO3)[nH]c2c(Cc3ccccn3)cnn12]

LC/MS (ES, m/z): [M+H]$^+$ 347.0
$^1$H-NMR (300 MHz, DMSO) δ 8.50 (d, J=3.9 Hz, 1H), 7.70-7.76 (m, 2H), 7.42 (d, J=1.5 Hz, 1H), 7.35-7.39 (m, 1H), 7.21-7.30 (m, 2H), 7.13-7.15 (t, J=8.1 Hz, 1H), 6.16 (s, 2H), 5.94 (s, 1H), 4.22 (s, 2H)

Example 212

5-(1H-Benzo[d][1,2,3]triazol-5-yl)-2-methyl-3-phenylpyrazolo[1,5-a]pyrimidin-7(4H)-one

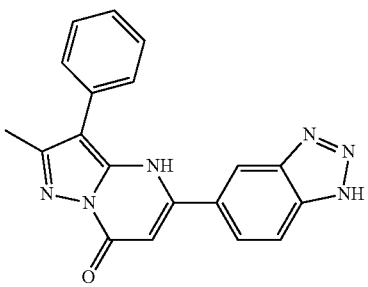

LC/MS (ES, m/z): [M+H]$^+$ 343.1
$^1$H-NMR (300 MHz, CDCl$_3$) δ$^1$H NMR (300 MHz, CDCl$_3$) δ 8.35 (s, 1H), 7.98 (d, J=7.5 Hz, 2H), 7.82-7.86 (m, 1H), 7.68 (d, J=8.7 Hz, 1H), 7.38-7.44 (t, J=7.8 Hz, 2H), 7.10-7.15 (t, J=7.5 Hz, 1H), 6.06 (s, 1H), 2.49-2.52 (m, 3H)

Example 213

5-(1H-Benzo[d][1,2,3]triazol-5-yl)-3-(pyridin-3-yl)pyrazolo[1,5-a]pyrimidin-7(4H)-one

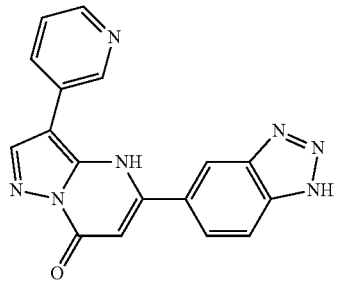 [SMILES: O=c1cc(-c2ccc3[nH]nnc3c2)[nH]c2c(-c3cccnc3)cnn12]

LC/MS (ES, m/z):[M+H]⁺ 330.1
¹H-NMR (300 MHz, DMSO) δ 9.48 (d, J=2.1 Hz, 1H), 8.55-8.61 (m, 2H), 8.31 (s, 1H), 8.20-8.28 (m, 2H), 7.94 (d, J=8.7 Hz, 1H), 7.35-7.39 (m, 1H), 6.18 (s, 1H)

Example 214

5-(1H-Benzo[d][1,2,3]triazol-5-yl)-7-oxo-N-propyl-4,7-dihydropyrazolo[1,5-a]pyrimidine-3-carboxamide

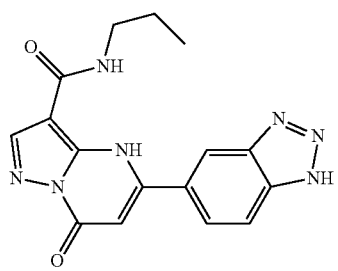 [SMILES: CCCNC(=O)c1cnn2c(=O)cc(-c3ccc4[nH]nnc4c3)[nH]c12]

LC/MS (ES, m/z): [M+H]⁺. 338.1
¹H-NMR (300 MHz, DMSO) δ 11.51 (s, 1H), 8.42-8.48 (m, 3H), 8.07 (s, 1H), 7.85-7.87 (m, 1H), 6.38 (s, 1H), 3.22-3.29 (m, 2H), 1.53-1.60 (m, 2H), 0.90-0.95 (t, J=7.5 Hz, 3H)

Example 215

5-(1H-Benzo[d][1,2,3]triazol-5-yl)-2-hydroxy-3-phenylpyrazolo[1,5-a]pyrimidin-7(4H)-one

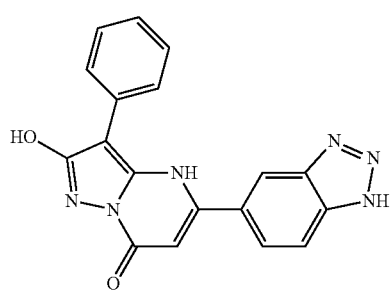

LC/MS. (ES, m/z): [M+H]⁺. 345.0
¹H-NMR (300 MHz, DMSO) δ 12.07 (s, 1H), 11.43 (s, 1H), 8.30-8.60 (m, 1H), 7.90-8.20 (m, 1H), 7.80-7.86 (m, 1H), 7.65-7.68 (m, 2H), 7.41-7.47 (t, J=7.8 Hz, 2H), 7.25-7.30 (t, J=7.5 Hz, 1H), 6.05 (s, 1H)

Example 216

5-(1H-Benzo[d][1,2,3]triazol-5-yl)-3-(4-chlorophenyl)-2-methylpyrazolo[1,5-a]pyrimidin-7(4H)-one

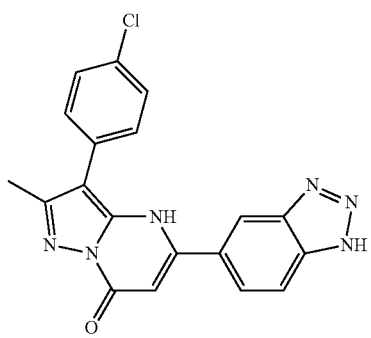 [SMILES: Cc1nn2c(=O)cc(-c3ccc4[nH]nnc4c3)[nH]c2c1-c1ccc(Cl)cc1]

LC/MS (ES, m/z): [M+H]⁺ 377.0
¹H-NMR (300 MHz, DMSO) δ 8.39 (s, 1H), 8.04 (d, J=8.4 Hz, 2H), 7.90 (d, J=1.5 Hz, 1H), 7.73 (d, J=8.4 Hz, 1H), 7.43-7.46 (m, 2H), 6.11 (s, 1H), 2.50 (s, 3H)

Example 217

2-Amino-5-(1H-benzo[d][1,2,3]triazol-5-yl)-3-(4-chlorophenyl)pyrazolo[1,5-a]pyrimidin-7(4H)-one

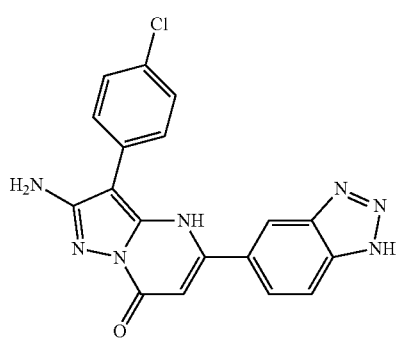 [SMILES: Nc1nn2c(=O)cc(-c3ccc4[nH]nnc4c3)[nH]c2c1-c1ccc(Cl)cc1]

LC/MS (ES, m/z): [M+H]⁺ 378.0
¹H-NMR (300 MHz, CD₃OD): δ 8.46 (s, 1H), 7.96-8.00 (m, 3H), 7.86 (d, J=8.7 Hz, 1H), 7.41 (d, J=8.4 Hz, 2H), 6.29 (s, 1H)

Example 218

5-(1H-Benzo[d][1,2,3]triazol-5-yl)-3-(4-chlorophenyl)pyrazolo[1,5-a]pyrimidin-7(4H)-one

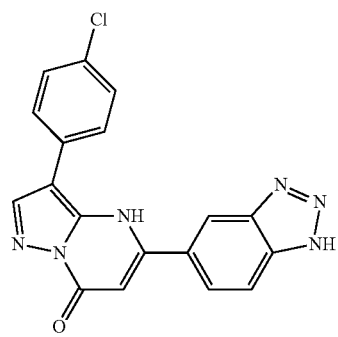 [SMILES: O=c1cc(-c2ccc3[nH]nnc3c2)[nH]c2c(-c3ccc(Cl)cc3)cnn12]

LC/MS (ES, m/z): [M+H]⁺. 363.0

¹H-NMR (300 MHz, DMSO) δ 8.38 (s, 1H), 8.30-8.33 (m, 2H), 8.18 (s, 1H), 7.82 (d, J=8.7 Hz, 1H), 7.69 (d, J=8.7 Hz, 1H), 7.37-7.40 (t, J=6.9 Hz, 2H), 6.09 (s, 1H)

Example 219

5-(1H-Indazol-5-yl)-2-methyl-3-(pyridin-2-yl)pyrazolo[1,5-a]pyrimidin-7(4H)-one

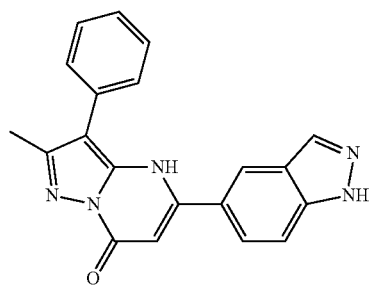

Step 1. 5-(1-Acetyl-1H-indazol-5-yl)-2-methyl-3-(pyridin-2-yl)pyrazolo[1,5-a]pyrimidin-7(4H)-one

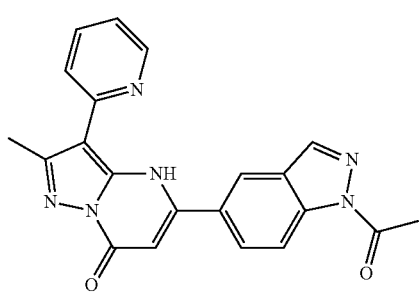 [SMILES: CC(=O)n1ncc2cc(-c3cc(=O)n4nc(C)c(-c5ccccn5)c4[nH]3)ccc21]

LC/MS (ES, m/z): [M+H]⁺ 385.1

Step 2. 5-(1H-Indazol-5-yl)-2-methyl-3-(pyridin-2-yl)pyrazolo[1,5-a]pyrimidin-7(4H)-one

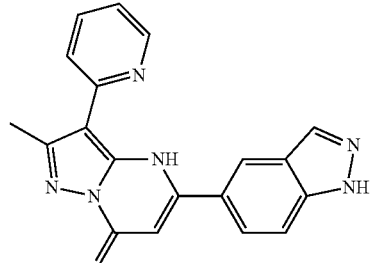

LC/MS (ES, m/z):[M+H]⁺ 343.0

¹H-NMR (300 MHz, DMSO) δ 8.87-8.90 (d, J=8.1 Hz, 1H), 8.45-8.50 (m, 2H), 8.17-8.20 (m, 2H), 7.72-7.78 (m, 1H), 7.59 (d, J=8.7 Hz, 1H), 6.96-7.00 (m, 1H), 6.08 (s, 1H), 3.40 (s, 3H)

Example 220

3-(4-Chlorophenyl)-5-(1H-indazol-5-yl)-2-methylpyrazolo[1,5-a]pyrimidin-7(4H)-one

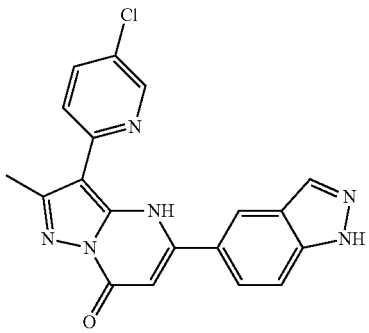 [SMILES: Cc1nn2c(=O)cc(-c3ccc4[nH]ncc4c3)[nH]c2c1-c1ccc(Cl)cn1]

LC/MS (ES, m/z): [M+H]+ 376.0

¹H-NMR (300 MHz, DMSO+H₂O) δ 8.42 (s, 1H), 8.12-8.15 (t, J=1.5 Hz, 2H), 8.01 (d, J=8.4 Hz, 2H), 7.56 (d, J=9.0 Hz, 1H), 7.42-7.45 (m, 2H), 6.08 (s, 1H), 2.48 (s, 3H)

Example 221

2-Amino-3-(4-chlorophenyl)-5-(1H-indazol-5-yl)pyrazolo[1,5-a]pyrimidin-7(4H)-one

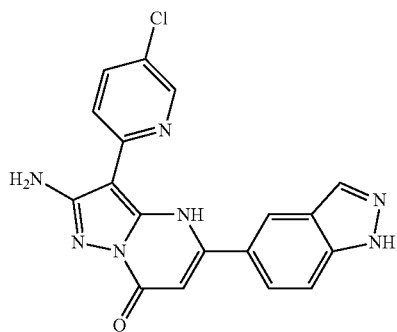 [SMILES: Nc1nn2c(=O)cc(-c3ccc4[nH]ncc4c3)[nH]c2c1-c1ccc(Cl)cn1]

LC/MS (ES, m/z): [M+H]+ 377.0

¹H-NMR (300 MHz, CD₃OD): δ 8.41 (s, 1H), 8.10-8.16 (m, 2H), 7.94 (d, J=8.7 Hz, 2H), 7.60 (d, J=8.7 Hz, 1H), 7.40 (d, J=8.4 Hz, 2H), 6.27 (s, 1H)

Example 222

3-(4-Chlorophenyl)-2-hydroxy-5-(1H-indazol-5-yl)pyrazolo[1,5-a]pyrimidin-7(4H)-one

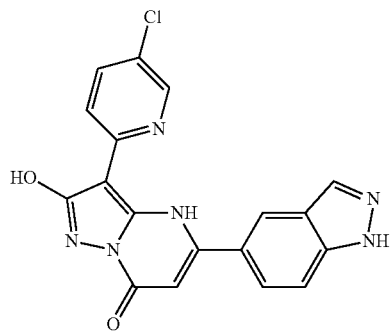 [SMILES: O=c1cc(-c2ccc3[nH]ncc3c2)[nH]c2c(-c3ccc(Cl)cn3)c(O)nn12]

LC/MS (ES, m/z): [M+H]+ 378.0

¹H-NMR (300 MHz, DMSO) δ 8.64 (d, J=8.7 Hz, 2H), 8.46 (s, 1H), 8.18 (s, 1H), 8.11 (d, J=9.0 Hz, 1H), 7.59-7.67 (m, 3H), 7.26-7.32 (t, J=8.7 Hz, 4H), 6.08 (s, 1H)

Example 223

2-Amino-5-(1H-benzo[d][1,2,3]triazol-5-yl)-7-oxo-N-propyl-4,7-dihydropyrazolo[1,5-a]pyrimidine-3-carboxamide

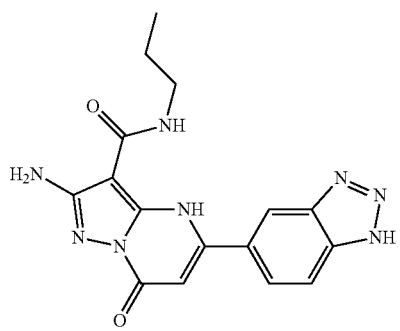 [SMILES: CCCNC(=O)c1c(N)nn2c(=O)cc(-c3ccc4[nH]nnc4c3)[nH]c12]

LC/MS (ES, m/z): [M+H]+353.0

¹H-NMR (300 MHz, CD₃OD): δ 8.46 (s, 1H), 7.82-7.91 (m, 2H), 6.40 (s, 1H), 3.43-3.48 (t, J=6.6 Hz, 2H), 1.73-1.80 (m, 2H), 1.10-1.15 (t, J=7.5 Hz, 3H)

Example 224

2-Amino-5-(3-methyl-1H-indazol-5-yl)-7-oxo-N-propyl-4,7-dihydropyrazolo[1,5-a]pyrimidine-3-carboxamide

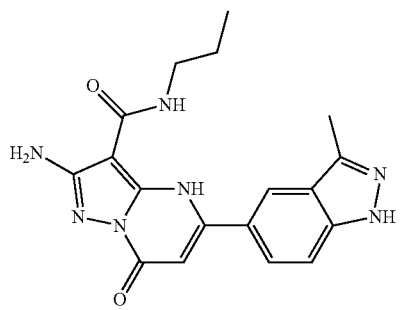 [SMILES: CCCNC(=O)c1c(N)nn2c(=O)cc(-c3ccc4[nH]nc(C)c4c3)[nH]c12]

Step 1. 5-(1-Acetyl-3-methyl-1H-indazol-5-yl)-2-amino-7-oxo-N-propyl-4,7-dihydropyrazolo[1,5-a]pyrimidine-3-carboxamide

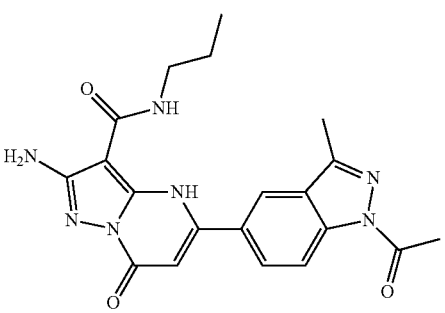 [SMILES: CCCNC(=O)c1c(N)nn2c(=O)cc(-c3ccc4c(c3)c(C)nn4C(C)=O)[nH]c12]

LC/MS (ES, m/z): [M+H]+ 408.0

Step 2. 2-Amino-5-(3-methyl-1H-indazol-5-yl)-7-oxo-N-propyl-4,7-dihydropyrazolo[1,5-a]pyrimidine-3-carboxamide

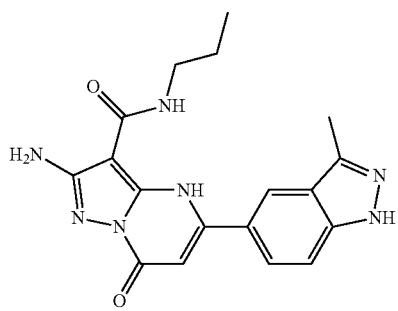 [SMILES: CCCNC(=O)c1c(N)nn2c(=O)cc(-c3ccc4[nH]nc(C)c4c3)[nH]c12]

LC/MS (ES, m/z): [M+H]+ 366.1
1H-NMR (300 MHz, DMSO) δ 8.51 (s, 1H), 8.37 (s, 1H), 7.98 (d, J=9.0 Hz, 1H), 7.48 (d, J=8.7 Hz, 1H), 6.20 (s, 1H), 2.54 (s, 3H), 1.60-1.67 (m, 2H), 1.02-1.07 (t, J=7.35 Hz, 3H)

Example 225

2-Amino-5-(4-chlorophenyl)-7-oxo-N-propyl-4,7-dihydropyrazolo[1,5-a]pyrimidine-3-carboxamide

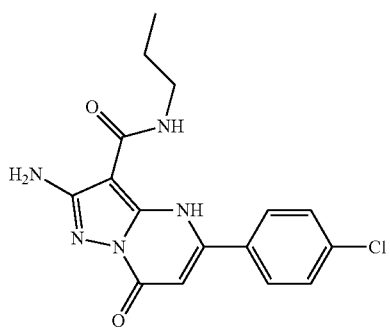 [SMILES: CCCNC(=O)c1c(N)nn2c(=O)cc(-c3ccc(Cl)cc3)[nH]c12]

LC/MS (ES, m/z): [M+H]+ 346.0
1H-NMR (300 MHz, CD3OD): δ 7.97-8.00 (m, 2H), 7.45-7.48 (m, 2H), 6.28 (s, 1H), 3.40-3.44 (t, J=6.9 Hz, 2H), 1.67-1.74 (m, 2H), 1.06-1.11 (t, J=7.5 Hz, 3H)

Example 226

2-Amino-5-(2,3-dihydrobenzo[b][1,4]dioxin-6-yl)-7-oxo-N-propyl-4,7-dihydropyrazolo[1,5-a]pyrimidine-3-carboxamide

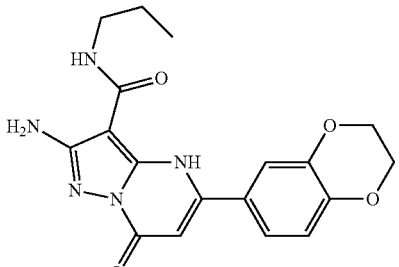

LC/MS (ES, m/z): [M+H]+ 370.1
1H-NMR (300 MHz, CD3OD): δ 7.52 (d, J=2.1 Hz, 1H), 7.46-7.49 (m, 1H), 6.89 (d, J=8.7 Hz, 1H), 6.21 (s, 1H), 4.31 (s, 4H), 3.40-3.44 (t, J=6.6 Hz, 2H), 1.68-1.75 (m, 2H), 1.07-1.12 (t, J=7.5 Hz, 3H)

Example 227

5-(Benzo[d][1,3]dioxol-5-yl)-2-hydroxy-7-oxo-N-propyl-4,7-dihydropyrazolo[1,5-a]pyrimidine-3-carboxamide

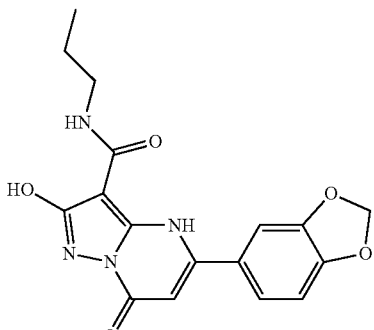

LC/MS (ES, m/z):[M+H]+ 357.0
1H-NMR (300 MHz, DMSO) δ 1H NMR (300 MHz, DMSO) δ 7.40 (d, J=1.8 Hz, 1H), 7.30 (d, J=2.1 Hz, 1H), 7.27 (d, J=1.8 Hz, 1H), 7.10 (d, J=8.4 Hz, 1H), 6.21 (s, 1H), 6.16 (s, 2H), 3.22-3.29 (m, 2H), 1.48-1.56 (m, 2H), 0.86-0.91 (t, J=7.5 Hz, 3H)

Example 228

5-(1H-Benzo[d][1,2,3]triazol-5-yl)-2-hydroxy-7-oxo-N-propyl-4,7-dihydropyrazolo[1,5-a]pyrimidine-3-carboxamide

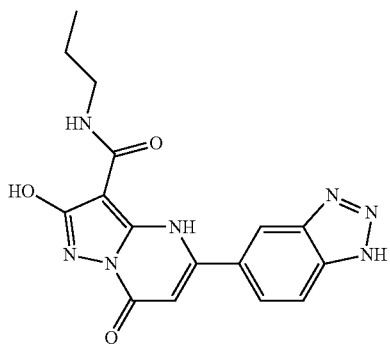 [SMILES: CCCNC(=O)c1c(O)nn2c(=O)cc(-c3ccc4[nH]nnc4c3)[nH]c12]

LC/MS (ES, m/z):[M+H]+ 354.1

1H-NMR (300 MHz, DMSO) δ 8.45 (s, 1H), 8.00 (d, J=8.7 Hz, 1H), 7.86 (d, J=8.7 Hz, 1H), 6.20 (s, 1H), 3.31-3.35 (m, 2H), 1.54-1.63 (m, 2H), 0.97-1.02 (t, J=7.2 Hz, 3H)

Example 229

5-(4-Methylbenzo[d][1,3]dioxol-5-yl)-3-(pyridin-2-yl)pyrazolo[1,5-a]pyrimidin-7(4H)-one

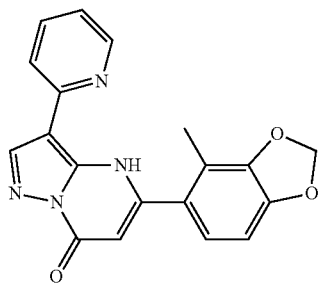 [SMILES: Cc1c(-c2cc(=O)n3ncc(-c4ccccn4)c3[nH]2)ccc2c1OCO2]

LC/MS (ES, m/z): [M+H]+ 347.0

1H-NMR (300 MHz, DMSO): δ 8.64 (s, 1H), 8.57 (d, J=4.8 Hz, 1H), 7.84-7.88 (m, 1H), 7.20-7.24 (m, 1H), 7.11 (d, J=8.1 Hz, 1H), 6.95 (d, J=8.1 Hz, 1H), 6.14 (s, 2H), 5.89 (s, 1H), 2.29 (s, 3H)

Example 230

2-Amino-5-(4-methylbenzo[d][1,3]dioxol-5-yl)-3-(pyridin-2-yl)pyrazolo[1,5-a]pyrimidin-7(4H)-one

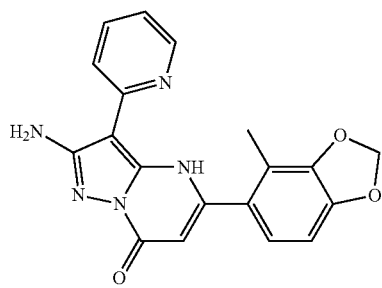 [SMILES: Cc1c(-c2cc(=O)n3nc(N)c(-c4ccccn4)c3[nH]2)ccc2c1OCO2]

LC/MS (ES, m/z): [M+H]+ 362.0

1H-NMR (300 MHz, DMSO): δ 8.55 (d, J=4.2 Hz, 1H), 7.80 (d, J=7.2 Hz, 1H), 7.71 (d, J=7.8 Hz, 1H), 7.06-7.17 (m, 2H), 6.92 (d, J=7.8 Hz, 1H), 6.12 (s, 2H), 5.73 (s, 1H), 2.27 (s, 3H)

Example 231

2-Hydroxy-5-(4-methylbenzo[d][1,3]dioxol-5-yl)-3-(pyridin-2-yl)pyrazolo[1,5-a]pyrimidin-7(4H)-one

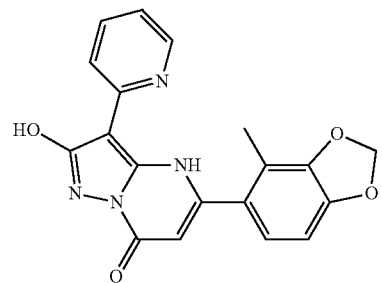 [SMILES: Cc1c(-c2cc(=O)n3nc(O)c(-c4ccccn4)c3[nH]2)ccc2c1OCO2]

LC/MS (ES, m/z): [M+H]+ 363.0

1H-NMR (300 MHz, DMSO): δ 8.48 (d, J=5.1 Hz, 1H), 8.25-8.26 (m, 1H), 8.04 (s, 1H), 7.18-7.22 (t, J=6.3 Hz, 1H), 7.04 (d, J=8.1 Hz, 1H), 6.88 (d, J=8.4 Hz, 1H), 6.10 (s, 2H), 5.86 (s, 1H), 2.29 (s, 3H)

Example 232

2-Methyl-5-(4-methylbenzo[d][1,3]dioxol-5-yl)-3-(pyridin-2-yl)pyrazolo[1,5-a]pyrimidin-7(4H)-one

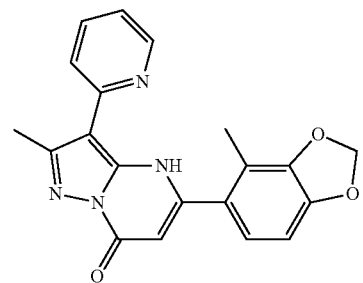 [SMILES: Cc1nn2c(=O)cc(-c3ccc4c(c3C)OCO4)[nH]c2c1-c1ccccn1]

LC/MS (ES, m/z): [M+H]+ 361.0

$^1$H-NMR (300 MHz, DMSO): δ 11.87 (s, 1H), 8.61 (d, J=4.5 Hz, 1H), 7.88-7.92 (t, J=6.9 Hz, 1H), 7.67 (d, J=8.1 Hz, 1H), 7.22-7.26 (m, 1H), 7.09 (d, J=8.1 Hz, 1H), 6.94 (d, J=7.8 Hz, 1H), 6.14 (s, 2H), 5.84 (s, 1H), 2.62 (s, 3H), 2.28 (s, 3H)

Example 233

5-(4-Methoxybenzo[d][1,3]dioxol-5-yl)-3-(pyridin-2-yl)pyrazolo[1,5-a]pyrimidin-7(4H)-one

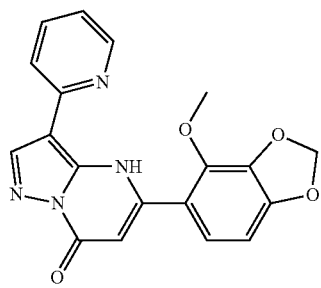 [SMILES: COc1c(-c2cc(=O)n3ncc(-c4ccccn4)c3[nH]2)ccc2c1OCO2]

LC/MS (ES, m/z): [M+H]+ 363.0

$^1$H-NMR (300 MHz, CD$_3$OD): δ 8.45-8.51 (m, 3H), 7.77-7.83 (m, 1H), 7.39 (d, J=7.2 Hz, 1H), 7.11-7.16 (m, 1H), 6.70 (d, J=8.1 Hz, 1H), 6.28 (s, 1H), 6.06 (s, 2H), 4.03 (s, 3H)

Example 234

2-Amino-5-(4-methoxybenzo[d][1,3]dioxol-5-yl)-3-(pyridin-2-yl)pyrazolo[1,5-a]pyrimidin-7(4H)-one

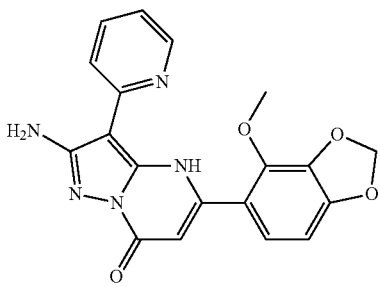 [SMILES: COc1c(-c2cc(=O)n3nc(N)c(-c4ccccn4)c3[nH]2)ccc2c1OCO2]

LC/MS (ES, m/z): [M+H]+ 378.0

$^1$H-NMR (300 MHz, CD$_3$OD): δ 8.54 (d, J=8.4 Hz, 1H), 8.44-8.45 (t, J=3.9 Hz, 1H), 7.65-7.71 (m, 1H), 7.38 (d, J=8.4 Hz, 1H), 6.93-6.97 (m, 1H), 6.68 (d, J=8.4 Hz, 1H), 6.21 (s, 1H), 6.03 (s, 2H), 3.98 (s, 3H)

Example 235

2-Hydroxy-5-(4-methoxybenzo[d][1,3]dioxol-5-yl)-3-(pyridin-2-yl)pyrazolo[1,5-a]pyrimidin-7(4H)-one

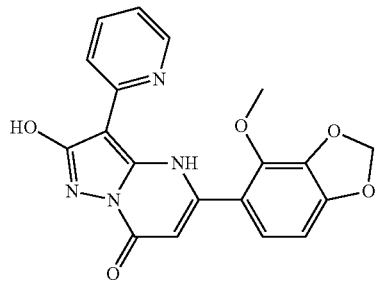 [SMILES: COc1c(-c2cc(=O)n3nc(O)c(-c4ccccn4)c3[nH]2)ccc2c1OCO2]

LC/MS (ES, m/z): [M+H]+ 379.0

$^1$H-NMR (300 MHz, CD$_3$OD): δ 8.45-8.50 (m, 1H), 8.41 (d, J=8.1 Hz, 1H), 7.77-7.83 (m, 1H), 7.39 (d, J=8.4 Hz, 1H), 7.11-7.16 (m, 1H), 6.70 (d, J=8.4 Hz, 1H), 6.10 (s, 1H), 6.06 (s, 2H), 4.03 (s, 3H)

Example 236

5-(6-Methyl-1H-benzo[d][1,2,3]triazol-5-yl)-3-(pyridin-2-yl)pyrazolo[1,5-a]pyrimidin-7(4H)-one

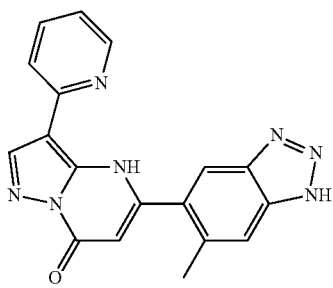 [SMILES: Cc1cc2[nH]nnc2cc1-c1cc(=O)n2ncc(-c3ccccn3)c2[nH]1]

LC/MS (ES, m/z): [M+H]+ 344.0

¹H-NMR (300 MHz, DMSO): δ 8.50 (d, J=8.1 Hz, 1H), 8.40 (d, J=3.9 Hz, 1H), 8.34 (s, 1H), 7.84 (s, 1H), 7.74 (s, 1H), 7.60-7.66 (m, 1H), 6.94-6.98 (m, 1H), 5.63 (s, 1H), 2.53 (s, 3H)

Example 237

5-(4-Methoxybenzo[d][1,3]dioxol-5-yl)-2-methyl-3-(pyridin-2-yl)pyrazolo[1,5-a]pyrimidin-7(4H)-one

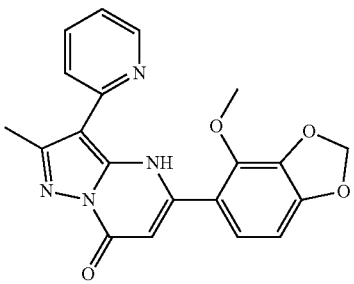 [SMILES: COc1c(-c2cc(=O)n3nc(C)c(-c4ccccn4)c3[nH]2)ccc2c1OCO2]

LC/MS (ES, m/z): [M+H]+ 377.0

¹H-NMR (300 MHz, CD₃OD): δ 8.58 (d, J=4.2 Hz, 1H), 8.04 (d, J=8.1 Hz, 1H), 7.80-7.86 (m, 1H), 7.30 (d, J=8.1 Hz, 1H), 7.16-7.21 (m, 1H), 6.68 (d, J=8.1 Hz, 1H), 6.17 (s, 1H), 6.05 (s, 2H), 4.04 (s, 3H), 2.67 (s, 1H)

Example 238

2-Amino-5-(6-methyl-1H-benzo[d][1,2,3]triazol-5-yl)-3-(pyridin-2-yl)pyrazolo[1,5-a]pyrimidin-7(4H)-one

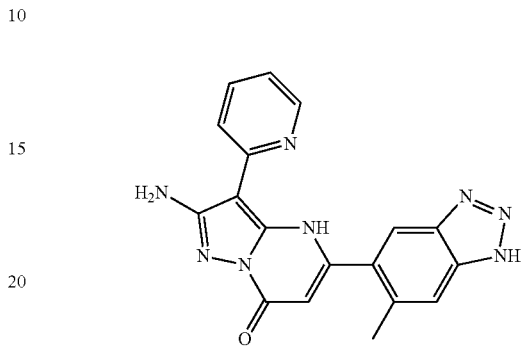

LC/MS (ES, m/z): [M+H]+ 359.1

¹H-NMR (300 MHz, DMSO) δ ¹H-NMR (300 MHz, DMSO) δ 8.57 (d, J=8.1 Hz, 1H), 8.38 (d, J=4.2 Hz, 1H), 7.85 (s, 1H), 7.75 (s, 1H), 7.57-7.62 (t, J=7.5 Hz, 1H), 6.86 (d, J=5.1 Hz, 1H), 5.66 (s, 1H), 2.55 (s, 3H)

Example 239

2-Hydroxy-5-(6-methyl-1H-benzo[d][1,2,3]triazol-5-yl)-3-(pyridin-2-yl)pyrazolo[1,5-a]pyrimidin-7(4H)-one

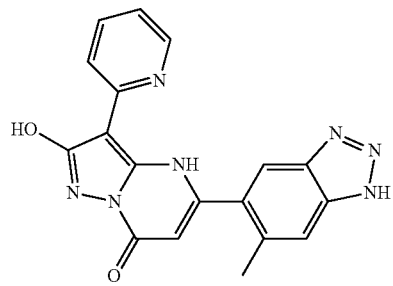 [SMILES: Cc1cc2[nH]nnc2cc1-c1cc(=O)n2nc(O)c(-c3ccccn3)c2[nH]1]

LC/MS (ES, m/z): [M+H]+ 360.0

¹H-NMR (300 MHz, DMSO) δ 8.35 (d, J=4.8 Hz, 1H), 8.25 (d, J=8.1 Hz, 1H), 7.82 (s, 1H), 7.69-7.74 (t, J=6.9 Hz, 2H), 6.94-6.98 (t, J=5.4 Hz, 1H), 5.62 (s, 1H), 2.53 (s, 3H)

Example 240

2-Amino-5-(4-methyl-1H-benzo[d][1,2,3]triazol-5-yl)-3-(pyridin-2-yl)pyrazolo[1,5-a]pyrimidin-7(4H)-one

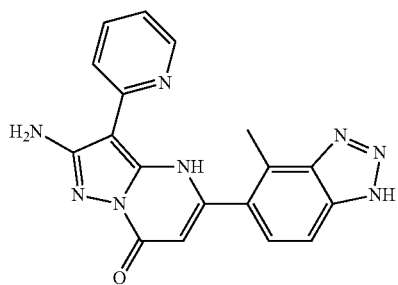 [SMILES: Cc1c(-c2cc(=O)n3nc(N)c(-c4ccccn4)c3[nH]2)ccc2[nH]nnc12]

LC/MS (ES, m/z): [M+H]+ 359.0

$^1$H-NMR (300 MHz, DMSO) δ 8.45 (d, J=4.5 Hz, 1H), 8.15-8.35 (m, 1H), 7.79 (s, 1H), 7.68-7.73 (m, 1H), 7.56 (d, J=8.1 Hz, 1H), 7.01 (s, 1H), 5.75 (s, 1H), 2.76 (s, 3H)

Example 241

2-Hydroxy-5-(4-methyl-1H-benzo[d][1,2,3]triazol-5-yl)-3-(pyridin-2-yl)pyrazolo[1,5-a]pyrimidin-7(4H)-one

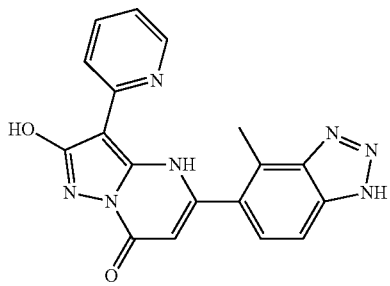 [SMILES: Cc1c(-c2cc(=O)n3nc(O)c(-c4ccccn4)c3[nH]2)ccc2[nH]nnc12]

LC/MS (ES, m/z): [M+H]+ 360.0

$^1$H-NMR (300 MHz, DMSO) δ 8.36 (d, J=4.5 Hz, 1H), 8.27 (d, J=8.1 Hz, 1H), 7.71-7.77 (m, 2H), 7.48 (d, J=8.4 Hz, 1H), 6.96-7.01 (m, 1H), 5.72 (s, 1H), 2.74 (s, 3H)

Example 242

2-Methyl-5-(4-methyl-1H-benzo[d][1,2,3]triazol-5-yl)-3-(pyridin-2-yl)pyrazolo[1,5-a]pyrimidin-7(4H)-one

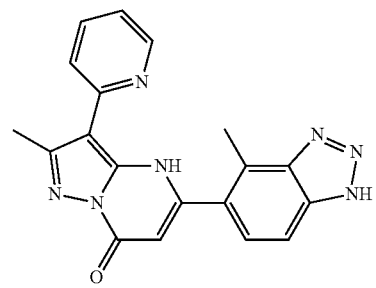 [SMILES: Cc1nn2c(=O)cc(-c3ccc4[nH]nnc4c3C)[nH]c2c1-c1ccccn1]

LC/MS (ES, m/z): [M+H]+ 358.1

$^1$H-NMR (300 MHz, DMSO) δ 8.59 (d, J=8.1 Hz, 1H), 8.45 (d, J=3.6 Hz, 1H), 7.71 (d, J=8.7 Hz, 1H), 7.59-7.65 (m, 1H), 7.49 (d, J=8.4 Hz, 1H), 6.94-6.97 (m, 1H), 5.65 (s, 1H), 2.73 (s, 3H), 2.65 (s, 3H)

Example 243

2-Amino-5-(6-methoxy-1H-benzo[d][1,2,3]triazol-5-yl)-3-(pyridin-2-yl)pyrazolo[1,5-a]pyrimidin-7(4H)-one

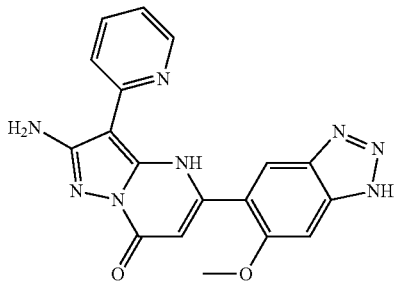 [SMILES: COc1cc2[nH]nnc2cc1-c1cc(=O)n2nc(N)c(-c3ccccn3)c2[nH]1]

LC/MS (ES, m/z): [M+H]+ 375.0

$^1$H-NMR (300 MHz, DMSO) δ 8.65 (d, J=8.1 Hz, 1H), 8.37-8.40 (t, J=7.2 Hz, 1H), 8.09 (d, J=3.6 Hz, 1H), 7.58-7.64 (m, 1H), 7.29 (s, 1H), 6.83-6.87 (t, J=6.0 Hz, 1H), 5.89 (s, 1H), 3.87 (s, 3H)

Example 244

2-Hydroxy-5-(6-methoxy-1H-benzo[d][1,2,3]triazol-5-yl)-3-(pyridin-2-yl)pyrazolo[1,5-a]pyrimidin-7(4H)-one

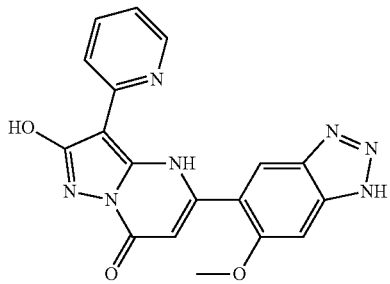 [SMILES: COc1cc2[nH]nnc2cc1-c1cc(=O)n2nc(O)c(-c3ccccn3)c2[nH]1]

LC/MS (ES, m/z): [M+H]⁺ 376.0

¹H-NMR (300 MHz, DMSO) δ 8.31-8.38 (m, 2H), 8.20 (s, 1H), 7.74-7.79 (m, 1H), 7.34 (s, 1H), 6.95-7.01 (m, 1H), 5.98 (s, 1H), 3.90 (s, 3H)

Example 245

5-(4-Methoxy-1H-benzo[d][1,2,3]triazol-5-yl)-3-(pyridin-2-yl)pyrazolo[1,5-a]pyrimidin-7(4H)-one

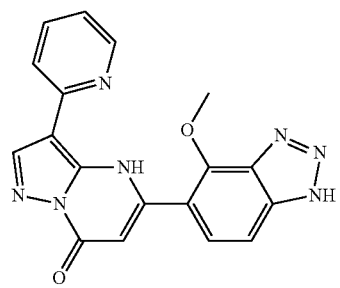 [SMILES: COc1c(-c2cc(=O)n3ncc(-c4ccccn4)c3[nH]2)ccc2[nH]nnc12]

LC/MS (ES, m/z): [M+H]⁺ 360.0

¹H-NMR (300 MHz, DMSO) δ 8.41-8.50 (m, 3H), 7.70-7.78 (m, 2H), 7.46 (d, J=8.7 Hz, 1H), 7.03-7.07 (t, J=5.7 Hz, 1H), 6.13 (s, 1H), 4.41 (s, 3H)

Example 246

2-Amino-5-(4-methoxy-1H-benzo[d][1,2,3]triazol-5-yl)-3-(pyridin-2-yl)pyrazolo[1,5-a]pyrimidin-7(4H)-one

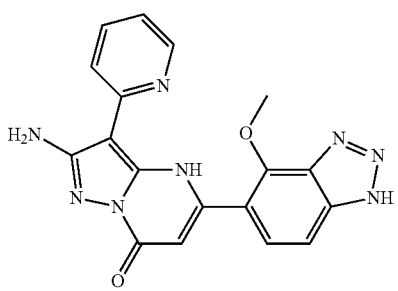 [SMILES: COc1c(-c2cc(=O)n3nc(N)c(-c4ccccn4)c3[nH]2)ccc2[nH]nnc12]

LC/MS (ES, m/z): [M+H]⁺ 375.1

¹H-NMR (300 MHz, DMSO): δ8.68 (s, 1H), 7.79-7.86 (m, 3H), 7.53 (s, 1H), 7.20-7.22 (m, 1H), 6.15 (s, 1H), 4.72 (s, 3H)

Example 247

2-Hydroxy-5-(4-methoxy-1H-benzo[d][1,2,3]triazol-5-yl)-3-(pyridin-2-yl)pyrazolo[1,5-a]pyrimidin-7(4H)-one

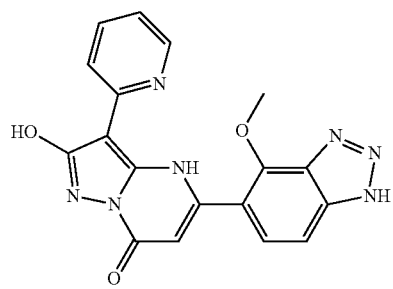 [SMILES: COc1c(-c2cc(=O)n3nc(O)c(-c4ccccn4)c3[nH]2)ccc2[nH]nnc12]

LC/MS (ES, m/z): [M+H]⁺ 376.1

¹H-NMR (300 MHz, DMSO): δ 8.38 (d, J=7.8 Hz, 2H), 7.73-7.78 (t, J=7.5 Hz, 1H), 7.46 (d, J=8.4 Hz, 1H), 7.32 (d, J=8.4 Hz, 1H), 6.95-6.99 (t, J=6.0 Hz, 1H), 6.31 (s, 1H), 4.36 (s, 3H)

Example 248

5-(4-Methoxy-1H-benzo[d][1,2,3]triazol-5-yl)-2-methyl-3-(pyridin-2-yl)pyrazolo[1,5-a]pyrimidin-7(4H)-one

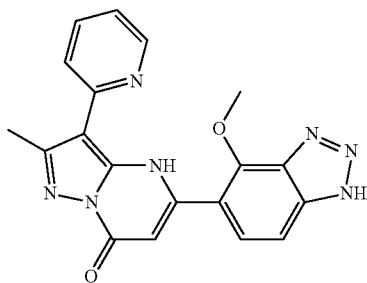 [SMILES: COc1c(-c2cc(=O)n3nc(C)c(-c4ccccn4)c3[nH]2)ccc2[nH]nnc12]

LC/MS (ES, m/z): [M+H]$^+$ 374.1

$^1$H-NMR (300 MHz, DMSO) δ 8.57 (d, J=4.2 Hz, 1H), 8.35 (d, J=7.2 Hz, 1H), 7.72-7.77 (t, J=7.8 Hz, 1H), 7.64 (d, J=8.7 Hz, 1H), 7.43 (d, J=8.7 Hz, 1H), 7.05-7.09 (t, J=5.1 Hz, 1H), 6.10 (s, 1H), 4.45 (s, 3H), 2.65 (s, 3H)

Example 249

5-(6-Fluoro-1H-benzo[d][1,2,3]triazol-5-yl)-3-(pyridin-2-yl)pyrazolo[1,5-a]pyrimidin-7(4H)-one

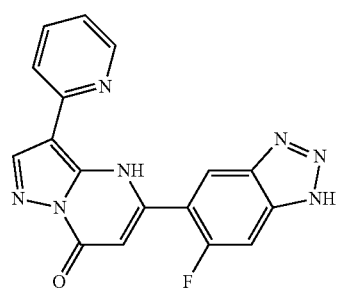 [SMILES: O=c1cc(-c2cc3nn[nH]c3cc2F)[nH]c2c(-c3ccccn3)cnn12]

LC/MS (ES, m/z): [M+H]$^+$. 348.0

$^1$H-NMR (300 MHz, DMSO) δ 8.62 (d, J=8.1 Hz, 1H), 8.42 (d, J=4.2 Hz, 2H), 8.37 (s, 1H), 7.70-7.80 (m, 2H), 7.00-7.03 (t, J=6.6 Hz, 1H), 5.98 (d, J=2.4 Hz, 1H)

Example 250

5-(4-Isopropoxybenzo[d][1,3]dioxol-5-yl)-3-(pyridin-2-yl)pyrazolo[1,5-a]pyrimidin-7(4H)-one

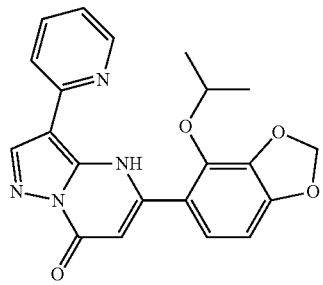 [SMILES: CC(C)Oc1c(-c2cc(=O)n3ncc(-c4ccccn4)c3[nH]2)ccc2c1OCO2]

LC/MS (ES, m/z): [M+H]$^+$ 391.1;

$^1$H-NMR (300 MHz, DMSO) δ 8.60 (d, J=8.1 Hz, 1H), 8.41 (d, J=3.9 Hz, 1H), 8.29 (s, 1H), 7.64-7.70 (m, 1H), 7.36 (d, J=8.7 Hz, 1H), 6.94-6.98 (m, 1H), 6.74 (d, J=8.1 Hz, 1H), 6.04 (s, 2H), 6.00 (s, 1H), 4.39-4.47 (m, 1H), 1.16 (d, J=6.0 Hz, 6H)

Example 251

5-(4-Isopropoxybenzo[d][1,3]dioxol-5-yl)-2-methyl-3-(pyridin-2-yl)pyrazolo[1,5-a]pyrimidin-7(4H)-one

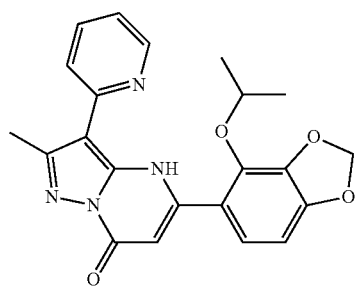 [SMILES: Cc1nn2c(=O)cc(-c3ccc4c(c3OC(C)C)OCO4)[nH]c2c1-c1ccccn1]

LC/MS (ES, m/z): [M+H]$^+$ 405.0

$^1$H-NMR (300 MHz, DMSO): δ 8.71 (d, J=8.1 Hz, 1H), 8.44 (d, J=3.9 Hz, 1H), 7.62-7.67 (m, 1H), 7.32 (d, J=8.1 Hz, 1H), 6.91-6.95 (m, 1H), 6.72 (d, J=8.4 Hz, 1H), 6.03 (s, 2H), 5.94 (s, 1H), 4.37-4.45 (m, 1H), 2.63 (s, 3H), 1.15 (d, J=6.0 Hz, 6H)

Example 252

4-(2-Methyl-7-oxo-3-(pyridin-2-yl)-4,7-dihydropyrazolo[1,5-a]pyrimidin-5-yl)phenyl methylcarbamate

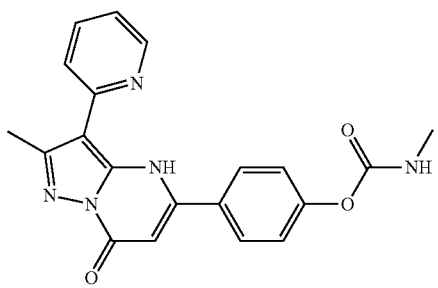

Step 1. 5-(4-hydroxyphenyl)-2-methyl-3-(pyridin-2-yl)pyrazolo[1,5-a]pyrimidin-7(4H)-one

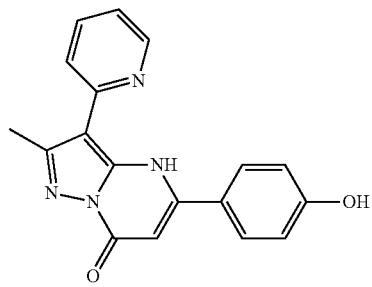 [SMILES: Cc1nn2c(=O)cc(-c3ccc(O)cc3)[nH]c2c1-c1ccccn1]

LC/MS (ES, m/z):[M+H]$^+$ 319.1
$^1$H-NMR (300 MHz, CD$_3$OD) δ 8.54-8.56 (m, 1H), 8.28-8.31 (m, 1H), 7.82-7.91 (m, 3H), 7.14-7.19 (m, 1H), 6.85-6.94 (m, 2H), 6.22 (s, 1H), 2.66 (s, 3H)

Step 2. 4-(2-Methyl-7-oxo-3-(pyridin-2-yl)-4,7-dihydropyrazolo[1,5-a]pyrimidin-5-yl)phenyl methylcarbamate

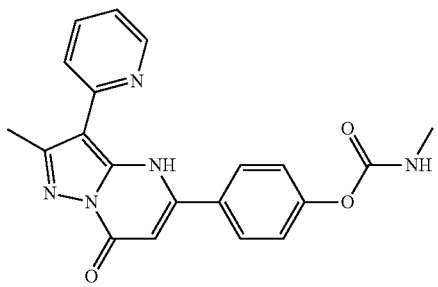

To a solution of 5-(4-hydroxyphenyl)-2-methyl-3-(pyridin-2-yl)pyrazolo[1,5-a]pyrimidin-7(4H)-one (100 mg, 0.31 mmol) in dichloromethane (40 mL) was added triethylamine (127 mg, 1.26 mmol) and a solution of isocyanatomethane (127 mg, 1.26 mmol) in toluene (1N, 8 mL) with stirring, and the resulting mixture was stirred for 3.5 hours at 40° C. The reaction was then quenched by the addition of water (80 mL), extracted with dichloromethane (3×30 mL), dried over anhydrous sodium sulfate, and concentrated under vacuum to give a residue, which was purified by silica gel column to afford 4-(2-methyl-7-oxo-3-(pyridin-2-yl)-4,7-dihydropyrazolo[1,5-a]pyrimidin-5-yl)phenyl methylcarbamate as a yellow solid (25.6 mg, 22%).

LC/MS (ES, m/z):[M+H]$^+$376.0
$^1$H-NMR (300 MHz, DMSO) δ 12.44 (s, 1H), 8.73 (d, J=4.8 Hz, 1H), 7.93-7.99 (m, 3H), 7.74-7.80 (m, 2H), 7.28-7.36 (m, 3H), 6.28 (s, 1H), 2.69 (d, J=4.5 Hz, 3H), 2.64 (s, 3H)

Example 253

4-(7-Oxo-3-(pyridin-2-yl)-4,7-dihydropyrazolo[1,5-a]pyrimidin-5-yl)phenyl methylcarbamate

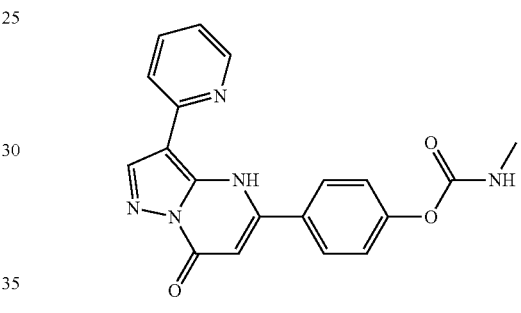

Step 1. 5-(4-Hydroxyphenyl)-3-(pyridin-2-yl)pyrazolo[1,5-a]pyrimidin-7(4H)-one

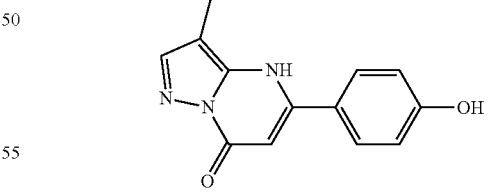

LC/MS (ES, m/z): [M+H]$^+$305.0
$^1$H-NMR (300 MHz, DMSO) δ 10.29 (s, 1H), 8.69 (d, J=5.1 Hz, 1H), 8.62 (s, 1H), 7.92 (d, J=3.6 Hz, 2H), 7.78 (d, J=8.7 Hz, 2H), 7.24-7.29 (m, 1H), 6.98 (d, J=8.7 Hz, 2H), 6.24 (s, 1H)

Step 2. 4-(7-oxo-3-(pyridin-2-yl)-4,7-dihydropyrazolo[1,5-a]pyrimidin-5-yl)phenyl methylcarbamate

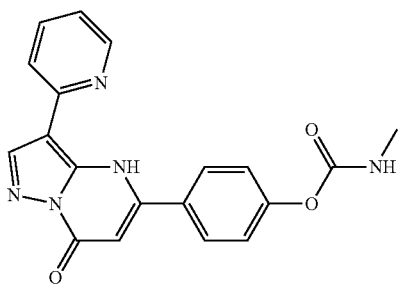 [SMILES: CNC(=O)Oc1ccc(-c2cc(=O)n3ncc(-c4ccccn4)c3[nH]2)cc1]

LC/MS (ES, m/z): [M+H]⁺362.0
¹H-NMR (300 MHz, DMSO) δ 8.66-8.66 (t, J=4.5 Hz, 1H), 7.90-8.15 (m, 4H), 7.78 (d, J=4.5 Hz, 1H), 7.36-7.35 (m, 3H), 5.76 (s, 1H), 2.70 (d, J=4.5 Hz, 3H)

Example 254

5-(4-(Oxazol-2-yl)phenyl)-3-(pyridin-2-yl)pyrazolo[1,5-a]pyrimidin-7(4H)-one

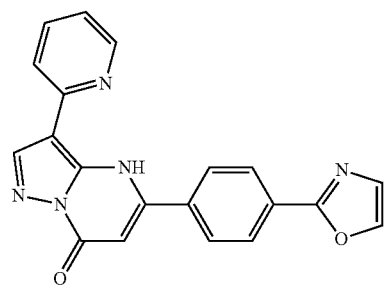 [SMILES: O=c1cc(-c2ccc(-c3ncco3)cc2)[nH]c2c(-c3ccccn3)cnn12]

LC/MS (ES, m/z): [M+H]⁺ 356.0
¹H-NMR (300 MHz, DMSO) δ 8.72 (d, J=7.8 Hz, 1H), 8.43-8.45 (m, 1H), 8.25-8.33 (m, 4H), 8.07 (d, J=8.7 Hz, 1H), 7.74-7.80 (m, 1H), 7.42 (s, 1H), 6.99-7.04 (m, 1H), 6.15 (s, 1H)

Example 255

5-(4-(1,3,4-Oxadiazol-2-yl)phenyl)-3-(pyridin-2-yl)pyrazolo[1,5-a]pyrimidin-7(4H)-one

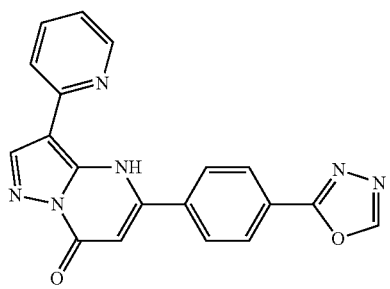 [SMILES: O=c1cc(-c2ccc(-c3nnco3)cc2)[nH]c2c(-c3ccccn3)cnn12]

Step 1. Methyl 4-(7-oxo-3-(pyridin-2-yl)-4,7-dihydropyrazolo[1,5-a]pyrimidin-5-yl)benzoate

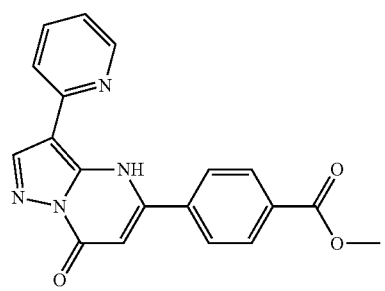 [SMILES: COC(=O)c1ccc(-c2cc(=O)n3ncc(-c4ccccn4)c3[nH]2)cc1]

LC/MS (ES, m/z): [M+H]⁺347.0
¹H-NMR (300 MHz, DMSO): δ 8.70 (d, J=7.8 Hz, 1H), 8.44 (d, J=4.2 Hz, 1H), 8.33 (s, 1H), 8.25 (d, J=8.4 Hz, 2H), 8.04-8.07 (d, J=8.4 Hz, 2H), 7.74-7.78 (m, 1H), 6.99-7.03 (m, 1H), 6.14 (s, 1H), 3.92 (s, 3H)

Step 2. 4-(7-oxo-3-(pyridin-2-yl)-4,7-dihydropyrazolo[1,5-a]pyrimidin-5-yl)benzohydrazide

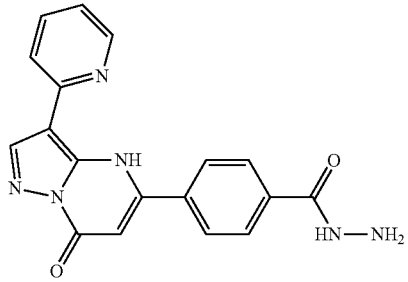 [SMILES: NNC(=O)c1ccc(-c2cc(=O)n3ncc(-c4ccccn4)c3[nH]2)cc1]

A solution of methyl 4-(7-oxo-3-(pyridin-2-yl)-4,7-dihydropyrazolo[1,5-a]pyrimidin-5-yl)benzoate (200 mg, 0.58 mmol) and N₂H₄H₂O (144 mg, 2.89 mmol) in methanol (20 ml) was stirred overnight at 90° C. Then the solids were collected by filtration to afford 4-(7-oxo-3-(pyridin-2-yl)-4,7-dihydropyrazolo[1,5-a]pyrimidin-5-yl)benzohydrazide as a yellow solid (160 mg, 80%).

LC/MS (ES, m/z): [M+H]⁺ 347.0
¹H-NMR (300 MHz, DMSO): δ 9.83 (s, 1H), 8.66 (d, J=7.8 Hz, 1H), 8.45 (d, J=4.2 Hz, 1H), 8.33 (s, 1H), 8.15 (d, J=8.4 Hz, 2H), 7.90-7.93 (t, J=8.4 Hz, 2H), 7.76-7.80 (t, J=6.9 Hz, 1H), 7.00-7.04 (t, J=6.6 Hz, 1H), 6.13 (s, 1H), 4.58 (s, 1H)

Step 3. 5-(4-(1,3,4-Oxadiazol-2-yl)phenyl)-3-(pyridin-2-yl)pyrazolo[1,5-a]pyrimidin-7(4H)-one

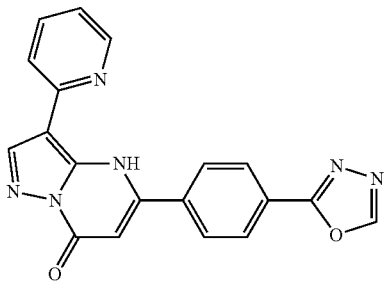 [SMILES: O=c1cc(-c2ccc(-c3nnco3)cc2)[nH]c2c(-c3ccccn3)cnn12]

To a solution of 4-(7-oxo-3-(pyridin-2-yl)-4,7-dihydropyrazolo[1,5-a]pyrimidin-5-yl)benzohydrazide (130 mg, 0.38 mmol,) in n-BuOH (10 ml) was added TsOH (4 mg, 0.02 mmol), and CH(OEt)$_3$ (3 ml). The resulting solution was stirred for 2 hours at 130° C. and then concentrated under vacuum to give a residue, which was purified by Pre-HPLC to afford 5-(4-(1,3,4-oxadiazol-2-yl)phenyl)-3-(pyridin-2-yl)pyrazolo[1,5-a]pyrimidin-7(4H)-one as a yellow solid (34.7 mg, 26%).

LC/MS (ES, m/z): [M+H]$^+$ 357.1

$^1$H-NMR (300 MHz, DMSO): δ 9.38 (s, 1H), 8.71 (d, J=8.1 Hz, 1H), 8.45 (d, J=4.2 Hz, 1H), 8.33-8.37 (t, J=5.85 Hz, 3H), 8.11 (d, J=8.1 Hz, 2H), 7.74-7.89 (t, J=6.9 Hz, 1H), 6.99-7.03 (t, J=5.7 Hz, 1H), 6.16 (s, 1H)

Example 256

4-(7-Oxo-3-(pyridin-2-yl)-4,7-dihydropyrazolo[1,5-a]pyrimidin-5-yl)benzonitrile

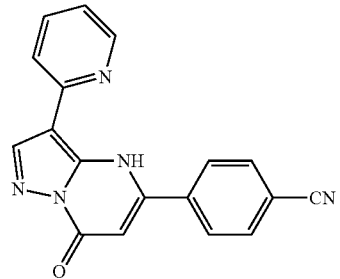

LC/MS (ES, m/z): [M+H]$^+$ 314.1

$^1$H-NMR (300 MHz, DMSO) δ 8.65-8.69 (t, J=6.3 Hz, 2H), 8.23-8.27 (m, 3H), 8.09-8.15 (m, 1H), 8.02 (d, J=8.4 Hz, 1H), 7.35-7.39 (t, J=8.4 Hz, 1H), 6.44 (s, 1H)

The activity of the compounds in Examples 1-256 as PASK modulators and CK2 inhibitors is illustrated in the following assays.

Biochemical Assay for hPASK Activity

PAS Kinase Luminescence Assay

One assay for purified hPASK activity utilizes the Kinase-Glo Luminescent Kinase Assay (Promega), which quantifies the amount of ATP remaining in solution following kinase reaction. The assay is carried out in a 96-well plate format and is performed by adding a volume of Kinase-Glo Reagent (Promega, catalog #V3771) equal to the volume of solution in the well of a completed kinase reaction. Kinase-Glo reagent contains Luciferase and its substrate. After addition to a kinase reaction it allows to measure luminescence. The amount of ATP left in solution at the time of Kinase-Glo Plus addition is directly proportional to the luminescence that is measured in each well, and inversely correlated with kinase activity.

Purified hPASK from insect cells (0.02 µg) is added to a 50 µL reaction mix containing 40 mM HEPES (pH 7.0), 100 mM KCl, 5 mM MgCl$_2$, 1 mM DTT and 1 µg of MBP protein. Inhibitory compounds are then added and the mixture is incubated for 10 min at 25° C. before adding 5 µL of ATP (at desired concentration). The reaction is allowed to proceed at 25° C. for 1 hour before adding 50 µL of Kinase-Glo reagent. The luminescence is measured as soon as 10 minutes after Kinase-Glo reagent is added.

Results are shown below in Table 1, where NT means not tested. Examples not listed in the table were not tested.

TABLE 1

| Example # | Full Length IC$_{50}$<br>+ indicates ≤10 µm<br>− indicates ≥10 µm | IC$_{50}$ Kinase Domain<br>+ indicates ≤10 µm<br>− indicates ≥10 µm |
|---|---|---|
| 1 | + | + |
| 2 | + | − |
| 3 | + | + |
| 4 | + | + |
| 5 | − | + |
| 6 | − | + |
| 7 | − | + |
| 8 | + | + |
| 9 | + | + |
| 10 | − | − |
| 11 | − | − |
| 12 | − | − |
| 13 | − | + |
| 14 | + | + |
| 15 | − | − |
| 16 | + | + |
| 17 | + | + |
| 18 | − | − |
| 19 | − | − |
| 20 | − | − |
| 21 | − | − |
| 22 | − | − |
| 23 | − | − |
| 24 | − | − |
| 25 | − | − |
| 26 | − | − |
| 27 | − | − |
| 28 | − | − |
| 29 | − | − |
| 30 | − | − |
| 31 | − | − |
| 32 | − | − |
| 33 | − | − |
| 34 | − | − |
| 35 | − | + |
| 36 | − | − |
| 37 | − | − |
| 38 | + | + |
| 39 | + | − |
| 40 | NT | + |
| 41 | NT | + |
| 42 | NT | + |
| 43 | NT | + |
| 44 | NT | + |
| 45 | NT | + |
| 46 | NT | + |
| 47 | NT | + |
| 48 | NT | + |
| 49 | NT | + |
| 50 | NT | + |
| 51 | NT | + |

TABLE 1-continued

| Example # | Full Length IC$_{50}$<br>+ indicates ≤10 µm<br>− indicates ≥10 µm | IC$_{50}$ Kinase Domain<br>+ indicates ≤10 µm<br>− indicates ≥10 µm |
|---|---|---|
| 52 | NT | + |
| 74 | NT | + |
| 78 | NT | + |

PASK ATP Radiochemical Assay

Purified PASK (UniProt #Q96RG2; human recombinant N-terminal GST tagged construct, residues 879-1323) from insect cells (final concentration 5 nM) is added to freshly prepared Base Reaction Buffer containing 20 mM HEPES (pH 7.5), 10 mM MgCl$_2$, 1 mM EGTA, 0.02% Brij35, 0.02 mg/ml BSA, 0.1 mM Na$_3$VO$_4$, 2 mM DTT, 1% DMSO and Myelin Basic Protein (20 µM final). Test compounds in DMSO are then added and the mixture, followed by delivery of $^{33}$P-ATP (specific activity 0.01 µCi/µl final) to initiate the reaction. The kinase reaction is incubated for 120 min at room temperature. The entire reaction mixture is washed through onto a P81 Phosphocellulose paper and washed three times for 10 minutes in 75 mM phosphoric acid and once in methanol prior to drying and scintillation counting.

Results for this assay are shown below in Table 2. Examples not listed in the table were not tested.

TABLE 2

| Example # | IC$_{50}$ Kinase Domain<br>+ indicates ≤10 µm<br>− indicates ≥10 µm |
|---|---|
| 71 | + |
| 72 | + |
| 73 | + |
| 74 | + |
| 75 | + |
| 76 | + |
| 77 | + |
| 79 | + |
| 81 | + |
| 92 | + |
| 93 | + |
| 95 | + |
| 96 | + |
| 97 | + |
| 95 | + |
| 96 | + |
| 97 | + |
| 98 | + |
| 99 | + |
| 100 | + |
| 102 | + |
| 103 | + |
| 106 | + |
| 107 | + |
| 108 | + |
| 109 | + |
| 110 | + |
| 111 | + |
| 113 | + |
| 114 | + |
| 116 | + |
| 117 | + |
| 119 | + |
| 121 | + |
| 122 | + |
| 123 | + |
| 125 | + |
| 126 | + |
| 127 | + |
| 128 | + |
| 129 | + |
| 130 | + |
| 131 | + |
| 133 | + |
| 135 | + |
| 137 | + |
| 141 | + |
| 142 | + |
| 143 | + |
| 144 | + |
| 145 | + |
| 147 | + |
| 148 | + |
| 149 | + |
| 150 | + |
| 152 | + |
| 155 | + |
| 156 | + |
| 158 | + |
| 159 | + |
| 160 | + |
| 161 | + |
| 163 | + |
| 164 | + |
| 171 | + |
| 191 | + |
| 193 | + |
| 197 | + |
| 198 | + |
| 199 | + |
| 201 | + |
| 205 | + |
| 210 | + |
| 213 | + |
| 214 | + |
| 217 | + |
| 218 | + |
| 223 | + |
| 224 | + |
| 225 | + |
| 227 | + |
| 234 | + |
| 235 | + |
| 237 | + |
| 243 | + |
| 245 | + |
| 249 | + |
| 254 | + |
| 256 | + |

PAS Kinase FRET Assay

The aim of the FRET assay is to determine the inhibition potential of test compounds on targeted kinase. This assay platform provides a homogenous screening method for measuring kinase activity by quantitating the amount of phospho-substrate in solution following a kinase reaction.

In the presence of kinase and ATP, the Ulight-peptide is phosphorylated and captured by an anti-phospho-substrate antibody, which brings the Eu chelate donor and Ulight acceptor dyes into close proximity. Upon excitation at 340 nm, the Eu chelate transfers its energy to the Ulight dye, resulting in a fluorescent light emission at 665 nm Titration of kinase at 1 mM ATP was achieved via the following protocol. After making serial three-fold dilutions of PASK (Invitrogen) in reaction buffer across the plate; 5 µl of kinase dilution and 5 µl substrate/ATP mix were added to the wells of the white Optiplate-384 (PerkinElmer). The contents of the plate were and incubated at RT for 1 h. The reaction was stopped by adding 5 µl of stop solution to each test well followed by mixing and incubation at RT for 10 minutes. 5 µl of detection mix (detection antibody diluted in detection buffer) was added; the contents of the plate were mixed and then incubated in the dark for 1 hour at RT. The signal was recorded at TR-FRET mode (665 nm/615 nm). The results were graphed to calculate the $EC_{50}$.

Titration of ATP at the $EC_{50}$ concentration of kinase to determine ATP Km, app. was performed using the following method. After making serial dilutions of ATP (Invitrogen), 5 µl of ATP dilution and 5 µl substrate/kinase mix were added to the wells of the white Optiplate-384 (PerkinElmer). The contents of the plate were and incubated at RT for 1 h. The reaction was stopped by adding 5 µl of stop solution to each test well followed by mixing and incubation at RT for 10 minutes. 5 µl of detection mix (detection antibody diluted in detection buffer) was added; the contents of the plate were mixed and then incubated in the dark for 1 hour at RT. The signal was recorded at TR-FRET mode (665 nm/615 nm). The results were graphed to calculate the $EC_{50}$ as the ATP Km, app.

Compound screening was done via the following method. 10 mM stock solution of test compound in DMSO was prepared by dissolving test compound in DMSO at RT for 1 hour, and then sonicating at 100% output for 8 minutes. If compound is not soluble under this condition, it was diluted to 3 mM. Kinase reaction buffer was prepared containing 10 mM $MgCl_2$, 50 mM HEPES, 1 mM EGTA, 0.01% TWEEN-20, 2 mM DTT. Serial dilutions of the test compounds were prepared at 4×final assay concentrations using Freedom EVO200® dispensing system as follows: $12 \times 10^{-5}$ M, $4 \times 10^{-5}$ M, $1.33 \times 10^{-5}$ M, $4.44 \times 10^{-6}$ M, $1.48 \times 10^{-6}$ M, $4.92 \times 10^{-7}$ M, $1.65 \times 10^{-7}$ M, $5.48 \times 10^{-7}$ M, $1.82 \times 10^{-8}$ M, $6.09 \times 10^{-9}$, $2.03 \times 10^{-9}$ M. Test compounds (2.5 µl at 4× the final assay concentration) was added to wells using Freedom EVO200® dispensing system. As a positive control, 2.5 µl of positive compound was added to assay wells, and 2.5 µl of DMSO to assay wells as vehicle control. Kinase solution was prepared in reaction buffer at 2×final assay concentration. Kinase solution (5 µl) was added to each well of the assay plate. The substrate and ATP solution was prepared in kinase reaction buffer at 4×final assay concentration. The kinase reaction was started by adding 2.5 µl of substrate+ATP mix solution to each well of the assay plate. The plate is mixed on a plate shaker; then covered and allowed to react for 2 hours in the dark at 25° C. without shaking. The reaction was stopped by adding 5 µl of stop solution to each test well followed by mixing and incubation at RT for 10 minutes in the dark. 5 µl of detection mix (detection antibody diluted in detection buffer) was added; the contents of the plate were mixed and then incubated in the dark for 1 hour at RT. The signal was recorded at TR-FRET mode (665 nm/615 nm).

Results are shown below in Table 3. Examples not listed in the table were not tested.

TABLE 3

| Example # | $IC_{50}$ Kinase Domain<br>+ indicates ≤10 µm<br>− indicates ≥10 µm |
|---|---|
| 70 | + |
| 71 | + |
| 72 | + |
| 73 | + |
| 75 | + |
| 76 | + |
| 80 | + |
| 81 | + |
| 82 | + |
| 83 | + |
| 84 | + |
| 85 | + |
| 86 | + |
| 87 | + |
| 88 | − |
| 89 | + |
| 90 | + |
| 91 | + |
| 92 | + |
| 93 | + |
| 94 | + |
| 96 | + |
| 97 | + |
| 98 | + |
| 99 | + |
| 100 | + |
| 101 | + |
| 102 | + |
| 103 | + |
| 104 | + |
| 105 | + |
| 106 | + |
| 107 | + |
| 108 | + |
| 109 | + |
| 110 | + |
| 111 | + |
| 112 | + |
| 113 | + |
| 114 | + |
| 115 | + |
| 116 | + |
| 117 | + |
| 118 | + |
| 119 | + |
| 120 | + |
| 121 | + |
| 122 | + |
| 123 | + |
| 124 | + |
| 125 | + |
| 126 | + |
| 127 | + |
| 128 | + |
| 129 | + |
| 130 | + |
| 131 | + |
| 132 | + |
| 133 | + |
| 134 | + |
| 135 | + |
| 136 | + |
| 137 | + |
| 138 | + |
| 139 | + |
| 140 | + |
| 141 | + |
| 142 | + |
| 143 | + |
| 144 | + |
| 145 | + |
| 146 | + |
| 147 | + |
| 148 | + |
| 149 | + |
| 150 | + |
| 151 | + |
| 152 | + |
| 153 | + |
| 154 | + |
| 155 | + |
| 156 | + |
| 157 | + |
| 158 | + |
| 159 | + |
| 160 | + |
| 161 | + |

TABLE 3-continued

| Example # | IC$_{50}$ Kinase Domain<br>+ indicates ≤10 μm<br>− indicates ≥10 μm |
|---|---|
| 162 | + |
| 163 | + |
| 164 | + |
| 165 | + |
| 166 | + |
| 167 | + |
| 168 | + |
| 169 | + |
| 170 | + |
| 171 | + |
| 172 | + |
| 173 | + |
| 174 | + |
| 175 | + |
| 176 | + |
| 177 | + |
| 178 | + |
| 179 | + |
| 180 | + |
| 181 | + |
| 182 | + |
| 183 | + |
| 184 | + |
| 185 | + |
| 186 | + |
| 187 | + |
| 188 | + |
| 189 | + |
| 190 | + |
| 191 | + |
| 192 | + |
| 193 | + |
| 194 | + |
| 195 | + |
| 196 | + |
| 197 | + |
| 198 | + |
| 199 | + |
| 200 | + |
| 201 | + |
| 202 | + |
| 203 | + |
| 204 | + |
| 205 | + |
| 206 | + |
| 207 | + |
| 208 | + |
| 209 | + |
| 210 | + |
| 211 | + |
| 212 | + |
| 213 | + |
| 214 | + |
| 215 | + |
| 216 | + |
| 217 | + |
| 218 | + |
| 219 | + |
| 220 | + |
| 221 | + |
| 222 | + |
| 223 | + |
| 224 | + |
| 225 | + |
| 226 | + |
| 227 | + |
| 228 | + |
| 229 | + |
| 230 | + |
| 231 | + |
| 232 | + |
| 233 | + |
| 234 | + |
| 235 | + |
| 236 | + |
| 237 | + |
| 238 | + |
| 239 | + |
| 240 | + |
| 241 | + |
| 242 | + |
| 243 | + |
| 244 | + |
| 245 | + |
| 246 | + |
| 247 | + |
| 248 | + |
| 249 | + |
| 250 | + |
| 251 | + |
| 252 | + |
| 253 | + |
| 254 | + |
| 255 | + |
| 256 | + |

Biochemical Assay for CK2 Activity

Purified CK2a2 (NP_001887; human full-length protein, GST tagged) from insect cells (final concentration 1.2 nM) is added to freshly prepared Base Reaction Buffer containing 20 mM Hepes (pH 7.5), 10 mM MgCl$_2$, 1 mM EGTA, 0.02% Brij35, 0.02 mg/ml BSA, 0.1 mM Na$_3$VO$_4$, 2 mM DTT, 1% DMSO and CK2 sub [RRRDDDSDDD] (20 μM final). Test compounds in DMSO are then added and the mixture, followed by delivery of $^{33}$P-ATP (specific activity 0.01 μCi/μl final) to initiate the reaction. The kinase reaction is incubated for 120 min at room temperature. The entire reaction mixture is washed through onto a P81 Phosphocellulose paper and washed three times for 10 minutes in 75 mM phosphoric acid and once in methanol prior to drying and scintillation counting.

Results are shown below in Table 4. Examples not listed in the table were not tested.

TABLE 4

| Example # | IC$_{50}$ CK2 a2<br>+ indicates ≤10 μm<br>− indicates ≥10 μm |
|---|---|
| 40 | + |
| 43 | + |
| 44 | + |
| 45 | + |
| 47 | + |
| 48 | + |
| 50 | + |
| 51 | + |
| 53 | + |
| 54 | + |
| 55 | + |
| 56 | + |
| 61 | + |
| 62 | − |
| 63 | − |
| 64 | − |
| 65 | − |
| 66 | − |
| 67 | − |
| 68 | − |
| 69 | − |
| 70 | − |
| 71 | − |

TABLE 4-continued

| Example # | IC$_{50}$ CK2 a2<br>+ indicates ≤10 μm<br>− indicates ≥10 μm |
|---|---|
| 72 | + |
| 73 | + |
| 74 | − |
| 75 | + |
| 76 | + |
| 77 | + |
| 79 | + |
| 81 | + |
| 89 | + |
| 91 | + |
| 92 | + |
| 95 | + |
| 96 | + |
| 97 | + |
| 98 | + |
| 99 | + |
| 100 | + |
| 101 | + |
| 102 | + |
| 103 | + |
| 106 | + |
| 107 | + |
| 108 | + |
| 109 | + |
| 110 | + |
| 111 | + |
| 113 | + |
| 114 | + |
| 116 | + |
| 117 | + |
| 119 | + |
| 121 | + |
| 122 | − |
| 123 | − |
| 125 | + |
| 126 | + |
| 127 | + |
| 128 | − |
| 129 | − |
| 130 | + |
| 131 | + |
| 133 | + |
| 135 | + |
| 137 | − |
| 141 | + |
| 142 | + |
| 143 | + |
| 144 | + |
| 145 | + |
| 147 | + |
| 148 | + |
| 149 | + |
| 150 | + |
| 152 | + |
| 155 | + |
| 156 | + |
| 158 | + |
| 159 | + |
| 160 | + |
| 161 | + |
| 163 | + |
| 164 | + |
| 171 | + |
| 191 | + |
| 193 | + |
| 197 | + |
| 198 | + |
| 199 | + |
| 201 | + |
| 205 | + |
| 210 | + |
| 213 | + |
| 214 | + |
| 217 | + |
| 218 | + |
| 223 | + |
| 224 | + |
| 225 | + |
| 227 | + |
| 234 | + |
| 235 | + |
| 237 | + |
| 243 | − |
| 245 | + |
| 249 | + |
| 254 | − |
| 256 | − |

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of treatment of a disease comprising the administration of a therapeutically effective amount of a compound of structural Formula I

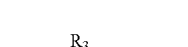

or a pharmaceutically acceptable salt, or ester thereof, wherein:
$R_1$ is chosen from hydrogen, hydroxyl, cyano, haloalkyl, and aryl, any of which may be optionally substituted;
$R_2$ is chosen from hydrogen, hydroxy, alkoxy, amino, alkylamino, dialkylamino, NHCOR$_{20}$, lower alkyl, lower haloalkyl, aryl, arylalkyl, heteroaryl and heteroarylalkyl, any of which may be optionally substituted;
$R_3$ is chosen from hydrogen, lower alkyl, cycloalkyl, aryl, heteroaryl, heterocycloalkyl, cycloalkylalkyl, arylalkyl, heteroarylalkyl, heterocycloalkylalkyl, and cyano, any of which may be optionally substituted;
$R_4$ is chosen from CH$_2$CO$_2$R$_5$, heteroaryl, cycloalkyl, heteroarylalkyl, and cycloalkylalkyl, any of which may be optionally substituted;
$R_5$ is chosen from hydrogen and lower alkyl; and
$R_{20}$ is chosen from lower alkyl, arylalkyl, aryl, heteroaryl, and heteroarylalkyl to a patient suffering from said disease,
wherein said disease is chosen from metabolic syndrome, obesity, insulin resistance, type II diabetes, and dyslipidemia.

2. The method of claim 1 wherein said dyslipidemia is hyperlipidemia.

* * * * *